US008262868B2

(12) United States Patent
Brooks et al.

(10) Patent No.: US 8,262,868 B2
(45) Date of Patent: Sep. 11, 2012

(54) SPECTRAL CHEMISTRY

(75) Inventors: Juliana H. J. Brooks, Columbus, OH (US); Bentley J. Blum, New York, NY (US)

(73) Assignee: GR Intellectual Reserve, LLC, Havre de Grace, MD (US)

(*) Notice: Subject to any disclaimer, the term of this patent is extended or adjusted under 35 U.S.C. 154(b) by 447 days.

(21) Appl. No.: 10/203,797

(22) PCT Filed: Sep. 11, 2001

(86) PCT No.: PCT/US01/28392
§ 371 (c)(1), (2), (4) Date: Nov. 27, 2002

(87) PCT Pub. No.: WO02/22797
PCT Pub. Date: Mar. 21, 2002

(65) Prior Publication Data
US 2004/0089532 A1  May 13, 2004

Related U.S. Application Data

(60) Continuation-in-part of application No. 09/919,679, filed on Aug. 1, 2001, now abandoned, which is a continuation of application No. 09/460,025, filed on Dec. 13, 1999, now abandoned, which is a division of application No. 09/098,883, filed on Jun. 17, 1998, now Pat. No. 6,033,531.

(60) Provisional application No. 60/231,620, filed on Sep. 11, 2000, provisional application No. 60/049,910, filed on Jun. 18, 1997.

(51) Int. Cl.
*C07C 1/00* (2006.01)
(52) U.S. Cl. ............ 204/157.15; 204/157.21; 204/157.4
(58) Field of Classification Search ............... 435/173.1; 204/157.15, 157.21, 157.4
See application file for complete search history.

(56) References Cited

U.S. PATENT DOCUMENTS

| | | | | |
|---|---|---|---|---|
| 2,161,292 A | 1/1939 | Hahnemann | | 607/156 |
| 3,092,561 A | 6/1963 | Lampe | | |
| 4,012,301 A | 3/1977 | Rich | | 204/157.41 |
| 4,115,280 A | 9/1978 | Pratt | | 422/186.1 |
| 4,287,036 A | 9/1981 | Tsutsui et al. | | 204/157.46 |
| 4,481,091 A | 11/1984 | Brus | | 204/157.15 |
| 4,548,686 A * | 10/1985 | Stevens et al. | | 204/157.94 |
| 4,755,269 A | 7/1988 | Brumer | | 204/157.4 |
| 4,774,026 A | 9/1988 | Kitamori | | 204/157.4 |
| 4,861,484 A | 8/1989 | Lichtin et al. | | 210/638 |
| 5,015,349 A | 5/1991 | Suib | | 204/168 |
| 5,174,877 A | 12/1992 | Cooper | | 204/193 |
| 5,395,490 A | 3/1995 | Hoff | | 204/157.15 |
| 6,217,712 B1 | 4/2001 | Mohr | | 204/157.15 |
| 6,294,174 B1 | 9/2001 | Krsmanovic et al. | | |
| 6,728,642 B2 | 4/2004 | Bloch et al. | | |
| 6,765,216 B2 | 7/2004 | Kagadei | | |

OTHER PUBLICATIONS

Mueller et al. "Nitroxyl (HNO), an intermediate in (light-induced) rearrangement reactions of nitrooxy compounds and nitrosoamines," Helv. Chimica Acta (1984) 67(4): 953-958.*
Miura et al. "Studies on the reaction of D-amino acid oxidase with beta-cyano-D-alanine. Observation of an intermediary stable charge transfer complex" J. Biochem. (1980) 87(5): 1469-1481.*
Wilson, A. "Reaction between hydrogen peroxide and ruthenium tetroxide in acid solutions" J. Inorg. Nuclear Chem. (1958) 7: 149-152.*
Kasal et al. the Journal of Physical Chemistry (1978) 62(5); 619-621.*
Acres et al. Platinum Metals Rev. (1966) 10(2): 60-64.*
Vladimirov, et al.; Photoreactivation of Superoxide Dismutase by Intensive Red (Laser) Light; pp. 281-286; 1988; Free Radical Biology & Medicine, vol. 5.
Volman, D.H.; Hydrogen Peroxide Photocatalyzed Reaction of Hydrogen and Oxygen; pp. 2458-2459; 1955; Journal of Chemical Physics, vol. 23, No. 12.
Volman, D.H.; Photochemical Oxygen-Hydrogen Reaction at 1849 A; pp. 288-292; 1956; Journal of Chemical Physics, vol. 25, No. 2.
Verheij, et al.; Hydrogen adsorption on oxygen covered Pt(111); pp. 185-201; 1995; Surface Science, vol. 324, Issues 2-3; Abstract.
Mitchell, et al.; Water formation on Pt(111): Reaction of an intermediate with H2(g); pp. 283-300; 1986; Surface Science, vol. 166, Issues 2-3; Abstract.
Verheij, L.K.; Kinetic modelling of the hydrogen-oxygen reaction on Pt(111) at low temperature (< 170 K); pp. 100-110; 1997; Surface Science, vol. 371, Issue 1; Abstract.
Mitchell, et al.; Identification of the intermediate in the water formation reaction on Pt(111); pp. 84-88; 1987; Chemical Physics Letters, vol. 135, Issues 1-2; Abstract.
Gdowski, et al.; The kinetics and mechanism of the hydrogen-oxygen reaction on Pt(S)-[9(111) × (100)]; pp. 184-206; 1982; Surface Science, vol. 119, Issues 2-3; Abstract.
Sansonetti, et al., Atlas of the Spectrum of a Platinum/Neon Hollow-Cathode Lamp in the Region 1130-4330 A; Accessed on the Internet at: physics.nist.gov/PhysRefData/platinum/contents.html,;on Jul. 9, 2003; Originally online Jun. 20, 1994.
Chou, et al.; Auditory perception of radio-frequency electromagnetic fields; pp. 1321-1333; 1982; The Journal of the Acoustical Society of America.

(Continued)

*Primary Examiner* — Susan Hanley
(74) *Attorney, Agent, or Firm* — Mark G. Mortenson

(57) ABSTRACT

The invention relates to controlling the formation of water in a reaction system comprising hydrogen, oxygen and atomic hydrogen by irradiating the reaction system with electromagnetic emissions from a platinum lamp such that the atomic hydrogen is direct resonance targeted. Physical platinum may also be present in the reaction system.

20 Claims, 44 Drawing Sheets

OTHER PUBLICATIONS

K. Kraus, et al.; The use of a Cap-Shaped Coll for Transcranial Magnetic Stimulation of the Motor Cortex; pp. 353-362; 1993; The Journal of Clinical Neurophysiology, vol. 10, No. 3.

C. Johnson, et al.; Nonionizing Electromagnetic Wave Effects in Biological Materials and Systems; pp. 692-719; 1972; Proceedings of the IEEE, vol. 60, No. 6.

J. Raloff; Medicinal EMF's: Harnessing electric and magnetic fields for healing and health; pp. 316-318; Science News, vol. 156.

S. Webb, et al.; Inhibition of Bacterial Cell Growth by 136 gc Microwaves; pp. 374-375; 1968; Nature, vol. 218.

S. Webb, et al.; Absorption of Microwaves by Microorganisms; pp. 1199-1200; 1969; Nature, vol. 222.

R. Coghill, et al.; Extra Low Frequency Electric and Magnetic Fields in the Bedplace of Children Diagnosed with Leukemia: A Case-Control Study; pp. 1-2; 1997; Bener Digest Update, vol. VII, Issue 1.

J. Weaver, et al.; Theoretical Limits on the Threshold for the Response of Long Cells to Weak Extremely Low Frequency Electric Fields Due to Ionic and Molecular Flux Rectification; pp. 1-9; 1998; Biophysical Journal, vol. 75, No. 5.

M. Jensen; Electromagnetic fields may trigger enzymes; p. 119; 1998; Science News, vol. 153.

Plants: Forest Overachievers; 1 Page; 1995; Popular Science.

Polk, C., & Postow, E. (1986). *Handbook of Biological Effects of Electromagnetic Fields*. Boca Raton, FL: CRC Press LLC. Introduction, pp. 27-35; Chapter 1, pp. 99-118; Chapter 2, pp. 121-138; Chapter 5, pp. 197-219.

Blank, M. (1995). *Electromagnetic Fields: Biological Interactions and Mechanisms*. An American Chemical Society Publication. Preface, pp. xiii-xiv; Chapter 1, pp. 1-10; Chapter 11, pp. 191-223; Chapter 14, pp. 261-275; Chapter 15, pp. 277-285; Chapter 23, pp. 423-436; and Chapter 24, pp. 437-450.

United States Environmental Protection Agency. (1990). Evaluation of the Potential Carcinogenicity of Electromagnetic Fields: Review Draft. EPA/600/6-90/005B. Executive Summary, pp. 1-1-1-6; Chapter 2, pp. 2-1-2-37.

Lynes, B. (1987). *The Cancer Cure That Worked! Fifty Years of Suppression*. Compcare Pubns. Introduction and Foreward, pp. 1-10; Chapter 13, pp. 87-107.

Scherer, W. (1996). Biological Effects of Radiofrequenzy Radiation. *Biological Effects of Radiofrequency and Microwave Radiation: Application, Hazards, and Safeguards*. Retrieved Dec. 30, 1997 from wysiwyg://135/http://www.reach.net/~scherer/p/biofx.htm.

Jennum, P., et al. (1996). Paired transcranial magnetic stimulations and motor evoked potentials. *Electromyography and Clinical Neurophysiology*, vol. 36, pp. 341-348.

Paros, L., & Kirsch, D. Cranial Electrotherapy Stimulation (CES): A Very Safe and Effective Non-Pharmocological Treatment for Anxiety. the Anxiety-Panic internet resource, pp. 1-12. Retrieved Jul. 20, 1998 from http://www.algy.com/anxiety/cranial.html.

Stuchly, M. (1995). Interactions of Electromagnetic Fields with Living Systems. Retrieved on Dec. 30, 1997 from http://bme01.engr.latech.edu/cdrom/340.html.

(1997). Physical Characteristics and Possible Biological Effects of Microwaves Applied in Wireless Communication. *Microwave News—FDA Workshop Abstracts*. Retrieved Aug. 5, 1997 from http://www.microwavenews.com/FDA_Workshop_Abstracts.html.

Cosic, I, "Resonant Recognition Model of Protein-Protein and Protein-DNA Recognition", Bioinstrumentation and Biosensors, (1991), 475-510, Marcel Dekker, Inc., New York.

Cosic, I, "Virtual Spectroscopy for Fun and Profit, Bio/Technology", (1995), 236-238, vol. 13, Nature Publishing Group.

Cosic et al, "Studies on protein-DNA interactions using the resonant recognition model", Eur. J. Biochem. (1992), 613-619, 205.

Cosic, et al, "Resonant recognition model and protein topography", Eur. J. Biochem. (1991), 113-119, 198.

Cosic, et al, "Prediction of 'hot spots' in SV40 enhancer and relation with experimental data", Eur. J. Biochem. (1987), 247-252, 170.

Cosic, et al, "Prediction of 'hot spots' in interleukin-2 based on informational spectrum characteristics of growth-regulating factors. Comparison with experimental data", Biochimie, (1989), 333-342, 71, Societe de Chimie biologique, Elsevier, Paris.

Cosic, I, Macromolecular Bioactivity: Is It Resonant Interaction Between Macromolecules?—Theory and Applications, IEEE Transactions on Biomedical Engineering, (1994) 1101-1114, vol. 41, No. 12.

Cosic et al, "'Hot Spot' Amino Acid Distribution in Ha-ras Oncogene Product p21:Relationship to Guanine Binding Site", Journal of Molecular Recognition, (1991), 57-62, vol. 4, John Wiley & Sons, Ltd.

Cosic et al, "Enhancer Binding Proteins Predicted by Informational Spectrum Method", Biochemical and Biophysical Research Communications, (1986), 831-838, vol. 141, No. 2, Academic Press, Inc.

Paolini, B.P. & Khakoo, M.A. An Intense Atomic Hydrogen Source With a Movable Nozzle Output, Review of Scientific Instruments, 1998, 3132-3135, 69 (9).

Atomic Hydrogen Blowtorch, Lateral Science. http://www.lateralscience.co.uk/AtomicH/atomicH.html. May 3, 2012.

Bischler, U. & Bertel, E. Simple Source of Atomic Hydrogen for Ultrahigh Vacuum Applications, J. Vac. Sci. Technol. A, 1993, 458-460, 11 (2).

Vetterhoffer, J., Campargue, A., Chenevier, M. & Stoeckel, F. Temperature Measurement of Atomic Hydrogen Produced by Hot-Filament Dissociation in a CH4-H2 Mixture, Diamond and Related Materials, 1993, 481-485, 2.

Van Den Bold, H.J. & Smit, J.A. Optical Investigation of an Atomic Hydrogen Flame, Physica, 1946, 475-490, XII (7).

Langmuir, I. Flames of Atomic Hydrogen, Science, 1925, 138.

\* cited by examiner

Initial Frequencies (Hz)

| | | |
|---|---|---|
| 400 | and | 100 |
| 400 + 100 = 500 | and | 400 - 100 = 300 |
| 500 + 300 = 800 | and | 500 - 300 = 200 |
| 800 + 200 = 1000 | and | 800 - 200 = 600 |
| 1000 + 600 = 1600 | and | 1000 - 600 = 400 |

| Sum (Added) Frequencies (Hz) | Difference (Subtracted) Frequencies (Hz) |
|---|---|
| 400 | 100 |
| 500 | 300 |
| 800 | 200 |
| 1000 | 600 |
| 1600 | 400 |
| 2000 | 1200 |
| 3200 | 800 |

Fig. 6d
Fig. 6c
Fig. 6b
Fig. 6a
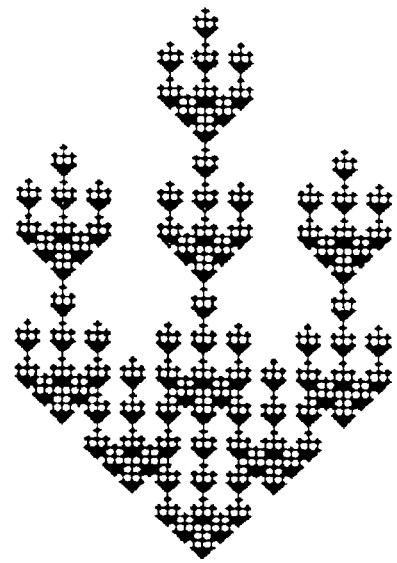
Fig. 7a
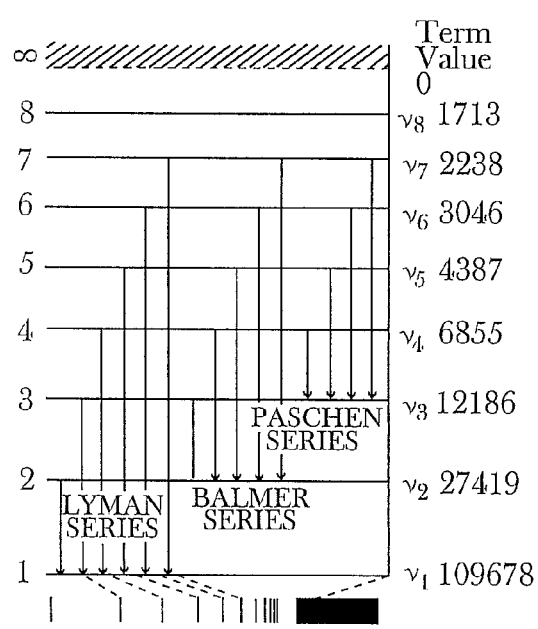
Fig. 7b
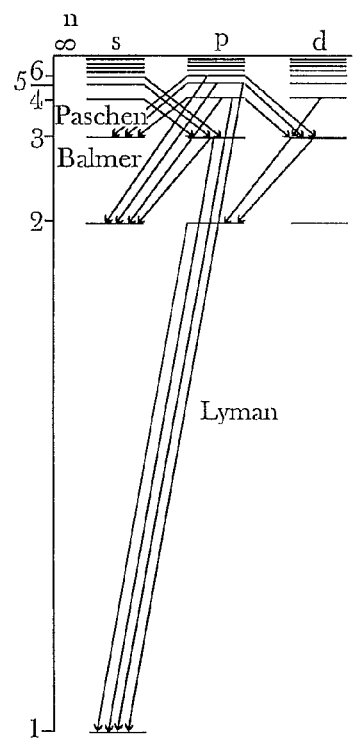

Frequency Curves - THz (relative intensity)

| V | IV | III | II | I |
|---|---|---|---|---|
| 40 (6) | 74 (15) | 160 (40) | 456 (300) | 2466 (1000) |
| 64 (4) | 114 (8) | 234 (20) | 616 (80) | 2923 (300) |
|  | 138 (5) | 274 (12) | 690 (30) | 3082 (100) |
|  |  | 298 (7) | 731 (15) | 3156 (50) |
|  |  | 314 (5) | 755 (8) | 3196 (30) |
|  |  |  | 770 (6) | 3220 (20) |
|  |  |  | 781 (5) | 3236 (15) |

Spectral pattern at low temperature

Spectral pattern at moderate temperature

Separate and distinct spectral curves at low temperature

Overlapping spectral curves at higher temperature, allowing resonant energy transfer ○ Oxygen
● Aluminum or silicon Emission spectrum
T = 50K High resolution spectrum Rotational and Vibrational Frequencies for LiF

| Rotational Transition | | | | |
|---|---|---|---|---|
| 0→1 | 89,740.46 | 88,319.18 | 86,921.20 | |
| 1→2 | 179,470.35 | 176,627.91 | 173,832.04 | 171,082.27 |
| 2→3 | 269,179.18 | 264,915.79 | 260,722.24 | 256,597.84 |
| 3→4 | 358,856.19 | 353,172.23 | 347,581.39 | 342,082.66 |
| 4→5 | 448,491.07 | | | |
| Vibrational Level | 0 | 1 | 2 | 3 |

Fig. 43a

Rotational and Vibrational Frequencies for LiF

Differences Between Rotational And Vibrational Frequencies (MHz) For LiF

| Rotational Transition | | | |
|---|---|---|---|
| 0→1 | 1,421.28 | 1,397.98 | |
| 1→2 | 2,842.44 | 2,795.87 | 2,749.77 |
| 2→3 | 4,263.39 | 4,193.55 | 4,124.40 |
| 3→4 | 5,683.96 | 5,590.84 | 5,498.73 |
| 4→5 | 7,104.24 | | |
| Vibrational Level | 0 | 1 | 2 | 3 |

Fig. 43b

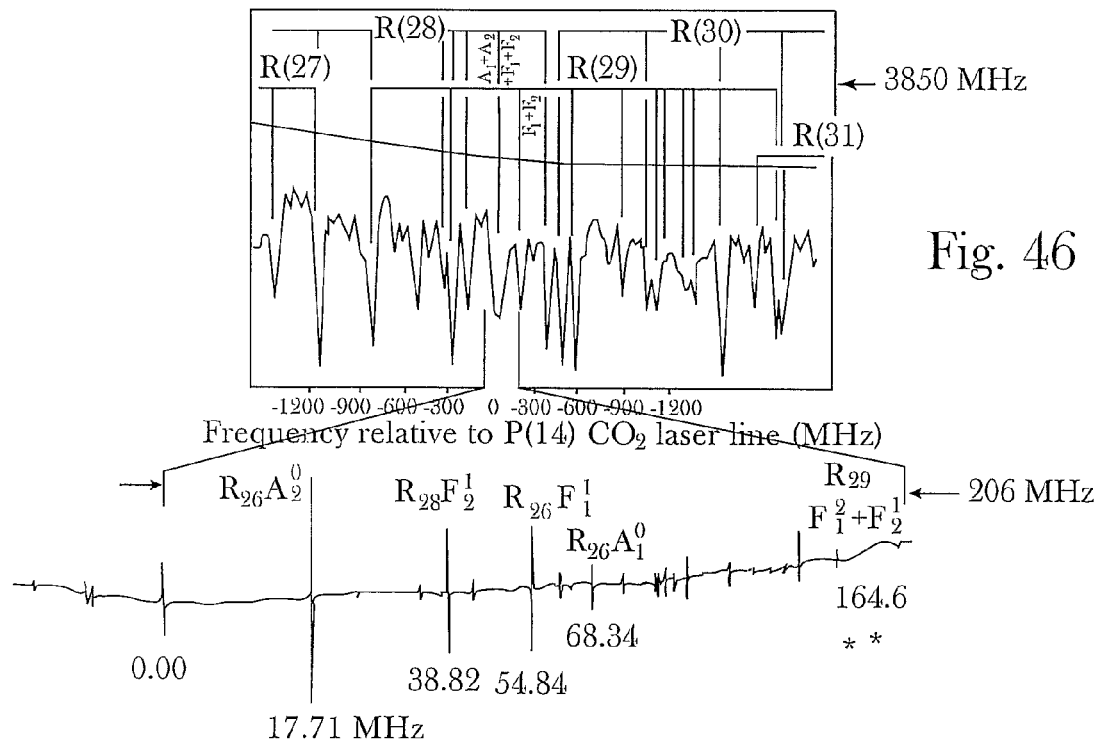
Fig. 46
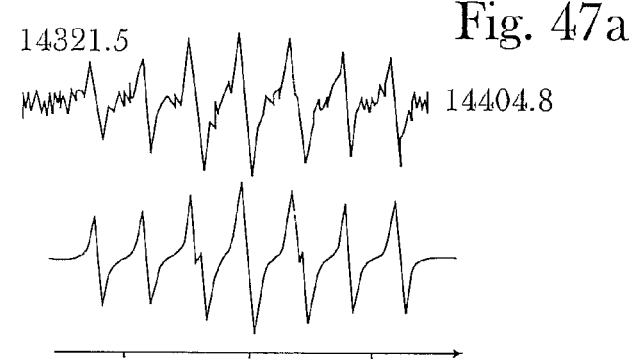
Fig. 48
Fig. 47a
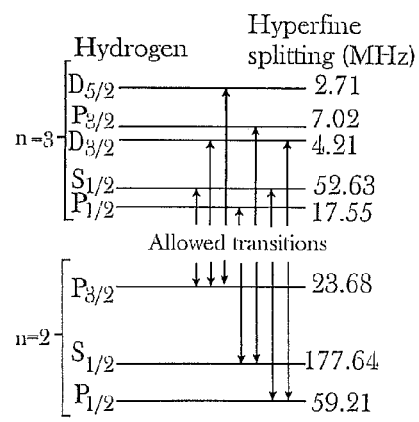
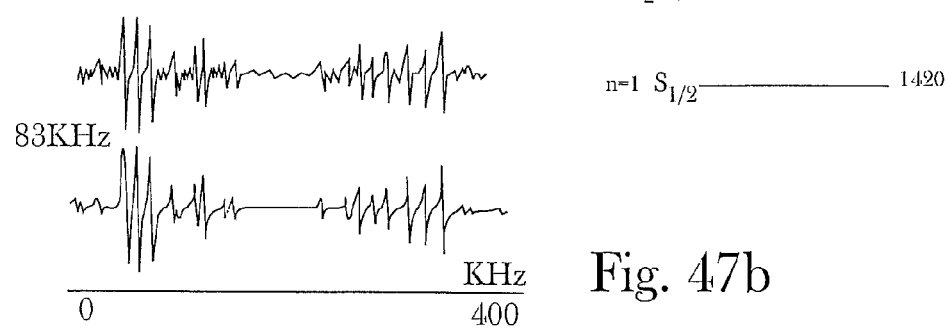
Fig. 47b

Fig. 49
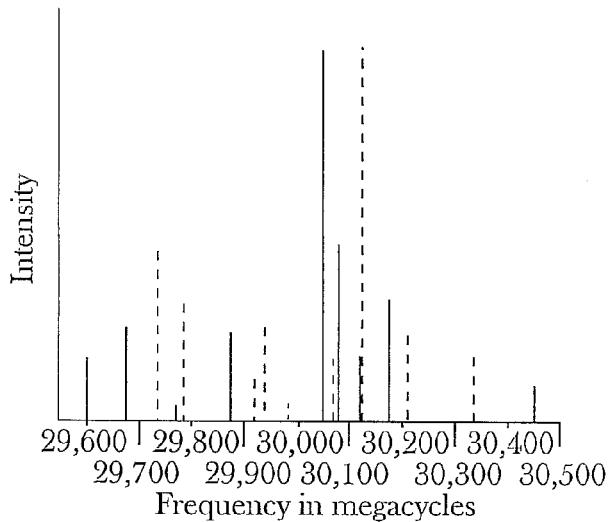
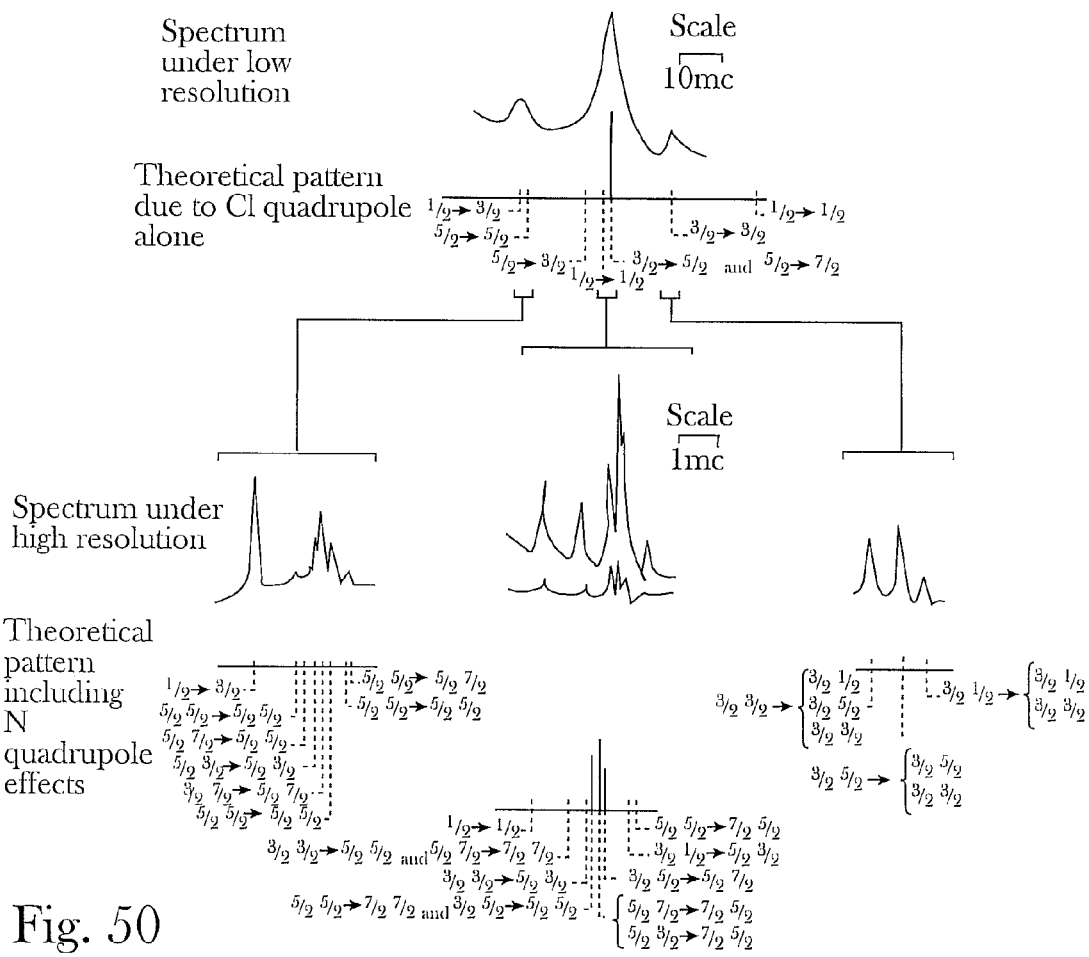
Fig. 50

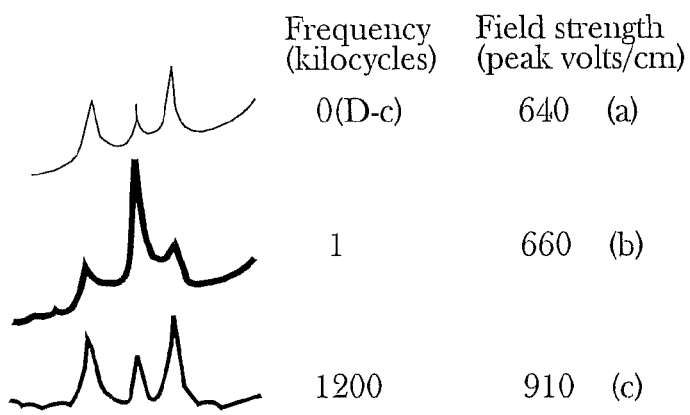
Fig. 60
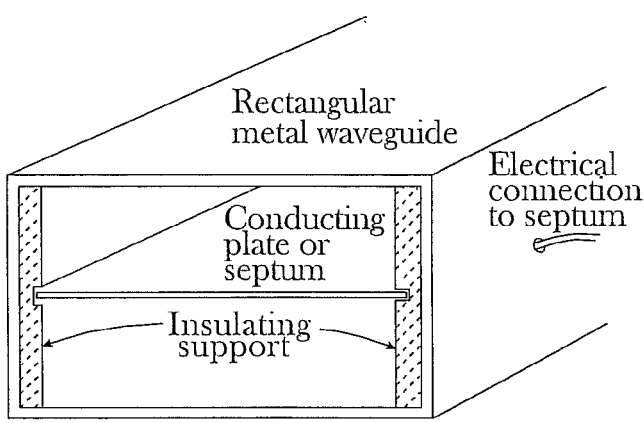
Fig. 61a
Fig. 61b
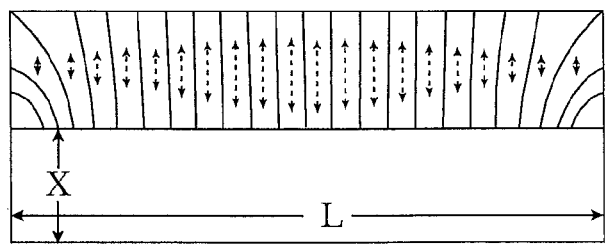

Fig. 65a
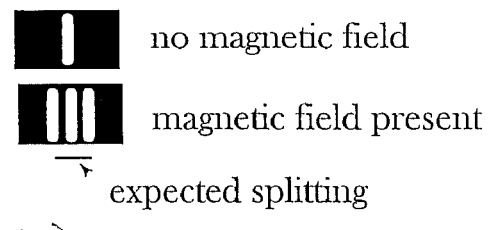
(a)
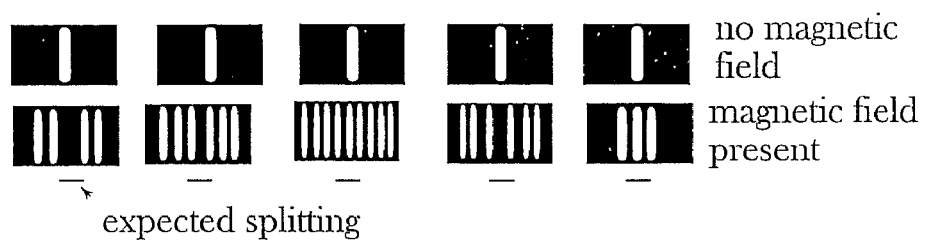
expected splitting
(b)
Fig. 65b
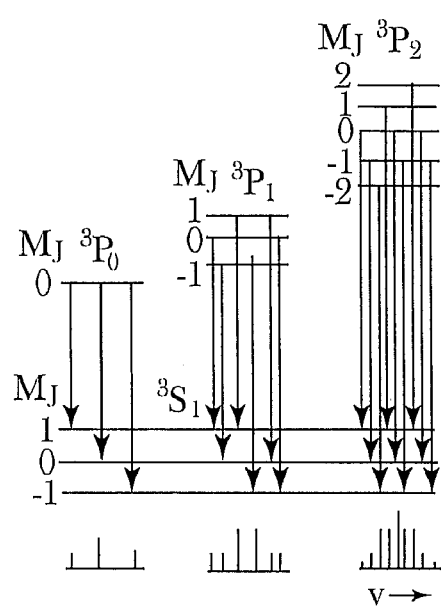
Fig. 66

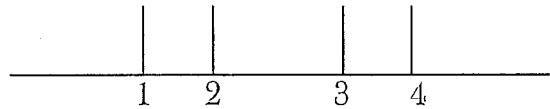
Fig. 67a
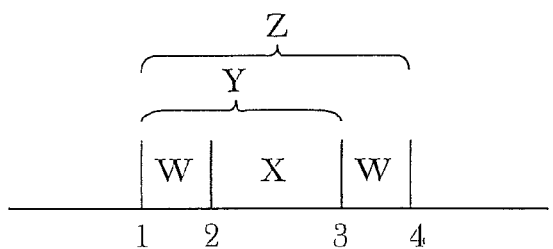
Fig. 67b
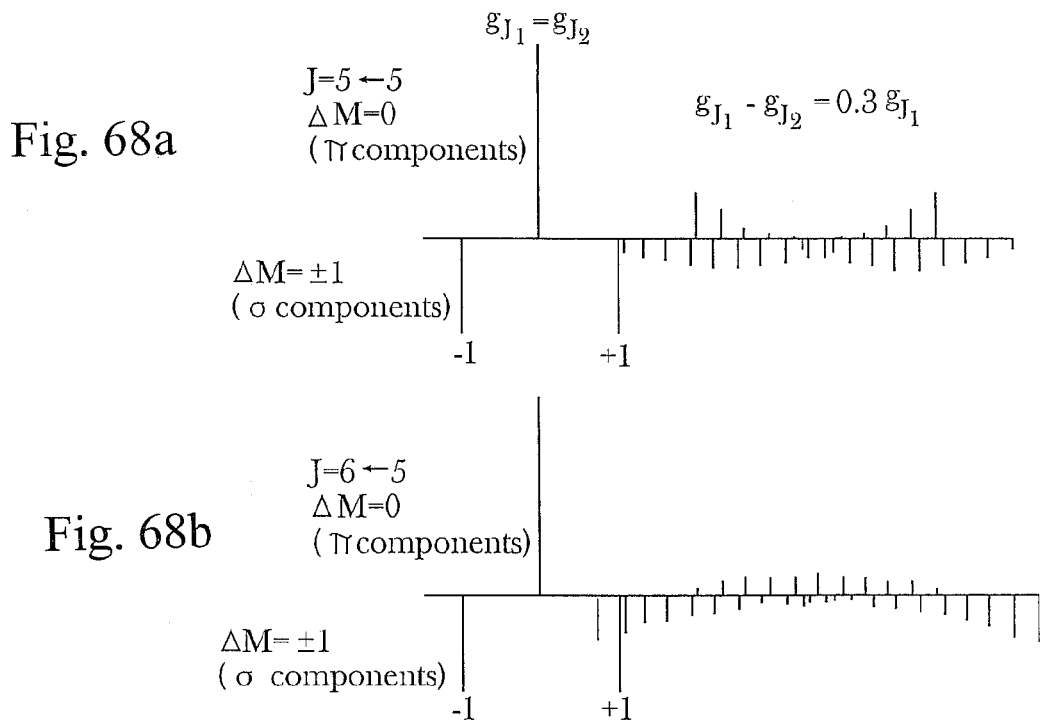
Fig. 68a
Fig. 68b

| 100 | 7.7144 | 10.786 | 15.732 | 24.2382 | 40.1965 | 64.4367 | 74.0016 | 114.2 | 138.428 | 159.881 | 233.882 | 274.081 | 298.319 | 314.051 | 456.811 |
|---|---|---|---|---|---|---|---|---|---|---|---|---|---|---|---|
| 364.501 | 0 | 0 | 0 | 0 | 0 | 0 | 0 | 0 | 0 | 0 | 0 | 0 | 0 | 0 | 0 |
| 421.428 | 0 | 0 | 0 | 0 | 0 | 0 | 0 | 0 | 0 | 0 | 0 | 0 | 0 | 0 | 0 |
| 438.127 | 0 | 0 | 0 | 0 | 0 | 0 | 0 | 0 | 0 | 0 | 0 | 0 | 0 | 0 | 0 |
| 443.127 | 0 | 0 | 0 | 0 | 0 | 0 | 0 | 0 | 0 | 0 | 0 | 0 | 0 | 0 | 0 |
| 443.479 | 0 | 0 | 0 | 0 | 0 | 5.99283 | 0 | 0 | 0 | 0 | 0 | 0 | 0 | 0 | 0 |
| 449.757 | 0 | 0 | 0 | 0 | 0 | 0 | 0 | 0 | 0 | 0 | 0 | 0 | 0 | 0 | 0 |
| 459.561 | 0 | 0 | 0 | 0 | 0 | 0 | 0 | 0 | 0 | 0 | 0 | 0 | 0 | 0 | 1.00602 |
| 473.862 | 0 | 0 | 0 | 0 | 0 | 0 | 0 | 0 | 0 | 0 | 0 | 0 | 0 | 0 | 0 |
| 474.478 | 0 | 43.9562 | 0 | 0 | 0 | 0 | 0 | 0 | 0 | 0 | 0 | 0 | 0 | 0 | 0 |
| 497.495 | 0 | 0 | 0 | 0 | 0 | 0 | 0 | 0 | 0 | 0 | 0 | 0 | 0 | 0 | 0 |
| 512.318 | 0 | 0 | 0 | 0 | 0 | 0 | 0 | 0 | 0 | 0 | 0 | 0 | 0 | 0 | 0 |
| 513.333 | 0 | 0 | 0 | 0 | 0 | 0 | 0 | 0 | 0 | 0 | 0 | 0 | 0 | 0 | 0 |
| 520.151 | 0 | 0 | 0 | 0 | 0 | 0 | 0 | 0 | 0 | 0 | 0 | 0 | 0 | 0 | 0 |
| 547.216 | 0 | 0 | 0 | 0 | 0 | 0 | 0 | 0 | 0 | 0 | 1.99655 | 0 | 0 | 0 | 0 |
| 547.489 | 0 | 0 | 0 | 0 | 0 | 0 | 0 | 0 | 0 | 0 | 1.99754 | 0 | 0 | 0 | 0 |
| 556.12 | 0 | 0 | 0 | 0 | 0 | 0 | 0 | 0 | 0 | 0 | 0 | 0 | 0 | 0 | 0 |
| 558.378 | 0 | 0 | 0 | 0 | 0 | 0 | 0 | 0 | 0 | 0 | 0 | 0 | 0 | 0 | 0 |
| 565.537 | 0 | 0 | 0 | 0 | 0 | 0 | 0 | 0 | 0 | 0 | 0 | 0 | 0 | 0 | 0 |
| 573.474 | 0 | 0 | 0 | 0 | 0 | 0 | 0 | 0 | 0 | 0 | 0 | 0 | 0 | 0 | 0 |
| 592.536 | 0 | 0 | 0 | 0 | 0 | 0 | 8.00707 | 0 | 0 | 0 | 0 | 0 | 0 | 0 | 0 |
| 594.35 | 0 | 0 | 0 | 0 | 0 | 0 | 0 | 0 | 0 | 0 | 0 | 0 | 1.99233 | 0 | 0 |
| 614.388 | 0 | 0 | 0 | 0 | 0 | 0 | 0 | 0 | 0 | 0 | 0 | 0 | 0 | 0 | 0 |
| 658.534 | 0 | 0 | 0 | 0 | 0 | 0 | 0 | 0 | 0 | 0 | 0 | 0 | 0 | 0 | 0 |
| 663.126 | 0 | 0 | 0 | 0 | 0 | 0 | 0 | 0 | 0 | 0 | 0 | 0 | 0 | 0 | 0 |
| 666.389 | 0 | 0 | 0 | 0 | 0 | 0 | 9.00506 | 0 | 0 | 0 | 0 | 0 | 0 | 0 | 0 |
| 674.365 | 0 | 0 | 0 | 0 | 0 | 0 | 0 | 0 | 0 | 0 | 0 | 0 | 0 | 0 | 0 |
| 674.821 | 0 | 0 | 0 | 0 | 0 | 0 | 0 | 0 | 0 | 0 | 0 | 0 | 0 | 0 | 0 |
| 682.614 | 0 | 0 | 0 | 0 | 0 | 0 | 0 | 0 | 0 | 0 | 0 | 0 | 0 | 0 | 0 |
| 692.832 | 0 | 0 | 0 | 0 | 0 | 0 | 0 | 0 | 5.00464 | 0 | 0 | 0 | 0 | 0 | 0 |
| 715.081 | 0 | 0 | 0 | 0 | 0 | 0 | 0 | 0 | 0 | 0 | 0 | 0 | 0 | 0 | 0 |
| 719.866 | 0 | 0 | 0 | 0 | 0 | 0 | 0 | 0 | 0 | 0 | 0 | 0 | 0 | 0 | 0 |
| 727.883 | 0 | 0 | 0 | 0 | 0 | 0 | 0 | 0 | 0 | 0 | 0 | 0 | 0 | 0 | 0 |
| 750.124 | 0 | 0 | 0 | 0 | 0 | 0 | 0 | 0 | 0 | 0 | 0 | 0 | 0 | 0 | 0 |
| 755.838 | 0 | 0 | 0 | 0 | 0 | 0 | 0 | 0 | 0 | 0 | 0 | 0 | 0 | 0 | 0 |
| 759.276 | 0 | 0 | 0 | 0 | 0 | 0 | 0 | 0 | 0 | 0 | 0 | 0 | 0 | 0 | 0 |
| 764.2 | 0 | 0 | 0 | 0 | 0 | 0 | 0 | 0 | 0 | 0 | 0 | 0 | 0 | 0 | 0 |
| 768.555 | 0 | 0 | 0 | 0 | 0 | 0 | 0 | 0 | 0 | 0 | 0 | 0 | 0 | 0 | 0 |
| 785.066 | 0 | 0 | 0 | 0 | 0 | 0 | 0 | 0 | 0 | 0 | 0 | 0 | 0 | 0 | 0 |
| 808.823 | 0 | 0 | 0 | 0 | 0 | 0 | 0 | 0 | 0 | 0 | 0 | 0 | 0 | 0 | 0 |
| 810.27 | 0 | 0 | 0 | 0 | 0 | 0 | 0 | 0 | 0 | 0 | 0 | 0 | 0 | 0 | 0 |
| 815.975 | 0 | 0 | 0 | 0 | 0 | 0 | 0 | 0 | 0 | 0 | 0 | 0 | 0 | 0 | 0 |
| 816.431 | 0 | 0 | 0 | 0 | 0 | 0 | 0 | 0 | 0 | 0 | 0 | 0 | 0 | 0 | 0 |
| 818.412 | 0 | 0 | 0 | 0 | 0 | 0 | 0 | 0 | 0 | 0 | 0 | 0 | 0 | 0 | 0 |
| 822.889 | 0 | 0 | 0 | 0 | 0 | 0 | 0 | 0 | 0 | 0 | 0 | 3.03236 | 0 | 0 | 0 |
| 823.88 | 0 | 0 | 0 | 0 | 0 | 0 | 0 | 0 | 0 | 0 | 0 | 3.00597 | 0 | 0 | 0 |
| 826.305 | 0 | 0 | 0 | 33.991 | 0 | 0 | 0 | 0 | 0 | 0 | 0 | 0 | 0 | 0 | 0 |
| 860.17 | 0 | 0 | 0 | 0 | 0 | 0 | 0 | 0 | 0 | 0 | 0 | 0 | 0 | 0 | 0 |
| 860.624 | 0 | 0 | 0 | 0 | 0 | 0 | 0 | 0 | 0 | 0 | 0 | 0 | 0 | 0 | 0 |
| 874.558 | 0 | 0 | 0 | 0 | 0 | 0 | 0 | 0 | 0 | 0 | 0 | 0 | 0 | 0 | 0 |
| 879.639 | 0 | 0 | 0 | 0 | 0 | 0 | 0 | 0 | 0 | 0 | 0 | 0 | 0 | 0 | 0 |
| 901.957 | 0 | 0 | 0 | 0 | 0 | 13.9976 | 0 | 0 | 0 | 0 | 0 | 0 | 0 | 0 | 0 |
| 904.338 | 0 | 0 | 0 | 0 | 0 | 0 | 0 | 0 | 0 | 0 | 0 | 0 | 0 | 0 | 0 |
| 907.95 | 0 | 0 | 0 | 0 | 0 | 0 | 0 | 0 | 0 | 0 | 0 | 0 | 0 | 0 | 0 |
| 911.162 | 0 | 0 | 0 | 0 | 0 | 0 | 0 | 0 | 0 | 0 | 0 | 0 | 0 | 0 | 1.99461 |
| 913.453 | 0 | 0 | 0 | 0 | 0 | 0 | 7.99871 | 0 | 0 | 0 | 0 | 0 | 0 | 0 | 1.99963 |
| 917.24 | 0 | 0 | 0 | 0 | 0 | 0 | 0 | 0 | 0 | 0 | 0 | 0 | 0 | 0 | 2.00792 |
| 920.761 | 0 | 0 | 0 | 0 | 0 | 0 | 0 | 0 | 0 | 0 | 0 | 0 | 0 | 0 | 0 |
| 921.877 | 0 | 0 | 0 | 0 | 0 | 0 | 0 | 0 | 0 | 0 | 0 | 0 | 0 | 0 | 0 |
| 922.336 | 0 | 0 | 0 | 0 | 0 | 0 | 0 | 0 | 0 | 0 | 0 | 0 | 0 | 0 | 0 |
| 927.168 | 0 | 0 | 0 | 0 | 0 | 0 | 0 | 0 | 0 | 0 | 0 | 0 | 0 | 0 | 0 |
| 928.067 | 0 | 0 | 58.9923 | 0 | 0 | 0 | 0 | 0 | 0 | 0 | 0 | 0 | 0 | 0 | 0 |
| 935.67 | 0 | 0 | 0 | 0 | 0 | 0 | 0 | 0 | 0 | 0 | 4.00061 | 0 | 0 | 0 | 0 |
| 936.644 | 0 | 0 | 0 | 0 | 0 | 0 | 0 | 0 | 0 | 0 | 4.00477 | 0 | 0 | 0 | 0 |
| 949.744 | 0 | 0 | 0 | 0 | 0 | 0 | 0 | 0 | 0 | 0 | 0 | 0 | 0 | 0 | 0 |
| 954.939 | 0 | 0 | 0 | 0 | 0 | 0 | 0 | 0 | 0 | 0 | 0 | 0 | 0 | 0 | 0 |
| 967.06 | 0 | 0 | 0 | 0 | 0 | 15.0079 | 0 | 0 | 0 | 0 | 0 | 0 | 0 | 0 | 0 |
| 975.906 | 0 | 0 | 0 | 0 | 0 | 0 | 0 | 0 | 0 | 0 | 0 | 0 | 0 | 0 | 0 |
| 978.238 | 0 | 0 | 0 | 0 | 0 | 0 | 0 | 0 | 0 | 0 | 0 | 0 | 0 | 0 | 0 |
| 985.304 | 0 | 0 | 0 | 0 | 0 | 0 | 0 | 0 | 0 | 0 | 0 | 0 | 0 | 0 | 0 |
| 987.312 | 0 | 0 | 0 | 0 | 0 | 0 | 0 | 0 | 0 | 0 | 0 | 0 | 0 | 0 | 0 |
| 993.338 | 0 | 0 | 0 | 0 | 0 | 0 | 0 | 0 | 0 | 0 | 0 | 0 | 0 | 0 | 0 |
| 998.553 | 0 | 0 | 0 | 0 | 0 | 0 | 0 | 0 | 0 | 0 | 0 | 0 | 0 | 0 | 0 |
| 999.965 | 0 | 0 | 0 | 0 | 0 | 0 | 0 | 0 | 0 | 0 | 0 | 0 | 0 | 0 | 0 |
| 1012.56 | 0 | 0 | 0 | 0 | 0 | 0 | 0 | 0 | 0 | 0 | 0 | 0 | 0 | 0 | 0 |
| 1013.12 | 0 | 0 | 0 | 0 | 0 | 0 | 0 | 0 | 0 | 0 | 0 | 0 | 0 | 0 | 0 |
| 1018.06 | 0 | 0 | 0 | 42.0023 | 0 | 0 | 0 | 0 | 0 | 0 | 0 | 0 | 0 | 0 | 0 |

Fig. 69a

| 100 | 7.7144 | 10.786 | 15.732 | 24.2362 | 40.1985 | 64.4367 | 74.0016 | 114.2 | 138.428 | 159.881 | 235.882 | 274.081 | 298.319 | 314.051 | 456.811 |
|---|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 8.99229 | 0 | 0 | 0 | 0 | 0 | 0 | 0 |
| 1028.96 | 0 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 | 0 |
| 1031.67 | 0 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 | 0 |
| 1035.96 | 0 | 0 | 0 | 0 | 0 | 0 | 13.9992 | 0 | 0 | 0 | 0 | 0 | 0 | 0 | 0 |
| 1036.19 | 0 | 0 | 0 | 0 | 0 | 0 | 14.0023 | 0 | 0 | 0 | 0 | 0 | 0 | 0 | 0 |
| 1037.99 | 0 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 | 0 |
| 1057.58 | 0 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 | 0 |
| 1081.02 | 0 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 | 0 |
| 1082.35 | 0 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 | 0 |
| 1088.63 | 0 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 3.99422 | 0 | 0 | 0 |
| 1096.55 | 0 | 0 | 0 | 0 | 0 | 0 | 0 | 0 | 0 | 0 | 0 | 4.00082 | 0 | 0 | 0 |
| 1098.17 | 0 | 0 | 0 | 0 | 0 | 0 | 0 | 0 | 0 | 0 | 0 | 4.00674 | 0 | 0 | 0 |
| 1102.57 | 0 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 8.00308 | 0 | 0 | 0 | 0 | 0 | 0 | 0 |
| 1109.36 | 0 | 0 | 0 | 0 | 0 | 0 | 14.991 | 0 | 0 | 0 | 0 | 0 | 0 | 0 | 0 |
| 1110.99 | 0 | 103.003 | 0 | 0 | 0 | 0 | 0 | 0 | 0 | 0 | 0 | 0 | 0 | 0 | 0 |
| 1119.82 | 0 | 0 | 0 | 0 | 0 | 0 | 0 | 0 | 0 | 7.00408 | 0 | 0 | 0 | 0 | 0 |
| 1120.9 | 0 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 | 0 |
| 1132.62 | 0 | 105.088 | 71.9947 | 0 | 0 | 0 | 0 | 0 | 0 | 0 | 0 | 0 | 0 | 0 | 0 |
| 1135.86 | 0 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 | 0 |
| 1181.82 | 0 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 | 0 |
| 1187.63 | 0 | 0 | 0 | 48.9963 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 3.99485 | 0 | 0 |
| 1192 | 0 | 0 | 0 | 0 | 0 | 0 | 0 | 0 | 0 | 0 | 0 | 0 | 3.99572 | 0 | 0 |
| 1192.46 | 0 | 0 | 0 | 0 | 0 | 0 | 0 | 0 | 0 | 0 | 0 | 0 | 3.99726 | 0 | 0 |
| 1195.11 | 0 | 0 | 0 | 0 | 0 | 0 | 0 | 0 | 0 | 0 | 0 | 0 | 4.00615 | 0 | 0 |
| 1196.33 | 0 | 0 | 0 | 0 | 0 | 0 | 0 | 0 | 0 | 0 | 0 | 0 | 0 | 0 | 0 |
| 1199.89 | 0 | 0 | 0 | 0 | 0 | 0 | 0 | 0 | 0 | 0 | 0 | 0 | 0 | 0 | 0 |
| 1201.18 | 0 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 | 0 |
| 1228.63 | 0 | 0 | 0 | 0 | 0 | 0 | 0 | 0 | 0 | 0 | 0 | 0 | 0 | 0 | 0 |
| 1230.33 | 0 | 0 | 0 | 0 | 0 | 0 | 0 | 0 | 0 | 0 | 0 | 0 | 0 | 0 | 0 |
| 1234.17 | 0 | 0 | 0 | 0 | 0 | 0 | 0 | 0 | 0 | 0 | 0 | 0 | 0 | 0 | 0 |
| 1234.63 | 0 | 0 | 0 | 0 | 0 | 0 | 0 | 0 | 0 | 0 | 0 | 0 | 0 | 0 | 0 |
| 1234.71 | 0 | 0 | 0 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 | 0 |
| 1251.13 | 0 | 115.9960 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 3.99492 | 0 | 0 |
| 1256.04 | 0 | 0 | 0 | 0 | 0 | 0 | 10.9986 | 0 | 0 | 0 | 0 | 0 | 3.99548 | 0 | 0 |
| 1257.71 | 0 | 0 | 0 | 0 | 0 | 0 | 16.9957 | 0 | 0 | 0 | 0 | 0 | 4.0048 | 0 | 0 |
| 1265.87 | 0 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 | 0 |

Fig. 69b

| 100 | 7.7144 | 10.786 | 15.732 | 24.2382 | 40.1995 | 64.4357 | 74.0016 | 114.2 | 138.438 | 159.881 | 233.882 | 274.081 | 298.319 | 314.051 | 456.811 |
|---|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 | 0 |
| 1288.82 | 0 | 0 | 0 | 0 | 0 | 20.0013 | 0 | 0 | 0 | 0 | 0 | 0 | 0 | 0 | 0 |
| 1293.16 | 0 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 | 0 |
| 1307.77 | 0 | 0 | 0 | 0 | 0 | 0 | 0 | 0 | 0 | 0 | 0 | 0 | 0 | 0 | 0 |
| 1309.56 | 0 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 | 0 |
| 1321.35 | 0 | 0 | 83.9912 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 | 0 |
| 1348.83 | 0 | 0 | 0 | 0 | 0 | 0 | 0 | 0 | 0 | 0 | 0 | 0 | 0 | 0 | 0 |
| 1361.32 | 0 | 0 | 0 | 0 | 0 | 0 | 0 | 0 | 0 | 0 | 0 | 0 | 0 | 0 | 0 |
| 1378.57 | 0 | 0 | 0 | 0 | 0 | 0 | 0 | 0 | 0 | 0 | 0 | 0 | 0 | 0 | 0 |
| 1384.61 | 0 | 0 | 0 | 0 | 0 | 0 | 0 | 0 | 10.0017 | 0 | 0 | 0 | 0 | 0 | 0 |
| 1398.14 | 0 | 0 | 0 | 0 | 0 | 0 | 0 | 0 | 0 | 0 | 0 | 0 | 0 | 0 | 0 |
| 1408.04 | 0 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 8.99507 | 0 | 0 | 0 | 0 | 0 |
| 1450.02 | 0 | 0 | 0 | 0 | 0 | 0 | 0 | 0 | 0 | 0 | 0 | 0 | 0 | 0 | 0 |
| 1462.85 | 0 | 0 | 0 | 0 | 0 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 | 0 |

Fig. 69c

| 180 | 456.816 | 616.698 | 690.691 | 730.891 | 755.131 | 770.863 | 781.649 | 2466 | 2923 | 3083 | 3157 | 3197 | 3221 | 3236.7 | 18.5004 | 39.9702 | 58.4706 |
|---|---|---|---|---|---|---|---|---|---|---|---|---|---|---|---|---|---|
| 364.501 | 0 | 0 | 0 | 0 | 0 | 0 | 0 | 0 | 0 | 0 | 0 | 0 | 0 | 0 | 0 | 0 | 0 |
| 421.428 | 0 | 0 | 0 | 0 | 0 | 0 | 0 | 0 | 0 | 0 | 0 | 0 | 0 | 0 | 0 | 0 | 0 |
| 438.127 | 0 | 0 | 0 | 0 | 0 | 0 | 0 | 0 | 0 | 0 | 0 | 0 | 0 | 0 | 0 | 0 | 0 |
| 443.127 | 0 | 0 | 0 | 0 | 0 | 0 | 0 | 0 | 0 | 0 | 0 | 0 | 0 | 0 | 0 | 0 | 0 |
| 443.479 | 0 | 0 | 0 | 0 | 0 | 0 | 0 | 0 | 0 | 0 | 0 | 0 | 0 | 0 | 0 | 0 | 0 |
| 449.757 | 0 | 0 | 0 | 0 | 0 | 0 | 0 | 0 | 0 | 0 | 0 | 0 | 0 | 0 | 0 | 0 | 0 |
| 459.561 | 1.00601 | 0 | 0 | 0 | 0 | 0 | 0 | 0 | 0 | 0 | 0 | 0 | 0 | 0 | 0 | 0 | 0 |
| 473.662 | 0 | 0 | 0 | 0 | 0 | 0 | 0 | 0 | 0 | 0 | 0 | 0 | 0 | 0 | 0 | 0 | 0 |
| 474.476 | 0 | 0 | 0 | 0 | 0 | 0 | 0 | 0 | 0 | 0 | 0 | 0 | 0 | 0 | 0 | 0 | 0 |
| 497.495 | 0 | 0 | 0 | 0 | 0 | 0 | 0 | 0 | 0 | 0 | 0 | 0 | 0 | 0 | 0 | 0 | 0 |
| 512.918 | 0 | 0 | 0 | 0 | 0 | 0 | 0 | 0 | 0 | 0 | 0 | 0 | 0 | 0 | 0 | 0 | 0 |
| 513.333 | 0 | 0 | 0 | 0 | 0 | 0 | 0 | 0 | 0 | 0 | 0 | 0 | 0 | 0 | 0 | 0 | 0 |
| 520.151 | 0 | 0 | 0 | 0 | 0 | 0 | 0 | 0 | 0 | 0 | 0 | 0 | 0 | 0 | 0 | 0 | 0 |
| 547.216 | 0 | 0 | 0 | 0 | 0 | 0 | 0 | 0 | 0 | 0 | 0 | 0 | 0 | 0 | 0 | 0 | 0 |
| 547.489 | 0 | 0 | 0 | 0 | 0 | 0 | 0 | 0 | 0 | 0 | 0 | 0 | 0 | 0 | 0 | 0 | 0 |
| 556.12 | 0 | 0 | 0 | 0 | 0 | 0 | 0 | 0 | 0 | 0 | 0 | 0 | 0 | 0 | 0 | 0 | 0 |
| 558.378 | 0 | 0 | 0 | 0 | 0 | 0 | 0 | 0 | 0 | 0 | 0 | 0 | 0 | 0 | 0 | 0 | 0 |
| 565.537 | 0 | 0 | 0 | 0 | 0 | 0 | 0 | 0 | 0 | 0 | 0 | 0 | 0 | 0 | 0 | 0 | 0 |
| 573.474 | 0 | 0 | 0 | 0 | 0 | 0 | 0 | 0 | 0 | 0 | 0 | 0 | 0 | 0 | 30.9979 | 0 | 0 |
| 592.536 | 0 | 0 | 0 | 0 | 0 | 0 | 0 | 0 | 0 | 0 | 0 | 0 | 0 | 0 | 0 | 0 | 0 |
| 594.35 | 0 | 0 | 0 | 0 | 0 | 0 | 0 | 0 | 0 | 0 | 0 | 0 | 0 | 0 | 0 | 0 | 0 |
| 614.388 | 0 | 0.99627 | 0 | 0 | 0 | 0 | 0 | 0 | 0 | 0 | 0 | 0 | 0 | 0 | 0 | 0 | 0 |
| 658.534 | 0 | 0 | 0 | 0 | 0 | 0 | 0 | 0 | 0 | 0 | 0 | 0 | 0 | 0 | 0 | 0 | 0 |
| 663.126 | 0 | 0 | 0 | 0 | 0 | 0 | 0 | 0 | 0 | 0 | 0 | 0 | 0 | 0 | 0 | 0 | 0 |
| 666.389 | 0 | 0 | 0 | 0 | 0 | 0 | 0 | 0 | 0 | 0 | 0 | 0 | 0 | 0 | 0 | 0 | 0 |
| 674.365 | 0 | 0 | 0 | 0 | 0 | 0 | 0 | 0 | 0 | 0 | 0 | 0 | 0 | 0 | 0 | 0 | 0 |
| 674.621 | 0 | 0 | 0 | 0 | 0 | 0 | 0 | 0 | 0 | 0 | 0 | 0 | 0 | 0 | 0 | 0 | 0 |
| 682.614 | 0 | 0 | 0 | 0 | 0 | 0 | 0 | 0 | 0 | 0 | 0 | 0 | 0 | 0 | 0 | 0 | 0 |
| 692.832 | 0 | 0 | 1.0031 | 0 | 0 | 0 | 0 | 0 | 0 | 0 | 0 | 0 | 0 | 0 | 0 | 0 | 0 |
| 715.081 | 0 | 0 | 0 | 0 | 0 | 0 | 0 | 0 | 0 | 0 | 0 | 0 | 0 | 0 | 0 | 0 | 0 |
| 719.866 | 0 | 0 | 0 | 0 | 0 | 0 | 0 | 0 | 0 | 0 | 0 | 0 | 0 | 0 | 0 | 0 | 0 |
| 727.883 | 0 | 0 | 0 | 0.99588 | 0 | 0 | 0 | 0 | 0 | 0 | 0 | 0 | 0 | 0 | 0 | 0 | 0 |
| 750.124 | 0 | 0 | 0 | 0 | 0.99337 | 0 | 0 | 0 | 0 | 0 | 0 | 0 | 0 | 0 | 0 | 0 | 0 |
| 755.838 | 0 | 0 | 0 | 0 | 1.00094 | 0 | 0 | 0 | 0 | 0 | 0 | 0 | 0 | 0 | 0 | 18.9961 | 0 |
| 759.276 | 0 | 0 | 0 | 0 | 1.00549 | 0 | 0 | 0 | 0 | 0 | 0 | 0 | 0 | 0 | 0 | 0 | 0 |
| 764.2 | 0 | 0 | 0 | 0 | 0 | 0.99136 | 0 | 0 | 0 | 0 | 0 | 0 | 0 | 0 | 0 | 0 | 0 |
| 768.555 | 0 | 0 | 0 | 0 | 0 | 0.99701 | 0 | 0 | 0 | 0 | 0 | 0 | 0 | 0 | 0 | 0 | 0 |
| 785.066 | 0 | 0 | 0 | 0 | 0 | 0 | 1.00437 | 0 | 0 | 0 | 0 | 0 | 0 | 0 | 0 | 0 | 0 |
| 808.823 | 0 | 0 | 0 | 0 | 0 | 0 | 0 | 0 | 0 | 0 | 0 | 0 | 0 | 0 | 0 | 0 | 0 |
| 810.27 | 0 | 0 | 0 | 0 | 0 | 0 | 0 | 0 | 0 | 0 | 0 | 0 | 0 | 0 | 0 | 0 | 0 |
| 815.975 | 0 | 0 | 0 | 0 | 0 | 0 | 0 | 0 | 0 | 0 | 0 | 0 | 0 | 0 | 0 | 0 | 0 |
| 816.431 | 0 | 0 | 0 | 0 | 0 | 0 | 0 | 0 | 0 | 0 | 0 | 0 | 0 | 0 | 0 | 0 | 0 |
| 818.412 | 0 | 0 | 0 | 0 | 0 | 0 | 0 | 0 | 0 | 0 | 0 | 0 | 0 | 0 | 0 | 0 | 13.997 |
| 822.899 | 0 | 0 | 0 | 0 | 0 | 0 | 0 | 0 | 0 | 0 | 0 | 0 | 0 | 0 | 0 | 0 | 0 |
| 823.38 | 0 | 0 | 0 | 0 | 0 | 0 | 0 | 0 | 0 | 0 | 0 | 0 | 0 | 0 | 0 | 0 | 0 |
| 826.305 | 0 | 0 | 0 | 0 | 0 | 0 | 0 | 0 | 0 | 0 | 0 | 0 | 0 | 0 | 0 | 0 | 0 |
| 860.17 | 0 | 0 | 0 | 0 | 0 | 0 | 0 | 0 | 0 | 0 | 0 | 0 | 0 | 0 | 0 | 0 | 0 |
| 860.624 | 0 | 0 | 0 | 0 | 0 | 0 | 0 | 0 | 0 | 0 | 0 | 0 | 0 | 0 | 0 | 0 | 0 |
| 874.558 | 0 | 0 | 0 | 0 | 0 | 0 | 0 | 0 | 0 | 0 | 0 | 0 | 0 | 0 | 0 | 0 | 0 |
| 879.939 | 0 | 0 | 0 | 0 | 0 | 0 | 0 | 0 | 0 | 0 | 0 | 0 | 0 | 0 | 0 | 22.0074 | 0 |
| 901.957 | 0 | 0 | 0 | 0 | 0 | 0 | 0 | 0 | 0 | 0 | 0 | 0 | 0 | 0 | 0 | 0 | 0 |
| 904.338 | 0 | 0 | 0 | 0 | 0 | 0 | 0 | 0 | 0 | 0 | 0 | 0 | 0 | 0 | 0 | 0 | 0 |
| 907.95 | 0 | 0 | 0 | 0 | 0 | 0 | 0 | 0 | 0 | 0 | 0 | 0 | 0 | 0 | 0 | 0 | 0 |
| 911.162 | 1.99459 | 0 | 0 | 0 | 0 | 0 | 0 | 0 | 0 | 0 | 0 | 0 | 0 | 0 | 0 | 0 | 0 |
| 913.453 | 1.99951 | 0 | 0 | 0 | 0 | 0 | 0 | 0 | 0 | 0 | 0 | 0 | 0 | 0 | 0 | 0 | 0 |
| 917.24 | 2.0079 | 0 | 0 | 0 | 0 | 0 | 0 | 0 | 0 | 0 | 0 | 0 | 0 | 0 | 0 | 0 | 0 |
| 920.761 | 0 | 0 | 0 | 0 | 0 | 0 | 0 | 0 | 0 | 0 | 0 | 0 | 0 | 0 | 0 | 0 | 0 |
| 921.877 | 0 | 0 | 0 | 0 | 0 | 0 | 0 | 0 | 0 | 0 | 0 | 0 | 0 | 0 | 0 | 0 | 0 |
| 922.336 | 0 | 0 | 0 | 0 | 0 | 0 | 0 | 0 | 0 | 0 | 0 | 0 | 0 | 0 | 0 | 0 | 0 |
| 927.168 | 0 | 0 | 0 | 0 | 0 | 0 | 0 | 0 | 0 | 0 | 0 | 0 | 0 | 0 | 0 | 0 | 0 |
| 928.067 | 0 | 0 | 0 | 0 | 0 | 0 | 0 | 0 | 0 | 0 | 0 | 0 | 0 | 0 | 0 | 0 | 0 |
| 935.67 | 0 | 0 | 0 | 0 | 0 | 0 | 0 | 0 | 0 | 0 | 0 | 0 | 0 | 0 | 0 | 0 | 16.0024 |
| 936.644 | 0 | 0 | 0 | 0 | 0 | 0 | 0 | 0 | 0 | 0 | 0 | 0 | 0 | 0 | 0 | 0 | 0 |
| 949.744 | 0 | 0 | 0 | 0 | 0 | 0 | 0 | 0 | 0 | 0 | 0 | 0 | 0 | 0 | 0 | 0 | 0 |
| 954.939 | 0 | 0 | 0 | 0 | 0 | 0 | 0 | 0 | 0 | 0 | 0 | 0 | 0 | 0 | 0 | 0 | 0 |
| 967.06 | 0 | 0 | 0 | 0 | 0 | 0 | 0 | 0 | 0 | 0 | 0 | 0 | 0 | 0 | 0 | 0 | 0 |
| 975.906 | 0 | 0 | 0 | 0 | 0 | 0 | 0 | 0 | 0 | 0 | 0 | 0 | 0 | 0 | 0 | 0 | 0 |
| 978.208 | 0 | 0 | 0 | 0 | 0 | 0 | 0 | 0 | 0 | 0 | 0 | 0 | 0 | 0 | 0 | 0 | 0 |
| 985.304 | 0 | 0 | 0 | 0 | 0 | 0 | 0 | 0 | 0 | 0 | 0 | 0 | 0 | 0 | 0 | 0 | 0 |
| 987.312 | 0 | 0 | 0 | 0 | 0 | 0 | 0 | 0 | 0 | 0 | 0 | 0 | 0 | 0 | 0 | 0 | 0 |
| 993.388 | 0 | 0 | 0 | 0 | 0 | 0 | 0 | 0 | 0 | 0 | 0 | 0 | 0 | 0 | 0 | 0 | 0 |
| 998.553 | 0 | 0 | 0 | 0 | 0 | 0 | 0 | 0 | 0 | 0 | 0 | 0 | 0 | 0 | 0 | 0 | 0 |
| 999.985 | 0 | 0 | 0 | 0 | 0 | 0 | 0 | 0 | 0 | 0 | 0 | 0 | 0 | 0 | 0 | 0 | 0 |
| 1012.56 | 0 | 0 | 0 | 0 | 0 | 0 | 0 | 0 | 0 | 0 | 0 | 0 | 0 | 0 | 0 | 0 | 0 |
| 1013.12 | 0 | 0 | 0 | 0 | 0 | 0 | 0 | 0 | 0 | 0 | 0 | 0 | 0 | 0 | 0 | 0 | 0 |
| 1018.06 | 0 | 0 | 0 | 0 | 0 | 0 | 0 | 0 | 0 | 0 | 0 | 0 | 0 | 0 | 0 | 0 | 0 |

Fig. 69d

| 100 | 456.816 | 616.088 | 690.691 | 730.891 | 755.131 | 770.863 | 781.649 | 2466 | 2923 | 3083 | 3157 | 3197 | 3221 | 3236.7 | 19.5004 | 39.9702 | 58.4706 |
|---|---|---|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 0 | 0 | 0 | 0 | 0 | 0 | 0 | 0 | 0 | 0 |
| 1028.55 | 0 | 0 | 0 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 | 0 | 0 | 0 |
| 1031.67 | 0 | 0 | 0 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 | 0 | 0 | 0 |
| 1035.96 | 0 | 0 | 0 | 0 | 0 | 0 | 0 | 0 | 0 | 0 | 0 | 0 | 0 | 0 | 55.9966 | 0 | 0 |
| 1036.19 | 0 | 0 | 0 | 0 | 0 | 0 | 0 | 0 | 0 | 0 | 0 | 0 | 0 | 0 | 56.0091 | 0 | 0 |
| 1037.99 | 0 | 0 | 0 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 | 0 | 0 | 0 |
| 1057.58 | 0 | 0 | 0 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 | 0 | 0 | 0 |
| 1081.02 | 0 | 0 | 0 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 | 0 | 0 | 0 |
| 1082.35 | 0 | 0 | 0 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 | 0 | 0 | 0 |
| 1088.63 | 0 | 0 | 0 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 0 | 0 | 0 | 0 | 0 | 0 |
| 1096.55 | 0 | 0 | 0 | 0 | 0 | 0 | 0 | 0 | 0 | 0 | 0 | 0 | 0 | 0 | 0 | 0 | 0 |
| 1098.17 | 0 | 0 | 0 | 0 | 0 | 0 | 0 | 0 | 0 | 0 | 0 | 0 | 0 | 0 | 0 | 0 | 0 |
| 1102.57 | 0 | 0 | 0 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 0 | 0 | 0 | 0 | 0 | 0 | 0 | 0 | 0 | 0 |
| 1109.36 | 0 | 0 | 0 | 0 | 0 | 0 | 0 | 0 | 0 | 0 | 0 | 0 | 0 | 0 | 0 | 0 | 0 |
| 1110.93 | 0 | 0 | 0 | 0 | 0 | 0 | 0 | 0 | 0 | 0 | 0 | 0 | 0 | 0 | 0 | 0 | 19.0008 |
| 1119.82 | 0 | 0 | 0 | 0 | 0 | 0 | 0 | 0 | 0 | 0 | 0 | 0 | 0 | 0 | 0 | 0 | 0 |
| 1126.9 | 0 | 0 | 0 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 | 0 | 0 | 0 |
| 1132.62 | 0 | 0 | 0 | 0 | 0 | 0 | 0 | 0 | 0 | 0 | 0 | 0 | 0 | 0 | 0 | 0 | 0 |
| 1135.86 | 0 | 0 | 0 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 | 0 | 0 | 0 |
| 1181.92 | 0 | 0 | 0 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 | 0 | 0 | 0 |
| 1187.63 | 0 | 0 | 0 | 0 | 0 | 0 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 0 | 0 | 0 | 0 | 0 |
| 1192 | 0 | 0 | 0 | 0 | 0 | 0 | 0 | 0 | 0 | 0 | 0 | 0 | 0 | 0 | 0 | 0 | 0 |
| 1192.46 | 0 | 0 | 0 | 0 | 0 | 0 | 0 | 0 | 0 | 0 | 0 | 0 | 0 | 0 | 0 | 0 | 0 |
| 1195.11 | 0 | 0 | 0 | 0 | 0 | 0 | 0 | 0 | 0 | 0 | 0 | 0 | 0 | 0 | 0 | 0 | 0 |
| 1196.33 | 0 | 0 | 0 | 0 | 0 | 0 | 0 | 0 | 0 | 0 | 0 | 0 | 0 | 0 | 0 | 0 | 0 |
| 1199.89 | 0 | 0 | 0 | 0 | 0 | 0 | 0 | 0 | 0 | 0 | 0 | 0 | 0 | 0 | 0 | 0 | 0 |
| 1201.18 | 0 | 0 | 0 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 | 0 | 0 | 0 |
| 1228.63 | 0 | 1.9923 | 0 | 0 | 0 | 0 | 0 | 0 | 0 | 0 | 0 | 0 | 0 | 0 | 0 | 0 | 0 |
| 1230.33 | 0 | 1.9596 | 0 | 0 | 0 | 0 | 0 | 0 | 0 | 0 | 0 | 0 | 0 | 0 | 0 | 0 | 0 |
| 1234.17 | 0 | 2.00129 | 0 | 0 | 0 | 0 | 0 | 0 | 0 | 0 | 0 | 0 | 0 | 0 | 0 | 0 | 0 |
| 1234.63 | 0 | 2.00203 | 0 | 0 | 0 | 0 | 0 | 0 | 0 | 0 | 0 | 0 | 0 | 0 | 0 | 0 | 0 |
| 1234.71 | 0 | 2.00216 | 0 | 0 | 0 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 | 0 | 0 | 0 |
| 1251.13 | 0 | 0 | 0 | 0 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 0 | 0 | 0 | 0 | 0 |
| 1256.04 | 0 | 0 | 0 | 0 | 0 | 0 | 0 | 0 | 0 | 0 | 0 | 0 | 0 | 0 | 0 | 0 | 0 |
| 1257.71 | 0 | 0 | 0 | 0 | 0 | 0 | 0 | 0 | 0 | 0 | 0 | 0 | 0 | 0 | 0 | 0 | 0 |
| 1265.87 | 0 | 0 | 0 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 | 0 | 0 | 0 |

Fig. 69e

| 100 | 456.816 | 616.688 | 690.691 | 730.891 | 755.131 | 770.863 | 781.649 | 2406 | 2923 | 3083 | 3157 | 3197 | 3221 | 3236.7 | 18.5004 | 39.9702 | 58.4706 |
|---|---|---|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 | 0 | 0 | 0 |
| 1288.82 | 0 | 0 | 0 | 0 | 0 | 0 | 0 | 0 | 0 | 0 | 0 | 0 | 0 | 0 | 0 | 0 | 0 |
| 1293.16 | 0 | 0 | 0 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 | 0 | 0 | 0 |
| 1307.77 | 0 | 0 | 0 | 0 | 0 | 0 | 0 | 0 | 0 | 0 | 0 | 0 | 0 | 0 | 0 | 0 | 0 |
| 1309.56 | 0 | 0 | 0 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 | 0 | 0 | 0 |
| 1321.35 | 0 | 0 | 0 | 0 | 0 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 | 0 | 0 | 0 |
| 1348.83 | 0 | 0 | 0 | 0 | 0 | 0 | 0 | 0 | 0 | 0 | 0 | 0 | 0 | 0 | 0 | 0 | 0 |
| 1361.32 | 0 | 0 | 0 | 0 | 0 | 0 | 0 | 0 | 0 | 0 | 0 | 0 | 0 | 0 | 0 | 0 | 0 |
| 1378.57 | 0 | 0 | 1.99593 | 0 | 0 | 0 | 0 | 0 | 0 | 0 | 0 | 0 | 0 | 0 | 0 | 0 | 0 |
| 1384.61 | 0 | 0 | 2.00467 | 0 | 0 | 0 | 0 | 0 | 0 | 0 | 0 | 0 | 0 | 0 | 0 | 0 | 0 |
| 1398.14 | 0 | 0 | 0 | 0 | 0 | 0 | 0 | 0 | 0 | 0 | 0 | 0 | 0 | 0 | 0 | 0 | 0 |
| 1408.04 | 0 | 0 | 0 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 0 | 0 | 0 | 0 | 0 | 0 | 0 | 0 |
| 1450.02 | 0 | 0 | 0 | 0 | 0 | 0 | 0 | 0 | 0 | 0 | 0 | 0 | 0 | 0 | 0 | 0 | 0 |
| 1462.85 | 0 | 0 | 0 | 2.00146 | 0 | 0 | 0 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 | 0 | 0 | 0 |

Fig. 69f

SPECTRAL CHEMISTRY

CROSS REFERENCE TO RELATED APPLICATIONS AND PATENT

This application claims the benefit of U.S. Provisional Application Ser. No. 60/231,620, entitled, A Frequency Based Theory Of Catalysts, which was filed Sep. 11, 2000 now abandoned. This application is also a Continuation-In-Part of U.S. patent application Ser. No. 09/919,679, entitled, Spectral Catalysts, filed Aug. 1, 2001, now abandoned which is a Continuation of U.S. patent application Ser. No. 09/460,025, entitled Spectral Catalysts, filed Dec. 13, 1999, now abandoned, which is a Divisional of U.S. patent application Ser. No. 09/098,883, originally filed on Jun. 17, 1998, now U.S. Pat. No. 6,033,531, which issued on Mar. 7, 2000, which claims the benefit of U.S. Provisional Application Ser. No. 60/049,910, entitled, Spectral Catalysts, filed Jun. 18, 1997. This application also claims the benefit of U.S. Provisional Application Ser. No. 60/049,910.

TECHNICAL FIELD

This invention relates to a novel method to affect, control and/or direct a reaction pathway (e.g., organic, inorganic, biologic or other reaction) by, for example, exposing one or more participants in a reaction system to at least one spectral energy pattern (e.g., at least one spectral pattern comprising at least one frequency of electromagnetic radiation) which can be made to correspond to at least a portion of a spectral catalyst or a spectral energy catalyst. The invention also relates to mimicking various mechanisms of action of various catalysts in reaction systems under various environmental reaction conditions. The invention further discloses methods for simulating, at least partially, one or more environmental reaction conditions by the application of one or more spectral environmental reaction conditions. The invention specifically discloses different means for achieving the matching of energy frequencies between, for example, applied energy and matter (e.g., solids, liquids, gases, plasmas and/or combinations or portions thereof), to achieve energy transfer to, for example, at least one participant in a reaction system by taking into account various energy considerations in the reaction system. The invention also discloses an approach for designing or determining appropriate physical catalyst(s) to be used in a reaction system.

BACKGROUND OF THE INVENTION

Chemical reactions are driven by energy. The energy comes in many different forms including chemical, thermal, mechanical, acoustic, and electromagnetic. Various features of each type of energy are thought to contribute in different ways to the driving of chemical reactions. Irrespective of the type of energy involved, chemical reactions are undeniably and inextricably intertwined with the transfer and combination of energy. An understanding of energy is, therefore, vital to an understanding of chemical reactions.

A chemical reaction can be controlled and/or directed either by the addition of energy to the reaction medium in the form of thermal, mechanical, acoustic and/or electromagnetic energy or by means of transferring energy through a physical catalyst. These methods are traditionally not that energy efficient and can produce, for example, either unwanted by-products, decomposition of required transients, and/or intermediates and/or activated complexes and/or insufficient quantities of preferred products of a reaction.

It has been generally believed that chemical reactions occur as a result of collisions between reacting molecules. In terms of the collision theory of chemical kinetics, it has been expected that the rate of a reaction is directly proportional to the number of the molecular collisions per second:

rate α number of collisions/sec

This simple relationship explains the dependence of reaction rates on concentration. Additionally, with few exceptions, reaction rates have been believed to increase with increasing temperature because of increased collisions.

The dependence of the rate constant k of a reaction can be expressed by the following equation, known as the Arrhenius equation:

$$k=Ae^{-E_a/RT}$$

where $E_a$ is the activation energy of the reaction which is the minimum amount of energy required to initiate a chemical reaction, R is the gas constant, T is the absolute temperature and e is the base of the natural logarithm scale. The quantity A represents the collision rate and shows that the rate constant is directly proportional to A and, therefore, to the collision rate. Furthermore, because of the minus sign associated with the exponent $E_a/RT$, the rate constant decreases with increasing activation energy and increases with increasing temperature.

Normally, only a small fraction of the colliding molecules, typically the fastest-moving ones, have enough kinetic energy to exceed the activation energy, therefore, the increase in the rate constant k can now be explained with the temperature increase. Since more high-energy molecules are present at a higher temperature, the rate of product formation is also greater at the higher temperature. But, with increased temperatures there are a number of problems which are introduced into the reaction system. With thermal excitation other competing processes, such as bond rupture, may occur before the desired energy state can be reached. Also, there are a number of decomposition products which often produce fragments that are extremely reactive, but they can be so short-lived because of their thermodynamic instability, that a preferred reaction may be dampened.

Radiant or light energy is another form of energy that may be added to the reaction medium that also may have negative side effects but which may be different from (or the same as) those side effects from thermal energy. Addition of radiant energy to a system produces electronically excited molecules that are capable of undergoing chemical reactions.

A molecule in which all the electrons are in stable orbitals is said to be in the ground electronic state. These orbitals may be either bonding or non-bonding. If a photon of the proper energy collides with the molecule the photon may be absorbed and one of the electrons may be promoted to an unoccupied orbital of higher energy. Electronic excitation results in spatial redistribution of the valence electrons with concomitant changes in internuclear configurations. Since chemical reactions are controlled to a great extent by these factors, an electronically excited molecule undergoes a chemical reaction that may be distinctly different from those of its ground-state counterpart.

The energy of a photon is defined in terms of its frequency or wavelength, $$E=h\nu=hc/\lambda$$

where E is energy; h is Plank's constant, $6.6 \times 10^{-34}$ J·sec; $\nu$ is the frequency of the radiation, $\sec^{-1}$; c is the speed of light; and $\lambda$ is the wavelength of the radiation. When a photon is absorbed, all of its energy is imparted to the absorbing species. The primary act following absorption depends on the wavelength of the incident light. Photochemistry studies photons whose energies lie in the ultraviolet region (100-4000 Å) and in the visible region (4000-7000 Å) of the electromagnetic spectrum. Such photons are primarily a cause of electronically excited molecules.

Since the molecules are imbued with electronic energy upon absorption of light, reactions occur from different potential-energy surfaces from those encountered in thermally excited systems. However, there are several drawbacks of using the known techniques of photochemistry, that being, utilizing a broad band of frequencies thereby causing unwanted side reactions, undue experimentation, and poor quantum yield. Some good examples of photochemistry are shown in the following patents.

In particular, U.S. Pat. No. 5,174,877 issued to Cooper, et. al., (1992) discloses an apparatus for the photocatalytic treatment of liquids. In particular, it is disclosed that ultraviolet light irradiates the surface of a prepared slurry to activate the photocatalytic properties of the particles contained in the slurry. The transparency of the slurry affects, for example, absorption of radiation. Moreover, discussions of different frequencies suitable for achieving desirable photocatalytic activity are disclosed.

Further, U.S. Pat. No. 4,755,269 issued to Brumer, et. al., (1998) discloses a photodisassociation process for disassociating various molecules in a known energy level. In particular, it is disclosed that different disassociation pathways are possible and the different pathways can be followed due to selecting different frequencies of certain electromagnetic radiation. It is further disclosed that the amplitude of electromagnetic radiation applied corresponds to amounts of product produced.

Selective excitation of different species is shown in the following three (3) patents. Specifically, U.S. Pat. No. 4,012,301 to Rich, et. al., (1977) discloses vapor phase chemical reactions that are selectively excited by using vibrational modes corresponding to the continuously flowing reactant species. Particularly, a continuous wave laser emits radiation that is absorbed by the vibrational mode of the reactant species.

U.S. Pat. No. 5,215,634 issued to Wan, et al., (1993) discloses a process of selectively converting methane to a desired oxygenate. In particular, methane is irradiated in the presence of a catalyst with pulsed microwave radiation to convert reactants to desirable products. The physical catalyst disclosed comprises nickel and the microwave radiation is applied in the range of about 1.5 to 3.0 GHz.

U.S. Pat. No. 5,015,349 issued to Suib, et. al., (1991) discloses a method for cracking a hydrocarbon to create cracked reaction products. It is disclosed that a stream of hydrocarbon is exposed to a microwave energy which creates a low power density microwave discharge plasma, wherein the microwave energy is adjusted to achieve desired results. A particular frequency desired of microwave energy is disclosed as being 2.45 GHz.

Physical catalysts are well known in the art. Specifically, a physical catalyst is a substance which alters the reaction rate of a chemical reaction without appearing in the end product. It is known that some reactions can be speeded up or controlled by the presence of substances which themselves appear to remain unchanged after the reaction has ended. By increasing the velocity of a desired reaction relative to unwanted reactions, the formation of a desired product can be maximized compared with unwanted by-products. Often only a trace of physical catalyst is necessary to accelerate the reaction. Also, it has been observed that some substances, which if added in trace amounts, can slow down the rate of a reaction. This looks like the reverse of catalysis, and, in fact, substances which slow down a reaction rate have been called negative catalysts or poisons. Known physical catalysts go through a cycle in which they are used and regenerated so that they can be used again and again. A physical catalyst operates by providing another path for the reaction which can have a higher reaction rate or slower rate than available in the absence of the physical catalyst. At the end of the reaction, because the physical catalyst can be recovered, it appears the physical catalyst is not involved in the reaction. But, the physical catalyst must somehow take part in the reaction, or else the rate of the reaction would not change. The catalytic act has historically been represented by five essential steps originally postulated by Ostwald around the late 1800's:

1. Diffusion to the catalytic site (reactant);
2. Bond formation at the catalytic site (reactant);
3. Reaction of the catalyst-reactant complex;
4. Bond rupture at the catalytic site (product); and
5. Diffusion away from the catalytic site product).

The exact mechanisms of catalytic actions are unknown in the art but it is known that physical catalysts can speed up a reaction that otherwise would take place too slowly to be practical.

There are a number of problems involved with known industrial catalysts: firstly, physical catalysts can not only lose their efficiency but also their selectivity, which can occur due to, for example, overheating or contamination of the catalyst; secondly, many physical catalysts include costly metals such as platinum or silver and have only a limited life span, some are difficult to rejuvenate, and the precious metals not easily reclaimed. There are numerous physical limitations associated with physical catalysts which render them less than ideal participants in many reactions.

Accordingly, what is needed is an understanding of the catalytic process so that biological processing, chemical processing, industrial processing, etc., can be engineered by more precisely controlling the multitude of reaction processes that currently exist, as well as developing completely new reaction pathways and/or reaction products. Examples of such understandings include methods to catalyze reactions without the drawbacks of: (1) known physical catalysts; and (2) utilizing energy with much greater specificity than the prior art teachings which utilize less than ideal thermal and electromagnetic radiation methods and which result in numerous inefficiencies.

SUMMARY OF THE INVENTION

Definitions

For purposes of this invention, the terms and expressions below, appearing in the Specification and Claims, are intended to have the following meanings:

"Activated complex", as used herein, means the assembly of atom(s) (charged or neutral) which corresponds to the maximum in the reaction profile describing the transformation of reactant(s) into reaction product(s). Either the reactant or reaction product in this definition could be an intermediate in an overall transformation involving more than one step.

"Applied spectral energy pattern", as used herein, means the totality of: (a) all spectral energy patterns that are externally applied; and/or (b) spectral environmental reaction conditions input into a reaction system.

"Catalytic spectral energy pattern", as used herein, means at least a portion of a spectral energy pattern of a physical catalyst which when applied to a reaction system in the form of a beam or field can catalyze the reaction system.

"Catalytic spectral pattern", as used herein, means at least a portion of a spectral pattern of a physical catalyst which when applied to a reaction system can catalyze the reaction system by the following:
 a) completely replacing a physical chemical catalyst;
 b) acting in unison with a physical chemical catalyst to increase the rate of reaction;
 c) reducing the rate of reaction by acting as a negative catalyst; or
 d) altering the reaction pathway for formation of a specific reaction product.

"Direct resonance targeting", as used herein, means the application of energy to a reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve direct resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy providers providing energy to at least one of said forms of matter by interacting with at least one frequency thereof, excluding electronic and vibrational frequencies in said reactants, to produce at least one desired reaction product and/or at least one desired reaction product at a desired reaction rate.

"Environmental reaction condition", as used herein, means and includes traditional reaction variables such as temperature, pressure, surface area of catalysts, physical catalyst size and shape, solvents, physical catalyst support materials, poisons, promoters, concentrations, electromagnetic radiation, electric fields, magnetic fields, mechanical forces, acoustic fields, reaction vessel size, shape and composition and combinations thereof, etc., which may be present and are capable of influencing, positively or negatively, reaction pathways in a reaction system.

"Frequency", as used herein, means the number of times which a physical event (e.g., wave, field and/or motion) varies from the equilibrium value through a complete cycle in a unit of time (e.g., one second; and one cycle/sec=1 Hz). The variation from equilibrium can be positive and/or negative, and can be, for example, symmetrical, asymmetrical and/or proportional with regard to the equilibrium value.

"Harmonic targeting", as used herein, means the application of energy to a reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve harmonic resonance with at least one of the following forms of matter: reactants; transients; intermediates; activated complexes; physical catalysts; reaction products; promoters, poisons; solvents; physical catalyst support materials; reaction vessels; and/or mixtures or components thereof, said spectral energy providers providing energy to at least one of said forms of matter by interacting with at least one frequency thereof, excluding electronic and vibrational frequencies in said reactants, to produce at least one desired reaction product and/or at least one desired reaction product at a desired reaction rate.

"Intermediate", as used herein, means a molecule, ion and/or atom which is present between a reactant and a reaction product in a reaction pathway or reaction profile. It corresponds to a minimum in the reaction profile of the reaction between reactant and reaction product. A reaction which involves an intermediate is typically a stepwise reaction.

"Non-harmonic heterodyne targeting", as used herein, means the application of energy to a reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction condition to achieve non-harmonic heterodyne resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Participant", as used herein, means reactant, transient, intermediate, activated complex, physical catalyst, promoter, poison and/or reaction product comprised of molecules, ions and/or atoms (or components thereof).

"Reactant", as used herein, means a starting material or starting component in a reaction system. A reactant can be any inorganic, organic and/or biologic atom, molecule, ion, compound, substance, and/or the like.

"Reaction coordinate", as used herein, means an intra- or inter-molecular/atom configurational variable whose change corresponds to the conversion of reactant into reaction product.

"Reaction pathway", as used herein, means those steps which lead to the formation of reaction product(s). A reaction pathway may include intermediates and/or transients and/or activated complexes. A reaction pathway may include some or all of a reaction profile.

"Reaction product", as used herein, means any product of a reaction involving a reactant. A reaction product may have a different chemical composition from a reactant or a substantially similar (or exactly the same) chemical composition but exhibit a different physical or crystalline structure and/or phase.

"Reaction profile", as used herein means a plot of energy (e.g., molecular potential energy, molar enthalpy, or free energy) against reaction coordinate for the conversion of reactant(s) into reaction product(s).

"Reaction system", as used herein, means the combination of reactants, intermediates, transients, activated complexes, physical catalysts, poisons, promoters, spectral catalysts, spectral energy catalysts, reaction products, environmental reaction conditions, spectral environmental reaction conditions, applied spectral energy pattern, etc., that are involved in any reaction pathway.

"Resultant energy pattern", as used herein, means the totality of energy interactions between the applied spectral energy pattern with all participants and/or components in the reaction systems.

"Spectral catalyst", as used herein, means electromagnetic energy which acts as a catalyst in a reaction system, for example, electromagnetic energy having a spectral pattern which affects, controls, or directs a reaction pathway.

"Spectral energy catalyst", as used herein, means energy which acts as a catalyst in a reaction system having a spectral energy pattern which affects, controls and/or directs a reaction pathway.

"Spectral energy pattern", as used herein, means a pattern formed by one or more energies and/or components emitted or absorbed by a molecule, ion, atom and/or component(s) thereof and/or which is present by and/or within a molecule, ion, atom and/or component(s) thereof.

"Spectral environmental reaction condition", as used herein, means at least one frequency and/or field which simulates at least a portion of at least one environmental reaction condition in a reaction system.

"Spectral pattern", as used herein, means a pattern formed by one or more electromagnetic frequencies emitted or absorbed after excitation of an atom or molecule. A spectral pattern may be formed by any known spectroscopic technique.

"Targeting", as used herein, means the application of energy to a reaction system by at least one of the following spectral energy providers: spectral energy catalyst; spectral catalyst; spectral energy pattern; spectral pattern; catalytic spectral energy pattern; catalytic spectral pattern; applied spectral energy pattern; and spectral environmental reaction conditions, to achieve direct resonance and/or harmonic resonance and/or non-harmonic heterodyne-resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Transient", as used herein, means any chemical and/or physical state that exists between reactant(s) and reaction product(s) in a reaction pathway or reaction profile.

This invention overcomes many of the deficiencies associated with the use of various known physical catalysts in a variety of different environments. More importantly, this invention, for the first time ever, discloses a variety of novel spectral energy techniques, referred to sometimes herein as spectral chemistry, that can be utilized in a number of reactions, including very basic reactions, which may be desirable to achieve or to permit to occur in a virtually unlimited number of areas. These spectral energy techniques can be used in, for example, any types of biological reactions (i.e., plant and animal), physical reactions, chemical reactions (i.e., organic or inorganic) industrial (i.e., any industrial reactions of large scale or small scale), and/or energy reactions of any type, etc.

These novel spectral energy techniques (now referred to as spectral chemistry) are possible to achieve due to the fundamental discoveries contained herein that disclose various means for achieving the transfer of energy between, for example, two entities. The invention teaches that the key for transferring energy between two entities (e.g., one entity sharing energy with another entity) is that when frequencies match, energy transfers. For example, matching of frequencies of spectral energy patterns of two different forms of matter; or matching of frequencies of a spectral energy pattern of matter with energy in the form of a spectral energy catalyst. The entities may both be comprised of matter (solids, liquids, gases and/or plasmas and/or mixtures and/or components thereof), both comprised of various form(s) of energy, or one comprised of various form(s) of energy and the other comprised of matter (solids, liquids, gases and/or plasmas and/or mixtures and/or components thereof).

More specifically, all matter can be represented by spectral energy patterns, which can be quite simple to very complex in appearance, depending on, for example, the complexity of the matter. One example of a spectral energy pattern is a spectral pattern which likewise can be quite simple to quite complex in appearance, depending on, for example, the complexity of the matter. In the case of matter represented by spectral patterns, matter can exchange energy with other matter if, for example, the spectral patterns of the two forms of matter match, at least partially, or can be made to match or overlap, at least partially (e.g., spectral curves or spectral patterns comprising one or more electromagnetic frequencies may overlap with each other). In general, but not in all cases, the greater the overlap in spectral patterns (and thus, the greater the overlap of frequencies comprising the spectral patterns), the greater the amount of energy transferred. Likewise, for example, if the spectral pattern of at least one form of energy can be caused to match or overlap, at least partially, with the spectral pattern of matter, energy will also transfer to the matter. Thus, energy can be transferred to matter by causing frequencies to match.

As discussed elsewhere herein, energy (E), frequency (v) and wavelength ($\lambda$) and the speed of light (c) in a vacuum are interrelated through, for example, the following equation:

$$E=hv=hc/\lambda$$

When a frequency or set of frequencies corresponding to at least a first form of matter can be caused to match with a frequency or set of frequencies corresponding to at least a second form of matter, energy can transfer between the different forms of matter and permit at least some interaction and/or reaction to occur involving at least one of the two different forms of matter. For example, solid, liquid, gas and/or plasma (and/or mixtures and/or portions thereof) forms of matter can interact and/or react and form a desirable reaction product or result. Any combination(s) of the above forms of matter (e.g., solid/solid, solid/liquid, solid/gas, solid/plasma, solid/gas/plasma, solid/liquid/gas, etc., and/or mixtures and/or portions thereof) are possible to achieve for desirable interactions and/or reactions to occur.

Further, matter (e.g., solids, liquids, gases and/or plasmas and/or mixtures and/or portions thereof) can be caused, or influenced, to interact and/or react with other matter and/or portions thereof in, for example, a reaction system along a desired reaction pathway by applying energy, in the form of, for example, a catalytic spectral energy pattern, a catalytic spectral pattern, a spectral energy pattern, a spectral energy catalyst, a spectral pattern, a spectral catalyst, a spectral environmental reaction condition and/or combinations thereof, which can collectively result in an applied spectral energy pattern.

In these cases, interactions and/or reactions may be caused to occur when the applied spectral energy pattern results in, for example, some type of modification to the spectral energy pattern of one or more of the forms of matter in the reaction system. The various forms of matter include: reactants; transients; intermediates; activated complexes; physical catalysts; reaction products; promoters; poisons; solvents; physical catalyst support materials; reaction vessels; and/or mixtures of components thereof. For example, the applied spectral energy provider (i.e., at least one of spectral energy catalyst; spectral catalyst; spectral energy pattern; spectral pattern; catalytic spectral energy pattern; catalytic spectral pattern; applied spectral energy pattern and spectral environmental reaction conditions) when targeted appropriately to, for example, a participant and/or component in the reaction system, can result in the generation of, and/or desirable interaction with, one or more participants. Specifically, the applied spectral energy provider can be targeted to achieve very specific desirable results and/or reaction product and/or reaction product at a desired rate. The targeting can occur by a direct resonance approach, (i.e., direct resonance targeting), a harmonic resonance approach (i.e., harmonic targeting) and/or a non-harmonic heterodyne resonance approach (i.e., non-harmonic heterodyne targeting). The spectral energy provider can be targeted to, for example, interact with at least one frequency of an atom or molecule, including, but not limited to, electronic frequencies, vibrational frequencies, rotational frequencies, rotational-vibrational frequencies, fine splitting frequencies, hyperfine splitting frequencies, magnetic field induced frequencies, electric field induced frequencies, natural oscillating frequencies, and all components and/or portions thereof (discussed in greater detail later herein). These approaches may result in, for example, the mimicking of at least one mechanism of action of a physical catalyst in a reaction system. For example, in some cases, desirable results may be achieved by utilizing a single applied spectral energy pattern targeted to a single participant; while in other cases, more than one applied spectral energy pattern may be targeted to a single participant or multiple participants, by, for example, multiple approaches. Specifically, combinations of direct resonance targeting, harmonic targeting and non-harmonic heterodyne targeting, which can be made to interact with one or more frequencies occurring in atoms and/or molecules, could be used sequentially or substantially continuously. Further, in certain cases, the spectral energy provider targeting may result in various interactions at predominantly the upper energy levels of one or more of the various forms of matter present in a reaction system.

The invention further recognizes and explains that various environmental reaction conditions are capable of influencing reaction pathways in a reaction system when using a spectral energy catalyst such as a spectral catalyst. The invention teaches specific methods for controlling various environmental reaction conditions in order to achieve desirable results in a reaction (e.g., desirable reaction product(s) in one or more desirable reaction pathway(s)) and/or interaction. The invention further discloses an applied spectral energy approach which permits the simulation, at least partially, of desirable environmental reaction conditions by the application of at least one, for example, spectral environmental reaction conditions. Thus, environmental reaction conditions can be controlled and used in combination with at least one spectral energy pattern to achieve a desired reaction pathway. Alternatively, traditionally utilized environmental reaction conditions can be modified in a desirable manner (e.g., application of a reduced temperature and/or reduced pressure) by supplementing and/or replacing the traditional environmental reaction condition(s) with at least one spectral environmental reaction condition.

The invention also provides a method for determining desirable physical catalysts (i.e., comprising previously known materials or materials not previously known to function as a physical catalyst) which can be utilized in a reaction system to achieve a desired reaction pathway and/or desired reaction rate. In this regard, the invention may be able to provide a recipe for a physical and/or spectral catalyst for a particular reaction system where no physical catalyst previously existed. In this embodiment of the invention, spectral energy patterns are determined or calculated by the techniques of the invention and corresponding physical catalysts can be supplied or manufactured and thereafter included in the reaction system to generate the calculated required spectral energy patterns. In certain cases, one or more existing physical species could be used or combined in a suitable manner, if a single physical species was deemed to be insufficient, to obtain the appropriate calculated spectral energy pattern to achieve a desired reaction pathway and/or desired reaction rate. Such catalysts can be used alone, in combination with other physical catalysts, spectral energy catalysts, controlled environmental reaction conditions and/or spectral environmental reaction conditions to achieve a desired resultant energy pattern and consequent reaction pathway and/or desired reaction rate.

The invention discloses many different permutations of the basic theme stated throughout namely, that when frequencies match, energy transfers. It should be understood that these many different permutations can be used alone to achieve desirable results (e.g., desired reaction pathways and/or a desired reaction rates) or can be used in a limitless combination of permutations, to achieve desired results (e.g., desired reaction pathways and/or desired reaction rates). However, common to all of these seemingly complicated permutations and combinations is the basic understanding first provided by this invention that in order to control or enable any reaction, so long as frequencies of two entities match (e.g., spectral patterns overlap), energy can be transferred. If energy is transferred, desirable interactions and/or reactions can result.

Moreover, this concept can also be used in the reverse. Specifically, if a reaction is occurring because frequencies match, the reaction can be slowed or stopped by causing the frequencies to no longer match or at least match to a lesser degree. In this regard, one or more reaction system components (e.g., environmental reaction condition, spectral environmental reaction condition and/or an applied spectral energy pattern) can be modified and/or applied so as to minimize, reduce or eliminate frequencies from matching. This also permits reactions to be started and stopped with ease providing for novel control in a myriad of reactions.

To simplify the disclosure and understanding of the invention, specific categories or sections have been created in the "Summary of the Invention" and in the "Detailed Description of the Preferred Embodiments". However, it should be understood that these categories are not mutually exclusive and that some overlap exists. Accordingly, these artificially created sections should not be used in an effort to limit the scope of the invention defined in the appended claims.

I. Wave Energies

In general, thermal energy has traditionally been used to drive chemical reactions by applying heat and increasing the temperature of a reaction system. The addition of heat increases the kinetic (motion) energy of the chemical reactants. It has been believed that a reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (EM) energy consists of waves of electric and magnetic fields. EM energy may also increase the kinetic energy and heat in reaction systems. It also may energize electronic orbitals or vibrational motion in some reactions.

Both acoustic and electromagnetic energy consist of waves. Energy waves and frequency have some interesting properties, and may be combined in some interesting ways. The manner in which wave energy transfers and combines, depends largely on the frequency. For example, when two waves of energy, each having the same amplitude, but one at a frequency of 400 Hz and the other at 100 Hz are caused to interact, the waves will combine and their frequencies will add, to produce a new frequency of 500 Hz (i.e., the "sum" frequency). The frequency of the waves will also subtract when they combine to produce a frequency of 300 Hz (i.e., the "difference" frequency). All wave energies typically add and subtract in this manner, and such adding and subtracting is referred to as heterodyning. Common results of heterodyning are familiar to most as harmonics in music. The importance of heterodyning will be discussed in greater detail later herein.

Another concept important to the invention is wave interactions or interference. In particular, wave energies are known to interact constructively and destructively. This phenomena is important in determining the applied spectral energy pattern. FIGS. 1a-1c show two different incident sine waves 1 (FIG. 1a) and 2 (FIG. 1b) which correspond to two different spectral energy patterns having two different wavelengths $\lambda_1$ and $\lambda_2$ (and thus different frequencies) which could be applied to a reaction system. Assume arguendo that the energy pattern of FIG. 1a corresponds to an electromagnetic spectral pattern and that FIG. 1b corresponds to one spectral environmental reaction condition. Each of the sine waves 1 and 2 has a different differential equation which describes its individual motion. However, when the sine waves are combined into the resultant additive wave 1+2 (FIG. 1c), the resulting complex differential equation, which describes the totality of the combined energies (i.e., the applied spectral energy pattern) actually results in certain of the input energies being high (i.e., constructive interference shown by a higher amplitude) at certain points in time, as well as being low (i.e., destructive interference shown by a lower amplitude) at certain points in time.

Specifically, the portions "X" represent areas where the electromagnetic spectral pattern of wave 1 has constructively interfered with the spectral environmental reaction condition wave 2, whereas the portions "Y" represent areas where the two waves 1 and 2 have destructively interfered. Depending upon whether the portions "X" corresponds to desirable or undesirable wavelengths, frequencies or energies (e.g., causing the applied spectral energy pattern to have positive or negative interactions with, for example, one or more participants and/or components in the reaction system), then the portions "X" could enhance a positive effect in the reaction system or could enhance a negative effect in the reaction system. Similarly, depending on whether the portions "Y" correspond to desirable or undesirable wavelengths, frequencies, or energies, then the portions "Y" may correspond to the effective loss of either a positive or negative effect.

It should be clear from this particular analysis that constructive interferences (i.e., the points "X") could, for example, maximize both positive and negative effects in a reaction system. Accordingly, this simplified example shows that by combining, for example, certain frequencies from a spectral pattern with one or more other frequencies from, for example, at least one spectral environmental reaction condition, that the applied spectral energy pattern that is actually applied to the reaction system can be a combination of constructive and destructive interference(s). Accordingly, these factors should also be taken into account when choosing appropriate spectral energy patterns that are to be applied to a reaction system. In this regard, it is noted that in practice many desirable incident wavelengths can be applied to a reaction system. Moreover, it should also be clear that wave interaction effects include, but are not limited to, heterodyning, direct resonance, indirect resonance, additive waves, subtractive waves, constructive or destructive interference, etc. Further, as discussed in detail later herein, additional effects such as electric effects and/or magnetic field effects can also influence spectral energy patterns (e.g., spectral patterns).

II. Spectral Catalysts and Spectroscopy

A wide variety of reactions can be advantageously affected and directed with the assistance of a spectral energy catalyst having a specific spectral energy pattern (e.g., spectral pattern or electromagnetic pattern) which transfers a predetermined quanta of targeted energy to initiate, control and/or promote desirable reaction pathways and/or desirable reaction rates within a reaction system. This section discusses spectral catalysts in more detail and explains various techniques for using spectral catalysts in reaction systems. For example, a spectral catalyst can be used in a reaction system to replace and provide the additional energy normally supplied by a physical catalyst. The spectral catalyst can actually mimic or copy the mechanisms of action of a physical catalyst. The spectral catalyst can act as both a positive catalyst to increase the rate of a reaction or as a negative catalyst or poison to decrease the rate of reaction. Furthermore, the spectral catalyst can augment a physical catalyst by utilizing both a physical catalyst and a spectral catalyst in a reaction system. The spectral catalyst can improve the activity of a physical chemical catalyst. Also, the spectral catalyst can partially replace a specific quantity or amount of the physical catalyst, thereby reducing the high cost of physical catalysts in many industrial reactions.

In the present invention, the spectral energy catalyst provides targeted energy (e.g., electromagnetic radiation comprising a specific frequency or combination of frequencies), in a sufficient amount for a sufficient duration to initiate and/or promote and/or direct a chemical reaction (e.g., follow a particular reaction pathway). The total combination of targeted energy applied at any point in time to the reaction system is referred to as the applied spectral energy pattern. The applied spectral energy pattern may be comprised of a single spectral catalyst, multiple spectral catalysts and/or other spectral energy catalysts as well. With the absorption of targeted energy into a reaction system (e.g., electromagnetic energy from a spectral catalyst), a reactant may be caused to proceed through one or several reaction pathways including: energy transfer which can, for example, excite electrons to higher energy states for initiation of chemical reaction, by causing frequencies to match; ionize or dissociate reactants which may participate in a chemical reaction; stabilize reaction products; energize and/or stabilize intermediates and/or transients and/or activated complexes that participate in a reaction pathway; and/or cause one or more components in a reaction system to have spectral patterns which at least partially overlap.

For example, in a simple reaction system, if a chemical reaction provides for at least one reactant "A" to be converted into at least one reaction product "B", a physical catalyst "C" may be utilized. In contrast, a portion of the catalytic spectral energy pattern (e.g., in this section the catalytic spectral pattern) of the physical catalyst "C" may be applied in the form of, for example, an electromagnetic beam to catalyze the reaction.

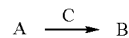

Substances A and B=unknown frequencies, and C=30 Hz;

Therefore, Substance $A+30\ HZ \rightarrow$ Substance $B$

In the present invention, for example, the spectral pattern (e.g., electromagnetic spectral pattern) of the physical catalyst "C" can be determined by known methods of spectroscopy. Utilizing spectroscopic instrumentation, the spectral pattern of the physical catalyst is preferably determined under conditions approximating those occurring in the reaction system using the physical catalyst (e.g., spectral energy patterns as well as spectral patterns can be influenced by environmental reaction conditions, as discussed later herein). Spectroscopy is a process in which the energy differences between allowed states of any system are measured by determining the frequencies of the corresponding electromagnetic energy which is either being absorbed or emitted. Spectroscopy in general deals with the interaction of electromagnetic radiation with matter. When photons interact with, for example, atoms or molecules, changes in the properties of atoms and molecules are observed.

Atoms and molecules are associated with several different types of motion. The entire molecule rotates, the bonds vibrate, and even the electrons move, albeit so rapidly that electron density distributions have historically been the primary focus of the prior art. Each of these kinds of motion is quantified. That is, the atom, molecule or ion can exist only in distinct states that correspond to discrete energy amounts. The energy difference between the different quantum states depends on the type of motion involved. Thus, the frequency of energy required to bring about a transition is different for the different types of motion. That is, each type of motion corresponds to the absorption of energy in different regions of the electromagnetic spectrum and different spectroscopic instrumentation may be required for each spectral region. The total motion energy of an atom or molecule may be considered to be at least the sum of its electronic, vibrational and rotational energies.

In both emission and absorption spectra, the relation between the energy change in the atom or molecule and the frequency of the electromagnetic energy emitted or absorbed is given by the so-called Bohr frequency condition:

$$\Delta E = h\nu$$

where h is Planck's constant; $\nu$ is the frequency; and $\Delta E$, is the difference of energies in the final and initial states.

Electronic spectra are the result of electrons moving from one electronic energy level to another in an atom, molecule or ion. A molecular physical catalyst's spectral pattern includes not only electronic energy transitions but also may involve transitions between rotational and vibrational energy levels. As a result, the spectra of molecules are much more complicated than those of atoms. The main changes observed in the atoms or molecules after interaction with photons include excitation, ionization and/or rupture of chemical bonds, all of which may be measured and quantified by spectroscopic methods including emission or absorption spectroscopy which give the same information about energy level separation.

In emission spectroscopy, when an atom or molecule is subjected to a flame or an electric discharge, such atoms or molecules may absorb energy and become "excited." On their return to their "normal" state they may emit radiation. Such an emission is the result of a transition of the atom or molecule from a high energy or "excited" state to one of lower state. The energy lost in the transition is emitted in the form of electromagnetic energy. "Excited" atoms usually produce line spectra while "excited" molecules tend to produce band spectra.

In absorption spectroscopy, the absorption of nearly monochromatic incident radiation is monitored as it is swept over a range of frequencies. During the absorption process the atoms or molecules pass from a state of low energy to one of high energy. Energy changes produced by electromagnetic energy absorption occur only in integral multiples of a unit amount of energy called a quantum, which is characteristic of each absorbing species. Absorption spectra may be classified into four types: rotational; rotation-vibration; vibrational; and electronic.

The rotational spectrum of a molecule is associated with changes which occur in the rotational states of the molecule. The energies of the rotational states differ only by a relatively small amount, and hence, the frequency which is necessary to effect a change in the rotational levels is very low and the wavelength of electromagnetic energy is very large. The energy spacing of molecular rotational states depends on bond distances and angles. Pure rotational spectra are observed in the far infrared and microwave and radio regions (See Table 1).

Rotation-vibrational spectra are associated with transitions in which the vibrational states of the molecule are altered and may be accompanied by changes in rotational states. Absorption occurs at higher frequencies or shorter wavelength and usually occurs in the middle of the infrared region (See Table 1).

Vibrational spectra from different vibrational energy levels occur because of motion of bonds. A stretching vibration involves a change in the interatomic distance along the axis of the bond between two atoms. Bending vibrations are characterized by a change in the angle between two bonds. The vibrational spectra of a molecule are typically in the near-infrared range.

Electronic spectra are from transitions between electronic states for atoms and molecules and are accompanied by simultaneous changes in the rotational and vibrational states in molecules. Relatively large energy differences are involved, and hence absorption occurs at rather large frequencies or relatively short wavelengths. Different electronic states of atoms or molecules correspond to energies in the infrared, ultraviolet-visible or x-ray region of the electromagnetic spectrum (See Table 1).

TABLE 1

Approximate Boundaries

| Region Name | Energy, J | Wavelength | Frequency, Hz |
| --- | --- | --- | --- |
| X-ray | $2 \times 10^{-14}$-$2 \times 10^{-17}$ | 10-2-10 nm | $3 \times 10^{19}$-$3 \times 10^{16}$ |
| Vacuum Ultraviolet | $2 \times 10^{-17}$-$9.9 \times 10^{-19}$ | 10-200 nm | $3 \times 10^{16}$-$1.5 \times 10^{15}$ |
| Near ultraviolet | $9.9 \times 10^{-19}$-$5 \times 10^{-19}$ | 200-400 nm | $1.5 \times 10^{15}$-$7.5 \times 10^{14}$ |
| Visible | $5 \times 10^{-19}$-$2.5 \times 10^{-19}$ | 400-800 nm | $7.5 \times 10^{14}$-$3.8 \times 10^{14}$ |
| Near Infrared | $2.5 \times 10^{-19}$-$6.6 \times 10^{-20}$ | 0.8-2.5 um | $3.8 \times 10^{14}$-$1 \times 10^{14}$ |
| Fundamental Infrared | $6.6 \times 10^{-20}$-$4 \times 10^{-21}$ | 2.5-50 um | $1 \times 10^{14}$-$6 \times 10^{12}$ |

TABLE 1-continued

Approximate Boundaries

| Region Name | Energy, J | Wavelength | Frequency, Hz |
|---|---|---|---|
| Far infrared | $4 \times 10^{-21}$-$6.6 \times 10^{-22}$ | 50-300 um | $6 \times 10^{12}$-$1 \times 10^{12}$ |
| Microwave | $6.6 \times 10^{-22}$-$4 \times 10^{-25}$ | 0.3 mm-0.5 m | $1 \times 10^{12}$-$6 \times 10^{8}$ |
| Radiowave | $4 \times 10^{-25}$-$6.6 \times 10^{-34}$ | $0.5$-$300 \times 10^{6}$m | $6 \times 10^{8}$-1 |

Electromagnetic radiation as a form of energy can be absorbed or emitted, and therefore many different types of spectroscopy may be used in the present invention to determine a desired spectral pattern of a spectral catalyst (e.g., a spectral pattern of a physical catalyst) including, but not limited to, x-ray, ultraviolet, infrared, microwave, atomic absorption, flame emissions, atomic emissions, inductively coupled plasma, DC argon plasma, arc-source emission, spark-source emission, high-resolution laser, radio, Raman and the like.

In order to study the electronic transitions, the material to be studied may need to be heated to a high temperature, such as in a flame, where the molecules are atomized and excited. Another very effective way of atomizing gases is the use of gaseous discharges. When a gas is placed between charged electrodes, causing an electrical field, electrons are liberated from the electrodes and from the gas atoms themselves and may form a plasma or plasma-like conditions. These electrons will collide with the gas atoms which will be atomized, excited or ionized. By using high frequency fields, it is possible to induce gaseous discharges without using electrodes. By varying the field strength, the excitation energy can be varied. In the case of a solid material, excitation by electrical spark: or arc can be used. In the spark or arc, the material to be analyzed is evaporated and the atoms are excited.

The basic scheme of an emission spectrophotometer includes a purified silica cell containing the sample which is to be excited. The radiation of the sample passes through a slit and is separated into a spectrum by means of a dispersion element. The spectral pattern can be detected on a screen, photographic film or by a detector.

An atom will most strongly absorb electromagnetic energy at the same frequencies it emits. Measurements of absorption are often made so that electromagnetic radiation that is emitted from a source passes through a wavelength-limiting device, and impinges upon the physical catalyst sample that is held in a cell. When a beam of white light passes through a material, selected frequencies from the beam are absorbed. The electromagnetic radiation that is not absorbed by the physical catalyst passes through the cell and strikes a detector. When the remaining beam is spread out in a spectrum, the frequencies that were absorbed show up as dark lines in the otherwise continuous spectrum. The position of these dark lines correspond exactly to the positions of lines in an emission spectrum of the same molecule or atom. Both emission and absorption spectrophotometers are available through regular commercial channels.

In 1885, Balmer discovered that hydrogen vibrates and produces energy at frequencies in the visible light region of the electromagnetic spectrum which can be expressed by a simple formula:

$$1/\lambda = R(1/2^2 - 1/m^2)$$

when $\lambda$ is the wavelength of the light, R is Rydberg's constant and m is an integer greater than or equal to 3 (e.g., 3, 4, or 5, etc.). Subsequently, Rydberg discovered that this equation could be adapted to result in all the wavelengths in the hydrogen spectrum by changing the $1/2^2$ to $1/n^2$, as in, $$1/\lambda = R(1/n^2 - 1/m^2)$$

where n is an integer $\geq 1$, and m is an integer $\geq n+1$. Thus, for every different number n, the result is a series of numbers for wavelength, and the names of various scientists were assigned to each such series which resulted. For instance, when n=2 and m$\geq$3, the energy is in the visible light spectrum and the series is referred to as the Balmer series. The Lyman series is in the ultraviolet spectrum with n=1, and the Paschen series is in the infrared spectrum with n=3.

In the prior art, energy level diagrams were the primary means used to describe energy levels in the hydrogen atom (see FIGS. 7a and 7b).

After determining the electromagnetic spectral pattern of a desired catalyst (e.g., a physical catalyst), the catalytic spectral pattern may be duplicated, at least partially, and applied to the reaction system. Any generator of one or more frequencies within an acceptable approximate range of, for example, frequencies of electromagnetic radiation may be used in the present invention. When duplicating one or more frequencies of, for example, a spectral pattern, it is not necessary to duplicate the frequency exactly. For instance, the effect achieved by a frequency of 1,000 THz, can also be achieved by a frequency very close to it, such as 1,001 or 999 THz. Thus, there will be a range above and below each exact frequency which will also catalyze a reaction. Specifically, FIG. 12 shows a typical bell-curve "B" distribution of frequencies around the desired frequency $f_0$, wherein desirable frequencies can be applied which do not correspond exactly to $f_0$, but are close enough to the frequency $f_0$ to achieve a desired effect, such as those frequencies between and including the frequencies within the range of $f_1$ and $f_2$. Note that $f_1$ and $f_2$ correspond to about one half the maximum amplitude, $a_{max}$, of the curve "B". Thus, whenever the term "exact" or specific reference to "frequency" or the like is used, it should be understood to have this meaning. In addition, harmonics of spectral catalyst frequencies, both above and below the exact spectral catalyst frequency, will cause sympathetic resonance with the exact frequency and will catalyze the reaction. Finally, it is possible to catalyze reactions by duplicating one or more of the mechanisms of action of the exact frequency, rather than using the exact frequency itself. For example, platinum catalyzes the formation of water from hydrogen and oxygen, in part, by energizing the hydroxyl radical at its frequency of roughly 1,060 THz. The reaction can also be catalyzed by energizing the hydroxy radical with its microwave frequency, thereby duplicating platinum's mechanism of action.

An electromagnetic radiation emitting source should have the following characteristics: high intensity of the desired wavelengths; long life; stability; and the ability to emit the electromagnetic energy in a pulsed and/or continuous mode.

Irradiating sources can include, but are not limited to, arc lamps, such as xenon-arc, hydrogen and deuterium, krypton-arc, high-pressure mercury, platinum, silver; plasma arcs, discharge lamps, such as As, Bi, Cd, Cs, Ge, Hg, K, P, Pb, Rb, Sb, Se, Sn, Ti, Tl and Zn; hollow-cathode lamps, either single or multiple elements such as Cu, Pt, and Ag; and sunlight and coherent electromagnetic energy emissions, such as masers and lasers.

Masers are devices which amplify or generate electromagnetic energy waves with great stability and accuracy. Masers operate on the same principal as lasers, but produce electromagnetic energy in the radio and microwave, rather than visible range of the spectrum. In masers, the electromagnetic energy is produced by the transition of molecules between rotational energy levels.

Lasers are powerful coherent photon sources that produce a beam of photons having the same frequency, phase and direction, that is, a beam of photons that travel exactly alike. Accordingly, for example, the predetermined spectral pattern of a desired catalyst can be generated by a series or grouping of lasers producing one or more required frequencies.

Any laser capable of emitting the necessary electromagnetic radiation with a frequency or frequencies of the spectral catalyst may be used in the present invention. Lasers are available for use throughout much of the spectral range. They can be operated in either a continuous or a pulsed mode. Lasers that emit lines and lasers that emit a continuum may be used in the present invention. Line sources may include argon ion laser, ruby laser, the nitrogen laser, the Nd:YAG laser, the carbon dioxide laser, the carbon monoxide laser and the nitrous oxide-carbon dioxide laser. In addition to the spectral lines that are emitted by lasers, several other lines are available, by addition or subtraction in a crystal of the frequency emitted by one laser to or from that emitted by another laser. Devices that combine frequencies and may be used in the present invention include difference frequency generators and sum frequency mixers. Other lasers that may be used in this invention include, but are not limited to: crystal, such as $Al_2O_3$ doped with $Cr^{3+}$, $Y_3Al_5O_{12}$ doped with $Nd^{3+}$; gas, such as He—Ne, Kr-ion; glass, chemical, such as vibrationally excited HCL and HF; dye, such as Rhodamine 6G in methanol; and semiconductor lasers, such as $Ga_{1-x}Al_xAs$. Many models can be tuned to various frequency ranges, thereby providing several different frequencies from one instrument and applying them to the reaction system (See Examples in Table 2).

TABLE 2

SEVERAL POPULAR LASERS

| Medium | Type | Emitted wavelength, nm |
|---|---|---|
| Ar | Gas | 334, 351.1, 363.8, 454.5, 457.9, 465.8, 472.7, 476.5, 488.0, 496.5, 501.7, 514.5, 528.7 |
| Kr | Gas | 350.7, 356.4, 406.7, 413.1, 415.4, 468.0, 476.2, 482.5, 520.8, 530.9, 568.2, 647.1, 676.4, 752.5, 799.3 |
| He—Ne | Gas | 632.8 |
| He—Cd | Gas | 325.0, 441.6 |
| $N_2$ | Gas | 337.1 |
| XeF | Gas | 351 |
| KrF | Gas | 248 |
| ArF | Gas | 193 |
| Ruby | Solid | 693.4 |
| Nd:YAG | Solid | 266, 355, 532 |
| $Pb_{1-x}Cd_xS$ | Solid | $2.9 \times 10^3$-$2.6 \times 10^4$ |
| $Pb_{1-x}Se_x$ | Solid | $2.9 \times 10^3$-$2.6 \times 10^4$ |
| $Pb_{1-x}Sn_xSe$ | Solid | $2.9 \times 10^3$-$2.6 \times 10^4$ |
| $Pb_{1-x}Sn_xTe$ | Solid | $2.9 \times 10^3$-$2.6 \times 10^4$ |

The coherent light from a single laser or a series of lasers is simply brought to focus or introduced to the region where a desired reaction is to take place. The light source should be close enough to avoid a "dead space" in which the light does not reach the reaction system, but far enough apart to assure complete incident-light absorption. Since ultraviolet sources generate heat, such sources may need to be cooled to maintain efficient operation. Irradiation time, causing excitation of the reaction system, may be individually tailored for each reaction: some short-term for a continuous reaction with large surface exposure to the light source; or long light-contact time for other systems.

An object of this invention is to provide a spectral energy pattern (e.g., a spectral pattern of electromagnetic energy) to the reaction system by applying at least a portion of (or substantially all of) a required spectral energy catalyst (e.g., a spectral catalyst) determined and calculated by, for example, waveform analysis of the spectral patterns of, for example, the reactant(s) and the reaction product(s). Accordingly, in the case of a spectral catalyst, a calculated electromagnetic pattern will be a spectral pattern or will act as a spectral catalyst to generate a preferred reaction pathway and/or preferred reaction rate. In basic terms, spectroscopic data for identified substances can be used to perform a simple waveform calculation to arrive at, for example, the correct electromagnetic energy frequency, or combination of frequencies, needed to catalyze a reaction. In simple terms, $A \rightarrow B$ Substance $A$=50 Hz, and Substance $B$=80 Hz 80 Hz–50 Hz=30 Hz:

Therefore, Substance $A$+30 Hz→Substance $B$.

The spectral energy pattern (e.g., spectral patterns) of both the reactant(s) and reaction product(s) can be determined. In the case of a spectral catalyst, this can be accomplished by the spectroscopic means mentioned earlier. Once the spectral patterns are determined (e.g., having a specific frequency or combination of frequencies) within an appropriate set of environmental reaction conditions, the spectral energy pattern(s) (e.g., electromagnetic spectral pattern(s)) of the spectral energy catalyst (e.g., spectral catalyst) can be determined. Using the spectral energy pattern (s) (e.g., spectral patterns) of the reactant(s) and reaction product(s), a waveform analysis calculation can determine the energy difference between the reactant(s) and reaction product(s) and at least a portion of the calculated spectral energy pattern (e.g., electromagnetic spectral pattern) in the form of a spectral energy pattern (e.g., a spectral pattern) of a spectral energy catalyst (e.g., a spectral catalyst) can be applied to the reaction system to cause the reaction system to follow along the desired reaction pathway. The specific frequency or frequencies of the calculated spectral energy pattern (e.g., spectral pattern) corresponding to the spectral energy catalyst (e.g., spectral catalyst) will provide the necessary energy input into the reaction system to affect and initiate a desired reaction pathway.

Performing the waveform analysis calculation to arrive at, for example, the correct electromagnetic energy frequency or frequencies can be accomplished by using complex algebra, Fourier transformation or Wavelet Transforms, which is available through commercial channels under the trademark Mathematical and supplied by Wolfram, Co. It should be noted that only a portion of a calculated spectral energy catalyst (e.g., spectral catalyst) may be sufficient to catalyze a reaction or a substantially complete spectral energy catalyst (e.g., spectral catalyst) may be applied depending on the particular circumstances.

In addition, at least a portion of the spectral energy pattern (e.g., electromagnetic pattern of the required spectral catalyst) may be generated and applied to the reaction system by, for example, the electromagnetic radiation emitting sources defined and explained earlier.

The use of a spectral catalyst may be applicable in many different areas of technology ranging from biochemical processes to industrial reactions.

The specific physical catalysts that may be replaced or augmented in the present invention may include any solid, liquid, gas or plasma catalyst, having either homogeneous or heterogeneous catalytic activity. A homogeneous physical catalyst is defined as a catalyst whose molecules are dispersed in the same phase as the reacting chemicals. A heterogeneous physical catalyst is defined as one whose molecules are not in the same phase as the reacting chemicals. In addition, enzymes which are considered biological catalysts are to be included in the present invention. Some examples of physical catalysts that may be replaced or augmented comprise both elemental and molecular catalysts, including, not limited to, metals, such as silver, platinum, nickel, palladium, rhodium, ruthenium and iron; semiconducting metal oxides and sulfides, such as $NiO_2$, Zn), MgO, $Bi_2O_3/MoO_3$, $TiO_2$, $SrTiO_3$, CdS, CdSe, SiC, GaP, $Wo_2$ and $MgO_3$; copper sulfate; insulating oxides such as $Al_2O_3$, $SiO_2$ and MgO; and Ziegler-Natta catalysts, such as titanium tetrachloride, and trialkyaluminum.

III. Targeting

The frequency and wave nature of energy has been discussed herein. Additionally, Section I entitled "Wave Energies" disclosed the concepts of various potential interactions between different waves. The general concepts of "targeting", "direct resonance targeting", "harmonic targeting" and "non-harmonic heterodyne targeting" (all defined terms herein) build on these and other understandings.

Targeting has been defined generally as the application of a spectral energy provider (e.g., spectral energy catalyst, spectral catalyst, spectral energy pattern, spectral pattern, catalytic spectral energy pattern, catalytic spectral pattern, spectral environmental reaction conditions and applied spectral energy pattern) to a reaction system. The application of these types of energies to a reaction system can result in interaction(s) between the applied spectral energy provider(s) and matter (including all components thereof) in the reaction system. This targeting can result in at least one of direct resonance, harmonic resonance, and/or non-harmonic heterodyne resonance with at least a portion, for example, at least one form of matter in a reaction system. In this invention, targeting should be generally understood as meaning applying a particular spectral energy provider (e.g., a spectral energy pattern) to another entity comprising matter (or any component thereof) to achieve a particular desired result (e.g., desired reaction product and/or desired reaction product at a desired reaction rate). Further, the invention provides techniques for achieving such desirable results without the production of, for example, undesirable transients, intermediates, activated complexes and/or reaction products. In this regard, some limited prior art techniques exist which have applied certain forms of energies (as previously discussed) to reaction systems. These certain forms of energies have been limited to direct resonance and harmonic resonance with some electronic frequencies and/or vibrational frequencies of some reactants. These limited forms of energies used by the prior art were due to the fact that the prior art lacked an adequate understanding of the spectral energy mechanisms and techniques disclosed herein. Moreover, it has often been the case in the prior art that at least some undesirable intermediate, transient, activated complex and/or reaction product was formed, and/or a less than optimum reaction rate for a desired reaction pathway occurred. The present invention overcomes the limitations of the prior art by specifically targeting, for example, various forms of matter in a reaction system (and/or components thereof), with, for example, an applied spectral energy pattern. Heretofore, such selective targeting of the invention was never disclosed or suggested. Specifically, at best, the prior art has been reduced to using random, trial and error or feedback-type analyses which, although may result in the identification of a single spectral catalyst frequency, such approach may be very costly and very time-consuming, not to mention potentially unreproducible under a slightly different set of reaction conditions. Such trial and error techniques for determining appropriate catalysts also have the added drawback, that having once identified a particular catalyst that works, one is left with no idea of what it means. If one wishes to modify the reaction, including simple reactions using size and shape, another trial and error analysis becomes necessary rather than a simple, quick calculation offered by the techniques of the present invention.

Accordingly, whenever use of the word "targeting" is made herein, it should be understood that targeting does not correspond to undisciplined energy bands being applied to a reaction system; but rather to well defined, targeted, applied spectral energy patterns, each of which has a particular desirable purpose in, for example, a reaction pathway to achieve a desired result and/or a desired result at a desired reaction rate.

IV. Environmental Reaction Conditions

Environmental reaction conditions are important to understand because they can influence, positively or negatively, reaction pathways in a reaction system. Traditional environmental reaction conditions include temperature, pressure, surface area of catalysts, catalyst size and shape, solvents, support materials, poisons, promoters, concentrations, electromagnetic radiation, electric fields, magnetic fields, mechanical forces, acoustic fields, reaction vessel size, shape and composition and combinations thereof, etc.

The following reaction can be used to discuss the effects of environmental reaction conditions which may need to be taken into account in order to cause the reaction to proceed along the simple reaction pathway shown below.

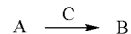

Specifically, in some instances, reactant A will not form into reaction product B in the presence of any catalyst C unless the environmental reaction conditions in the reaction system include certain maximum or minimum conditions of environmental reaction conditions such as pressure and/or temperature. In this regard, many reactions will not occur in the presence of a physical catalyst unless the environmental reactions conditions include, for example, an elevated temperature and/or an elevated pressure. In the present invention, such environmental reaction conditions should be taken into consideration when applying a particular spectral energy catalyst (e.g., a spectral catalyst). Many specifics of the various environmental reaction conditions are discussed in greater detail in the Section herein entitled "Description of the Preferred Embodiments".

V. Spectral Environmental Reaction Conditions

If it is known that certain reaction pathways will not occur within a reaction system (or not occur at a desirable rate) even when a catalyst is present unless, for example, certain minimum or maximum environmental reaction conditions are present (e.g., the temperature and/or pressure is/are elevated), then an additional frequency or combination of frequencies (i.e., an applied spectral energy pattern) can be applied to the reaction system. In this regard, spectral environmental reaction condition(s), can be applied instead of, or to supplement, those environmental reaction conditions that are naturally present, or need to be present, in order for a desired reaction pathway and/or desired reaction rate to be followed. The environmental reaction conditions that can be supplemented or replaced with spectral environmental reaction conditions include, for example, temperature, pressure, surface area of catalysts, catalyst size and shape, solvents, support materials, poisons, promoters, concentrations, electric fields, magnetic fields, etc.

Still further, a particular frequency or combination of frequencies and/or fields that can produce one or more spectral environmental reaction conditions can be combined with one or more spectral energy catalysts and/or spectral catalysts to generate an applied spectral energy pattern. Accordingly, various considerations can be taken into account for what particular frequency or combination of frequencies and/or fields may be desirable to combine with (or replace) various environmental reaction conditions, for example.

As an example, in a simple reaction, assume that a first reactant "A" has a frequency or simple spectral pattern of 3 THz and a second reactant "B" has a frequency or simple spectral pattern of 7 THz. At room temperature, no reaction occurs. However, when reactants A and B are exposed to high temperatures, their frequencies, or simple spectral patterns, both shift to 5 THz. Since their frequencies match, they transfer energy and a reaction occurs. By applying a frequency of 2 THz, at room temperature, the applied 2 THz frequency will heterodyne with the 3 THz pattern to result in, both 1 Thz and 5 THz heterodyned frequencies; while the applied frequency of 2 THz will heterodyne with the spectral pattern of 7 THz of reactant "B" and result in heterodyned frequencies of 5 THz and 9 THz in reactant "B". Thus, the heterodyned frequencies of 5 THz are generated at room temperature in each of the reactants "A" and "B". Accordingly, frequencies in each of the reactants match and thus energy can transfer between the reactants "A" and "B". When the energy can transfer between such reactants, all desirable reactions along a reaction pathway may be capable of being achieved. However, in certain reactions, only some desirable reactions along a reaction pathway are capable of being achieved by the application of a singular frequency. In these instances, additional frequencies and/or fields may need to be applied to result in all desirable steps along a reaction pathway being met, including but not limited to, the formation of all required reaction intermediates and/or transients.

Thus, by applying a frequency, or combination of frequencies and/or fields (i.e., creating an applied spectral energy pattern) which corresponds to at least one spectral environmental reaction condition, the spectral energy patterns (e.g., spectral patterns of, for example, reactant(s), intermediates, transients, catalysts, etc.) can be effectively modified which may result in broader spectral energy patterns (e.g., broader spectral patterns), in some cases, or narrower spectral energy patterns (e.g., spectral patterns) in other cases. Such broader or narrower spectral energy patterns (e.g., spectral patterns) may correspond to a broadening or narrowing of line widths in a spectral energy pattern (e.g., a spectral pattern). As stated throughout herein, when frequencies match, energy transfers. In this particular embodiment, frequencies can be caused to match by, for example, broadening the spectral pattern of one or more participants in a reaction system. For example, as discussed in much greater detail later herein, the application of temperature to a reaction system typically causes the broadening of one or more spectral patterns (e.g., line width broadening) of, for example, one or more reactants in the reaction system. It is this broadening of spectral patterns that can cause spectral patterns of one or more reactants to, for example, overlap. The overlapping of the spectral patterns can cause frequencies to match, and thus energy to transfer. When energy is transferred, reactions can occur. The scope of reactions which occur, include all of those reactions along any particular reaction pathway. Thus, the broadening of spectral pattern(s) can result in, for example, formation of reaction product, formation of and/or stimulation and/or stabilization of reaction intermediates and/or transients, catalyst frequencies, poisons, promoters, etc. All of the environmental reaction conditions that are discussed in detail in the section entitled "Detailed Description of the Preferred Embodiments" can be at least partially stimulated in a reaction system by the application of a spectral environmental reaction condition.

Similarly, spectral patterns can be caused to become non-overlapping by changing, for example, at least one spectral environmental reaction condition, and thus changing the applied spectral energy pattern. In this instance, energy will not transfer (or the rate at which energy transfers can be reduced) and reactions will not occur (or the rates of reactions can be slowed).

Spectral environmental reaction conditions can be utilized to start and/or stop reactions in a reaction pathway. Thus, certain reactions can be started, stopped, slowed and/or speeded up by, for example, applying different spectral environmental reaction conditions at different times during a reaction and/or at different intensities. Thus, spectral environmental reaction conditions are capable of influencing, positively or negatively, reaction pathways and/or reaction rates in a reaction system.

VI. Designing Physical and Spectral Catalysts

Moreover, by utilizing the above techniques to design (e.g., calculate or determine) a desirable spectral energy pattern, such as a desirable spectral pattern for a spectral energy catalyst (e.g., spectral catalyst) rather than applying the spectral energy catalyst (e.g., spectral catalyst) per se, for example, the designed spectral pattern can be used to design and/or determine an optimum physical and/or spectral catalyst that could be used in the reaction system. Further, the invention may be able to provide a recipe for a physical and/or spectral catalyst for a particular reaction system where no catalyst previously existed. For example in a reaction where:

where A=reactant, B=product and I=known intermediate, and there is no known catalyst, either a physical or spectral catalyst that could be designed which, for example, resonates with the intermediate "I", thereby catalyzing the reaction.

As a first step, the designed spectral pattern could be compared to known spectral patterns for existing materials to determine if similarities exist between the designed spectral pattern and spectral patterns of known, materials. If the designed spectral pattern at least partially matches against a spectral pattern of a known material, then it is possible to utilize the known material as a physical catalyst in a reaction system. In this regard, it may be desirable to utilize the known material alone or in combination with a spectral energy catalyst and/or a spectral catalyst. Still further, it may be possible to utilize environmental reaction conditions and/or spectral environmental reaction conditions to cause the known material to behave in a manner which is even closer to the designed energy pattern or spectral pattern. Further, the application of different spectral energy patterns may cause the designed catalyst to behave in different manners, such as, for example, encouraging a first reaction pathway with the application of a first spectral energy pattern and encouraging a second reaction pathway with the application of a second spectral energy pattern. Likewise, the changing of one or more environmental reaction conditions could have a similar effect.

Further, this designed catalyst has applications in all types of reactions including, but not limited to, chemical (organic and inorganic), biological, physical, energy, etc.

Still further, in certain cases, one or more physical species could be used or combined in a suitable manner, for example, physical mixing or by a chemical reaction, to obtain a physical catalyst material exhibiting the appropriate designed spectral energy pattern (e.g., spectral pattern) to achieve a desired reaction pathway. Accordingly, a combination of designed catalyst(s) (e.g., a physical catalyst which is known or manufactured expressly to function as a physical catalyst), spectral energy catalyst(s) and/or spectral catalyst(s) can result in a resultant energy pattern (e.g., which in this case can be a combination of physical catalyst(s) and/or spectral catalyst(s)) which is conducive to forming desired reaction product(s) and/or following a desired reaction pathway at a desired reaction rate. In this regard, various line width broadening and/or narrowing of spectral energy pattern(s) and/or spectral pattern(s) may occur when the designed catalyst is combined with various spectral energy patterns and/or spectral patterns.

It is important to consider the energy interactions between all components of the reaction system when calculating or determining an appropriate designed catalyst. There will be a particular combination of specific energy pattern(s) (e.g., electromagnetic energy) that will interact with the designed catalyst to form an applied spectral energy pattern. The particular frequencies, for example, of electromagnetic radiation that should be caused to be applied to a reaction system should be as many of those frequencies as possible, when interacting with the frequencies of the designed catalyst, that can result in desirable effects to one or more participants in the reaction system, while eliminating as many of those frequencies as possible which result in undesirable effects within the reaction system.

VII. Spectral Pharmaceuticals

Many pharmaceutical agents act as catalysts in biochemical reactions. While there are several types of exceptions, the effects of the preponderance of drugs result from their interaction with functional macromolecular components of the host organism. Such interaction alters the function of the pertinent cellular components and thereby initiates the series of biochemical and physiological changes that are characteristic of the response to the drug.

A drug is usually described by its prominent effect or by the action thought to be the basis of that effect. However, such descriptions should not obscure the fact that no drug produces only a single effect. Morphine is correctly described as an analgesic, but it also suppresses the cough reflex, causes sedation, respiratory depression, constipation, bronchiolar constriction, release of histamine, antidiuresis, and a variety of other side effects. A drug is adequately characterized only in terms of its full spectrum of effects and few drugs are sufficiently selective to be described as specific.

One of the objects of this invention is to provide a more targeted mode for achieving a desired response from a biological system by introducing a spectral energy catalyst (e.g., a spectral catalyst) in place of, or to augment, pharmaceutical agents which may mimic the effect or mechanism of action of a given enzyme, and thereby, limit the occurrence of unwanted side effects commonly associated with pharmaceutical agents. Moreover, certain reactions can be achieved with spectral catalysts that are not achievable with any specific physical catalyst pharmaceutical.

A first embodiment of this aspect of the invention involves DHEA and melatonin which are both pharmaceuticals thought to be involved in slowing and/or reversing the aging process. The electromagnetic spectral pattern for DHEA and melatonin could be emitted from light bulbs present in the home or the workplace. The resultant EM radiation can be absorbed directly into the central nervous system via the optic nerves and tracts, producing anti-aging effects at the site of the genesis of the aging phenomenon, namely, the central nervous system and the pineal-hypothalamus-pituitary system.

A second embodiment of this aspect of the invention involves a lowering of LDL cholesterol levels with pharmaceutical spectral patterns emitted by, for example, coils in the mattress of a bed or in a mattress pad that negatively catalyzes HMG CoA reductase. Thus, desirable effects can be achieved by targeting appropriate biologics with unique spectral patterns designed to produce a desired reaction product.

A third embodiment of this aspect of the invention involves the treatment of bacterial, fungal, parasitic, and viral illnesses using spectral pharmaceuticals. Specifically, by generating the catalytic spectral pattern of known drug catalysts, similar effects to physical drug catalysts can be achieved.

Another embodiment of this aspect of the invention provides a treatment for asthma which involves the autonomic nervous system playing a key role in the control of bronchometer tone both in normal airways and in those of individuals with bronchospastic disease. The effects of the autonomic nervous system are thought to be mediated through their action on the stores of cyclic adenosine monophosphate (AMP) and cyclic guanosine monophosphate (GMP) in bronchial smooth muscle cells. Further, acetycholine, or stimulation by the vagus nerve, is thought to provide an increase in the amounts of cyclic GMP relative to cyclic AMP, leading to smooth muscle contraction and asthma attacks. Conversely, an increase within bronchial smooth muscle cells in the levels of cyclic AMP relative to cyclic GMP leads to relaxation of the bronchial muscles and thus provides a treatment for asthma. The enzyme, adenylate cyclase, catalyses the formation of cyclic AMP. Accordingly, by applying (e.g. a pendant worn around the neck) the catalytic spectral pattern for adenylate cyclase, relief from asthma could be achieved.

Some of the most amazing physical catalysts are enzymes which catalyze the multitudinous reactions in living organisms. Of all the intricate processes that have evolved in living systems, none are more striking or more essential than enzyme catalysis. The amazing fact about enzymes is that not only can they increase the rate of biochemical reactions by factors ranging from $10^6$ to $10^{12}$, but they are also highly specific. An enzyme acts only on certain molecules while leaving the rest of the system unaffected. Some enzymes have been found to have a high degree of specificity while others can catalyze a number of reactions. If a biological reaction can be catalyzed by only one enzyme, then the loss of activity or reduced activity of that enzyme could greatly inhibit the specific reaction and could be detrimental to a living organism. If this situation occurs, a catalytic spectral energy pattern could be determined for the exact enzyme or mechanism, then genetic deficiencies could be augmented by providing the spectral energy catalyst to replace the enzyme.

VIII. Objects of the Invention

All of the above information disclosing the invention should provide a comprehensive understanding of the main aspects of the invention. However, in order to understand the invention further, the invention shall now be discussed in terms of some of the representative objects or goals to be achieved.

1. One object of this invention is to control or direct a reaction pathway in a reaction system by applying a spectral energy pattern in the form of a spectral catalyst having at least one electromagnetic energy frequency which may initiate, activate, and/or affect at least one of the participants involved in the reaction system.

2. Another object of the invention is to provide an efficient, selective and economical process for replacing a known physical catalyst in a reaction system comprising the steps of:
   duplicating at least a portion of a spectral pattern of a physical catalyst (e.g., at least one frequency of a spectral pattern of a physical catalyst) to form a catalytic spectral pattern; and
   applying to the reaction system at least a portion of the catalytic spectral pattern.

3. Another object of the invention is to provide a method to augment a physical catalyst in a reaction system with its own catalytic spectral pattern comprising the steps of:
   determining an electromagnetic spectral pattern of the physical catalyst; and
   duplicating at least one frequency of the spectral pattern of the physical catalyst with at least one electromagnetic energy emitter source to form a catalytic spectral pattern; and
   applying to the reaction system at least one frequency of the catalytic spectral pattern at a sufficient intensity and for a sufficient duration to catalyze the formation of reaction product(s) in the reaction system.

4. Another object of the invention is to provide an efficient, selective and economical process for replacing a known physical catalyst in a reaction system comprising the steps of:
   duplicating at least a portion of a spectral pattern of a physical catalyst (e.g., at least one frequency of a spectral pattern of a physical catalyst) to form a catalytic spectral pattern; and
   applying to the reaction system at least a portion of the catalytic spectral pattern; and,
   applying at least one additional spectral energy pattern which forms an applied spectral energy pattern when combined with said catalytic spectral pattern.

5. Another object of the invention is to provide a method to replace a physical catalyst in a reaction system comprising the steps of:
   determining an electromagnetic spectral pattern of the physical catalyst;
   duplicating at least one frequency of the electromagnetic spectral pattern of the physical catalyst with at least one electromagnetic energy emitter source to form a catalytic spectral pattern;
   applying to the reaction system at least one frequency of the catalytic spectral pattern; and
   applying at least one additional spectral energy pattern to form an applied spectral energy pattern, said applied spectral energy pattern being applied at a sufficient intensity and for a sufficient duration to catalyze the formation of at least one reaction product in the reaction system.

6. Another object of this invention is to provide a method to affect and/or direct a reaction system with a spectral catalyst by augmenting a physical catalyst comprising the steps of:
   duplicating at least a portion of a spectral pattern of a physical catalyst (e.g., at least one frequency of a spectral pattern of the physical catalyst) with at least one electromagnetic energy emitter source to form a catalytic spectral pattern;
   applying to the reaction system, (e.g., irradiating) at least a portion of the catalytic spectral pattern (e.g., an electromagnetic spectral pattern having a frequency range of from about radio frequency to about ultraviolet frequency) at a sufficient intensity and for a sufficient duration to catalyze the reaction system; and
   introducing the physical catalyst into the reaction system.

The above method may be practiced by introducing the physical catalyst into the reaction system before, and/or during, and/or after applying said catalytic spectral pattern to the reaction system.

7. Another object of this invention is to provide a method to affect and/or direct a reaction system with a spectral energy catalyst by augmenting a physical catalyst comprising the steps of:
   applying at least one spectral energy catalyst at a sufficient intensity and for a sufficient duration to catalyze the reaction system;
   introducing the physical catalyst into the reaction system.

The above method may be practiced by introducing the physical catalyst into the reaction system before, and/or during, and/or after applying the spectral energy catalyst to the reaction system.

8. Another object of this invention is to provide a method to affect and/or direct a reaction system with a spectral catalyst and a spectral energy catalyst by augmenting a physical catalyst comprising the steps of:
   applying at least one spectral catalyst at a sufficient intensity and for a sufficient duration to at least partially catalyze the reaction system;
   applying at least one spectral energy catalyst at a sufficient intensity and for a sufficient duration to at least partially catalyze the reaction system; and
   introducing the physical catalyst into the reaction system.

The above method may be practiced by introducing the physical catalyst into the reaction system before, and/or during, and/or after applying the spectral catalyst and/or the spectral energy catalyst to the reaction system. Moreover, the spectral catalyst and spectral energy catalyst may be applied simultaneously to form an applied spectral energy pattern or they may be applied sequentially either at the same time or at different times from when the physical catalyst is introduced into the reaction system.

9. Another object of this invention is to provide a method to affect and/or direct a reaction system with a spectral catalyst and a spectral energy catalyst and a spectral environmental reaction condition, with or without a physical catalyst, comprising the steps of:
   applying at least one spectral catalyst at a sufficient intensity and for a sufficient duration to catalyze a reaction pathway;
   applying at least one spectral energy catalyst at a sufficient intensity and for a sufficient duration to catalyze a reaction pathway;
   applying at last one spectral environmental reaction condition at a sufficient intensity and for a sufficient duration to catalyze a reaction pathway, whereby when any of said at least one spectral catalyst, said at least one spectral energy catalyst and/or at least one spectral environmental reaction condition are applied at the same time, they form an applied spectral energy pattern; and introducing the physical catalyst into the reaction system.

The above method may be practiced by introducing the physical catalyst into the reaction system before, and/or during, and/or after applying any one of, or any combination of, the spectral catalyst and/or the spectral energy catalyst and/or the spectral environmental reaction condition to the reaction system. Likewise, the spectral catalyst and/or the spectral energy catalyst and/or the spectral environmental reaction condition can be provided sequentially or continuously.

10. Another object of this invention is to provide a method to affect and direct a reaction system with an applied spectral energy pattern and a spectral energy catalyst comprising the steps of:

applying at least one applied spectral energy pattern at a sufficient intensity and for a sufficient duration to catalyze the reaction system, whereby said at least one applied spectral energy pattern comprises at least two members selected from the group consisting of catalytic spectral energy pattern, catalytic spectral pattern, spectral catalyst, spectral energy catalyst, spectral energy pattern, spectral environmental reaction condition and spectral pattern; and applying at least one spectral energy catalyst to the reaction system.

The above method may be practiced by introducing the applied spectral energy pattern into the reaction system before, and/or during, and/or after applying the spectral energy catalyst to the reaction system. Moreover, the spectral energy catalyst and the applied spectral energy pattern can be provided sequentially or continuously. If applied continuously, a new applied spectral energy pattern is formed.

11. Another object of this invention is to provide a method to affect and direct a reaction system with a spectral energy catalyst comprising the steps of:

determining at least a portion of a spectral energy pattern for starting reactant(s) in said reaction system;

determining at least a portion of a spectral energy pattern for reaction product(s) in said reaction system;

calculating an additive spectral energy pattern (e.g., at least one electromagnetic frequency) from said reactant(s) and reaction product(s) spectral energy patterns to determine a required spectral energy catalyst (e.g., a spectral catalyst);

generating at least a portion of the required spectral energy catalyst (e.g., at least one electromagnetic frequency of the required spectral catalyst); and applying to the reaction system (e.g., irradiating with electromagnetic energy) said at least a portion of the required spectral energy catalyst (e.g., spectral catalyst) to form desired reaction product(s).

12. Another object of the invention is to provide a method to affect and direct a reaction system with a spectral energy catalyst comprising the steps of:

targeting at least one participant in said reaction system with at least one spectral energy catalyst to cause the formation and/or stimulation and/or stabilization of at least one transient and/or at least one intermediate to result in desired reaction product(s).

13. Another object of the invention is to provide a method for catalyzing a reaction system with a spectral energy pattern to result in at least one reaction product comprising:

applying at least one spectral energy pattern for a sufficient time and at a sufficient intensity to cause the formation and/or stimulation and/or stabilization of at least one transient and/or at least one intermediate to result in desired reaction product(s) at a desired reaction rate.

14. Another object of the invention is to provide a method to affect and direct a reaction system with a spectral energy catalyst and at least one of the spectral environmental reaction condition comprising the steps of:

applying at least one applied spectral energy catalyst to at least one participant in said reaction system; and applying at least one spectral environmental reaction condition to said reaction system to cause the formation and/or stimulation and/or stabilization of at least one transient and/or at least one intermediate to permit desired reaction product(s) to form.

15. Another object of the invention is to provide a method for catalyzing a reaction system with a spectral energy catalyst to result in at least one reaction product comprising:

applying at least one frequency (e.g., electromagnetic) which heterodynes with at least one reactant frequency to cause the formation of and/or stimulation and/or stabilization of at least one transient and/or at least one intermediate to result in desired reaction product(s).

16. Another object of the invention is to provide a method for catalyzing a reaction system with at least one spectral energy pattern resulting in at least one reaction product comprising:

applying a sufficient number of frequencies (e.g., electromagnetic) and/or fields (e.g., electric and/or magnetic) to result in an applied spectral energy pattern which stimulates all transients and/or intermediates required in a reaction pathway to result in desired reaction product(s).

17. Another object of the invention is to provide a method for catalyzing a reaction system with a spectral energy catalyst resulting in at least one reaction product comprising:

targeting at least one participant in said reaction system with at least one frequency and/or field to form, indirectly, at least one transient and/or at least one intermediate, whereby formation of said at least one transient and/or at least one intermediate results in the formation of an additional at least one transient and/or at least one additional intermediate.

18. It is another object of the invention to provide a method for catalyzing a reaction system with a spectral energy catalyst resulting in at least one reaction product comprising:

targeting at least one spectral energy catalyst to at least one participant in said reaction system to form indirectly at least one transient and/or at least one intermediate, whereby formation of said at least one transient and/or at least one intermediate results in the formation of an additional at least one transient and/or at least one additional intermediate.

19. It is a further object of the invention to provide a method for directing a reaction system along a desired reaction pathway comprising:

applying at least one targeting approach selected from the group of approaches consisting of direct resonance targeting, harmonic targeting and non-harmonic heterodyne targeting.

In this regard, these targeting approaches can cause the formation and/or stimulation and/or stabilization of at least one transient and/or at least one intermediate to result in desired reaction product(s).

20. It is another object of the invention to provide a method for catalyzing a reaction system comprising:

applying at least one frequency to at least one participant and/or at least one component in said reaction system to cause the formation and/or stimulation and/or stabilization of at least one transient and/or at least one intermediate to result in desired reaction product(s), whereby said at least one frequency comprises at least one frequency selected from the group consisting of direct resonance frequencies, harmonic resonance frequencies, non-harmonic heterodyne resonance frequencies, electronic frequencies, vibrational frequencies, rotational frequencies, rotational-vibrational frequencies, fine splitting frequencies, hyperfine splitting frequencies, electric field splitting frequencies, magnetic field splitting frequencies, cyclotron resonance frequencies, orbital frequencies and nuclear frequencies.

In this regard, the applied frequencies can include any desirable frequency or combination of frequencies which resonates directly, harmonically or by a non-harmonic heterodyne technique, with at least one participant and/or at least one component in said reaction system.

21. It is another object of the invention to provide a method for directing a reaction system along with a desired reaction pathway with a spectral energy pattern comprising:

applying at least one frequency and/or field to cause the spectral energy pattern (e.g., spectral pattern) of at least one participant and/or at least one component in said reaction system to at least partially overlap with the spectral energy pattern (e.g., spectral pattern) of at least one other participant and/or at least one other component in said reaction system to permit the transfer of energy between said at least two participants and/or components.

22. It is another object of the invention to provide a method for catalyzing a reaction system with a spectral energy pattern resulting in at least one reaction product comprising:

applying at least one spectral energy pattern to cause the spectral energy pattern of at least one participant and/or component in said reaction system to at least partially overlap with a spectral energy pattern of at least one other participant and/or component in said reaction system to permit the transfer of energy between the at least two participants and/or components, thereby causing the formation of said at least one reaction product.

23. It is a further object of the invention to provide a method for catalyzing a reaction system with a spectral energy catalyst resulting in at least one reaction product comprising:

applying at least one frequency and/or field to cause spectral energy pattern (e.g., spectral pattern) broadening of at least one participant (e.g., at least one reactant) and/or component in said reaction system to cause a transfer of energy to occur resulting in transformation (e.g., chemically, physically, phase or otherwise) of at least one participant and/or at least one component in said reaction system.

In this regard, the transformation may result in a reaction product which is of a different chemical composition and/or different physical or crystalline composition and/or phases than any of the chemical and/or physical or crystalline compositions and/or phases of any starting reactant. Thus, only transients may be involved in the conversion of a reactant into a reaction product.

24. It is a further object of the invention to provide a method for catalyzing a reaction system with a spectral energy catalyst resulting in at least one reaction product comprising:

applying an applied spectral energy pattern to cause spectral energy pattern (e.g., spectral pattern) broadening of at least one participant (e.g., at least one reactant) and/or component in said reaction system to cause a transfer of energy to occur resulting in transformation (e.g., chemically, physically, phase or otherwise) of at least one participant and/or at least one component in said reaction system.

In this regard, the transformation may result in a reaction product which is of a different chemical composition and/or different physical or crystalline composition and/or phase than any of the chemical and/or physical or crystalline compositions and/or phases of any starting reactant. Thus, only transients may be involved in the conversion of a reactant into a reaction product.

25. Another object of the invention is to provide a method for controlling a reaction and/or directing a reaction pathway by utilizing at least one spectral environmental reaction condition, comprising:

forming a reaction system; and applying at least one spectral environmental reaction condition to direct said reaction system along a desired reaction pathway.

In this regard, the applied spectral environmental reaction condition can be used alone or in combination with other environmental reaction conditions to achieve desired results. Further, additional spectral energy patterns may also be applied, simultaneously and/or continuously with said spectral environmental reaction condition.

26. Another object of the invention is to provide a method for designing a catalyst where no catalyst previously existed (e.g., a physical catalyst and/or spectral energy catalyst), to be used in a reaction system, comprising:

determining a required spectral pattern to obtain a desired reaction and/or desired reaction pathway and/or desired reaction rate; and designing a catalyst (e.g., material, or combination of materials, and/or spectral energy catalysts) that exhibit (s) a spectral pattern that approximates the required spectral pattern.

In this regard, the designed catalyst material may comprise be a physical admixing of one or more materials and/or more materials that have been combined by an appropriate reaction, such as a chemical reaction. The designed material may be enhanced in function by one or more spectral energy patterns that may also be applied to the reaction system. Moreover, the application of different spectral energy patterns may cause the designed material to behave in different manners, such as, for example, encouraging a first reaction pathway with the application of a first spectral energy pattern and encouraging a second reaction pathway with the application of a second spectral energy pattern. Likewise, the changing of one or more environmental reaction conditions could have a similar effect.

Further, this designed material has applications in all types of reactions including, but not limited to, chemical (organic and inorganic), biological, physical, etc.

While not wishing to be bound by any particular theory or explanation of operation, it is believed that when frequencies match, energy transfers. The transfer of energy can be a sharing of energy between two entities and/or, for example, a transfer of energy from one entity into another entity. The entities may both be, for example, matter, or one entity may be matter and the other energy (e.g. energy may be a spectral energy pattern such as electromagnetic frequencies, and/or an electric field and/or a magnetic field).

BRIEF DESCRIPTION OF THE FIGURES

FIG. 2a shows a low amplitude wave and FIG. 2b shows a high amplitude wave.

FIG. 3a shows a time vs. amplitude plot and FIG. 3b shows a frequency vs. amplitude plot.

FIG. 6 shows fractal diagrams.

FIGS. 7a and 7b show hydrogen energy level diagrams.

FIG. 13a shows a narrow resonance curve with a high Q and FIG. 13b shows a broad resonance curve with a low Q.

FIG. 15a is at a low temperature, FIG. 15b is at a moderate temperature and FIG. 15c is at a high temperature.

FIG. 17a shows distinct spectral curves at low temperature; and FIG. 17b shows overlapping of spectral curves at a higher temperature.

FIG. 21a corresponds to a spectral pattern representing the absorption of water vapor in air and FIG. 21b is a spectral pattern which corresponds to the absorption of $NH_3$ at one atmosphere pressure.

FIG. 23a is a standard spectral curve not showing any self-absorption; FIG. 23b shows the shifting of resonant frequency due to self absorption; FIG. 23c shows a self-reversal spectral pattern due to self-absorption; and FIG. 23d shows an attenuation example of a self-reversal spectral pattern.

FIG. 39b shows the same spectrum of FIG. 39a at a lower resolution (i.e., not showing any fine frequencies).

FIG. 43a shows rotational and vibrational frequencies (MHz) for LiF. FIG. 43b shows differences between rotational and vibrational frequencies for LiF.

FIG. 46 shows a fine structure spectrum for $SF_6$ from zero to 300 being magnified.

FIGS. 47a and 47b show the magnification of two curves from fine structure of $SF_6$ showing hyperfine structure frequencies. Note the regular spacing of the hyperfine structure curves. FIG. 47a shows magnification of the curve marked with a single asterisk (*) in FIG. 46 and FIG. 47b shows the magnification of the curved marked with a double asterisk (**) in FIG. 46.

FIG. 48 shows an energy level diagram corresponding to the hyperfine splitting for the hyperfine structure in the n=2 to n=3 transition for hydrogen.

FIG. 49 shows the hyperfine structure in the J=1→2 rotational transition of $CH_3I$.

FIG. 50 shows the hyperfine structure of the J=1→2 transition for ClCN in the ground vibrational state.

FIG. 59a shows the J=4→5 transitions; and FIG. 59b shows the J=4→4 transitions. The electric field is large enough for complete spectral resolution.

FIG. 60 shows the Stark effect for the OCS molecule on the J=1→2 transition with applied electric fields at various frequencies. The "a", curve represents the Stark effect with a static DC electric field; the "b" curve represents broadening and blurring of the Stark frequencies with a 1 KHz electric field; and the "c" curve represents normal Stark type effect with electric field of 1,200 KHz.

FIG. 61a shows a construction of a Stark waveguide and FIG. 61b shows a distribution of fields in the Starck waveguide.

FIG. 65a is a pictorial which shows a normal Zeeman effect and FIG. 65b is a pictorial which shows an anomolous Zeeman effect.

FIG. 66 shows anomalous Zeeman effect for zinc $^3P \rightarrow ^3S$.

FIG. 67a shows a graphic representation of four Zeeman splitting frequencies and FIG. 67b shows a graphic representation of four new heterodyned differences.

FIGS. 68a and 68b show graphs of typical Zeeman splitting patterns for two different transitions in a paramagnetic molecule.

FIG. 69 shows the frequencies of hydrogen listed horizontally across the Table; and the frequencies of platinum listed vertically on the Table.

DESCRIPTION OF THE PREFERRED EMBODIMENTS

In general, thermal energy is used to drive chemical reactions by applying heat and increasing the temperature. The addition of heat increases the kinetic (motion) energy of the chemical reactants. A reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (EM) energy consists of waves of electric and magnetic fields. EM energy may also increase the kinetic energy and heat in reaction systems. It may energize electronic orbitals or vibrational motion in some reactions.

Figure 1A:
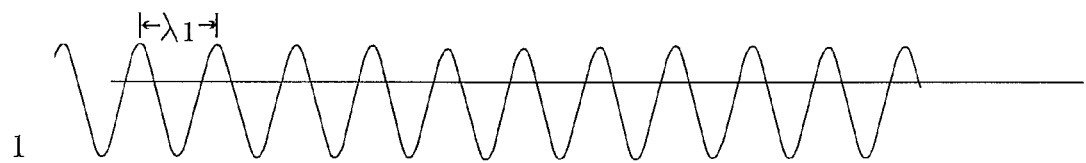
FIGS. 1a and 1b show a graphic representation of an acoustic or electromagnetic wave.
Figure 1B:
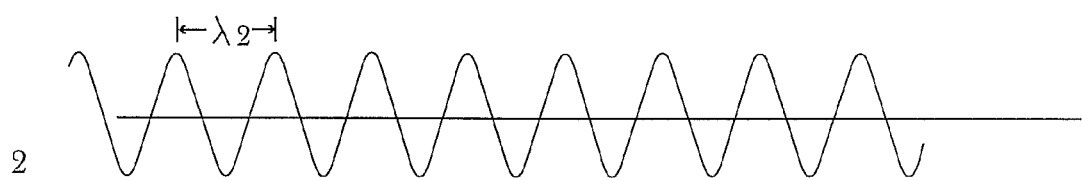
Figure 1C:
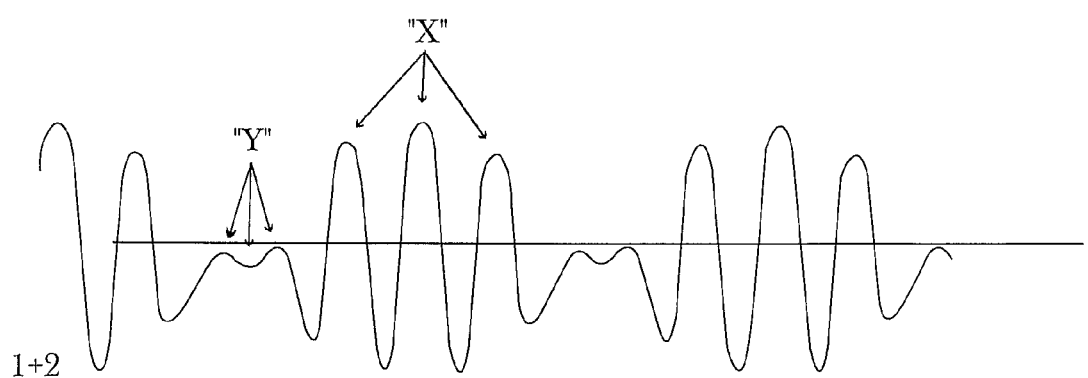
FIG. 1c shows the combination wave which results from the combining of the waves in FIG. 1a and FIG. 1b.
Figure 2A:
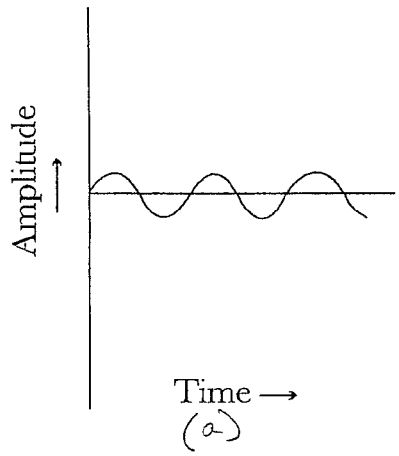
FIGS. 2a and 2b show waves of different amplitudes but the same frequency.
Figure 2B:
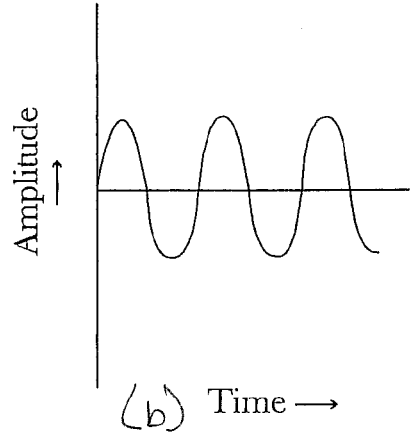

Both acoustic and electromagnetic energy may consist of waves. The number of waves in a period of time can be counted. Waves are often drawn, as in FIG. 1a. Usually, time is placed on the horizontal X-axis. The vertical Y-axis shows the strength or intensity of the wave. This is also called the amplitude. A weak wave will be of weak intensity and will have low amplitude (see FIG. 2a). A strong wave will have high amplitude (see FIG. 2b). Traditionally, the number of waves per second is counted, to obtain the frequency.

Frequency=Number of waves/time=Waves/second=Hz.

Another name for "waves per second", is "hertz" (abbreviated "Hz"). Frequency is drawn on wave diagrams by showing a different number of waves in a period of time (see FIG.

Figure 3A:
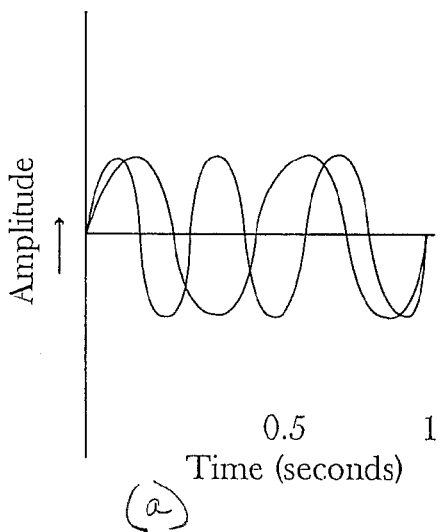
FIGS. 3a and 3b show frequency diagrams.
Figure 3B:
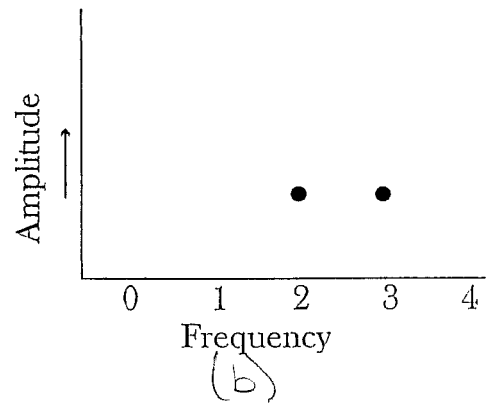

3a which shows waves having a frequency of 2 Hz and 3 Hz). It is also drawn by placing frequency itself, rather than time, on the X-axis (see FIG. 3b which shows the same 2 Hz and 3 Hz waves plotted differently).

Energy waves and frequency have some interesting properties, and may interact in some interesting ways. The manner in which wave energies interact, depends largely on the frequency. For example, when two waves of energy interact, each having the same amplitude, but one at a frequency of 400 Hz and the other at 100 Hz, the waves will add their frequencies, to produce a new frequency of 500 Hz (i.e., the "sum" frequency). The frequency of the waves will also subtract to produce a frequency of 300 HZ (i.e., the "difference" frequency). All wave energies typically add and subtract in this manner, and such adding and subtracting is referred to as heterodyning. Common results of heterodyning are familiar to most as harmonics in music.

Figures 4, 5:
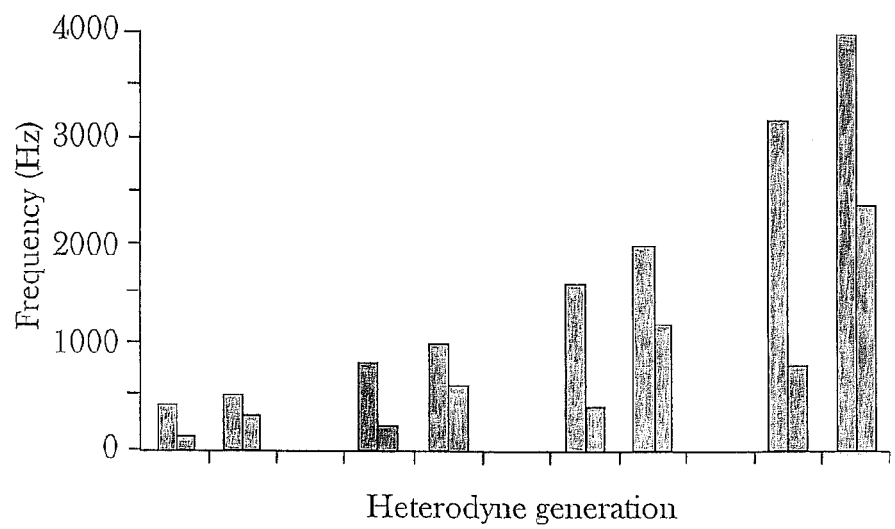
FIG. 4 shows a specific example of a heterodyne progression.
FIG. 5 shows a graphical example of the heterodyned series from FIG. 4.

There is a mathematical, as well as musical basis, to the harmonics produced by heterodyning. Consider, for example, a continuous progression of heterodyned frequencies. As discussed above, beginning with 400 Hz and 100 Hz, the sum frequency is 500 Hz and the difference frequency is 300 Hz. If these frequencies are further heterodyned (added and subtracted) then new frequencies of 800 (i.e., 500+300) and 200 (i.e., 500−300) are obtained. The further heterodyning of 800 and 200 results in 1,000 and 600 Hz as shown in FIG. 4.

A mathematical pattern begins to emerge. Both the sum and the difference columns contain alternating series of numbers that double with each set of heterodynes. In the sum column, 400 Hz, 800 Hz, and 1,600 Hz, alternates with 500 Hz, 1000 Hz, and 2000 Hz. The same sort of doubling phenomenon occurs in the difference column.

Heterodyning of frequencies is the natural process that occurs whenever waveform energies interact. Heterodyning results in patterns of increasing numbers that are mathematically derived. The number patterns are integer multiples of the original frequencies. These multiples are called harmonics. For example, 800 Hz and 1600 Hz are harmonics of 400 Hz. In musical terms, 800 Hz is one octave above 400 Hz, and 1600 Hz is two octaves higher. It is important to understand the mathematical heterodyne basis for harmonics, which occurs in all waveform energies, and thus in all of nature.

The mathematics of frequencies is very important. Frequency heterodynes increase mathematically in visual patterns (see FIG. 5). Mathematics has a name for these visual patterns of FIG. 5. These patterns are called fractals. A fractal is defined as a mathematical function which produces a series of self-similar patterns or numbers. Fractal patterns have spurred a great deal of interest historically because fractal patterns are found everywhere in nature. Fractals can be found in the patterning of large expanses of coastline, all the way down to microorganisms. Fractals are found in the behavior of organized insects and in the behavior of fluids. The visual patterns produced by fractals are very distinct and recognizable. A typical fractal pattern is shown in FIG. 6.

A heterodyne is a mathematical function, governed by mathematical equations, just like a fractal. A heterodyne also produces self-similar patterns of numbers, like a fractal. If graphed, a heterodyne series produces the same familiar visual shape and form which is so characteristic of fractals. It is interesting to compare the heterodyne series in FIG. 5, with the fractal series in FIG. 6.

Heterodynes are fractals; the conclusion is inescapable. Heterodynes and fractals are both mathematical functions which produce a series of self-similar patterns or numbers. Wave energies interact in heterodyne patterns. Thus, all wave energies interact as fractal patterns. Once it is understood that the fundamental process of interacting energies is itself a fractal process, it becomes easier to understand why so many creatures and systems in nature also exhibit fractal patterns. The fractal processes and patterns of nature are established at a fundamental or basic level.

Accordingly, since energy interacts by heterodyning, matter should also be capable of interacting by a heterodyning process. All matter whether in large or small forms, has what is called a natural oscillatory frequency. The natural oscillatory frequency ("NOF") of an object, is the frequency at which the object prefers to vibrate, once set in motion. The NOF of an object is related to many factors including size, shape, dimension, and composition. The smaller an object is, the smaller the distance it has to cover when it oscillates back and forth. The smaller the distance, the faster it can oscillate, and the higher its NOF.

For example, consider a wire composed of metal atoms. The wire has a natural oscillatory frequency. The individual metal atoms also have unique natural oscillatory frequencies. The NOF of the atoms and the NOF of the wire heterodyne by adding and subtracting, just the way energy heterodynes.

$$NOF_{atom} + NOF_{wire} = \text{Sum Frequency}_{atom+wire}$$

and $$NOF_{atom} - NOF_{wire} = \text{Difference Frequency}_{atom-wire}$$

If the wire is stimulated with the Difference Frequency$_{atom-wire}$, the difference frequency will heterodyne (add) with the NOF$_{wire}$ to produce NOF$_{atom}$, (natural oscillatory frequency of the atom) and the atom will absorb with the energy, thereby becoming stimulated to a higher energy level. Cirac and Zoeller reported this phenomenon in 1995, and they used a laser to generate the Difference Frequency.

$$\text{Difference Frequency}_{atom-wire} + NOF_{wire} = NOF_{atom}$$

Matter heterodynes with matter in a manner similar to the way in which wave energies heterodyne with other wave energies. This means that matter in its various states may also interact in fractal processes. This interaction of matter by fractal processes assists in explaining why so many creatures and systems in nature exhibit fractal processes and patterns. Matter, as well as energy, interacts by the mathematical equations of heterodynes, to produce harmonics and fractal patterns. That is why there are fractals everywhere around us.

Thus, energy heterodynes with energy, and matter heterodynes with matter. However, perhaps even more important is that matter can heterodyne with energy (and visa versa). In the metal wire discussion above, the Difference Frequency$_{atom-wire}$ in the experiment by Cirac and Zoeller was provided by a laser which used electromagnetic wave energy at a frequency equal to the Difference Frequency$_{atom-wire}$. The matter in the wire, via its natural oscillatory frequency, heterodyned with the electromagnetic wave energy frequency of the laser to produce the frequency of an individual atom of matter. This shows that energy and matter do heterodyne with each other.

In general, when energy encounters matter, one of three possibilities occur. The energy either bounces off the matter (i.e., is reflected energy), passes through the matter (i.e., is transmitted energy), or interacts and/or combines with the matter (e.g., is absorbed or heterodynes with the matter). If the energy heterodynes with the matter, new frequencies of energy and/or matter will be produced by mathematical processes of sums and differences. If the frequency thus produced matches an NOF of the matter, the energy will be, at least partially, absorbed, and the matter will be stimulated to, for example, a higher energy level, (i.e., it possesses more energy). A crucial factor which determines which of these three possibilities will happen is the frequency of the energy compared to the frequency of the matter. If the frequencies do not match, the energy will either be reflected, or will pass on through as transmitted energy. If the frequencies of the energy and the matter match either directly (e.g., are close to each other, as discussed in greater detail later herein), or match indirectly (e.g., heterodynes), then the energy is capable of interacting and/or combining with the matter.

Another term often used for describing the matching of frequencies is resonance. In this invention, use of the term resonance will typically mean that frequencies of matter and/or energy match. For example, if the frequency of energy and the frequency of matter match, the energy and matter are in resonance and the energy is capable of combining with the matter. Resonance, or frequency matching, is merely an aspect of heterodyning that permits the coherent transfer and combination of energy with matter.

In the example above with the wire and atoms, resonance could have been created with the atom, by stimulating the atom with a laser frequency exactly matching the NOF of the atom. In this case, the atom would be energized with its own resonant frequency and the energy would be transferred to the atom directly. Alternatively, as was performed in the actual wire/laser experiment, resonance could also have been created with the atom by using the heterodyning that naturally occurs between differing frequencies. Thus, the resonant frequency of the atom ($NOF_{atom}$) can be produced indirectly, as an additive (or subtractive) heterodyned frequency, between the resonant frequency of the wire ($NOF_{wire}$) and the applied frequency of the laser. Either direct resonance, or indirect resonance through heterodyned frequency matching, produces resonance and thus permits the combining of matter and energy. When frequencies match, energy transfers.

Heterodyning produces indirect resonance. Heterodyning also produces harmonics, (i.e., frequencies that are integer multiples of the resonant (NOF) frequency. For example, the music note "A" is approximately 440 Hz. If that frequency is doubled to about 880 Hz, the note "A" is heard an octave higher. This first octave is called the first harmonic. Doubling the note or frequency again, from 880 Hz to 1,760 Hz (i.e., four times the frequency of the original note) results in another "A", two octaves above the original note. This is called the third harmonic. Every time the frequency is doubled another octave is achieved, so these are the even integer multiples of the resonant frequency.

In between the first and third harmonic is the second harmonic, which is three times the original note. Musically, this is not an octave like the first and third harmonics. It is an octave and a fifth, equal to the second "E" above the original "A". All of the odd integer multiples are fifths, rather than octaves. Because harmonics are simply multiples of the fundamental natural oscillatory frequency, harmonics stimulate the NOF or resonant frequency indirectly. Thus by playing the high "A" at 880 Hz on a piano, the string for middle "A" at 440 Hz should also begin to vibrate due to the phenomenon of harmonics.

Matter and energy in chemical reactions respond to harmonics of resonant frequencies much the way musical instruments do. Thus, the resonant frequency of the atom ($NOF_{atom}$) can be stimulated indirectly, using one or more of its' harmonic frequencies. This is because the harmonic frequency heterodynes with the resonant frequency of the atom itself ($NOF_{atom}$). For example, in the wire/atom example above, if the laser is tuned to 800 THz and the atom resonates at 400 THz, heterodyning the two frequencies results in:

800 THz−400 THz=400 THz

The 800 THz (the atom's first harmonic), heterodynes with the resonant frequency of the atom, to produce the atom's own resonant frequency. Thus the first harmonic indirectly resonates with the atom's NOF, and stimulates the atom's resonant frequency as a first generation heterodyne.

Of course, the two frequencies will also heterodyne in the other direction, producing:

800 THz+400 THz=1,200 THz

The 1,200 THz frequency is not the resonant frequency of the atom. Thus, part of the energy of the laser will heterodyne to produce the resonant frequency of the atom. The other part of the energy of the laser heterodynes to a different frequency, that does not itself stimulate the resonant frequency of the atom. That is why the stimulation of an object by a harmonic frequency of particular strength of amplitude, is typically less than the stimulation by its' own resonant (NOF) frequency at the same particular strength.

Although it appears that half the energy of a harmonic is wasted, that is not necessarily the case. Referring again to the exemplary atom vibrating at 400 THz, exposing the atom to electromagnetic energy vibrating at 800 THz will result in frequencies subtracting and adding as follows:

800 THz−400 THz=400 THz and

800 THz+400 THz=1,200 THz

Figure 14:
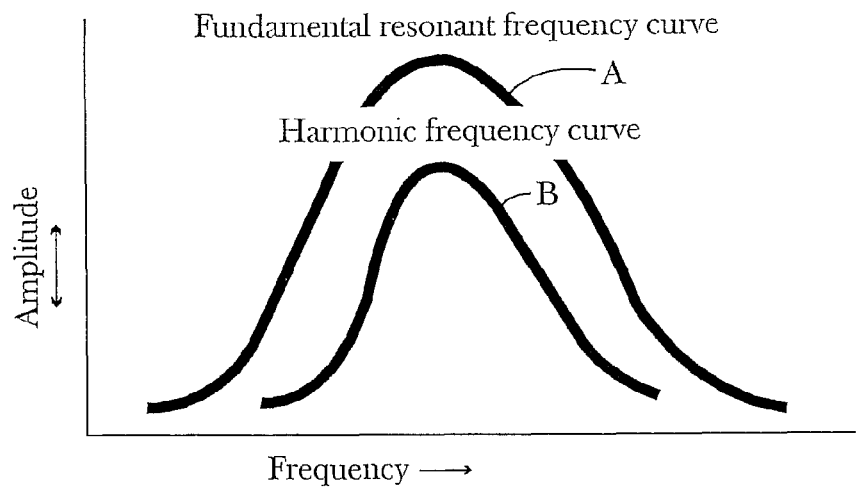
FIG. 14 shows two different energy transfer curves at fundamental resonance frequencies (curve A) and a harmonic frequency (curve B).

The 1,200 THz heterodyne, for which about 50% of the energy appears to be wasted, will heterodyne with other frequencies also, such as 800 THz. Thus, 1,200 THz−800 THz=400 THz Also, the 1,200 THz will heterodyne with 400 THz:

1,200 THz−400 THz=800 THz, thus producing 800 THz, and the 800 THz will heterodyne with 400 THz:

800 THz−400 THz=400 THz, thus producing 400 THz frequency again. When other generations of heterodynes of the seemingly wasted energy are taken into consideration, the amount of energy transferred by a first harmonic frequency is much greater than the previously suggested 50% transfer of energy. There is not as much energy transferred by this approach when compared to direct resonance, but this energy transfer is sufficient to produce a desired effect (see FIG. 14).

As stated previously, Ostwald's theories on catalysts and bond formation were based on the kinetic theories of chemistry from the turn of the century. However, it should now be understood that chemical reactions are interactions of matter, and that matter interacts with other matter through resonance and heterodyning of frequencies; and energy can just as easily interact with matter through a similar processes of resonance and heterodyning. With the advent of spectroscopy (discussed in more detail elsewhere herein), it is evident that matter produces, for example, electromagnetic energy at the same or substantially the same frequencies at which it vibrates. Energy and matter can move about and recombine with other energy or matter, as long as their frequencies match, because when frequencies match, energy transfers. In many respects, both philosophically and mathematically, both matter and energy can be fundamentally construed as corresponding to frequency. Accordingly, since chemical reactions are recombinations of matter driven by energy, chemical reactions are in effect, driven just as much by frequency.

Analysis of a typical chemical reaction should be helpful in understanding the normal processes disclosed herein. A representative reaction to examine is the formation of water from hydrogen and oxygen gases, catalyzed by platinum. Platinum has been known for some time to be a good hydrogen catalyst, although the reason for this has not been well understood.

This reaction is proposed to be a chain reaction, depending on the generation and stabilization of the hydrogen and hydroxy intermediates. The proposed reaction chain is:

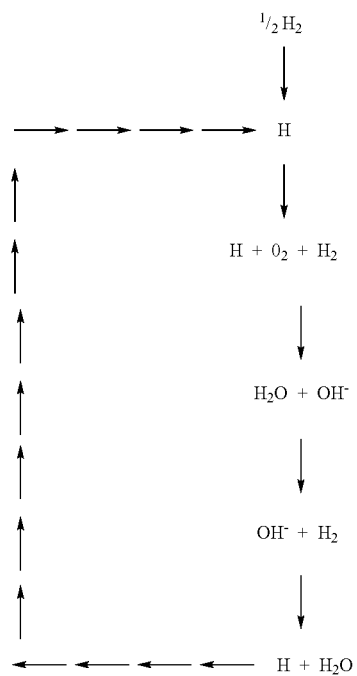

Generation of the hydrogen and hydroxy intermediates are thought to be crucial to this reaction chain. Under normal circumstances, hydrogen and oxygen gas can be mixed together for an indefinite amount of time, and they will not form water. Whenever the occasional hydrogen molecule splits apart, the hydrogen atoms do not have adequate energy to bond with an oxygen molecule to form water. The hydrogen atoms are very short-lived as they simply re-bond again to form a hydrogen molecule. Exactly how platinum catalyzes this reaction chain is a mystery to the prior art.

The present invention teaches that an important step to catalyzing this reaction is the understanding now provided that it is crucial not only to generate the intermediates, but also to energize and/or stabilize (i.e., maintain the intermediates for a longer time), so that the intermediates have sufficient energy to, for example, react with other components in the reaction system. In the case of platinum, the intermediates react with the reactants to form product and more intermediates (i.e., by generating, energizing and stabilizing the hydrogen intermediate, it has sufficient energy to react with the molecular oxygen reactant, forming water and the hydroxy intermediate, instead of falling back into a hydrogen molecule). Moreover, by energizing and stabilizing the hydroxy intermediates, the hydroxy intermediates can react with more reactant hydrogen molecules, and again water and more intermediates result from this chain reaction. Thus, generating energizing and/or stabilizing the intermediates, influences this reaction pathway. Paralleling nature in this regard would be desirable (e.g., nature can be paralleled by increasing the energy levels of the intermediates). Specifically, desirable, intermediates can be energized and/or stabilized by applying at least one appropriate electromagnetic frequency resonant with the intermediate, thereby stimulating the intermediate to a higher energy level. Interestingly, that is what platinum does (e.g., various platinum frequencies resonate with the intermediates on the reaction pathway for water formation). Moreover, in the process of energizing and stabilizing the reaction intermediates, platinum fosters the generation of more intermediates, which allows the reaction chain to continue, and thus catalyzes the reaction.

As a catalyst, platinum takes advantage of many of the ways that frequencies interact with each other. Specifically, frequencies interact and resonate with each other: 1) directly, by matching a frequency; or 2) indirectly, by matching a frequency through harmonics or heterodynes. In other words, platinum vibrates at frequencies which both directly match the natural oscillatory frequencies of the intermediates, and which indirectly match their frequencies, for example, by heterodyning harmonics with the intermediates.

Further, in addition to the specific intermediates of the reaction discussed above herein, it should be understood that in this reaction, like in all reactions, various transients or transient states also exist. In some cases, transients or transient states may only involve different bond angles between similar chemical species or in other cases transients may involve completely different chemistries altogether. In any event, it should be understood that numerous transient states exist between any particular combination of reactant and reaction product.

Figure 8A:
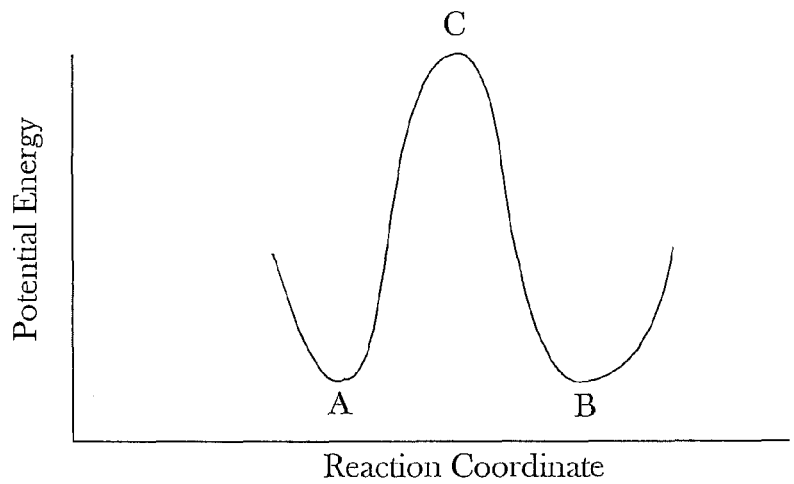
FIGS. 8a-8c show three different simple reaction profiles.

It should now be understood that physical catalysts produce effects by generating, energizing and/or stabilizing all manner of transients, as well as intermediates. In this regard, FIG. 8a shows a single reactant and a single product. The point "A" corresponds to the reactant and the point "B" corresponds to the reaction product. The point "C" corresponds to an activated complex. Transients correspond to all those points on the curve between reactant "A" and product "B", and can also include the activated complex "C".

Figure 8B:
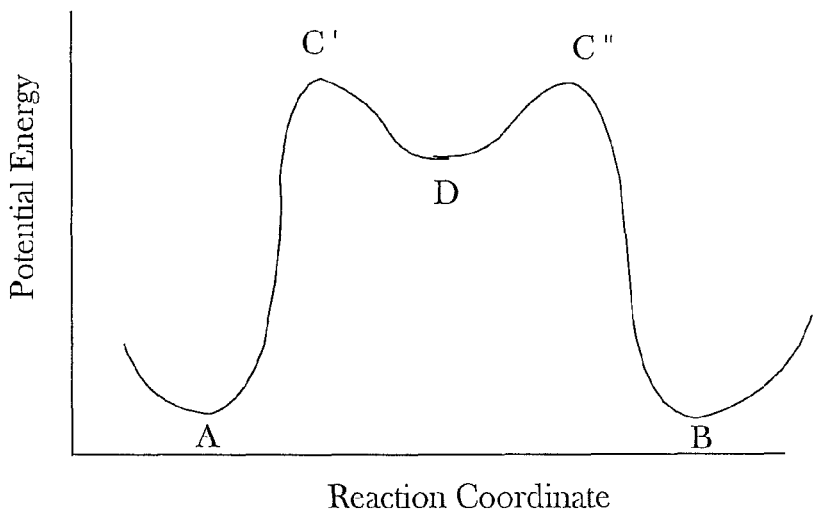
Figure 8C:
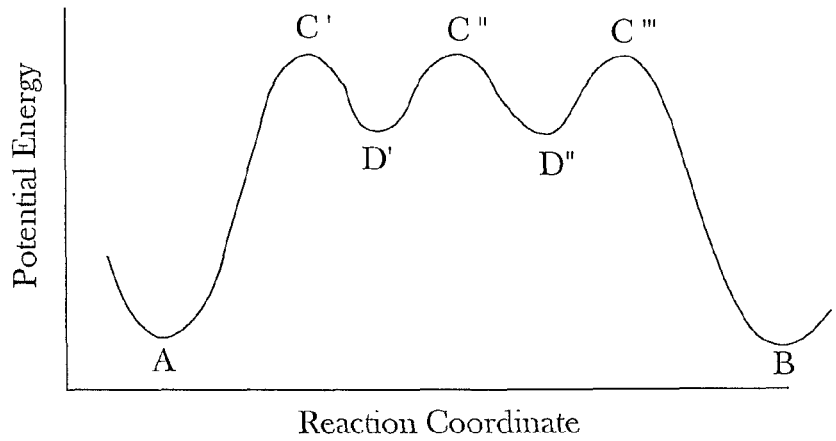

In a more complex reaction which involves formation of at least one intermediate, the reaction profile looks somewhat different. In this regard, reference is made to FIG. 8b, which shows reactant "A", product "B", activated complex "C' and C"", and intermediate "D". In this particular example, the intermediate "D" exists as a minimum in the energy reaction profile of the reaction, while it is surrounded by the activated complexes C' and C". However, again, in this particular reaction, transients correspond to anything between the reactant "A" and the reaction product "B", which in this particular example, includes the two activated complexes "C'" and "C"," as well as the intermediate "D". In the particular example of hydrogen and oxygen combining to form water, the reaction profile is closer to that shown in FIG. 8c. In this particular reaction profile, "D'" and "D""" could correspond generally to the intermediates of the hydrogen atom and hydroxy molecule.

Now, with specific reference to the reaction to form water, both intermediates are good examples of how platinum produces resonance in an intermediate by directly matching a frequency. Hydroxy intermediates vibrate strongly at frequencies of 975 THz and 1,060 THz. Platinum also vibrates at 975 THz and 1,060 THz. By directly matching the frequencies of the hydroxy intermediates, platinum can cause resonance in hydroxy intermediates, enabling them to be energized, stimulated and/or stabilized long enough to take part in chemical reactions. Similarly, platinum also directly matches frequencies of the hydrogen intermediates. Platinum resonates with about 10 out of about 24 hydrogen frequencies in its electronic spectrum (see FIG. 69). Specifically, FIG. 69 shows the frequencies of hydrogen listed horizontally across the Table and the frequencies of platinum listed vertically on the Table. Thus, by directly resonating with the intermediates in the above-described reaction, platinum facilitates the generation, energizing, stimulating, and/or stabilizing of the intermediates, thereby catalyzing the desired reaction.

Platinum's interactions with hydrogen are also a good example of matching frequencies through heterodyning. It is disclosed herein, and shown clearly in FIG. 69, that many of the platinum frequencies resonate indirectly as harmonics with the hydrogen atom intermediate (e.g., harmonic heterodynes). Specifically, fifty-six (56) frequencies of platinum (i.e., 33% of all its frequencies) are harmonics of nineteen (19) hydrogen frequencies (i.e., 80% of its 24 frequencies). Fourteen (14) platinum frequencies are first harmonics (2×) of seven (7) hydrogen frequencies. And, twelve (12) platinum frequencies are third harmonics (4×) of four (4) hydrogen frequencies. Thus, the presence of platinum causes massive indirect harmonic resonance in the hydrogen atom, as well as significant direct resonance.

Figure 9A:
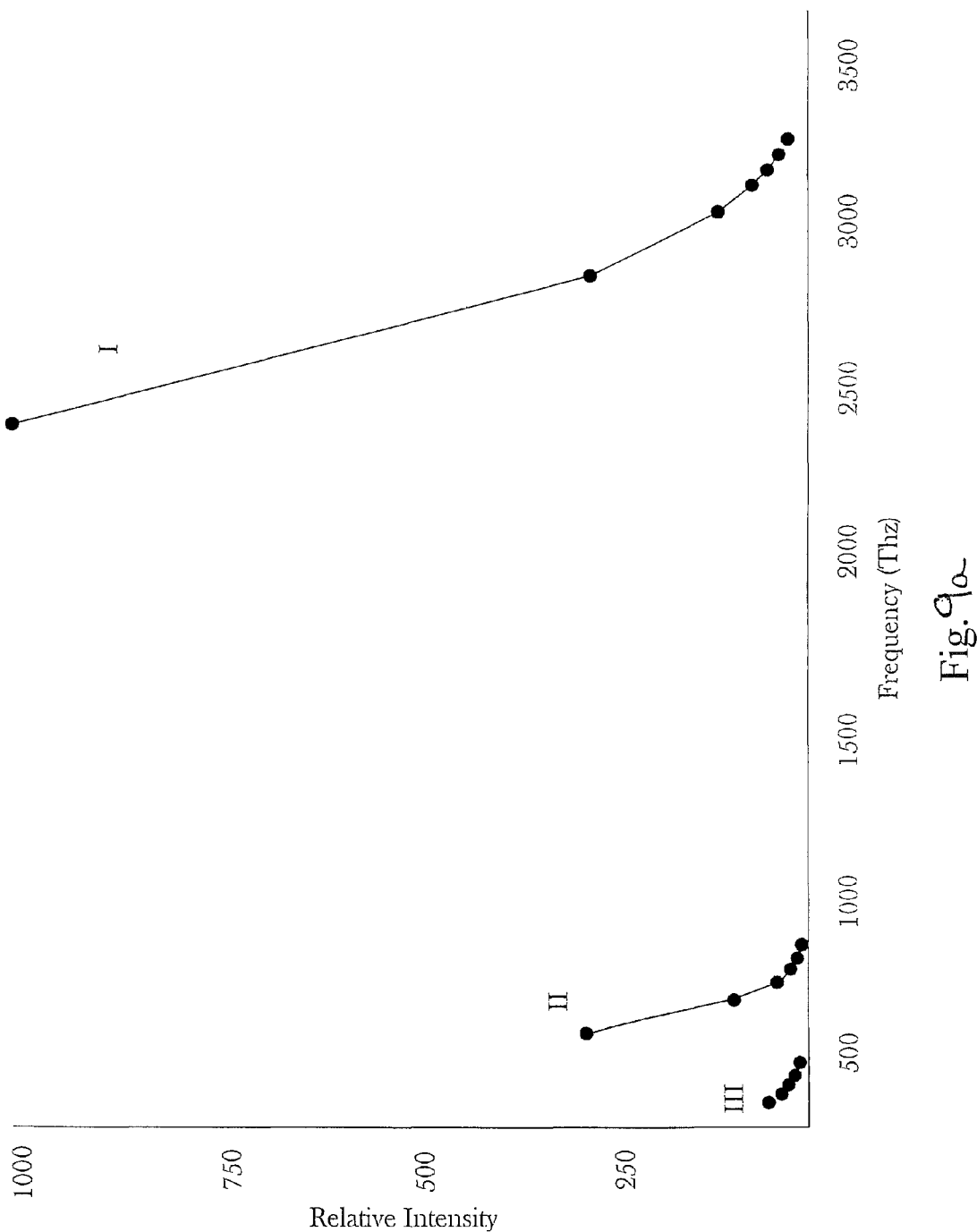
FIGS. 9a and 9b show fine frequency diagram curves for hydrogen.
Figures 9B, 10:
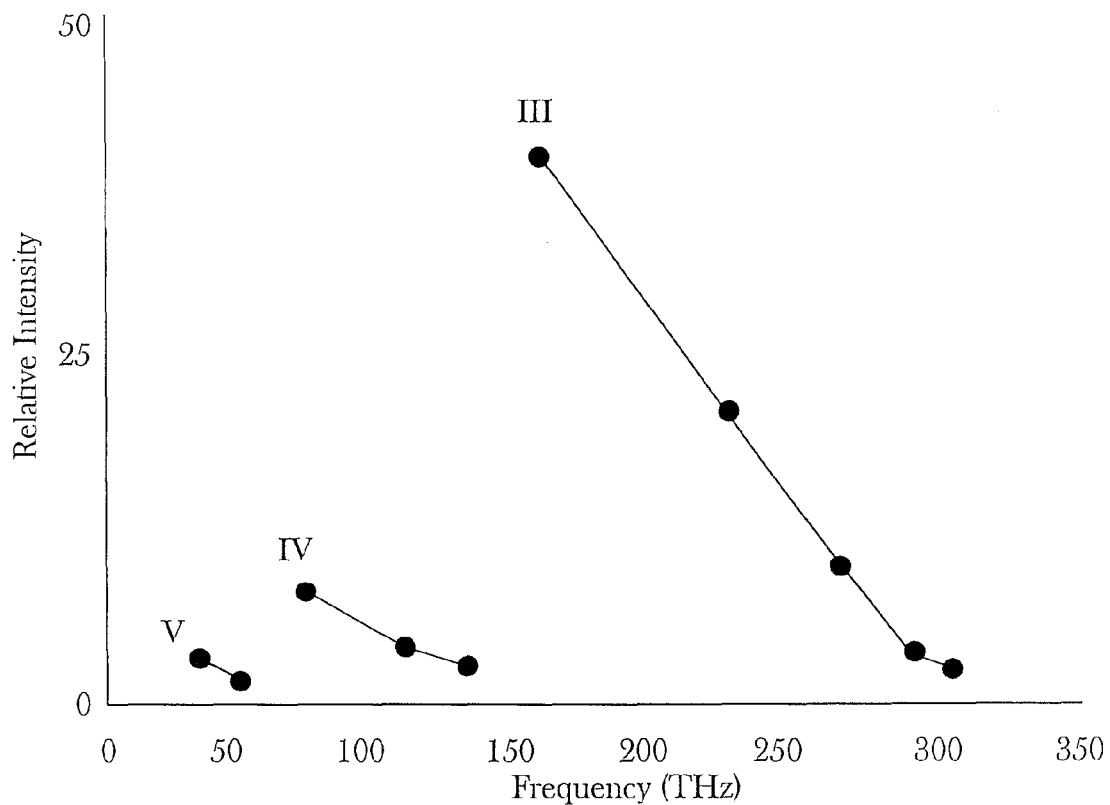
FIG. 10 shows various frequencies and intensities for hydrogen.

Further focus on the individual hydrogen frequencies is even more informative. FIGS. 9-10 show a different picture of what hydrogen looks like when the same information used to make energy level diagrams is plotted as actual frequencies and intensities instead. Specifically, the X-axis shows the frequencies emitted and absorbed by hydrogen, while the Y-axis shows the relative intensity for each frequency. The frequencies are plotted in terahertz (THz, $10^{12}$ Hz) and are rounded to the nearest THz. The intensities are plotted on a relative scale of 1 to 1,000. The highest intensity frequency that hydrogen atoms produce is 2,466 THz. This is the peak of curve I to the far right in FIG. 9a. This curve I shall be referred to as the first curve. Curve I sweeps down and to the right, from 2,466 THz at a relative intensity of 1,000 to 3,237 THz at a relative intensity of only about 15.

The second curve in FIG. 9a, curve II, starts at 456 THz with a relative intensity of about 300 and sweeps down and to the right. It ends at a frequency of 781 THz with a relative intensity of five (5). Every curve in hydrogen has this same downward sweep to the right. Progressing from right to left in FIG. 9, the curves are numbered I through V; going from high to low frequency and from high to low intensity.

The hydrogen frequency chart shown in FIG. 10 appears to be much simpler than the energy level diagrams. It is thus easier to visualize how the frequencies are organized into the different curves shown in FIG. 9. In fact, there is one curve for each of the series described by Rydberg. Curve "I" contains the frequencies in the Lyman series, originating from what quantum mechanics refers to as the first energy level. The second curve from the right, curve "II", equates to the second energy level, and so on.

The curves in the hydrogen frequency chart of FIG. 9 are composed of sums and differences (i.e., they are heterodyned). For example, the smallest curve at the far left, labeled curve "V", has two frequencies shown, namely 40 THz and 64 THz, with relative intensities of six (6) and four (4), respectively (see also FIG. 10). The next curve, IV, begins at 74 THz, proceeds to 114 THz and ends with 138 THz. The summed heterodyne calculations are thus:

$$40+74=114$$

$$64+74+138.$$

The frequencies in curve IV are the sum of the frequencies in curve V plus the peak intensity frequency in curve IV.

Alternatively, the frequencies in curve IV, minus the frequencies in curve V, yield the peak of curve IV:

$$114-40=74$$

$$138-64=74.$$

This is not just a coincidental set of sums or differences in curves IV and V. Every curve in hydrogen is the result of adding each frequency in any one curve, with the highest intensity frequency in the next curve.

These hydrogen frequencies are found in both the atom itself, and in the electromagnetic energy it radiates. The frequencies of the atom and its energy, add and subtract in regular fashion. This is heterodyning. Thus, not only matter and energy heterodyne interchangeably, but matter heterodynes its' own energy within itself.

Moreover, the highest intensity frequencies in each curve are heterodynes of heterodynes. For example, the peak frequency in Curve I of FIG. 9 is 2,466 THz, which is the third harmonic of 616 THz;

$$4 \times 616 \text{ THz} = 2,466 \text{ THz}.$$

Thus, 2,466 THz is the third harmonic of 616 THz (Recall that for heterodyned harmonics, the result is even multiples of the starting frequency, i.e., for the first harmonic 2× the original frequency and the third harmonic is 4× the original frequency. Multiplying a frequency by four (4) is a natural result of the heterodyning process.) Thus, 2,466 THz is a fourth generation heterodyne, namely the third harmonic of 616 THz.

The peak of curve II of FIG. 9, a frequency corresponding to 456 THz, is the third harmonic of 114 THz in curve IV. The peak of curve III, corresponding to a frequency of 160 THz, is the third harmonic of 40 THz in curve V. The peaks of the curves shown in FIG. 9 are not only heterodynes between the curves but are also harmonics of individual frequencies which are themselves heterodynes. The whole hydrogen spectrum turns out to be an incestuously heterodyned set of frequencies and harmonics.

Theoretically, this heterodyne process could go on forever. For example, if 40 is the peak of a curve, that means the peak is four (4) times a lower number, and it also means that the peak of the previous curve is 24 (64−40=24). It is possible to mathematically extrapolate backwards and downwards this way to derive lower and lower frequencies. Peaks of successive curves to the left are 24.2382, 15.732, and 10.786 THz, all generated from the heterodyne process. These frequencies are in complete agreement with the Rydberg formula for energy levels 6, 7 and 8, respectively. Not much attention has historically been given by the prior art to these lower frequencies and their heterodyning.

This invention teaches that the heterodyned frequency curves amplify the vibrations and energy of hydrogen. A low intensity frequency on curve IV or V has a very high intensity by the time it is heterodyned out to curve I. In many respects, the hydrogen atom is just one big energy amplification system. Moving from low frequencies to high frequencies, (i.e., from curve V to curve I in FIG. 9), the intensities increase dramatically. By stimulating hydrogen with 2,466 THz at an intensity of 1,000, the result will be 2,466 THz at 1,000 intensity. However, if hydrogen is stimulated with 40 THz at an intensity of 1,000, by the time it is amplified back out to curve I of FIG. 9, the result will be 2,466 THz at an intensity of 167,000. This heterodyning turns out to have a direct bearing on platinum, and on how platinum interacts with hydrogen. It all has to do with hydrogen being an energy amplification system. That is why the lower frequency curves are perceived as being higher energy levels. By understanding this process, the low frequencies of low intensity suddenly become potentially very significant.

Platinum resonates with most, if not all, of the hydrogen frequencies with one notable exception, the highest intensity curve at the far right in the frequency chart of FIG. 9 (i.e., curve I) representing energy level 1, and beginning with 2,466 THz. Platinum does not appear to resonate significantly with the ground state transition of the hydrogen atom. However, it does resonate with multiple upper energy levels of lower frequencies.

With this information, one ongoing mystery can be solved. Ever since lasers were developed, the prior art chemists believed that there had to be some way to catalyze a reaction using lasers. Standard approaches involved using the single highest intensity frequency of an atom (such as 2,466 THz of hydrogen) because it was apparently believed that the highest intensity frequency would result in the highest reactivity. This approach was taken due to considering only the energy level diagrams. Accordingly, prior art lasers are typically tuned to a ground state transition frequency. This use of lasers in the prior art has been minimally successful for catalyzing chemical reactions. It is now understood why this approach was not successful. Platinum, the quintessential hydrogen catalyst, does not resonate with the ground state transition of hydrogen. It resonates with the upper energy level frequencies, in fact, many of the upper level frequencies. Without wishing to be bound by any particular theory or explanation, this is probably why platinum is such a good hydrogen catalyst.

Einstein essentially worked out the statistics on lasers at the turn of the century when atoms at the ground energy level ($E_1$) are resonated to an excited energy level ($E_2$). Refer to the number of atoms in the ground state as "$N_1$" and the number of excited atoms as "$N_2$", with the total "$N_{total}$". Since there are only two possible states that atoms can occupy:

$$N_{total} = N_1 + N_2.$$

After all the mathematics are performed, the relationship which evolves is:

$$\frac{N_2}{N_{total}} = \frac{N_2}{N_1 + N_2} < \frac{1}{2}$$

In a two level system, it is predicted that there will never by more than 50% of the atoms in the higher energy level, $E_2$, at the same time.

If, however, the same group of atoms is energized at three (3) or more energy levels (i.e., a multi-level system), it is possible to obtain more than 50% of the atoms energized above the first level. By referring to the ground and energized levels as $E_1$, $E_2$, and $E_3$, respectively, and the numbers of atoms as $N_{total}$, $N_1$, $N_2$, and $N_3$, under certain circumstances, the number of atoms at an elevated energy level ($N_3$) can be more than the number at a lower energy level ($N_2$). When this happens, it is referred to as a "population inversion". Population inversion means that more of the atoms are at higher energy levels that at the lower energy levels.

Figure 11A:
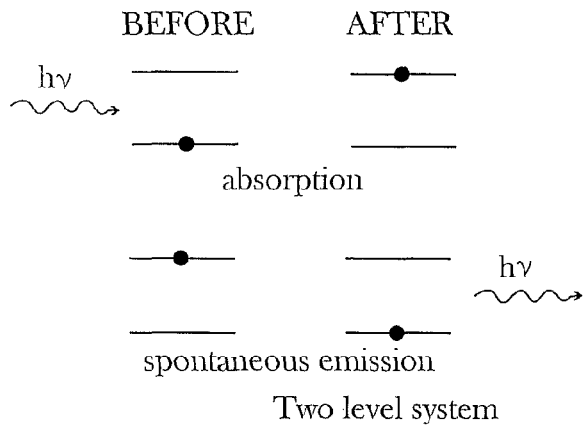
FIGS. 11a and 11b show two light amplification diagrams with stimulated emission/population inversions.
Figure 11B:
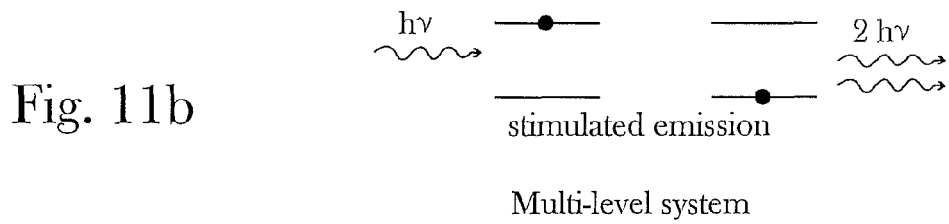

Population inversion in lasers is important. Population inversion causes amplification of light energy. For example, in a two-level system, one photon in results in one photon out. In a system with three (3) or more energy levels and population inversion, one photon in may result in 5, 10, or 15 photons out (see FIG. 11). The amount of photons out depends on the number of levels and just how energized each level becomes. All lasers are based on this simple concept of producing a population inversion in a group of atoms, by creating a multi-level energized system among the atoms. Lasers are simply devices to amplify electromagnetic wave energy (i.e., light) Laser is actually an abbreviation for Light Amplification System for Emitting Radiation.

By referring back to the interactions discussed herein between platinum and hydrogen, platinum energizes 19 upper level frequencies in hydrogen (i.e., 80% of the total hydrogen frequencies). But only three frequencies are needed for a population inversion. Hydrogen is stimulated at 19. This is a clearly multi-level system. Moreover, consider that seventy platinum frequencies do the stimulating. On average, every hydrogen frequency involved is stimulated by three or four (i.e., 70/19) different platinum frequencies; both directly resonant frequencies and/or indirectly resonant harmonic frequencies. Platinum provides ample stimulus, atom per atom, to produce a population inversion in hydrogen. Finally, consider the fact that every time a stimulated hydrogen atom emits some electromagnetic energy, that energy is of a frequency that matches and stimulates platinum in return.

Platinum and hydrogen both resonate with each other in their respective multi-level systems. Together, platinum and hydrogen form an atomic scale laser (i.e., an energy amplification system on the atomic level). In so doing, platinum and hydrogen amplify the energies that are needed to stabilize both the hydrogen and hydroxy intermediates, thus catalyzing the reaction pathway for the formation of water. Platinum is such a good hydrogen catalyst because it forms a lasing system with hydrogen on the atomic level, thereby amplifying their respective energies.

Further, this reaction hints that in order to catalyze a reaction system and/or control the reaction pathway in a reaction system it is possible for only a single transient and/or intermediate to be formed and/or energized by an applied frequency (e.g., a spectral catalyst) and that by forming and/or stimulating at least one transient and/or at least one intermediate that is required to follow for a desired reaction pathway (e.g., either a complex reaction or a simple reaction), then a frequency, or combination of frequencies, which result in such formation or stimulation of only one of such required transients and/or intermediates may be all that is required. Accordingly, the present invention recognizes that in some reaction systems, by determining at least one required transient and/or intermediate, and by applying at least one frequency which generates, energizes and/or stabilizes said at least one transient and/or intermediate, then all other transients and/or intermediates required for a reaction to proceed down a desired reaction pathway may be self-generated. However, in some cases, the reaction could be increased in rate by applying the appropriate frequency or spectral energy pattern, which directly stimulates all transients and/or intermediates that are required in order for a reaction to proceed down a desired reaction pathway. Accordingly, depending upon the particulars of any reaction system, it may be desirable for a variety of reasons, including equipment, environmental reaction conditions, etc., to provide or apply a frequency or spectral energy pattern which results in the formation and/or stimulation and/or stabilization of any required transients and/or intermediates. Thus, in order to determine an appropriate frequency or spectral energy pattern, it is first desirable to determine which transients and/or intermediates are present in any reaction pathway.

Specifically, once all known required transients and/or intermediates are determined, then, one can determine experimentally or empirically which transients and/or intermediates are essential to a reaction pathway and then determine, which transients and or intermediates can be self-generated by the stimulation and/or formation of a different transient or intermediate. Once such determinations are made, appropriate spectral energies (e.g., electromagnetic frequencies) can then be applied to the reaction system to obtain the desirable reaction product and/or desirable reaction pathway.

It is known that an atom of platinum interacts with an atom of hydrogen and/or a hydroxy intermediate. And, that is exactly what modern chemistry has taught for the last one hundred years, based on Ostwald's theory of catalysis. However, the prior art teaches that catalysts must participate in the reaction by binding to the reactants, in other words, the prior art teaches a matter: matter bonding interaction is required for physical catalysts. As previously stated, these reactions follow these steps:

1. Reactant diffusion to the catalyst site;
2. Bonding of reactant to the catalyst site;
3. Reaction of the catalyst-reactant complex;
4. Bond rupture at the catalytic site (product); and
5. Diffusion of the product away from the catalyst site.

However, according to the present invention, for example, energy:energy frequencies can interact as well as energy:matter frequencies. Moreover, matter radiates energy, with the energy frequencies being substantially the same as the matter frequencies. So platinum vibrates at the frequency of 1,060 THz, and it also radiates electromagnetic energy at 1,060 THz. Thus, according to the present invention, the distinction between energy frequencies and matter frequencies starts to look less important.

Resonance can be produced in, for example, the reaction intermediates by permitting them to come into contact with additional matter vibrating at substantially the same frequencies, such as those frequencies of a platinum atom (e.g., platinum stimulating the reaction between hydrogen and oxygen to form water). Alternatively, according to the present invention, resonance can be produced in the intermediates by introducing electromagnetic energy corresponding to one or more platinum energies, which also vibrate at the same frequencies, thus at least partially mimicking (an additional mechanism of platinum is resonance with the $H_2$ molecule, a pathway reactant) the mechanism of action of a platinum catalyst. Matter, or energy, it makes no difference as far as the frequencies are concerned, because when the frequencies match, energy transfers. Thus, physical catalysts are not required. Rather, the application of at least a portion of the spectral pattern of a physical catalyst may be sufficient (i.e. at least a portion of the catalytic spectral pattern). However, in another preferred embodiment, substantially all of a spectral pattern can be applied.

Still further, by understanding the catalyst mechanism of action, particular frequencies can be applied to, for example, one or more reactants in a reaction system and, for example, cause the applied frequencies to heterodyne with existing frequencies in the matter itself to result in frequencies which correspond to one or more platinum catalyst or other relevant spectral frequencies. For example, both the hydrogen atom and the hydrogen molecule have unique frequencies. By heterodyning the frequencies a subtractive frequency can be determined:

$$NOF_{H\ atom} - NOF_{H\ molecule} = \text{Difference}_{H\ atom-molecule}$$

The $\text{Difference}_{H\ atom-molecule}$ frequency applied to the $H_2$ molecule reactant will heterodyne with the molecule and energize the individual hydrogen atoms as intermediates. Similarly, any reaction participant can serve as the heterodyning backboard for stimulation of another participant. For example, $$\text{Difference}_{H\ atom-Oxygen\ molecule} + NOF_{oxygen\ molecule} = NOF_{H\ atom}$$

or $$\text{Difference}_{OH-water} + NOF_{water} = NOF_{OH}$$

This approach enables greater flexibility for choice of appropriate equipment to apply appropriate frequencies. However, the key to this approach is understanding catalyst mechanisms of action and the reaction pathway so that appropriate choices for application of frequencies can be made.

Specifically, whenever reference is made to, for example, a spectral catalyst duplicating at least a portion of a physical catalyst's spectral pattern, this reference is to all the different frequencies produced by a physical catalyst; including, but not necessarily limited to, electronic, vibrational, rotational, and NOF frequencies. To catalyze, control, and/or direct a chemical reaction then, all that is needed is to duplicate one or more frequencies from a physical catalyst, with, for example, an appropriate electromagnetic energy. The actual physical presence of the catalyst is not necessary. A spectral catalyst can substantially completely replace a physical catalyst, if desired.

A spectral catalyst can also augment or promote the activity of a physical catalyst. The exchange of energy at particular frequencies, between hydrogen, hydroxy, and platinum is primarily what drives the conversion to water. These participants interact and create a miniature atomic scale lasing system that amplify their respective energies. The addition of these same energies to a reaction system, using a spectral catalyst, does the same thing. The spectral catalyst amplifies the participant energies by resonating with them and when frequencies match, energy transfers and the chemicals (matter) can absorb the energy. Thus, a spectral catalyst can augment a physical catalyst, as well as replace it. In so doing, the spectral catalyst may increase the reaction rate, enhance specificity, and/or allow for the use of less physical catalyst.

Figure 12:
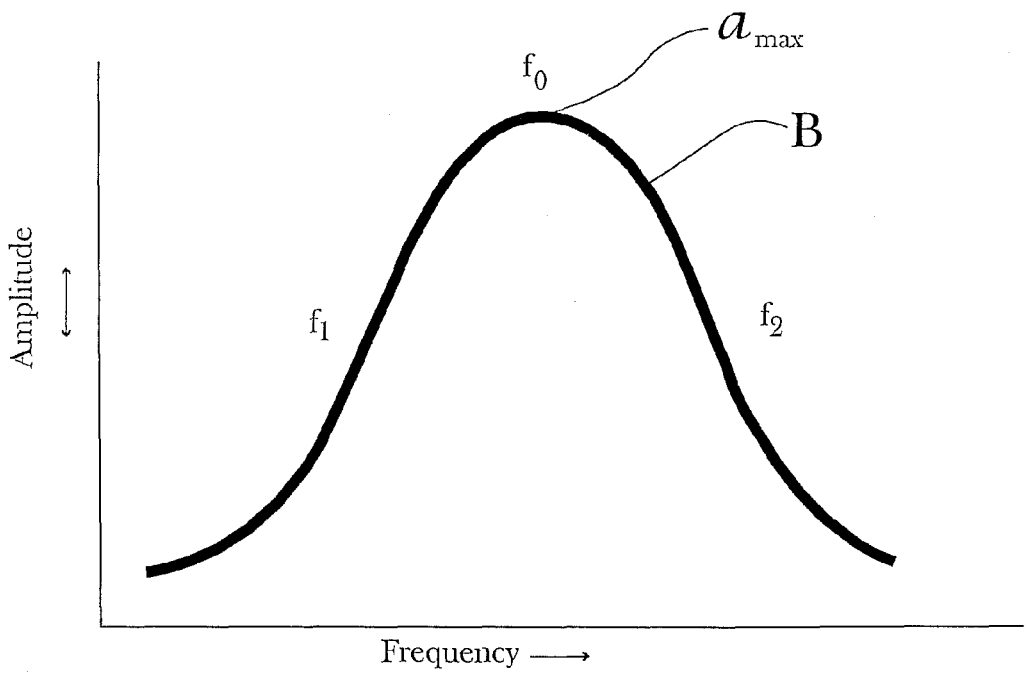
FIG. 12 shows a resonance curve where the resonance frequency is $f_o$, an upper frequency=$f_2$ and a lower frequency=$f_1$, wherein $f_1$ and $f_2$ are at about 50% of the amplitude of $f_o$.

FIG. 12 shows a basic bell-shaped curve produced by comparing how much energy an object absorbs, as compared to the frequency of the energy. This curve is called a resonance curve. As elsewhere herein stated, the energy transfer between, for example, atoms or molecules, reaches a maximum at the resonant frequency ($f_o$). The farther away an applied frequency is from the resonant frequency, $f_o$, the lower the energy transfer (e.g., matter to matter, energy to matter, etc.). At some point the energy transfer will fall to a value representing only about 50% of that at the resonant frequency $f_o$. The frequency higher than the resonant frequency, at which energy transfer is only about 50% is called "$f_2$." The frequency lower than the resonant frequency, at which about 50% energy transfer occurs, is labeled "$f_1$."

The resonant characteristics of different objects can be compared using the information from the simple exemplary resonance curve shown in FIG. 12. One such useful characteristic is called the "resonance quality" or "Q" factor. To determine the resonance quality for an object the following equation is utilized:

$$Q = \frac{f_0}{(f_2 - f_1)}$$

Figure 13A:
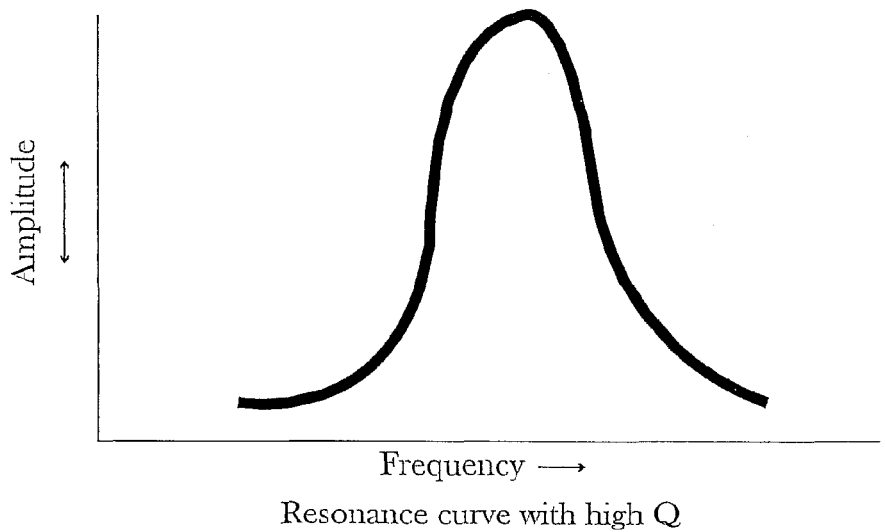
FIGS. 13a and 13b show two different resonance curves having different quality factors.
Figure 13B:
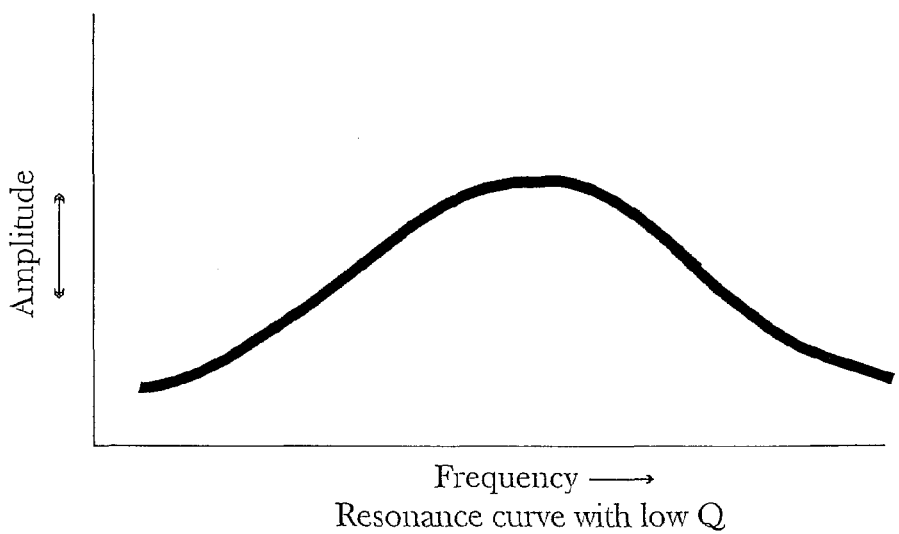

Accordingly, as shown from the equation, if the bell-shaped resonance curve is tall and narrow, then $(f_2-f_1)$ will be a very small number and Q, the resonance quality, will be high (see FIG. 13a). An example of a material with a high "Q" is a high quality quartz crystal resonator. If the resonance curve is low and broad, then the spread or difference between $f_2$ and $f_1$ will be relatively large. An example of a material with a low "Q" is a marshmallow. The dividing of the resonant frequency by this large number will produce a much lower Q value (see FIG. 13b).

Atoms and molecules, for example, have resonance curves which exhibit properties similar to larger objects such as quartz crystals and marshmallows. If the goal is to stimulate atoms in a reaction (e.g., hydrogen in the reaction to produce water as mentioned previously) a precise resonant frequency produced by a reaction system component or environmental reaction condition (e.g., hydrogen) can be used. It is not necessary to use the precise frequency, however. Use of a frequency that is near a resonant frequency of, for example, one or more reaction system components or environmental reaction conditions is adequate. There will not be quite as much of an effect as using the exact resonant frequency, because less energy will be transferred, but there will still be an effect. The closer the applied frequency is to the resonant frequency, the more the effect. The farther away the applied frequency is from the resonant frequency, the less effect that is present (i.e., the less energy transfer that occurs).

Harmonics present a similar situation. As previously stated, harmonics are created by the heterodyning (i.e., adding and subtracting) of frequencies, allowing the transfer of significant amounts of energy. Accordingly, for example, desirable results can be achieved in chemical reactions if applied frequencies (e.g., at least a portion of a spectral catalyst) are harmonics (i.e., matching heterodynes) with one or more resonant frequency(ies) of one or more reaction system components or environmental reaction conditions.

Further, similar to applied frequencies being close to resonant frequencies, applied frequencies which are close to the harmonic frequency can also produce desirable results. The amplitude of the energy transfer will be less relative to a harmonic frequency, but an effect will still occur. For example, if the harmonic produces 70% of the amplitude of the fundamental resonant frequency and by using a frequency which is merely close to the harmonic, for example, about 90% on the harmonic's resonance curve, then the total effect will be 90% of 70%, or about 63% total energy transfer in comparison to a direct resonant frequency. Accordingly, according to the present invention, when at least a portion of the frequencies of one or more reaction system components or environmental reaction conditions at least partially match, then at least some energy will transfer and at least some reaction will occur (i.e., when frequencies match, energy transfers).

Duplicating the Catalyst Mechanics of Action

As stated previously, to catalyze, control, and/or direct a chemical reaction, a spectral catalyst can be applied. The spectral catalyst may correspond to at least a portion of a spectral pattern of a physical catalyst or the spectral catalyst may correspond to frequencies which form or stimulate required participants (e.g., heterodyned frequencies) or the spectral catalyst may substantially duplicate environmental reaction conditions such as temperature or pressure. Thus, as now taught by the present invention, the actual physical presence of a catalyst is not required to achieve the desirable chemical reactions. The removal of a physical catalyst is accomplished by understanding the underlying mechanism inherent in catalysis, namely that desirable energy can be exchanged (i.e., transferred) between, for example, (1) at least one participant (e.g., reactant, transient, intermediate, activated complex, reaction product, promoter and/or poison) and/or at least one component in a reaction system and (2) an applied electromagnetic energy (e.g., spectral catalyst) when such energy is present at one or more specific frequencies. In other words, the targeted mechanism that nature has built into the catalytic process can be copied according to the teachings of the present invention. Nature can be further mimicked because the catalyst process reveals several opportunities for duplicating catalyst mechanisms of action, and hence improving the use of spectral catalysts, as well as the control of countless chemical reactions.

For example, the previously discussed reaction of hydrogen and oxygen to produce water, which used platinum as a catalyst, is a good starting point for understanding catalyst mechanisms of action. For example, this invention discloses that platinum catalyzes the reaction in several ways not contemplated by the prior art:

Platinum directly resonates with and energizes reaction intermediates and/or transients (e.g., atomic hydrogen and hydroxy radicals);
Platinum harmonically resonates with and energizes at least one reaction intermediate and or transient (e.g., atomic hydrogen); and
Platinum energizes multiple upper energy levels of at least one reaction intermediate and or transient (e.g., atomic hydrogen).

This knowledge can be utilized to improve the functioning of the spectral catalyst and/or spectral energy catalyst to design spectral catalysts and spectral energy catalysts which differ from actual catalytic spectral patterns, and to design physical catalysts, and to optimize environmental reaction conditions. For example, the frequencies of atomic platinum are in the ultraviolet, visible light, and infrared regions of the electromagnetic spectrum. The electronic spectra of virtually all atoms are in these same regions. However, these very high electromagnetic frequencies can be a problem for large-scale and industrial applications because wave energies having high frequencies typically do not penetrate matter very well (i.e., do not penetrate far into matter). The tendency of wave energy to be absorbed rather than transmitted, can be referred to as attenuation. High frequency wave energies have a high attenuation, and thus do not penetrate far into a typical industrial scale reaction vessel containing typical reactants for a chemical reaction. Thus, the duplication and application of at least a portion of the spectral pattern of platinum into a commercial scale reaction vessel will typically be a slow process because a large portion of the applied spectral pattern of the spectral catalysts may be rapidly absorbed near the edges of the reaction vessel.

Thus, in order to input energy into a large industrial-sized commercial reaction vessel, a lower frequency energy could be used that would penetrate farther into the reactants housed within the reaction vessel. The present invention teaches that this can be accomplished in a unique manner by copying nature. As discussed herein, the spectra of atoms and molecules are broadly classified into three (3) different groups: electronic, vibrational, and rotational. The electronic spectra of atoms and small molecules are said to result from transitions of electrons from one energy level to another, and have the corresponding highest frequencies, typically occurring in the ultraviolet (UV), visible, and infrared (IR) regions of the EM spectrum. The vibrational spectra are said to result primarily from this movement of bonds between individual atoms within molecules, and typically occur in the infrared and microwave regions. Rotational spectra occur primarily in the microwave and radiowave regions of the EM spectrum due, primarily, to the rotation of the molecules.

Microwave or radiowave radiation could be an acceptable frequency to be used as a spectral catalyst because it would penetrate well into a large reaction vessel. Unfortunately, platinum atoms do not produce frequencies in the microwave or radiowave portions of the electromagnetic spectrum because they do not have vibrational or rotational spectra. However, by copying the mechanism of action platinum, selected platinum frequencies can be used as a model for a spectral catalyst in the microwave portion of the spectrum. Specifically, as previously discussed, one mechanism of action of platinum in the reaction system to produce water involves energizing at least one reaction intermediate and/or transient. Reaction intermediates in this reaction are atomic hydrogen and the hydroxy radical. Atomic hydrogen has a high frequency electronic spectrum without vibrational or rotational spectra. The hydroxy radical, on the other hand, is a molecule, and has vibrational and rotational spectra as well as an electronic spectrum. Thus, the hydroxy radical emits, absorbs and heterodynes frequencies in the microwave portion of the electromagnetic spectrum.

Thus, to copy the mechanism of action of platinum in the reaction to form water, namely resonating with at least one reaction intermediate and/or transient, the hydroxy intermediate can be specifically targeted via resonance. However, instead of resonating with the hydroxy radical in its electronic spectrum, as physical platinum catalyst does, at least one hydroxy frequency in the microwave portion of the EM spectrum can be used to resonate with the hydroxy radical. Hydroxy radicals heterodyne at a microwave frequency of about 21.4 GHz. Energizing a reaction system of hydrogen and oxygen gas with a spectral catalyst at about 21.4 GHz will catalyze the formation of water. In this instance, the mechanism of action of the physical catalyst platinum has been partially copied and the mechanism has been shifted to a different region of the electromagnetic spectrum.

The second method discussed above for platinum catalyzing a reaction, involves harmonically energizing at least one reaction intermediate in the reaction system. For example, assume that one or more lasers was available to catalyze the hydrogen-oxygen reaction to form water, however, the frequency range of such lasers was only from, for example, 1,500 to 2,000 THz. Platinum does not produce frequencies in that portion of the EM spectrum. Moreover, the two hydroxy frequencies that platinum resonates with, 975 and 1,060 THz, are outside the frequency range that the lasers, in this example, can generate. Likewise, the hydrogen spectrum does not have any frequencies between 1,500 and 2,000 THz (see FIGS. 9-10).

However, according to the present invention, by again copying the mechanism of action of platinum, frequencies can be adapted or selected to be convenient and/or efficient for the equipment available. Specifically, harmonic frequencies corresponding to the reaction intermediates and/or transients, and also corresponding to frequencies capable of being generated by the lasers of this example, can be utilized. For the hydroxy radical, having a resonant frequency of 975 THz, the first harmonic is 1,950 THz. Thus, a laser of this example could be tuned to 1,950 THz to resonate harmonically with the hydroxy intermediate. The first harmonics of three different hydrogen frequencies also fall within the operational range of the lasers of this example. The fundamental frequencies are 755, 770 and 781 THz and the first harmonics are 1,510, 1,540, and 1,562 THz, respectively. Thus, a laser of this example could be tuned to the first harmonics 1,510, 1,540, and 1,562 THz in order to achieve a heterodyned matching of frequencies between electromagnetic energy and matter and thus achieve a transfer and absorption of said energy.

Thus, depending on how many lasers are available and the frequencies to which the lasers can be tuned, third or fourth harmonics could also be utilized. The third harmonic of the hydrogen frequency, 456 THz, occurs at 1,824 THz, which is also within the operating range of the lasers of this example. Similarly, the fourth harmonic of the hydrogen frequency, 314 THz, occurs at 1,570 THz, which again falls within the operating range of the lasers of this example. In summary, a mechanism of action of a physical catalyst can be copied, duplicated or mimicked while moving the relevant spectral catalyst frequencies, to a portion of the electromagnetic spectrum that matches equipment available for the reaction system and the application of electromagnetic energy.

The third method discussed above for platinum catalyzing this reaction involves energizing at least one reaction intermediate and/or transient at multiple upper energy levels and setting up, for example, an atomic scale laser system. Again, assume that the same lasers discussed above are the only electromagnetic energy sources available and assume that there are a total of ten (10) lasers available. There are four (4) first harmonics available for targeting within the operating frequency range of 1,500 to 2,000 THz. Some portion of the lasers should be adjusted to four (4) first harmonics and some should be adjusted to the third, fourth, and higher harmonics. Specifically, the present invention has discovered that a mechanism of action that physical platinum uses is to resonate with multiple upper energy levels of at least one reaction participant. It is now understood that the more upper energy levels that are involved, the better. This creates an atomic scale laser system with amplification of the electromagnetic energies being exchanged between the atoms of platinum and hydrogen. This amplification of energy catalyzes the reaction at a much faster rate than the reaction would ordinarily proceed. This mechanism of action can also be exploited to catalyze, for example, the reaction with the available lasers discussed above.

For example, rather than setting all ten (10) lasers to the four (4) first harmonics and energizing only four (4) levels, it should now be understood that it would be desirable to energize as many different energy levels as possible. This task can be accomplished by setting each of the ten (10) lasers to a different frequency. Even though the physical catalyst platinum is not present, the energizing of multiple upper energy levels in the hydrogen will amplify the energies being exchanged between the atoms, and the reaction system will form its' own laser system between the hydrogen atoms. This will permit the reaction to proceed at a much faster rate than it ordinarily would. Once again, nature can be mimicked by duplicating one of her mechanisms of action by specifically targeting multiple energy levels with a spectral catalyst to achieve energy transfer in a novel manner.

The preceding discussion on duplicating catalyst mechanisms of action is just the beginning of an understanding of many variables associated with the use of spectral catalysts. These additional variables should be viewed as potentially very useful tools for enhancing the performance of spectral energy, and/or physical catalysts. There are many factors and variables that affect both catalyst performance, and chemical reactions in general. For example, when the same catalyst is mixed with the same reactant, but exposed to different environmental reaction conditions such as temperature or pressure, different products can be produced. Consider the following example:

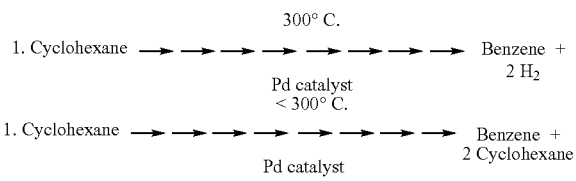

The same catalyst with the same reactant, produces quite different products in these two reactions, namely molecular hydrogen or cyclohexane, depending on the reaction temperature.

Many factors are known in the art which affect the direction and intensity with which a physical catalyst guides a reaction or with which a reaction proceeds in general. Temperature is but one of these factors. Other factors include pressure, volume, surface area of physical catalysts, solvents, support materials, contaminants, catalyst size and shape and composition, reactor vessel size, shape and composition, electric fields, magnetic fields, and acoustic fields. The present invention teaches that these factors all have one thing in common. These factors are capable of changing the spectral patterns (i.e., frequency pattern) of, for example, participants and/or reaction system components. Some changes in spectra are very well studied and thus much information is available for consideration and application thereof. The prior art does not contemplate, however, the spectral chemistry basis for each of these factors, and how they relate to catalyst mechanisms of action, and chemical reactions in general. Further, alternatively, effects of the aforementioned factors can be enhanced or diminished by the application of additional spectral, spectral energy, and/or physical catalyst frequencies. Moreover, these environmental reaction conditions can be at least partially simulated in a reaction system by the application of one or more corresponding spectral environmental reaction conditions (e.g., a spectral energy pattern which duplicates at least a portion of one or more environmental reaction conditions). Alternatively, one spectral environmental reaction condition (e.g., a spectral energy pattern corresponding to temperature) could be substituted for another (e.g., spectral energy pattern corresponding to pressure) so long as the goal of matching of frequencies was met.

Temperature

Figure 15A:
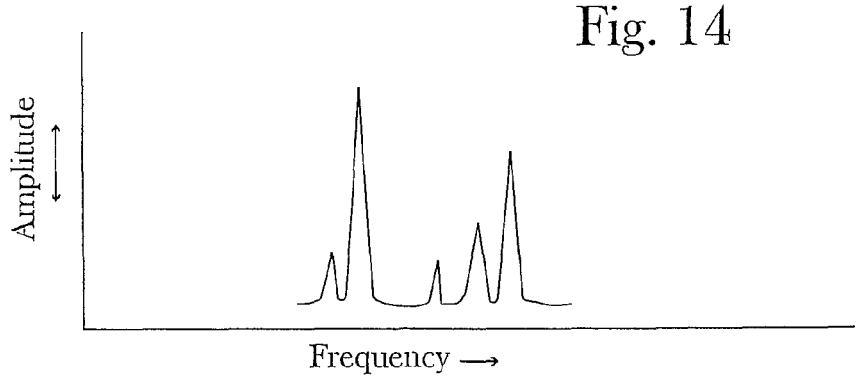
FIGS. 15a-c show how a spectral pattern varies at three different temperatures.
Figure 15B:
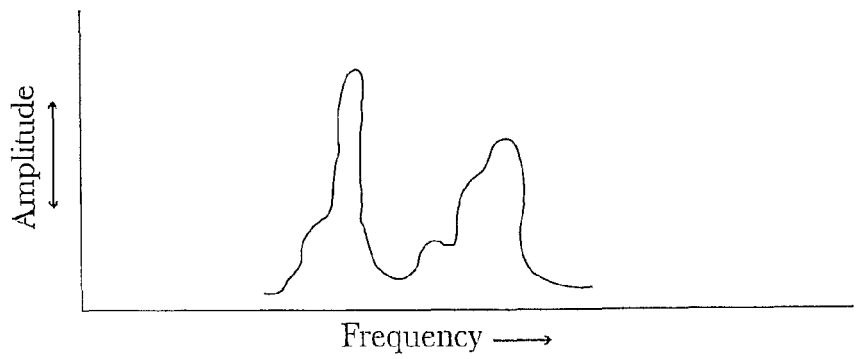
Figure 15C:
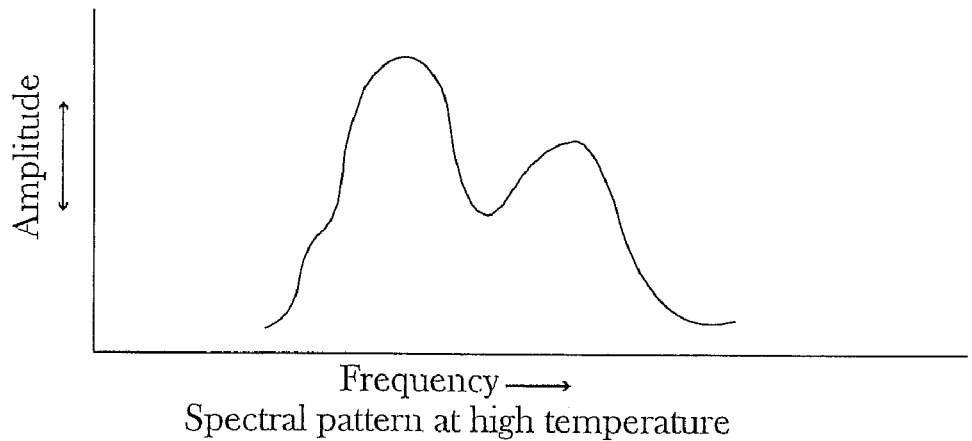

At very low temperatures, the spectral pattern of an atom or molecule has clean, crisp peaks (see FIG. 15a). As the temperature increases, the peaks begin to broaden, producing a bell-shaped curve of a spectral pattern (see FIG. 15b). At even higher temperatures, the bell-shaped curve broadens even more, to include more and more frequencies on either side of the primary frequency (see FIG. 15c). This phenomenon is called "broadening".

These spectral curves are very much like the resonance curves discussed in the previous section. Spectroscopists use resonance curve terminology to describe spectral frequency curves for atoms and molecules (see FIG. 16). The frequency at the top of the curve, $f_0$, is called the resonance frequency. There is a frequency ($f_2$) above the resonance frequency and another ($f_1$) below it (i.e., in frequency), at which the energy or intensity (i.e., amplitude) is 50% of that for the resonance frequency $f_0$. The quantity $f_2-f_1$ is a measure of how wide or narrow the spectral frequency curve is. This quantity ($f_2-f_1$) is the "line width". A spectrum with narrow curves has a small line width, while a spectrum with wide curves has a large line width.

Figure 17A:
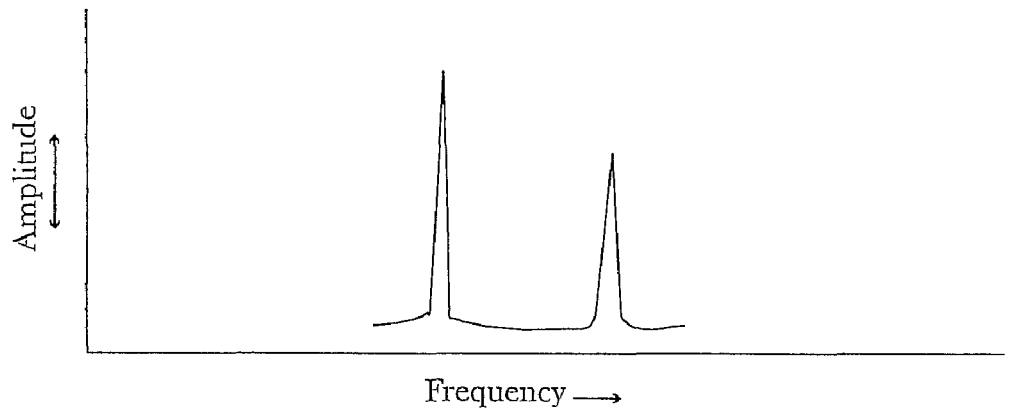
FIGS. 17a and 17b show two amplitude vs. frequency curves.
Figure 17B:
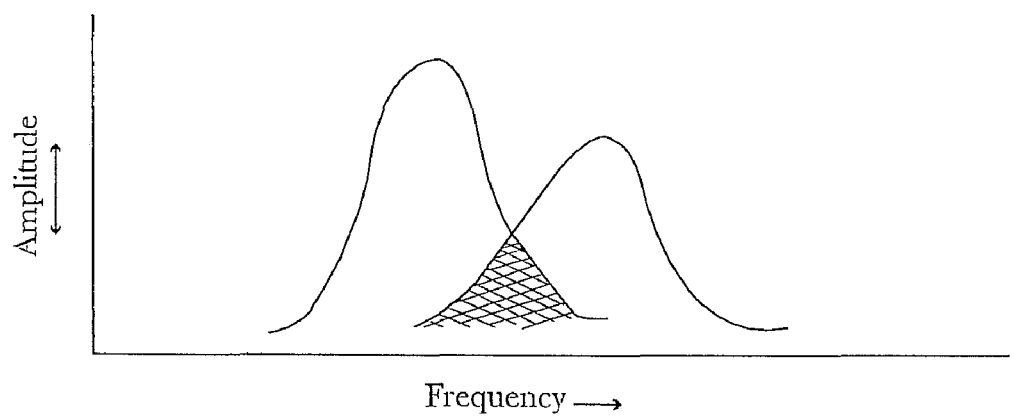

Temperature affects the line width of spectral curves. Line width can affect catalyst performance, chemical reactions and/or reaction pathways At low temperatures, the spectral curves of chemical species will be separate and distinct, with a lesser possibility for the transfer of resonant energy between potential reaction system components (see FIG. 17a). However, as the line widths of potentially reactive chemical species broaden, their spectral curves may start to overlap with spectral curves of other chemical species (see FIG. 17b). When frequencies match, or spectral energy patterns overlap, energy transfers. Thus, when temperatures are low, frequencies do not match and reactions are slow. At higher temperatures, resonant transfer of energy can take place and reactions can proceed very quickly or proceed along a different reaction pathway than they otherwise would have at a lower temperature.

Figure 18A:
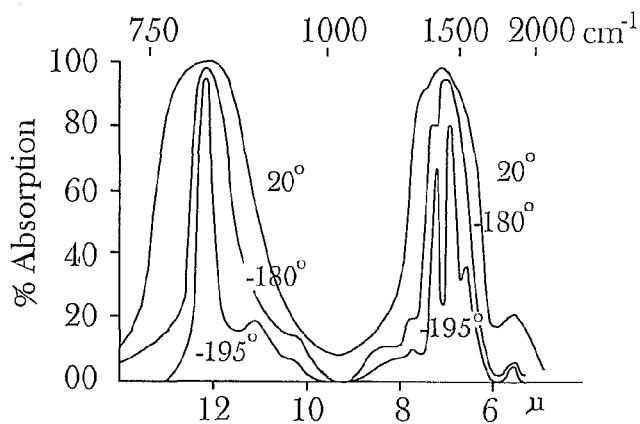
FIG. 18a shows the influence of temperature on the resolution of infrared absorption spectra.
Figure 18B:
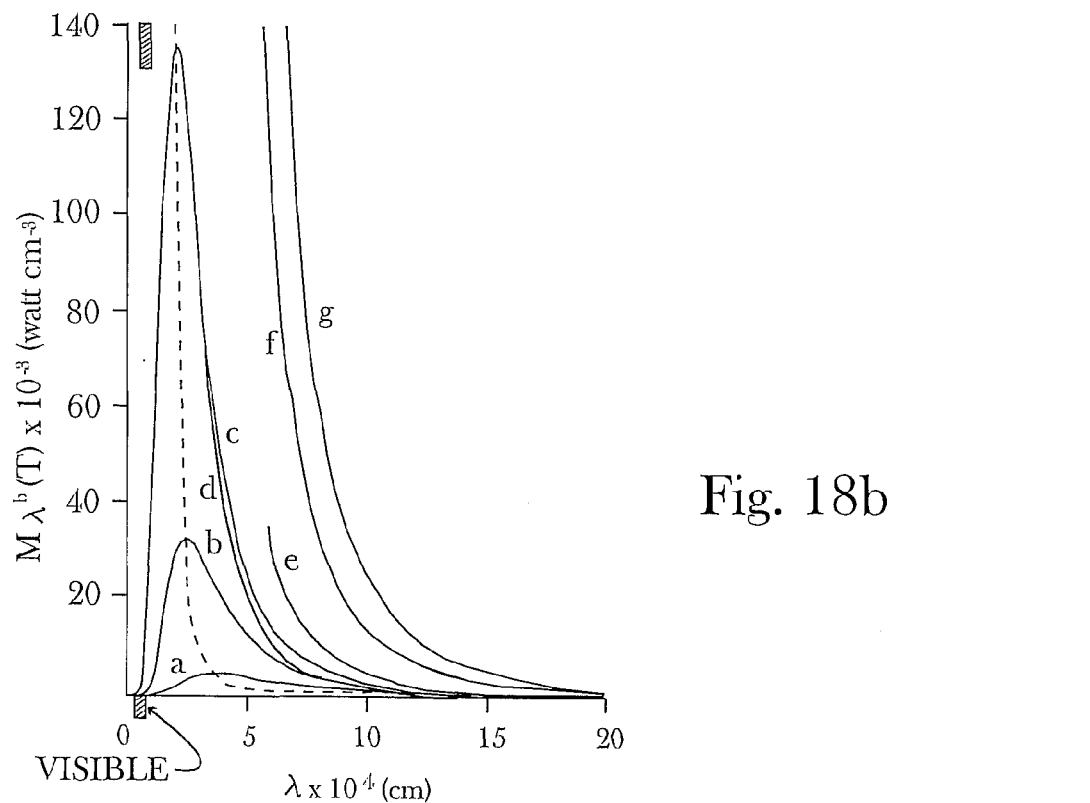
FIG. 18b shows blackbody radiation.
Figure 18C:
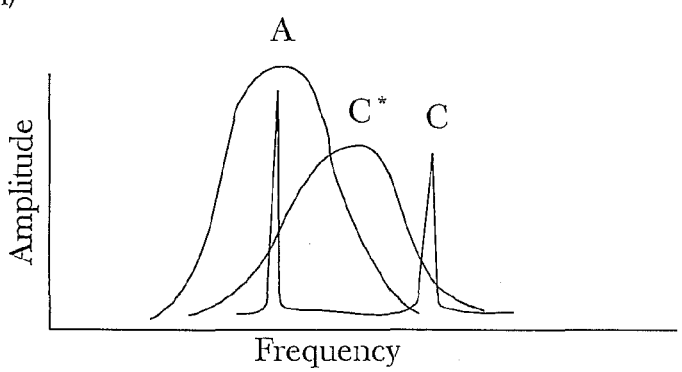
FIG. 18c shows curves A and C at low temperature, and broadened curves A and C* at higher temperature, with C* also shifted.

Besides affecting the line width of the spectral curves, temperature also can change, for example, the resonant frequency of reaction system components. For some chemical species, the resonant frequency will shift as temperature changes. This can be seen in the infrared absorption spectra in FIG. 18a and blackbody radiation graphs shown in FIG. 18b. Further, atoms and molecules do not all shift their resonant frequencies by the same amount or in the same direction, when they are at the same temperature. This can also affect catalyst performance. For example, if a catalyst resonant frequency shifts more with increased temperature than the resonant frequency of its targeted chemical species, then the catalyst could end up matching the frequency of a chemical species, and resonance may be created where none previously existed (see FIG. 18c). Specifically, FIG. 18c shows catalyst "C" at low temperature and "C*" at high temperature. The catalyst "C*" resonates with reactant "A" at high temperatures, but not at low temperatures.

The amplitude or intensity of a spectral line may be affected by temperature also. For example, linear and symmetric rotor molecules will have an increase in intensity as the temperature is lowered while other molecules will increase intensity as the temperature is raised. These changes of spectral intensity can also affect catalyst performance. Consider the example where a low intensity spectral curve of a catalyst is resonant with one or more frequencies of a specific chemical target. Only small amounts of energy can be transferred from the catalyst to the target chemical (e.g., a hydroxy intermediate). As temperature increases, the amplitude of the catalyst's curve increases also. In this example, the catalyst can transfer much larger amounts of energy to the chemical target when the temperature is raised.

If the chemical target is the intermediate chemical species for an alternative reaction route, the type and ratio of end products may be affected. By examining the above cyclohexene/palladium reaction again, at temperatures below 300° C., the products are benzene and hydrogen gas. However, when the temperature is above 300° C., the products are benzene and cyclohexane. Temperature is affecting the palladium and/ or other constituents in the reaction system (including, for example, reactants, intermediates, and/or products) in such a way that an alternative reaction pathway leading to the formation of cyclohexane is favored above 300° C. This could be a result of, for example, increased line width, altered resonance frequencies, or changes in spectral curve intensities for any of the components in the reaction system.

It is important to consider not only the spectral catalyst frequencies one may wish to use to catalyze a reaction, but also the reaction conditions under which those frequencies are supposed to work. For example, in the palladium/cyclohexene reaction at low temperatures, the palladium may match frequencies with an intermediate for the formation of hydrogen molecules ($H_2$). At temperatures above 300° C. the reactants and transients may be unaffected, but the palladium may have an increased line width, altered resonant frequency and/or increased intensity. The changes in the line width, resonant frequency and/or intensity may cause the palladium to match frequencies and transfer energy to an intermediate in the formation of cyclohexane instead. If a spectral catalyst was to be used to assist in the formation of cyclohexane at room temperature, the frequency for the cyclohexane intermediate would be more effective if used, rather than the spectral catalyst frequency used at room temperature.

Thus, it may be important to understand the reaction system dynamics in designing and selecting an appropriate spectral catalyst. The transfer of energy between different reaction system components will vary, depending on temperature. Once understood, this allows one to knowingly adjust temperature to optimize a reaction, reaction product, interaction and/or formation of reaction product at a desirable reaction rate, without the trial and error approaches of prior art. Further, it allows one to choose catalysts such as physical catalysts, spectral catalysts, and/or spectral energy patterns to optimize a desired reaction pathway. This understanding of the spectral impact of temperature allows one to perform customarily high temperature (and, sometimes high danger) chemical processes at safer, room temperatures. It also allows one to design physical catalysts which work at much broader temperature ranges (e.g., frigid arctic temperatures or hot furnace temperatures), as desired.

Pressure

Figure 19:
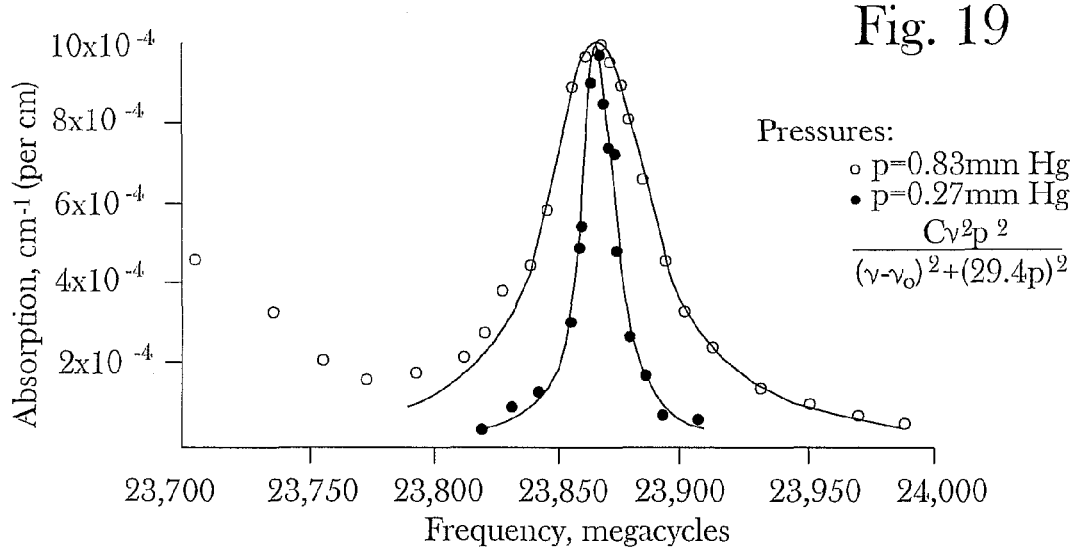
FIG. 19 shows spectral patterns which exhibit the effect of pressure broadening on the compound $NH_3$.

Pressure and temperature are directly related to each other. Specifically, from the ideal gas law, we know that $$PV=nRT$$

where P is pressure, V is volume, n is the number of moles of gas, R is the gas constant, and T is the absolute temperature. Thus, at equilibrium, an increase in temperature will result in a corresponding increase in pressure. Pressure also has an effect on spectral patterns. Specifically, increases in pressure can cause broadening and changes in spectral curves, just as increases in temperature do (see FIG. 19 which shows the pressure broadening effects on the $NH_3$ 3.3 absorption line).

Mathematical treatments of pressure broadening are generally grouped into either collision or statistical theories. In collision theories, the assumption is made that most of the time an atom or molecule is so far from other atoms or molecules that their energy fields do not interact. Occasionally, however, the atoms or molecules come so close together that they collide. In this case, the atom or molecule may undergo a change in wave phase (spectral) function, or may change to a different energy level. Collision theories treat the matter's emitted energy as occurring only when the atom or molecule is far from others, and is not involved in a collision. Because collision theories ignore spectral frequencies during collisions, collision theories fail to predict accurately chemical behavior at more than a few atmospheres of pressure, when collisions are frequent.

Statistical theories, however, consider spectral frequencies before, during and after collisions. They are based on calculating the probabilities that various atoms and/or molecules are interacting with, or perturbed by other atoms or molecules. The drawback with statistical treatments of pressure effects is that the statistical treatments do not do a good job of accounting for the effects of molecular motion. In any event, neither collision nor statistical theories adequately predict the rich interplay of frequencies and heterodynes that take place as pressure is increased. Experimental work has demonstrated that increased pressure can have effects similar to those produced by increased temperature, by:

1) broadening of the spectral curve, producing increased line width; and
2) shifting of the resonant frequency ($f_o$).

Figure 20:
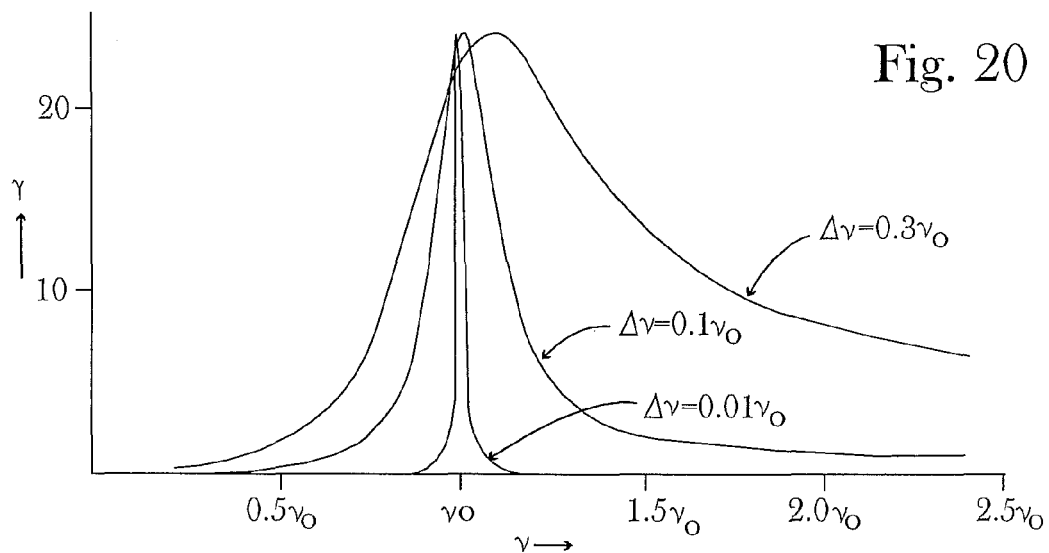
FIG. 20 shows the theoretical shape of pressure-broadened lines at three different pressures for a single compound.
Figure 21A:
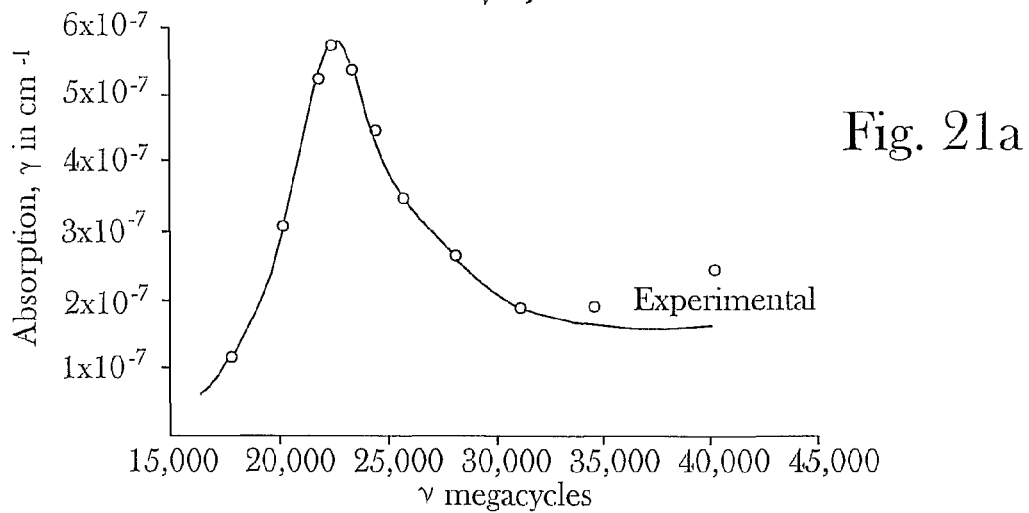
FIGS. 21a and 21b are two graphs which show experimental confirmation of changes in spectral patterns at increased pressures.
Figure 21B:
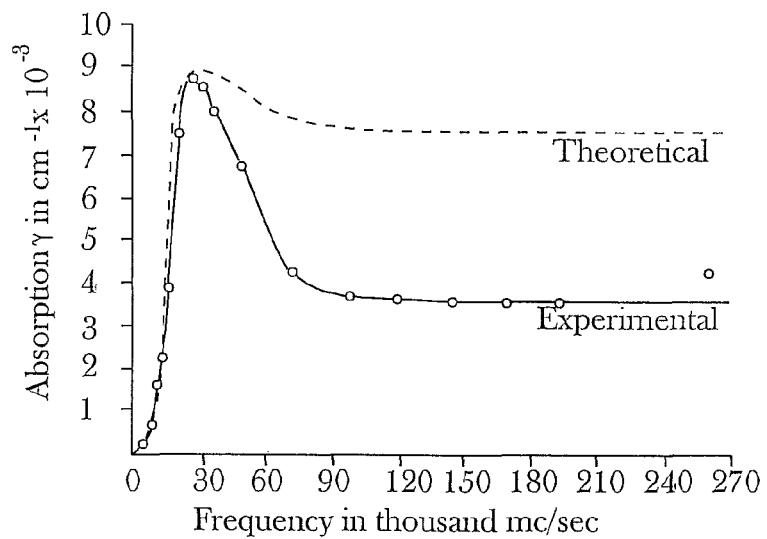

Pressure effects different from those produced by temperatures are: (1) pressure changes typically do not affect intensity, (see FIG. 20 which shows a theoretical set of curves exhibiting an unchanged intensity for three applied different pressures) as with temperature changes; and (2) the curves produced by pressure broadening are often less symmetric than the temperature-affected curves. Consider the shape of the three theoretical curves shown in FIG. 20. As the pressure increases, the curves become less symmetrical. A tail extending into the higher frequencies develops. This upper frequency extension is confirmed by the experimental work shown in FIG. 21. Specifically, FIG. 21a shows a pattern for the absorption by water vapor in air (10 g of $H_2O$ per cubic meter); and FIG. 21b shows the absorption in $NH_3$ at 1 atmosphere pressure.

Pressure broadening effects on spectral curves are broadly grouped into two types: resonance or "Holtsmark" broadening, and "Lorentz" broadening. Holtsmark broadening is secondary to collisions between atoms of the same element, and thus the collisions are considered to be symmetrical. Lorentz broadening results from collisions between atoms or molecules which are different. The collisions are asymmetric, and the resonant frequency, $f_o$, is often shifted to a lower frequency. This shift in resonant frequency is shown in FIG. 20. The changes in spectral curves and frequencies that accompany changes in pressure can affect catalysts, both physical and spectral, and chemical reactions and/or reaction pathways. At low pressures, the spectral curves tend to be fairly narrow and crisp, and nearly symmetrical about the resonant frequency. However, as pressures increase, the curves may broaden, shift, and develop high frequency tails.

At low pressures the spectral frequencies in the reaction system might be so different for the various atoms and molecules that there may be little or no resonant effect, and thus little or no energy transfer. At higher pressures, however, the combination of broadening, shifting and extension into higher frequencies can produce overlapping between the spectral curves, resulting in the creation of resonance, where none previously existed, and thus, the transfer of energy. The reaction system may proceed down one reaction pathway or another, depending on the changes in spectral curves produced by various pressure changes. One reaction pathway may be resonant and proceed at moderate pressure, while another reaction pathway may be resonant and predominate at higher pressures. As with temperature, it is important to consider the reaction system frequencies and mechanisms of action of various catalysts under the environmental reaction conditions one wishes to duplicate. Specifically, in order for an efficient transfer of energy to occur between, for example, a spectral catalyst and at least one reactant in a reaction system, there must be at least some overlap in frequencies.

For example, a reaction with a physical catalyst at 400 THz and a key transient at 500 THz may proceed slowly at atmospheric pressure. Where the frequency pressure is raised to about five (5) atmospheres, the catalyst broadens out through the 500 THz, for example, of the transient. This allows the transfer of energy between the catalyst and transient by, for example, energizing and stimulating the transient. The reaction then proceeds very quickly. Without wishing to be bound by any particular theory or explanation, it appears that, the speed of the reaction has much less to do with the number of collisions (as taught by the prior art) than it has to do with the spectral patterns of the reaction system components. In the above example, the reaction could be energized at low pressures by applying the 500 THz frequency to directly stimulate the key transient. This could also be accompanied indirectly using various heterodynes, (e.g., @1,000 THz harmonic, or a 100 THz non-harmonic heterodyne between the catalyst and transient (500 THz–400 THz=100 THz.).

As shown herein, the transfer of energy between different reaction system components will vary, depending on pressure. Once understood, this allows one to knowingly adjust pressure to optimize a reaction, without the trial and error approaches of prior art. Further, it allows one to choose catalysts such as physical catalysts, spectral catalysts, and/or spectral energy patterns to optimize one or more desired reaction pathways. This understanding of the spectral impact of pressure allows one to perform customarily high pressure (and thus, typically, high danger) chemical processes at safer, room pressures. It also allows one to design physical catalysts which work over a large range of acceptable pressures (e.g., low pressures approaching a vacuum to several atmospheres of pressure).

Surface Area

Traditionally, the surface are of a catalyst has been considered to be important because the available surface area controls the number of available binding sites. Supposedly, the more exposed binding sites, the more catalysis. In light of the spectral mechanisms disclosed in the present invention, surface area may be important for another reason.

Many of the spectral catalyst frequencies that correspond to physical catalysts are electronic frequencies in the visible light and ultraviolet regions of the spectrum. These high frequencies have relatively poor penetrance into, for example, large reaction vessels that contain one or more reactants. The high frequency spectral emissions from a catalyst such as platinum or palladium (or the equivalent spectral catalyst) will thus not travel very far into such a reaction system before such spectral emissions (or spectral catalysts) are absorbed. Thus, for example, an atom or molecule must be fairly close to a physical catalyst so that their respective electronic frequencies can interact.

Thus, surface area primarily affects the probability that a particular chemical species, will be close enough to the physical catalyst to interact with its electromagnetic spectra emission(s). With small surface area, few atoms or molecules will be close enough to interact. However, as surface area increases, so too does the probability that more atoms or molecules will be within range for reaction. Thus, rather than increasing the available number of binding sites, larger surface area probably increases the volume of the reaction system exposed to the spectral catalyst frequencies or patterns. This is similar to the concept of assuring adequate penetration of a spectral catalyst into a reaction system (e.g., assuming that there are adequate opportunities for species to interact with each other).

An understanding of the effects of surface area on catalysts and reaction system components allows one to knowingly adjust surface area and other reaction system components to optimize a reaction, reaction pathway and/or formation of reaction product(s), at a desirable reaction rate, without the drawbacks of the prior art. For instance, surface area is currently optimized by making catalyst particles as small as possible, thereby maximizing the overall surface area. The small particles have a tendency to, for example, sinter (merge or bond together) which decreases the overall surface area and catalytic activity. Rejuvenation of a large surface area catalyst can be a costly and time-consuming process. This process can be avoided with an understanding of the herein presented invention in the field of spectral chemistry. For example, assume a reaction is quickly catalyzed by a 3 $m^2$ catalyst bed (in a transfer of energy from catalyst to a key reactant and product). After sintering takes place, however, the surface area is reduced to 1 $m^2$. Thus, the transfer of energy from the catalyst is dramatically reduced, and the reaction slows down. The costly and time consuming process of rejuvenating the surface area can be avoided (or at least delayed) by augmenting the reaction system with one or more desirable spectral energy patterns. In addition, because spectral energy patterns can affect the final physical form or phase of a material, as well as its chemical formula, the sintering process itself may be reduced or eliminated.

Catalyst Size and Shape

In a related line of reasoning, catalyst size and shape are classically thought to affect physical catalyst activity. Selectivity of reactions controlled by particle size has historically been used to steer catalytic pathways. As with surface area, certain particle sizes are thought to provide a maximum number of active binding sites and thus maximize the reaction rate. The relationship between size and surface area has been previously discussed.

Figure 22A:
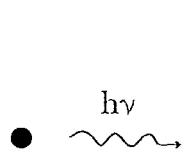
FIG. 22a shows a representation of radiation from a single atom and FIG. 22b shows a representation of radiation from a group of atoms.
Figure 22B:
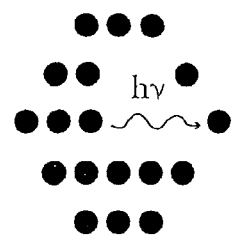
Figure 23A:
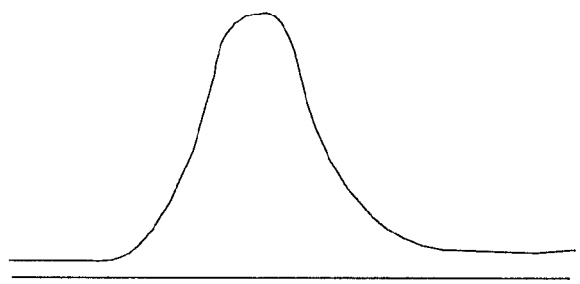
FIGS. 23a-d show four different spectral curves, three of which exhibit self-absorption patterns.
Figure 23B:
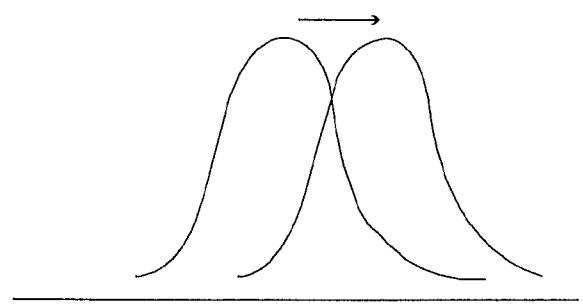
Figure 23C:
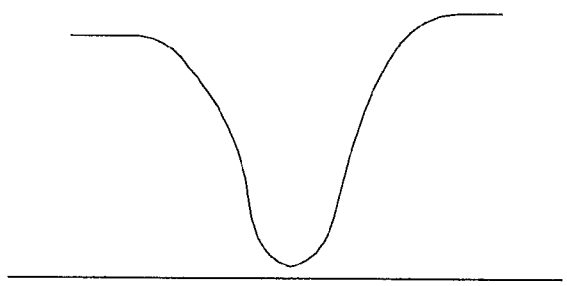
Figure 23D:
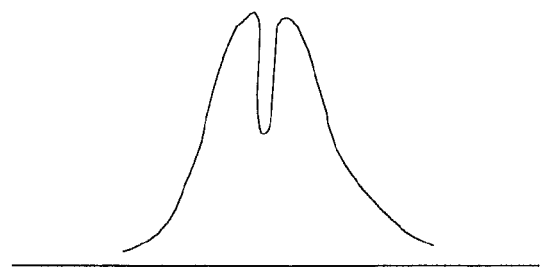

In light of the current understanding of the spectral mechanisms underlying the activity of physical catalysts and reactions in general, catalyst size and shape may be important for other reasons. One of those reasons is a phenomenon called "self absorption". When a single atom or molecule produces its' classical spectral pattern it radiates electromagnetic energy which travels outward from the atom or molecule into neighboring space. FIG. 22a shows radiation from a single atom versus radiation from a group of atoms as shown in FIG. 22b. As more and more atoms or molecules group together, radiation from the center of the group is absorbed by its' neighbors and may never make it out into space. Depending on the size and shape of the group of atoms, self absorption can cause a number of changes in the spectral emission pattern (see FIG. 23). Specifically, FIG. 23a shows a normal spectral curve produced by a single atom; FIG. 23b shows a resonant frequency shift due to self absorption; FIG. 23c shows a self-reversal spectral pattern produced by self absorption in a group of atoms and FIG. 23d shows a self-reversal spectral pattern produced by self absorption in a group of atoms. These changes include a shift in resonant frequency and self-reversal patterns.

The changes in spectral curves and frequencies that accompany changes in catalyst size and shape can affect catalysts, chemical reactions and/or reaction pathways. For example, atoms or molecules of a physical catalyst may produce spectral frequencies in the reaction system which resonate with a key transient and/or reaction product. With larger groups of atoms, such as in a sintered catalyst, the combination of resonant frequency shifting and self-reversal may eliminate overlapping between the spectral curves of chemical species, thereby minimizing or destroying conditions of resonance.

A reaction system may proceed down one reaction pathway or another, depending on the changes in spectral curves produced by the particle sizes. For example, a catalyst having a moderate particle size may proceed down a first reaction pathway while a larger size catalyst may direct the reaction down another reaction pathway.

The changes in spectral curves and frequencies that accompany changes in catalyst size and shape are relevant for practical applications. Industrial catalysts are manufactured in a range of sizes and shapes, depending on the design requirements of the process and the type of reactor used. Catalyst activity is typically proportional to the surface area of the catalyst bed in the reactor. Surface area increases as the size of the catalyst particles decreases. Seemingly, the smaller the catalyst particles, the better for industrial applications. This is not always the case, however. When a very fine bed of catalyst particles is used, high pressures may be required to force the reacting chemicals across or through the catalyst bed. The chemicals enter the catalyst bed under high pressure, and exit the bed (e.g., the other side) at a lower pressure. This large difference between entry and exit pressures is called a "pressure drop". A compromise is often required between catalyst size, catalyst activity, and pressure drop across the catalyst bed.

The use of spectral catalysts according to the present invention allows for much finer tuning of this compromise. For example, a large catalyst size can be used so that pressure drops across the catalyst bed are minimized. At the same time, the high level of catalyst activity obtained with a smaller catalyst size can still be obtained by, for example, augmenting the physical catalyst with at least a portion of one or more spectral catalyst(s).

For example, assume that a 10 mm average particle size catalyst has 50% of the activity of a 5 mm average particle size catalyst. With a 5 mm-diameter catalyst, however, the pressure drop across the reactor may be so large that the reaction cannot be economically performed. The compromise in historical processes has typically been to use twice as much of the 10 mm catalyst, to obtain the same, or approximately the same, amount of activity as with the original amount of 5 mm catalyst. However, an alternative desirable approach is to use the original amount of 10 mm physical catalyst and augment the physical catalyst with at least a portion of at least one spectral catalyst. Catalyst activity can be effectively doubled (or increased even more) by the spectral catalyst, resulting in approximately the same degree of activity (or perhaps even greater activity) as with the 5 mm catalyst. Thus, the present invention permits the size of the catalyst to be larger, while retaining favorable reactor vessel pressure conditions so that the reaction can be performed economically, using half as much (or less) physical catalyst as compared to traditional prior art approaches.

Another manner to approach the problem of pressure drops in physical catalyst beds, is to eliminate the physical catalyst completely. For example, in another embodiment of the invention, a fiberoptic sieve, (e.g., one with very large pores) can be used in a flow-through reactor vessel. If the pore size is designed to be large enough there can be virtually no pressure drop across the sieve, compared to a pressure drop accompanying the use of a 5 mm diameter or even a 10 mm diameter physical catalyst discussed above. According to the present invention, the spectral catalyst can be emitted through the fiberoptic sieve, thus catalyzing the reacting species as they flow by. This improvement over the prior art approaches has significant processing implications including lower costs, higher rates and improved safety, to mention only a few.

Industrial catalysts are also manufactured in a range of shapes, as well as sizes. Shapes include spheres, irregular granules, pellets, extrudate, and rings. Some shapes are more expensive to manufacture than others, while some shapes have superior properties (e.g., catalyst activity, strength, and less pressure drop) than others. While spheres are inexpensive to manufacture, a packed bed of spheres produces high pressure drops and the spheres are typically not very strong. Physical catalyst rings on the other hand, have superior strength and activity and produce very little pressure drop, but they are also relatively expensive to produce.

Spectral energy catalysts permit a greater flexibility in choosing catalyst shape. For example, instead of using a packed bed of inexpensive spheres, with the inevitable high pressure drop and resulting mechanical damage to the catalyst particles, a single layer of spheres augmented, for example, with a spectral energy catalyst can be used. This catalyst is inexpensive, activity is maintained, and large pressure drops are not produced, thus preventing mechanical damage and extending the useful life of physical catalyst spheres. Similarly, far smaller numbers of catalyst rings can be used while obtaining the same or greater catalyst activity by, for example, supplementing with at least a portion of a spectral catalyst. The process can proceed at a faster flow-through rate because the catalyst bed will be smaller relative to a bed that is not augmented with a spectral catalyst.

The use of spectral energy catalysts and/or spectral environmental reaction conditions to augment existing physical catalysts has the following advantages:

permit the use of less expensive shaped catalyst particles;
permit the use of fewer catalyst particles overall;
permit the use of stronger shapes of catalyst particles; and
permit the use of catalyst particle shapes with better pressure drop characteristics.

Their use to replace existing physical catalysts has similar advantages:

eliminate the use and expense of catalyst particles altogether;
allow use of spectral catalyst delivery systems that are stronger; and
delivery systems can be designed to incorporate superior pressure drop characteristics.

Catalyst size and shape are also important to spectral emission patterns because all objects have an NOF depending on their size and shape. The smaller an object is in dimension, the higher its NOF will be in frequency (because speed=length× frequency). Also, two (2) objects of the same size, but different shape will have different NOF's (e.g., the resonant NOF frequency of a 1.0 m diameter sphere, is different from the NOF for a 1.0 m edged cube). Wave energies (both acoustic and EM) will have unique resonant frequencies for particular objects. The objects, such as physical catalyst particles or powder granules of reactants in a slurry, will act like antennas, absorbing and emitting energies at their structurally resonant frequencies. With this understanding, one is further able to manipulate and control the size and shape of reaction system components (e.g., physical catalysts, reactants, etc.) to achieve desired effects. For example, a transient for a desired reaction pathway may produce a spectral rotational frequency of 30 GHz. Catalyst spheres 1 cm in diameter with structural EM resonant frequency of 30 GHz ($3 \times 10^8$ m/s $1 \times 10^{-2}$ m=$30 \times 10^9$ Hz), can be used to catalyze the reaction. The catalyst particles will structurally resonate with the rotational frequency of the transient, providing energy to the transient and catalyzing the reaction. Likewise, the structurally resonant catalyst particles may be farther energized by a spectral energy catalyst, such as, for example, 30 GHz microwave radiation. Thus understood, the spectral dynamics of chemical reactions can be much more precisely controlled than in prior art trial and error approaches.

Solvents

Typically, the term solvent is applied to mixtures for which the solvent is a liquid, however, it should be understood that solvents may also comprise solids, liquids, gases or plasmas and/or mixtures and/or components thereof. The prior art typically groups liquid solvents into three broad classes: aqueous, organic, and non-aqueous. If an aqueous solvent is used, it means that the solvent is water. Organic solvents include hydrocarbons such as alcohols and ethers. Non-aqueous solvents include inorganic non-water substances. Many catalyzed reactions take place in solvents.

Because solvents are themselves composed of atoms, molecules and/or ions they can have pronounced effects on chemical reactions. Solvents are comprised of matter and they emit their own spectral frequencies. The present invention teaches that these solvent frequencies undergo the same basic processes discussed earlier, including heterodyning, resonance, and harmonics. Spectroscopists have known for years that a solvent can dramatically affect the spectral frequencies produced by its' solutes. Likewise, chemists have known for years that solvents can affect catalyst activity. However, the spectroscopists and chemists in the prior art have apparently not associated these long studied changes in solute frequencies with changes in catalyst activity. The present invention recognizes that these changes in solute spectral frequencies can affect catalyst activity and chemical reactions and/or reaction pathways in general, changes include spectral curve broadening. Changes of curve intensity, gradual or abrupt shifting of the resonant frequency $f_o$, and even abrupt rearrangement of resonant frequencies.

Figure 24A:
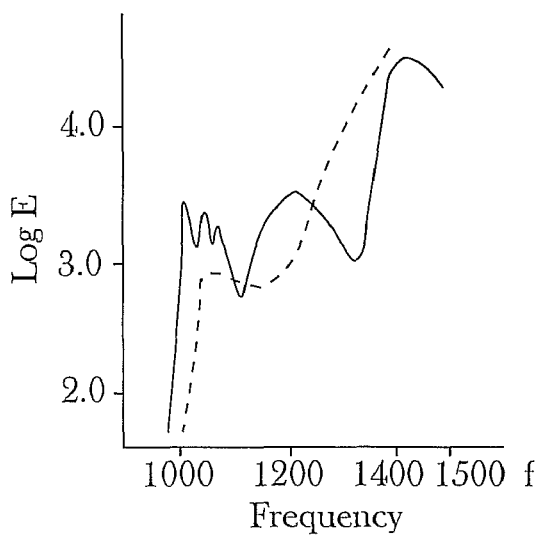
FIG. 24a shows an absorption spectra of alcohol and phthalic acid in hexane.

When reviewing FIG. 24a, the solid line represents a portion of the spectral pattern of phthalic acid in alcohol while the dotted line represents phthalic acid in the solvent hexane. Consider a reaction taking place in alcohol, in which the catalyst resonates with phthalic acid at a frequency of 1,250, the large solid curve in the middle. If the solvent is changed to hexane, the phthalic acid no longer resonates at a frequency of 1,250 and the catalyst can not stimulate and energize it. The change in solvent will render the catalyst ineffective.

Figure 24B:
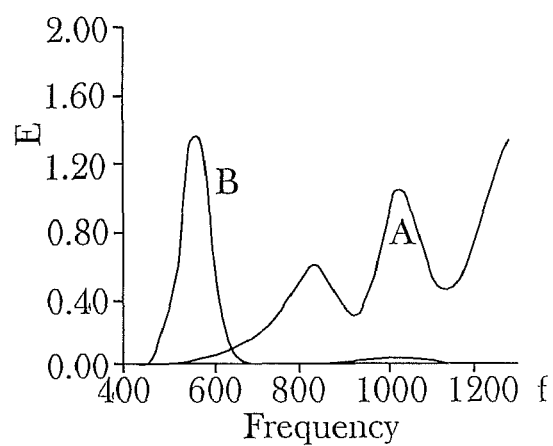
FIG. 24b shows an absorption spectra for the absorption of iodine in alcohol and carbon tetracholoride.

Similarly, in reference to FIG. 24b, iodine produces a high intensity curve at 580 when dissolved in carbon tetrachloride, as shown in curve B. In alcohol, as shown by curve A the iodine produces instead, a moderate intensity curve at 1,050 and a low intensity curve at 850. Accordingly, assume that a reaction uses a spectral catalyst that resonates directly with the iodine in carbon tetrachloride at 580. If the spectral catalyst does not change and the solvent is changed to alcohol, the spectral catalyst will no longer function because frequencies no longer match and energy will not transfer. Specifically, the spectral catalyst's frequency of 580 will no longer match and resonate with the new iodine frequencies of 850 and 1,050.

However, there is the possibility that the catalyst will change its spectral pattern with a change in the solvent. The catalyst could change in a similar manner to the iodine, in which case the catalyst may continue to catalyze the reaction regardless of the change in solvent. Conversely, the spectral catalyst pattern could change in a direction opposite to the spectral pattern of the iodine. In this instance, the catalyst will again fail to catalyze the original reaction. There is also the possibility that the change in the catalyst could bring the catalyst into resonance with a different chemical species and help the reaction proceed down an alternative reaction pathway.

Figure 24C:
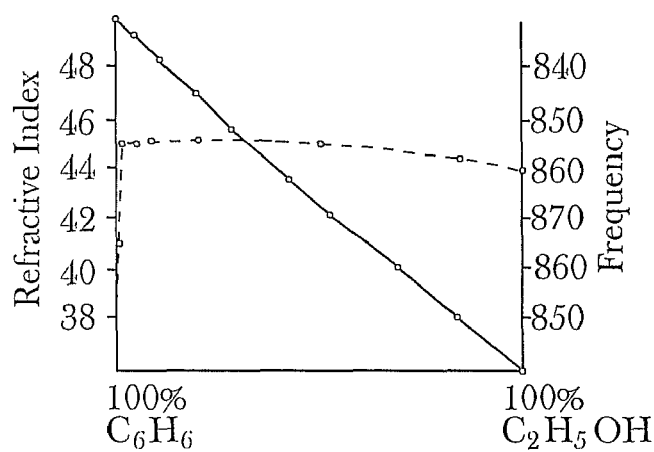
FIG. 24c shows the effect of mixtures of alcohol and benzene on the solute phenylazophenol.

Finally, consider the graph in FIG. 24c, which shows a variety of solvent mixtures ranging from 100% benzene at the far left, to a 50:50 mixture of benzene and alcohol in the center, to 100% alcohol at the far right. The solute is phenylazophenol. The phenylazophenol has a frequency of 855-860 for most of the solvent mixtures. For a 50:50 benzene:alcohol mixture the frequency is 855; or for a 98:2 benzene:alcohol mixture the frequency is still 855. However, at 99.5:0.5 benzene:alcohol mixture, the frequency abruptly changes to about 865. A catalyst active in 100% benzene by resonating with the phenylazophenol at 865, will lose its activity if there is even a slight amount of alcohol (e.g., 0.5%) in the solvent.

Thus understood, the principles of spectral chemistry presented herein can be applied to catalysis, and reactions and/or reaction pathways in general. Instead of using the prior art trial and error approach to the choice of solvents and/or other reaction system components, solvents can be tailored and/or modified to optimize the spectral environmental reaction conditions. For example, a reaction may have a key reaction participant which resonates at 400 THz, while the catalyst resonates at 800 THz transferring energy harmonically. Changing the solvent may cause the resonant frequencies of both the participant and the catalyst to abruptly shift to 600 THz. There the catalyst would resonate directly with the participant, transferring even more energy, and catalyzing the reaction system more efficiently.

Support Materials

Catalysts can be either unsupported or supported. An unsupported catalyst is a formulation of the pure catalyst, with substantially no other molecules present. Unsupported catalysts are rarely used industrially because these catalysts generally have low surface area and hence low activity. The low surface area can result from, for example, sintering, or coalescence of small molecules of the catalyst into larger particles in a process which reduces surface tension of the particles. An example of an unsupported catalyst is platinum alloy gauze, which is sometimes used for the selective oxidation of ammonia to nitric oxide. Another example is small silver granules, sometimes used to catalyze the reaction of methanol with air, to form formaldehyde. When the use of unsupported catalysts is possible, their advantages include straightforward fabrication and relatively simple installation in various industrial processes.

A supported catalyst is a formulation of the catalyst with other particles, the other particles acting as a supporting skeleton for the catalyst. Traditionally, the support particles are thought to be inert, thus providing a simple physical scaffolding for the catalyst molecules. Thus, one of the traditional functions of the support material is to give the catalyst shape and mechanical strength. The support material is also said to reduce sintering rates. If the catalyst support is finely divided similar to the catalyst, the support will act as a "spacer" between the catalyst particles, and hence prevent sintering. An alternative theory holds that an interaction takes place between the catalyst and support, thereby preventing sintering. This theory is supported by the many observations that catalyst activity is altered by changes in support material structure and composition.

Supported catalysts are generally made by one or more of the following three methods: impregnation, precipitation, and/or crystallization. Impregnation techniques use preformed support materials, which are then exposed to a solution containing the catalyst or its precursors. The catalyst or precursors diffuse into the pores of the support. Heating, or another conversion process, drives off the solvent and transforms the catalyst or precursors into the final catalyst. The most common support materials for impregnation are refractory oxides such as aluminas and aluminum hydrous oxides. These support materials have found their greatest use for catalysts that must operate under extreme conditions such as steam reforming, because they have reasonable mechanical strengths.

Precipitation techniques use concentrated solutions of catalyst salts (e.g., usually metal salts). The salt solutions are rapidly mixed and then allowed to precipitate in a finely divided form. The precipitate is then prepared using a variety of processes including washing, filtering, drying, heating, and pelleting. Often a graphitic lubricant is added. Precipitated catalysts have high catalytic activity secondary to high surface area, but they are generally not as strong as impregnated catalysts.

Figure 25A:
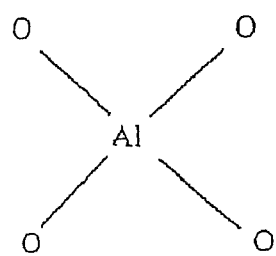
FIG. 25a shows a tetrahedral unit representation of aluminum oxide and FIG. 25b shows a representation of a tetrahedral units for silicon dioxide.
Figure 25B:
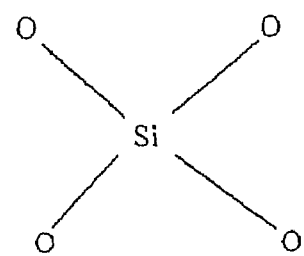
Figure 26A:
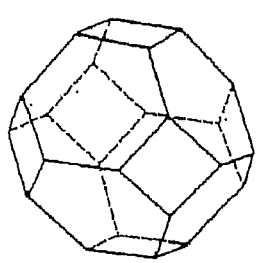
FIG. 26a shows a truncated octahedron crystal structure for aluminum or silicon combined with oxygen and FIG. 26b shows a plurality of truncated octahedrons joined together to represent zeolite.
Figure 26A:
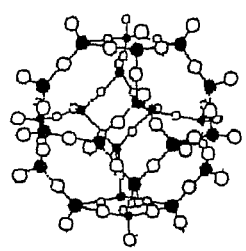
Figure 26B:
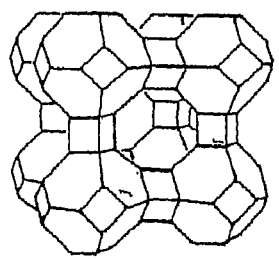
Figure 26C:
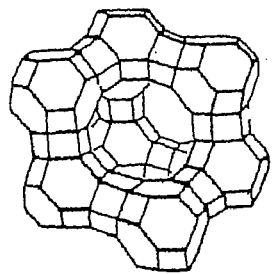
FIG. 26c shows truncated octahedrons for zeolites "X" and "Y" which are joined together by oxygen bridges.

Crystallization techniques produce support materials called zeolites. The structure of these crystallized catalyst zeolites is based on $SiO_4$ and $AlO_4$ (see FIG. 25a which shows the tetrahedral units of silicon; and FIG. 25b which shows the tetrahedral units of aluminum). These units link in different combinations to form structural families, which include rings, chains, and complex polyhedra. For example, the $SiO_4$ and $AlO_4$ tetrahdderal units can form truncated octahedron structures, which form the building blocks for A, X, and Y zeolites (see FIG. 26a which shows a truncated octahedron structure with lines representing oxygen atoms and corners are Al or Si atoms; FIG. 26b which shows zeolite with joined truncated octahedrons joined by oxygen bridges between square faces; and FIG. 26c which shows zeolites X and Y with joined truncated octahedrons joined by oxygen bridges between hexagonal faces).

The crystalline structure of zeolites gives them a well defined pore size and structure. This differs from the varying pore sizes found in impregnated or precipitated support materials. Zeolite crystals are made by mixing solutions of silicates and aluminates and the catalyst. Crystallization is generally induced by heating (see spectral effects of temperature in the Section entitled "Temperature"). The structure of the resulting zeolite depends on the silicon/aluminum ratio, their concentration, the presence of added catalyst, the temperature, and even the size of the reaction vessels used, all of which are environmental reaction conditions. Zeolites generally have greater specificity than other catalyst support materials (e.g., they do not just speed up the reaction). They also may steer the reaction towards a particular reaction pathway.

Support materials can affect the activity of a catalyst. Traditionally, the prior art has attributed these effects to geometric factors. However, according to the present invention, there are spectral factors to consider as well. It has been well established that solvents affect the spectral patterns produced by their solutes. Solvents can be liquids, solids, gases and/or plasmas Support materials can, in many cases, be viewed as nothing more than solid solvents for catalysts. As such, support materials can affect the spectral patterns produced by their solute catalysts.

Just as dissolved sugar can be placed into a solid phase solvent (ice), catalysts can be placed into support materials that are solid phase solvents. These support material solid solvents can have similar spectral effects on catalysts that liquid solvents have. Support materials can change spectral frequencies of their catalyst solutes by, for example, causing spectral curve broadening, changing of curve intensity, gradual or abrupt shifting of the resonant frequency $f_o$, and even abrupt rearrangement of resonant frequencies.

Thus, due to the disclosure herein, it should become clear to an artisan of ordinary skill that changes in support materials can have dramatic effects on catalyst activity. The support materials affect the spectral frequencies produced by the catalysts. The changes in catalyst spectral frequencies produce varying effects on chemical reactions and catalyst activity, including accelerating the rate of reaction and also guiding the reaction on a particular reaction path. Thus support materials can potentially influence the matching of frequencies and can thus favor the possibility of transferring energy between reaction system components and/or spectral energy patterns, thus permitting certain reactions to occur.

Poisoning

Poisoning of catalysts occurs when the catalyst activity is reduced by adding a small amount of another constituent, such as a chemical species. The prior art has attributed poisoning to chemical species that contain excess electrons (e.g., electron donor materials) and to adsorption of poisons onto the physical catalyst surface where the poison physically blocks reaction sites. However, neither of these theories satisfactorily explains poisoning.

Consider the case of nickel hydrogenation catalysts. These physical catalysts are substantially deactivated if only 0.1% sulphur compounds by weight are adsorbed onto them. It is difficult to believe that 0.1% sulphur by weight could contribute so many electrons as to inactivate the nickel catalyst. Likewise, it is difficult to believe that the presence of 0.1% sulphur by weight occupies so many reaction sites that it completely deactivates the catalyst. Accordingly, neither prior art explanation is satisfying.

Poisoning phenomena can be more logically understood in terms of spectral chemistry. In reference to the example in the Solvent Section using a benzene solvent and phenylazophenol as the solute, in pure benzene the phenylazophenol had a spectral frequency of 865 Hz. The addition of just a few drops of alcohol (0.5%) abruptly changed the phenylazophenol frequency to 855. If the expectation was for the phenylazophenol to resonate at 865, then the alcohol would have poisoned that particular reaction. The addition of small quantities of other chemical species can change the resonant frequencies ($f_o$) of catalysts and reacting chemicals. The addition of another chemical species can act as a poison to take the catalyst and reacting species out of resonance. (i.e., the presence of the additional species can remove any substantial overlapping of frequencies and thus prevent any significant transfer of energy).

Figure 27:
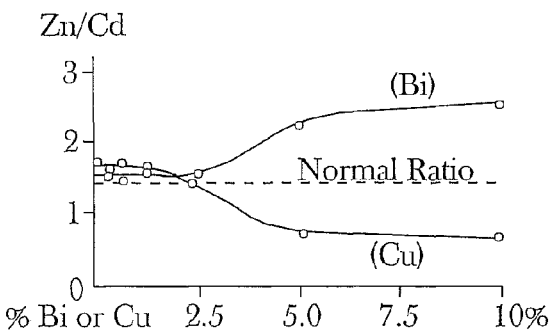
FIG. 27 is a graph which shows the influence of copper and bismuth on zinc/cadmium line ratios.

Besides changing resonant frequencies of chemical species, adding small amounts of other chemicals can also affect the spectral intensities of the catalyst and, for example, other atoms and molecules in the reaction system by either increasing or decreasing the spectral intensities. Consider cadmium and zinc mixed in an alumina-silica precipitate (see FIG. 27 which shows the influences of copper and bismuth on the zinc/cadmium line ratio). A normal ratio between the cadmium 3252.5 spectral line and the zinc 3345.0 spectral line was determined. The addition of sodium, potassium, lead, and magnesium had little or no effect on the Cd/Zn intensity ratio. However, the addition of copper reduced the relative intensity of the zinc line and increased the cadmium intensity. Conversely, addition of bismuth increased the relative intensity of the zinc line while decreasing cadmium.

Figure 28:
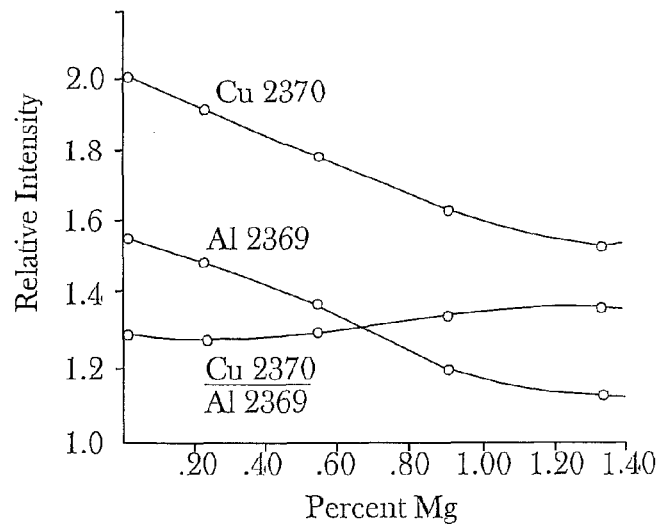
FIG. 28 is a graph which shows the influence of magnesium on copper/aluminum intensity ratio.

Also, consider the effect of small amounts of magnesium on a copper-aluminum mixture (see FIG. 28 which shows the influence of magnesium on the copper aluminum intensity ratio). Magnesium present at 0.6%, caused significant reductions in line intensity for copper and for aluminum. At 1.4% magnesium, the spectral intensities for both copper and aluminum were reduced by about a third. If the copper frequency is important for catalyzing a reaction, adding this small amount of magnesium would dramatically reduce the catalyst activity. Thus, it could be concluded that the copper catalyst had been poisoned by the magnesium.

In summary, poisoning effects on catalysts are due to spectral changes. Adding a small amount of another chemical species to a physical catalyst and/or reaction system can change the resonance frequencies or the spectral intensities of one or more chemical species (e.g., reactant). The catalyst might remain the same, while a crucial intermediate is changed. Likewise, the catalyst might change, while the intermediate stays the same. They might both change, or they might both stay the same and be oblivious to the added poison species. This understanding is important to achieving the goals of the present invention which include targeting species to cause an overlap in frequencies, or in this instance, specifically targeting one or more species so as to prevent any substantial overlap in frequencies and thus prevent reactions from occurring by blocking the transfer of energy.

Promoters

Just as adding a small amount of another chemical species to a catalyst and reaction system can poison the activity of the catalyst, the opposite can also happen. When an added species enhances the activity of a catalyst, it is called a promoter. For instance, adding a few percent calcium and potassium oxide to iron-alumina compounds promotes activity of the iron catalyst for ammonia synthesis. Promoters act by all the mechanisms discussed previously in the Sections entitled Solvents, Support Materials, and Poisoning. Not surprisingly, some support materials actually are promoters. Promoters enhance catalysts and specific reactions and/or reaction pathways by changing spectral frequencies and intensities. While a catalyst poison takes the reacting species out of resonance (i.e., the frequencies do not overlap), the promoter brings them into resonance (i.e., the frequencies do overlap). Likewise, instead of reducing the spectral intensity of crucial frequencies, the promoter may increase the crucial intensities.

Thus, if it was desired for phenylazophenol to react at 855 in a benzene solvent, alcohol could be added and the alcohol would be termed a promoter. If it was desired for the phenylazophenol too react at 865, alcohol could be added and the alcohol could be considered a poison. Thus understood, the differences between poisons and promoters are a matter of perspective, and depend on which reaction pathways and/or reaction products are desired. They both act by the same underlying spectral chemistry mechanisms of the present invention.

Concentration

Figure 29:
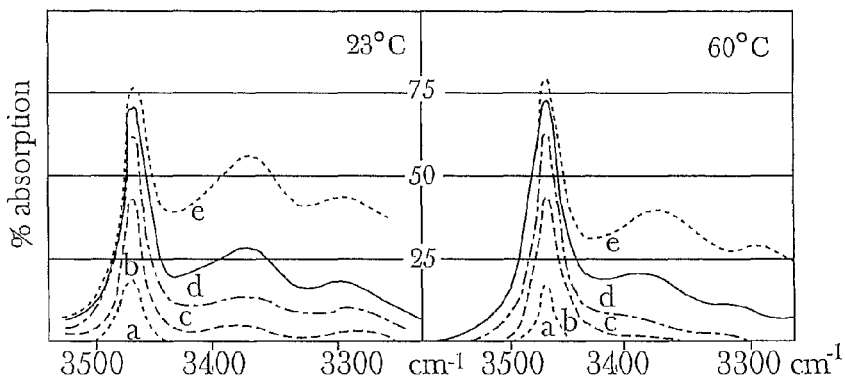
FIG. 29 shows the concentration effects on the atomic spectra frequencies of N-methyl urethane in carbon tetrachloride solutions at the following concentrations: a) 0.01M; b) 0.03M; c) 0.06M; d) 0.10M; 3) 0.15M.

Concentrations of chemical species are known to affect reaction rates and dynamics. Concentration also affects catalyst activity. The prior art explains these effects by the probabilities that various chemical species will collide with each other. At high concentrations of a particular species, there are many individual atoms or molecules present. The more atoms or molecules present, the more likely they are to collide with something else. However, this statistical treatment by the prior art does not explain the entire situation. FIG. 29 shows various concentrations of N-methyl urethane in a carbon tetrachloride solution. At low concentrations, the spectral lines have a relatively low intensity. However, as the concentration is increased, the intensities of the spectral curves increase also. At 0.01 molarity, the spectral curve at 3,460 $cm^{-1}$ is the only prominent frequency. However, at 0.15 molarity, the curves at 3,370 and 3,300 $cm^{-1}$ are also prominent.

As the concentration of a chemical species is changed, the spectral character of that species in the reaction mixture changes also. Suppose that 3,300 and 3,370 $cm^{-1}$ are important frequencies for a desired reaction pathway. At low concentrations the desired reaction pathway will not occur. However, if the concentrations are increased (and hence the intensities of the relevant frequencies) the reaction will proceed down the desired pathway. Concentration is also related to solvents, support structures, poisons and promoters, as previously discussed.

Fine Structure Frequencies

The field of science concerned generally with measuring the frequencies of energy and matter, known as spectroscopy, has already been discussed herein. Specifically, the three broad classes of atomic and molecular spectra were reviewed. Electronic spectra, which are due to electron transitions, have frequencies primarily in the ultraviolet (UV), visible, and infrared (IR) regions, and occur in atoms and molecules. Vibrational spectra, which are due to, for example, bond motion between individual atoms within molecules, are primarily in the IR, and occur in molecules. Rotational spectra are due primarily to rotation of molecules in space and have microwave or radiowave frequencies, and also occur in molecules.

The previous discussion of various spectra and spectroscopy has been oversimplified. There are actually at least three additional sets of spectra, which comprise the spectrum discussed above herein, namely, the fine structure spectra and the hyperfine structure spectra and the superfine structure spectra. These spectra occur in atoms and molecules, and extend, for example, from the ultraviolet down to the low radio regions. These spectra are often mentioned in prior art chemistry and spectroscopy books typically as an aside, because prior art chemists typically focus more on the traditional types of spectroscopy, namely, electronic, vibrational, and rotational.

The fine and hyperfine spectra are quite prevalent in the areas of physics and radio astronomy. For example, cosmologists map the locations of interstellar clouds of hydrogen, and collect data regarding the origins of the universe by detecting signals from outerspace, for example, at 1.420 GHz, a microwave frequency which is one of the hyperfine splitting frequencies for hydrogen. Most of the large databases concerning the microwave and radio frequencies of molecules and atoms have been developed by astronomers and physicists, rather than by chemists. This apparent gap between the use by chemists and physicists, of the fine and hyperfine spectra in chemistry, has apparently resulted in prior art chemists not giving much, if any, attention to these potentially useful spectra.

Figure 30A:
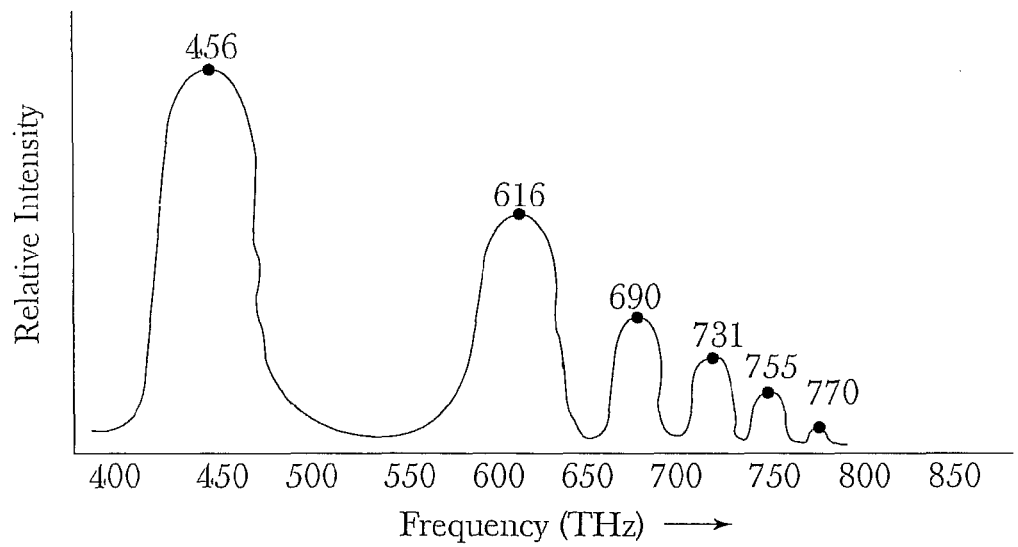
FIG. 30 shows plots corresponding to the emission spectrum of hydrogen. Specifically, FIG. 30a corresponds to Balmer Series 2 for hydrogen.
FIG. 30b corresponds to emission spectrum for the 456 THz frequency of hydrogen.
Figure 30B:
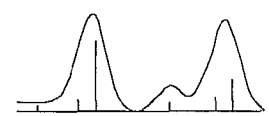
Figure 31:
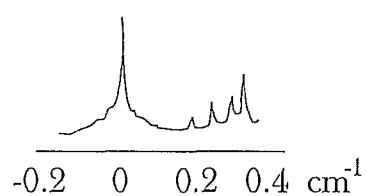
FIG. 31 corresponds to a high resolution laser saturation spectrum for the 456 THz frequency of hydrogen.

Referring again to FIGS. 9a and 9b, the Balmer series (i.e., frequency curve II), begins with a frequency of 456 THz (see FIG. 30a). Closer examination of this individual frequency shows that instead of there being just one crisp narrow curve at 456 THz, there are really seven different curves very close together that comprise the curve at 456 THz. The seven (7)

different curves are fine structure frequencies. FIG. 30b shows the emission spectrum for the 456 THz curve in hydrogen. A high-resolution laser saturation spectrum, shown in FIG. 31, gives even more detail. These seven different curves, which are positioned very close together, are generally referred to as a multiplet.

Although there are seven different fine structure frequencies shown, these seven frequencies are grouped around two major frequencies. These are the two, tall, relatively high intensity curves shown in FIG. 30b. These two high intensity curves are also shown in FIG. 31 at zero cm$^{-1}$ (456.676 THz), and at relative wavenumber 0.34 cm$^{-1}$ (456.686 THz). What appears to be a single frequency of (456 THz), is actually composed predominantly of two slightly different frequencies (456.676 and 456.686 THz), and the two frequencies are typically referred to as doublet and the frequencies are said to be split. The difference or split between the two predominant frequencies in the hydrogen 456 THz doublet is 0.010 THz (100 THz) or 0.34 cm$^{-1}$ wavnumbers. This difference frequency, 10 GHz, is called the fine splitting frequency for the 456 THz frequency of hydrogen.

Figure 32:
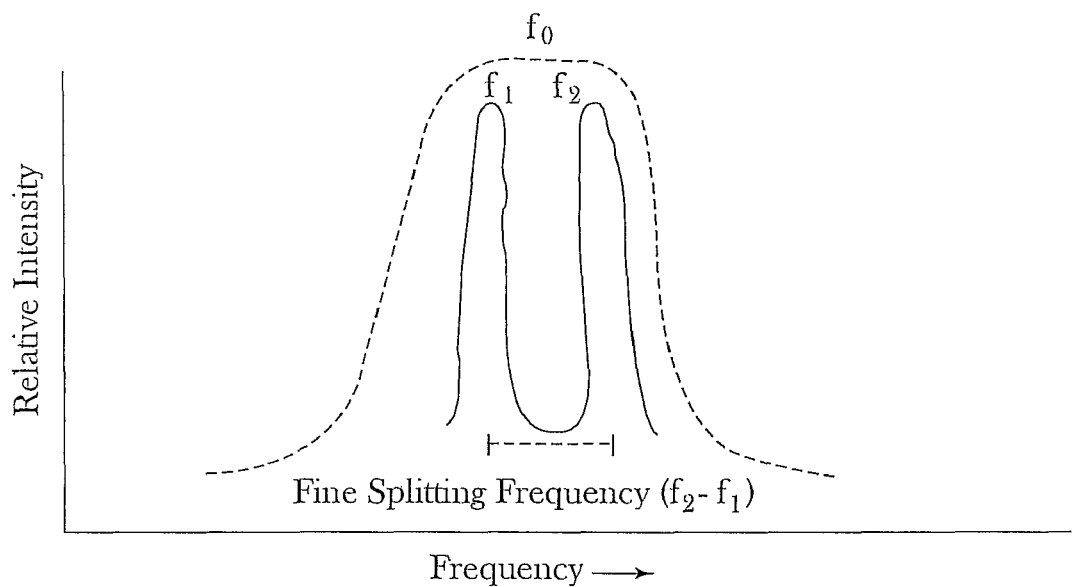
FIG. 32 shows fine splitting frequencies which exist under a typical spectral curve.

Thus, the individual frequencies that are typically shown in ordinary electronic spectra are composed of two or more distinct frequencies spaced very close together. The distinct frequencies spaced very close together are called fine structure frequencies. The difference, between two fine structure frequencies that are split apart by a very slight amount, is a fine splitting frequency (see FIG. 32 which shows $f_1$ and $f_2$ which comprise $f_0$ and which are shown as underneath $f_0$. The difference between $f_1$ and $f_2$ is known as the fine splitting frequency). This "difference" between two fine structure frequencies is important because such a difference between any two frequencies is a heterodyne.

Almost all the hydrogen frequencies shown in FIGS. 9a and 9b are doublets or multiplets. This means that almost all the hydrogen electronic spectrum frequencies have fine structure frequencies and fine splitting frequencies (which means that these heterodynes are available to be used as spectral catalysts, if desired). The present invention discloses that these "differences" or heterodynes can be quite useful for certain reactions. However, prior to discussing the use of these heterodynes, in the present invention, more must be understood about these heterodynes. Some of the fine splitting frequencies (i.e., heterodynes) for hydrogen are listed in Table 3. These fine splitting heterodynes range from the microwave down into the upper reaches of the radio frequency region.

TABLE 3

Fine Splitting Frequencies for Hydrogen

| Frequency (THz) | Orbital | Wavenumber (cm$^{-1}$) | Fine Splitting Frequency |
|---|---|---|---|
| 2,466 | 2p | 0.365 | 10.87 GHz |
| 456 | n2→3 | 0.340 | 10.02 GHz |
| 2,923 | 3p | 0.108 | 3.23 GHz |
| 2,923 | 3d | 0.036 | 1.06 GHz |
| 3,082 | 4p | 0.046 | 1.38 GHz |
| 3,082 | 4d | 0.015 | 448.00 MHz |
| 3,082 | 4f | 0.008 | 239.00 MHz |

There are more than 23 fine splitting frequencies (i.e., heterodynes) for just the first series or curve I in hydrogen. Lists of the fine splitting heterodynes can be found, for example, in the classic 1949 reference "Atomic Energy Levels" by Charlotte Moore. This reference also lists 133 fine splitting heterodyned intervals for carbon, whose frequencies range from 14.1 THz (473.3 cm$^{-1}$) down to 12.2. GHz (0.41 cm$^{-1}$). Oxygen has 287 fine splitting heterodynes listed from 15.9 THz (532.5 cm$^{-1}$) down to 3.88 GHz (0.13 cm$^{-1}$). The 23 platinum fine splitting intervals detailed are from 23.3 THz (775.9 cm$^{-1}$) to 8.62 THz in frequency (287.9 cm$^{-1}$).

Figure 33:
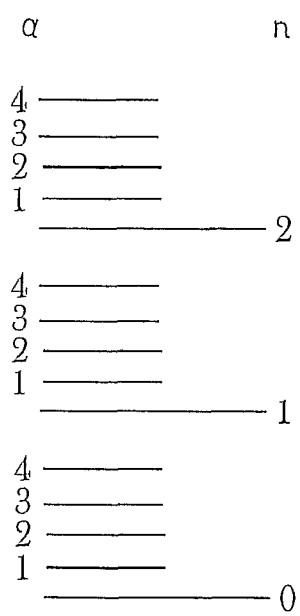
FIG. 33 corresponds to a diagram of atomic electron levels (n) in fine structure frequencies (a).
Figure 34:
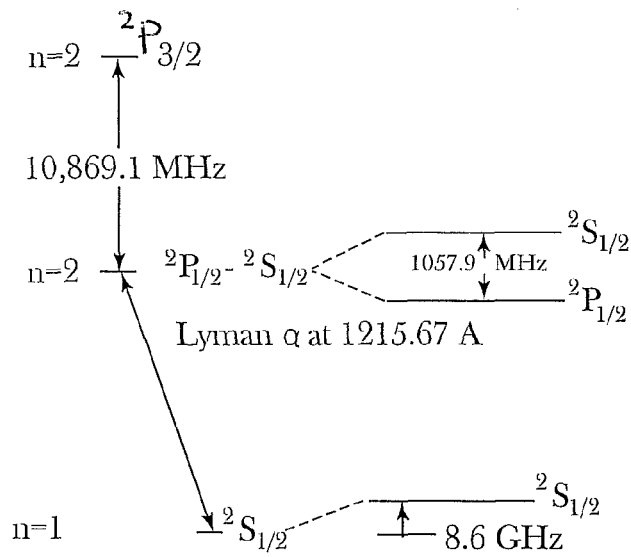
FIG. 34 shows fine structures of the n=1 and n=2 levels of a hydrogen atom.
Figure 35:
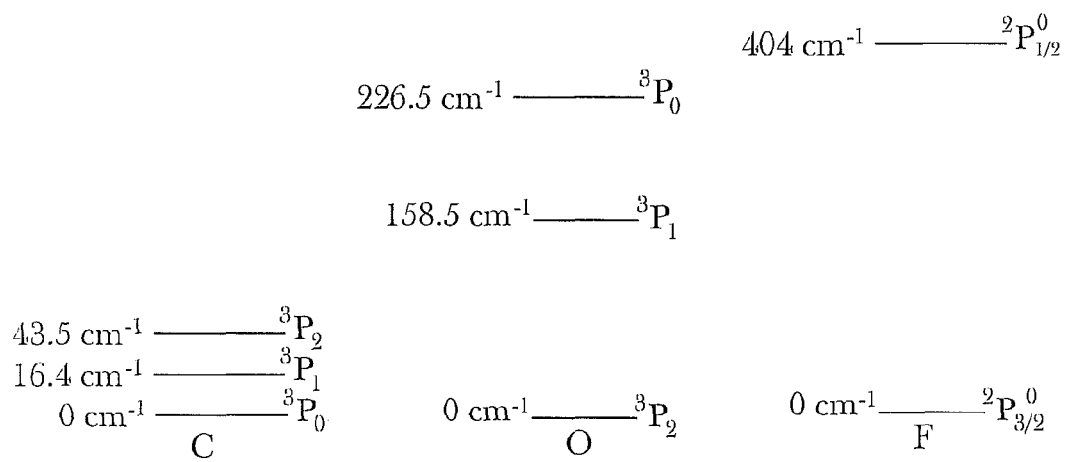
FIG. 35 shows multiplet splittings for the lowest energy levels of carbon, oxygen and fluorine: 43.5 cm$^{-1}$=1.3 THz; 16.4 cm$^{-1}$=490 GHz; 226.5 cm$^{-1}$=6.77 THz; 158.5 cm$^{-1}$=4.74 THz; 404 cm$^{-1}$=12.1 THz.

Diagrammatically, the magnification and resolution of an electronic frequency into several closely spaced fine frequencies is depicted in FIG. 33. The electronic orbit is designated by the orbital number n=0, 1, 2, etc. The fine structure is designated as α. A quantum diagram for the hydrogen fine structure is shown in FIG. 34. Specifically, shown is the fine structure of the n=1 and n=2 levels of the hydrogen atom. FIG. 35 shows the multiplet splittings for the lowest energy levels of carbon, oxygen, and fluorine, as represented by "C", "O" and "F", respectively.

In addition to the fine splitting frequencies for atoms (i.e., heterodynes), molecules also have similar fine structure frequencies. The origin and derivation for molecular fine structure and splitting is different from that for atoms, however, the graphical and practical results are quite similar. In atoms, the fine structure frequencies are said to result from the interaction of the spinning electron with its' own magnetic field. Basically, this means the electron cloud of a single atomic sphere, rotating and interacting with its' own magnetic field, produces the atomic fine structure frequencies. The prior art refers to this phenomena as "spin-orbit coupling". For molecules, the fine structure frequencies correspond to the actual rotational frequencies of the electronic or vibrational frequencies. So the fine structure frequencies for atoms and molecules both result from rotation. In the case of atoms, it is the atom spinning and rotating around itself, much the way the earth rotates around its axis. In the case of molecules, it is the molecule spinning and rotating through space.

Figure 36:
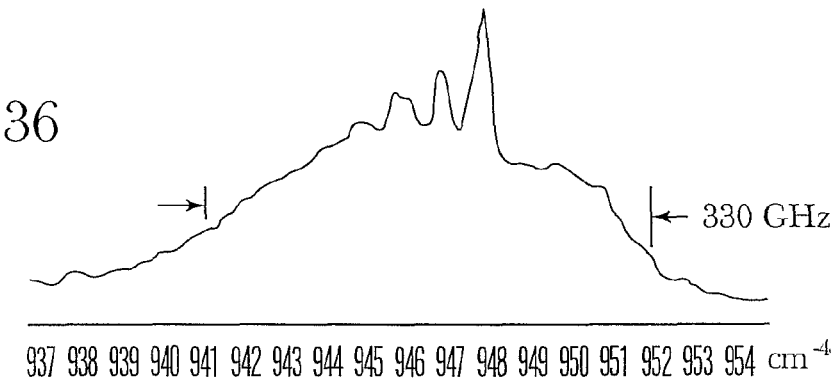
FIG. 36 shows a vibration band of $SF_6$ at a wavelength of 10 μm$^2$.

FIG. 36 shows the infrared absorption spectrum of the SF$_6$ vibration band near 28.3 THz (10.6 μm wavelength, wavenumber 948 cm$^{-1}$) of the SF$_6$ molecule. The molecule is highly symmetrical and rotates somewhat like a top. The spectral tracing was obtained with a high resolution grating spectrometer. There is a broad band between 941 and 952 cm$^{-1}$ (28.1 and 28.5 THz) with three sharp spectral curves at 946, 947, and 948 cm$^{-1}$ (28.3, 28.32, and 23.834 THz).

Figure 37A:
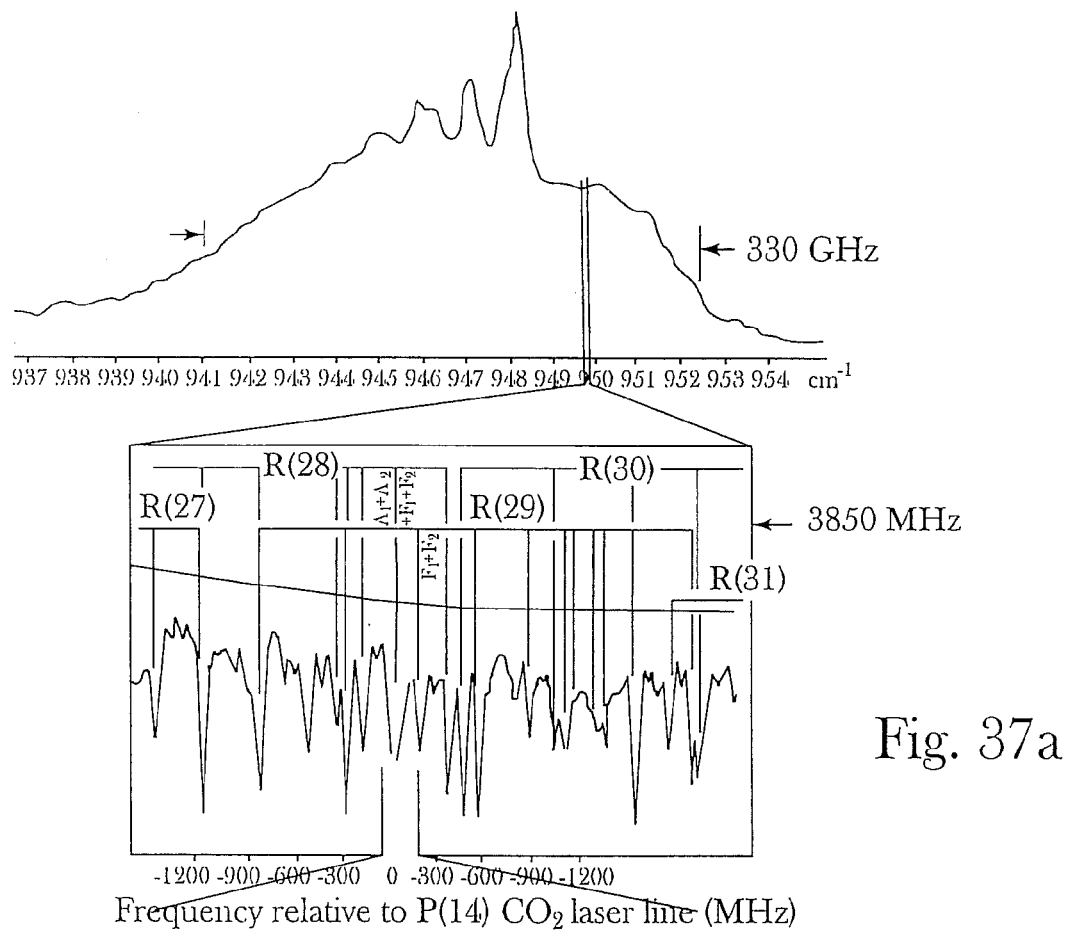
FIG. 37a shows a spectral pattern similar to that shown in FIG. 36, with a particular frequency magnified.
Figure 37B:
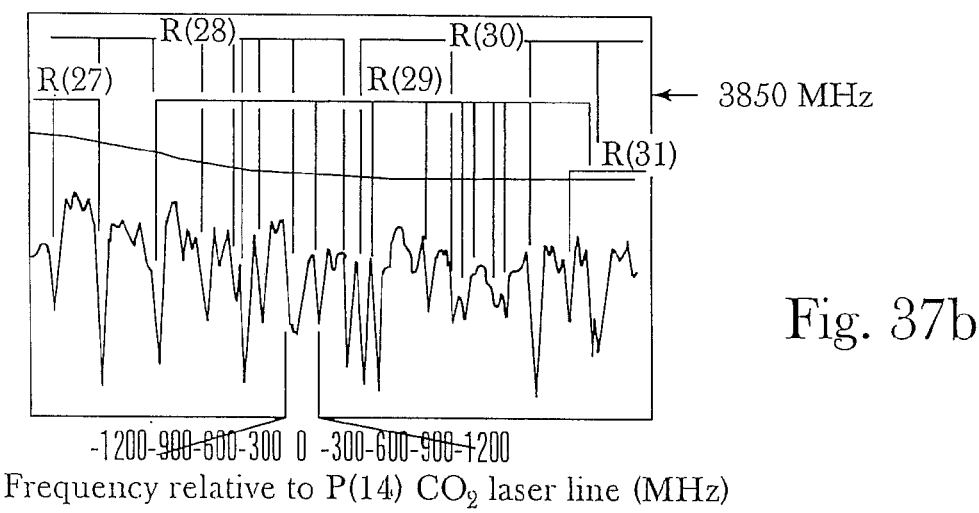
FIG. 37b shows fine structure frequencies in greater detail for the compound $SF_6$.
Figure 38:
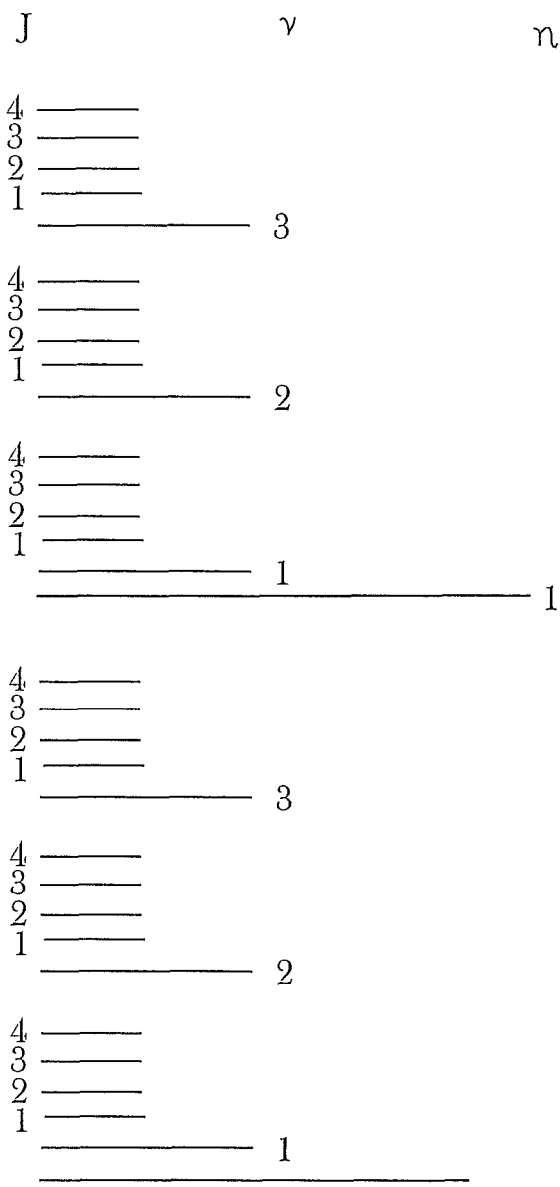
FIG. 38 shows an energy level diagram which corresponds to different energy levels for a molecule where rotational corresponds to "J", vibrational corresponds to "v" and electronic levels correspond to "n".

FIG. 37a shows a narrow slice being taken from between 949 and 950 cm$^{-1}$, which is blown up to show more detail in FIG. 37b. A tunable semiconductor diode laser was used to obtain the detail. There are many more spectral curves which appear when the spectrum is reviewed in finer detail. These curves are called the fine structure frequencies for this molecule. The total energy of an atom or molecule is the sum of its' electronic, vibrational, and rotational energies. Thus, the simple Planck equation discussed previously herein:

$$E=h\nu$$

can be rewritten as follows:

$$E=E_e+E_v+E_r$$

where E is the total energy, $E_e$ is the electronic energy, $E_v$ is the vibrational energy, and $E_r$ is the rotational energy. Diagrammatically, this equation is shown in FIG. 38 for molecules. The electronic energy, $E_e$, involves a change in the orbit of one of the electrons in the molecule. It is designated by the orbital number n=0, 1, 2, 3, etc. The vibrational energy, $E_v$, is produced by a change in the vibration rate between two atoms within the molecule, and is designated by a vibrational number v=1, 2, 3, etc. Lastly, the rotational energy, $E_r$, is the energy of rotation caused by the molecule rotating around its' center of mass. The rotational energy is designated by the quantum number J=1, 2, and 3, etc., as determined form angular momentum equations.

Thus, by examining the vibrational frequencies of $SF_6$ in more detail, the fine structure molecular frequencies become apparent. These fine structure frequencies are actually produced by the molecular rotations, "J", as a subset of each vibrational frequency. Just as the rotational levels "J" are substantially evenly separated in FIG. 38, they are also substantially evenly separated when plotted as frequencies.

Figure 39A:
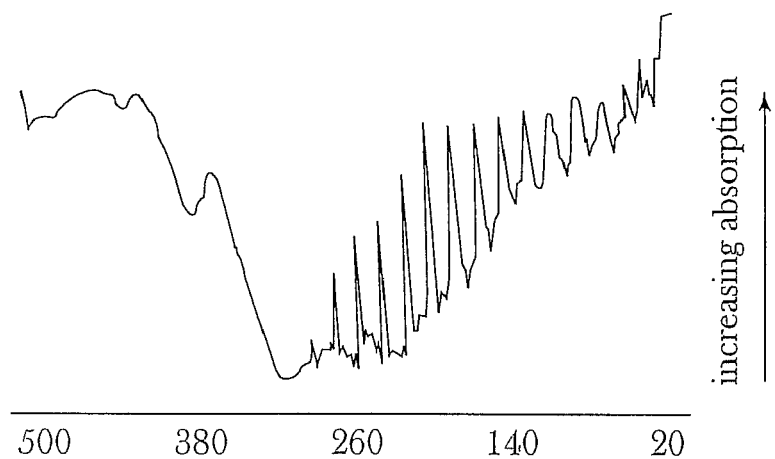
FIGS. 39a and 39b correspond to pure rotational absorption spectrum of gaseous hydrogen chloride as recorded with an interferometer.
Figure 39B:
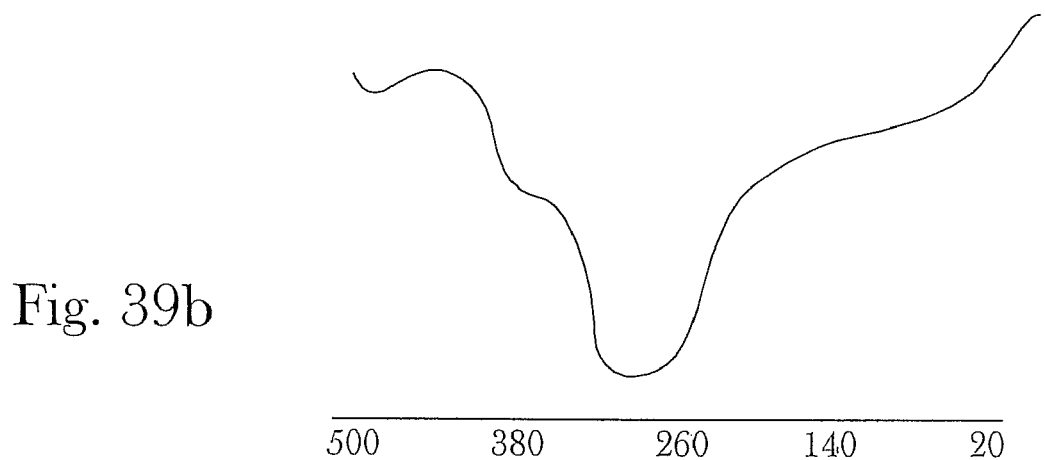

This concept may be easier to understand by viewing some additional frequency diagrams. For example, FIG. 39a shows the pure rotational absorption spectrum for gaseous hydrogen-chloride and FIG. 39b shows the same spectrum at low resolution. In FIG. 39a, the separate waves, that look something like teeth on a "comb", correspond to the individual rotational frequencies. The complete wave (i.e., that wave comprising the whole comb) that extends in frequency from 20 to 500 $cm^{-1}$ corresponds to the entire vibrational frequency. At low resolution or magnification, this set of rotational frequencies appear to be a single frequency peaking at about 20 $cm^{-1}$ (598 GHz) (see FIG. 39b). This is very similar to the way atomic frequencies such as the 456 THz hydrogen frequency appear (i.e., just one frequency at low resolution, that turn out to be several different frequencies at higher magnification).

Figure 40:
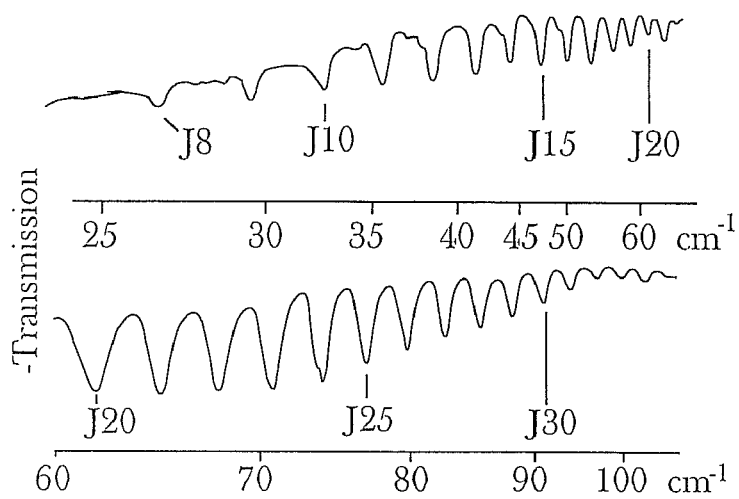
FIG. 40 corresponds to the rotational spectrum for hydrogen cyanide. "J" corresponds to the rotational level.

In FIG. 40, the rotational spectrum (i.e., fine structure) of hydrogen cyanide is shown, where "J" is the rotational level. Note again, the regular spacing of the rotational levels. (Note that this spectrum is oriented opposite of what is typical). This spectrum uses transmission rather than emission on the horizontal Y-axis, thus, intensity increases downward on the Y-axis, rather than upwards.

Figure 41:
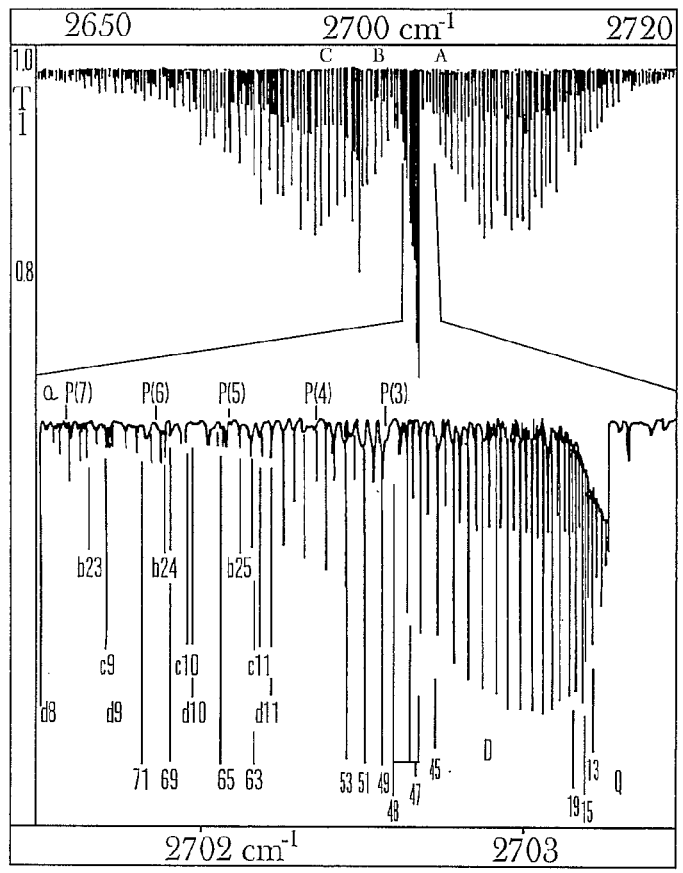
FIG. 41 shows a spectrum corresponding to the additive heterodyne of $v_1$ and $v_5$ in the spectral band showing the frequency band at A ($v_1-v_5$), B=$v_1-2v_5$.

Additionally, FIG. 41 shows the $v_1$–$v_5$ vibrational bands for FCCF (where $v_1$ is vibrational level 1 and $v_5$ vibrational level 5) which includes a plurality of rotational frequencies. All of the fine sawtooth spikes are the fine structure frequencies which correspond to the rotational frequencies. Note, the substantially regular spacing of the rotational frequencies. Also note, the undulating pattern of the rotational frequency intensity, as well as the alternating pattern of the rotational frequency intensities.

Consider the actual rotational frequencies (i.e., fine structure frequencies) for the ground state of carbon monoxide listed in Table 4.

TABLE 4

Rotational Frequencies and Derived Rotational Constant for CO in the Ground State

| J Transition | Frequency (MHz) | Frequency (GHz) |
|---|---|---|
| 0→1 | 115,271.204 | 115 |
| 1→2 | 230,537.974 | 230 |
| 2→3 | 345,795.989 | 346 |
| 3→4 | 461,040.811 | 461 |
| 4→5 | 576,267.934 | 576 |
| 5→6 | 691,472.978 | 691 |
| 6→7 | 806,651.719 | 807 |

Where; $B_o$=57,635.970 MHz

Each of the rotational frequencies is regularly spaced at approximately 115 GHz apart. Prior art quantum theorists would explain this regular spacing as being due to the fact that the rotational frequencies are related to Planck's constant and the moment of inertia (i.e., center of mass for the molecule) by the equation:

$$B = \frac{h}{8\pi^2 I}$$

where B is the rotational constant, h is Planck's constant, and I is the moment of inertia for the molecule. From there the prior art established a frequency equation for the rotational levels that corresponds to:

$$f=2B(J+1)$$

where f is the frequency, B is the rotational constant, and J is the rotational level. Thus, the rotational spectrum (i.e., fine structure spectrum) for a molecule turns out to be a harmonic series of lines with the frequencies all spaced or split (i.e., heterodyned) by the same amount. This amount has been referred to in the prior art as "2B", and "B" has been referred to as the "rotational constant". In existing charts and databases of molecular frequencies, "B" is usually listed as a frequency such as MHz. This is graphically represented for the first four rotational frequencies for CO in FIG. 42.

This fact is interesting for several reasons. The rotational constant "B", listed in many databases, is equal to one half of the difference between rotational frequencies for a molecule. That means that B is the first subharmonic frequency, to the fundamental frequency "2B", which is the heterodyned difference between all the rotational frequencies. The rotational constant B listed for carbon monoxide is 57.6 GHz (57,635.970 MHz). This is basically half of the 115 GHz difference between the rotational frequencies. Thus, according to the present invention, if it is desired to stimulate a molecule's rotational levels, the amount "2B" can be used, because it is the fundamental first generation heterodyne. Alternatively, the same "B" can be used because "B" corresponds to the first subharmonic of that heterodyne.

Further, the prior art teaches that if it is desired to use microwaves for stimulation, the microwave frequencies used will be restricted to stimulating levels at or near the ground state of the molecule (i.e., n=0 in FIG. 38). The prior art teaches that as you progress upward in FIG. 38 to the higher electronic and vibrational levels, the required frequencies will correspond to the infrared, visible, and ultraviolet regions. However, the prior art is wrong about this point.

By referring to FIG. 38 again, it is clear that the rotational frequencies are evenly spaced out no matter what electronic or vibrational level is under scrutiny. The even spacing shown in FIG. 38 is due to the rotational frequencies being evenly spaced as progression is made upwards through all the higher vibrational and electronic levels. Table 5 lists the rotational frequencies for lithium fluoride (LiF) at several different rotational and vibrational levels.

TABLE 5

Rotational Frequencies for Lithium Fluoride (LiF)

| Vibrational Level | Rotational Transition | Frequency (MHz) |
|---|---|---|
| 0 | 0→1 | 89,740.46 |
| 0 | 1→2 | 179,470.35 |
| 0 | 2→3 | 269,179.18 |
| 0 | 3→4 | 358,856.19 |
| 0 | 4→5 | 448,491.07 |
| 0 | 5→6 | 538,072.65 |
| 1 | 0→1 | 88,319.18 |
| 1 | 1→2 | 176,627.91 |

TABLE 5-continued

Rotational Frequencies for Lithium Fluoride (LiF)

| Vibrational Level | Rotational Transition | Frequency (MHz) |
|---|---|---|
| 1 | 2→3 | 264,915.79 |
| 1 | 3→4 | 353,172.23 |
| 1 | 4→5 | 441,386.83 |
| 2 | 0→1 | 86,921.20 |
| 2 | 1→2 | 173,832.04 |
| 2 | 2→3 | 260,722.24 |
| 2 | 3→4 | 347,581.39 |
| 3 | 1→2 | 171,082.27 |
| 3 | 2→3 | 256,597.84 |
| 3 | 3→4 | 342,082.66 |

It is clear from Table 5 that the differences between rotational frequencies, no matter what the vibrational level, is about 86,000 to about 89,000 MHz (i.e., 86-89 GHz). Thus, according to the present invention, by using a microwave frequency between about 86,000 MHz and 89,000 MHz, the molecule can be stimulated from the ground state level all the way up to its' highest energy levels. This effect has not been even remotely suggested by the prior art. Specifically, the rotational frequencies of molecules can be manipulated in a unique manner. The first rotational level has a natural oscillatory frequency (NOF) of 89,740 MHz. The second rotational level has an NOF of 179,470 MHz. Thus, $$NOF_{rotational\ 1\to 2} - NOF_{rotational\ 0\to 1} = \text{Subtracted Frequency}_{rotational\ 2-1};$$

or 179,470 MHz−89,740 MHz=89,730 MHz

Thus, the present invention has discovered that the NOF's of the rotational frequencies heterodyne by adding and subtracting in a manner similar to the manner that all frequencies heterodyne. Specifically, the two rotational frequencies heterodyne to produce a subtracted frequency. This subtracted frequency happens to be exactly twice as big as the derived rotational constant "B" listed in nuclear physics and spectroscopy manuals. Thus, when the first rotational frequency in the molecule is stimulated with the Subtracted Frequency$_{rotational\ 2-1}$, the first rotational frequency will heterodyne (i.e., in this case add) with the NOF$_{rotational\ 0\to 1}$ (i.e., first rotational frequency) to produce NOF$_{rotational\ 1\to 2}$, which is the natural oscillatory frequency of the molecule's second rotational level. In other words:

$$\text{Subtracted Frequency}_{rotational\ 2-1} + NOF_{rotational\ 0\to 1} = NOF_{rotational\ 1\to 2};$$

Or 89,730 MHz+89,740 MHz=179,470 MHz

Since the present invention has disclosed that the rotational frequencies are actually evenly spaced harmonics, the subtracted frequency will also add with the second level NOF to produce the third level NOF. The subtracted frequency will add with the third level NOF to produce the fourth level NOF. And so on and so on. Thus, according to the present invention, by using one single microwave frequency, it is possible to stimulate all the rotational levels in a vibratory band.

Moreover, if all the rotational levels for a vibrational frequency are excited, then the vibrational frequency will also be correspondingly excited. Further, if all the vibrational levels for an electronic level are excited, then the electronic level will be excited as well. Thus, according to the teachings of the present invention, it is possible to excite the highest levels of the electronic and vibrational structure of a molecule by using a single microwave frequency. This is contrary to the prior art teachings that the use of microwaves is restricted to the ground state of the molecule. Specifically, if the goal is to resonate directly with an upper vibrational or electronic level, the prior art teaches that microwave frequencies can not be used. If, however, according to the present invention, a catalytic mechanism of action is initiated by, for example, resonating with target species indirectly through heterodynes, then one or more microwave frequencies can be used to energize at least one upper level vibrational or electronic state. Accordingly, by using the teachings of the present invention in conjunction with the simple processes of heterodyning it becomes readily apparent that microwave frequencies are not limited to the ground state levels of molecules.

Figure 42:
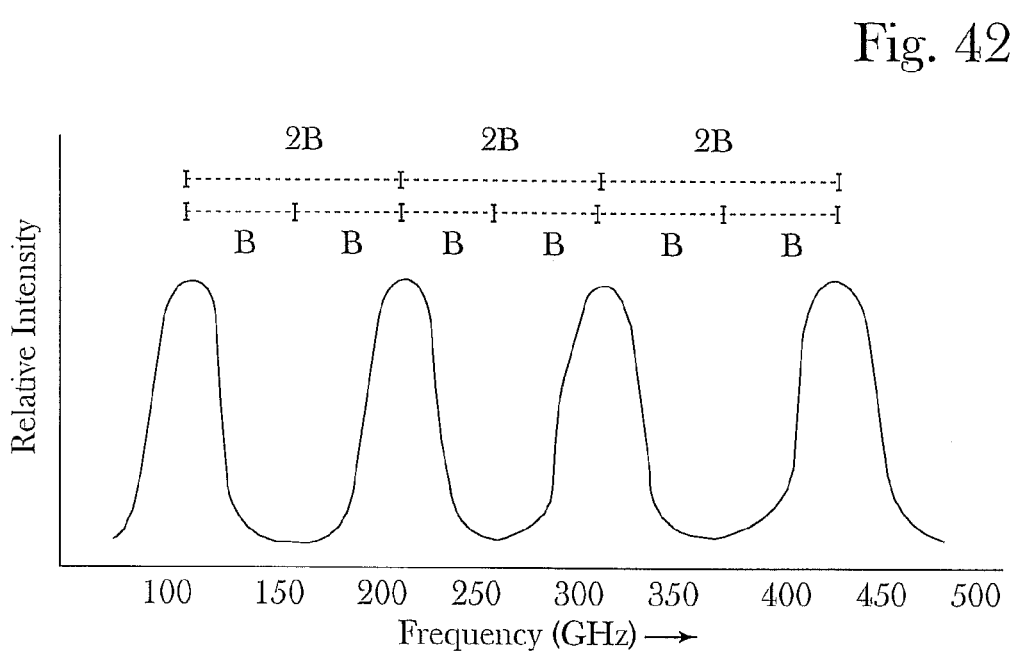
FIG. 42 shows a graphical representation of fine structure spectrum showing the first four rotational frequencies for CO in the ground state. The difference (heterodyne) between the molecular fine structure rotational frequencies is 2× the rotational constant B (i.e., $f_2-f_1=2B$). In this case, B=57.6 GHz (57,635.970 MHz).

The present invention has determined that catalysts can actually stimulate target species indirectly by utilizing at least one heterodyne frequency (e.g., harmonic). However, catalysts can also stimulate the target species by direct resonance with at least one fundamental frequency of interest. However, the rotational frequencies can result in use of both mechanisms. For example, FIG. 42 shows a graphical representation of fine structure spectrum showing the first four rotational frequencies for CO in the ground state. The first rotational frequency for CO is 115 GHz. The heterodyned difference between rotational frequencies is also 115 GHz. The first rotational frequency and the heterodyned difference between frequencies are identical. All of the upper level rotational frequencies are harmonics of the first frequency. This relationship is not as apparent when one deals only with the rotational constant "B" of the prior art. However, frequency-based spectral chemistry analyses, like those of the present invention, makes such concepts easier to understand.

Examination of the first level rotational frequencies for LiF shows that it is nearly identical to the heterodyned difference between it and the second level rotational frequency. The rotational frequencies are sequential harmonics of the first rotational frequency. Accordingly, if a molecule is stimulated with a frequency equal to 2B (i.e., a heterodyned harmonic difference between rotational frequencies) the present invention teaches that energy will resonate with all the upper rotational frequencies indirectly through heterodynes, and resonate directly with the first rotational frequency. This is an important discovery.

The prior art discloses a number of constants used in spectroscopy that relate in some way or another to the frequencies of atoms and molecule, just as the rotational constant "B" relates to the harmonic spacing of rotational fine structure molecular frequencies. The alpha (a) rotation-vibration constant is a good example of this. The alpha rotation-vibration frequency constant is related to slight changes in the frequencies for the same rotational level, when the vibrational level changes. For example, FIG. 43a shows the frequencies for the same rotational levels, but different vibrational levels for LiF. The frequencies are almost the same, but vary by a few percent between the different vibrational levels.

Referring to FIG. 43b, the differences between all the frequencies for the various rotational transitions at different vibrational levels of FIG. 43a are shown. The rotational transition 0→1 in the top line of FIG. 43b has a frequency of 89,740.46 MHz at vibrational level 0. At vibrational level 1, the 0→1 transition is 88,319.18 MHz. The difference between these two rotational frequencies is 1,421.28 MHz. At vibrational level 2, the 0→1 transition is 86,921.20 MHz. The difference between it and the vibrational level 1 frequency (88,319.18 MHz) is 1,397.98 MHz. These slight differences for the same J rotational level between different vibrational levels are nearly identical. For the J=0→1 rotational level they center around a frequency of 1,400 MHz.

For the J=1→2 transition, the differences center around 2,800 Hz, and for the J=2→3 transition, the differences center around 4,200 Hz. These different frequencies of 1,400, 2,800 and 4,200, Hz etc., are all harmonics of each other. Further, they are all harmonics of the alpha rotation-vibration constant. Just as the actual molecular rotational frequencies are harmonics of the rotational constant B, the differences between the rotational frequencies are harmonics of the alpha rotation-vibration constant. Accordingly, if a molecule is stimulated with a frequency equal to the alpha vibration-rotation frequencies, the present invention teaches that energy will resonate with all the rotational frequencies indirectly through heterodynes. This is an important discovery.

Figure 44:
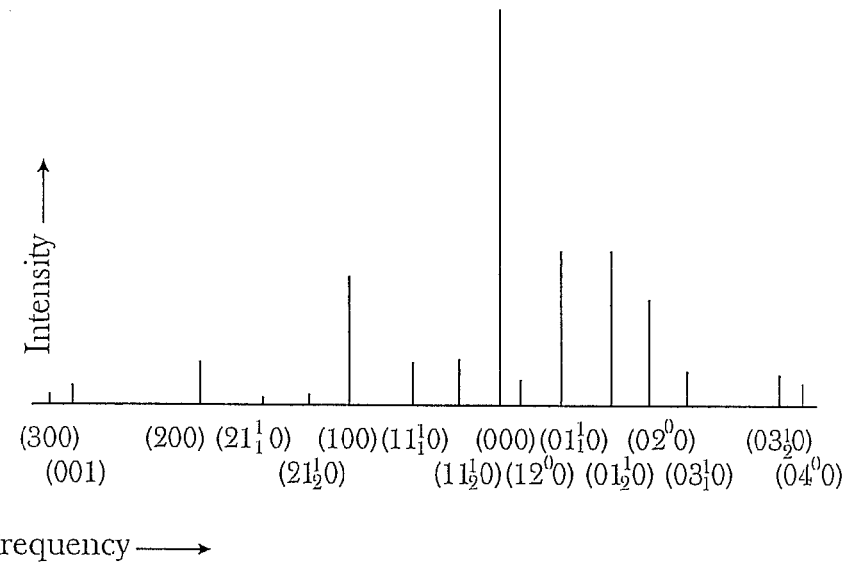
FIG. 44 shows the rotational transition J=1→2 for the triatomic molecule OCS. The vibrational state is given by vibrational quantum numbers in brackets ($v_1$, $v_2$, $v_3$), $v_2$ have a superscript [1]. In this case, l=1. A subscript 1 is applied to the lower-frequency component of the l-type doublet, and 2 to the higher-frequency components. The two lines at ($01^10$) and ($01^10$) are an l-type doublet, separated by $q_1$.

Consider the rotational and vibrational states for the triatomic molecule OCS shown in FIG. 44. FIG. 44 shows the same rotational level (J=1→2) for different vibrational states in the OCS molecule. For the ground vibrational (000) level, J=1→2 transition; and the excited vibrational state (100) J=1→2 transition, the difference between the two frequencies is equal to 4× $alpha_1$ ($4\alpha_1$). In another excited state, the frequency difference between the ground vibrational (000) level, J=1→2 transition, and the center of the two l-type doublets is 4× $alpha_2$ ($4\alpha_2$). In a higher excited vibrational state, the frequency difference between (000) and (02°0) is 8× $alpha_2$ ($8\alpha_2$). Thus, it can be seen that the rotation-vibration constants "a" are actually harmonics of molecular frequencies. Thus, according to the present invention, stimulating a molecule with an "a" frequency, or a harmonic of "a", will either directly resonate with or indirectly heterodyne harmonically with various rotational-vibrational frequencies of the molecule.

Another interesting constant is the l-type doubling constant. This constant is also shown in FIG. 44. Specifically, FIG. 44 shows the rotational transition J=1→2 for the triatomic molecule OCS. Just as the atomic frequencies are sometimes split into doublets or multiplets, the rotational frequencies are also sometimes split into doublets. The difference between them is called the l-type doubling constant. These constants are usually smaller (i.e., of a lower frequency) than the a constants. For the OCS molecule, the a constants are 20.56 and 10.56 MHz while the l-type doubling constant is 6.3 MHz. These frequencies are all in the radio-wave portion of the electromagnetic spectrum.

As discussed previously herein, energy is transferred by two fundamental frequency mechanisms. If frequencies are substantially the same or match, then energy transfers by direct resonance. Energy can also transfer indirectly by heterodyning, (i.e., the frequencies substantially match after having been added or subtracted with another frequency). Further, as previously stated, the direct or indirect resonant frequencies do not have to match exactly. If they are merely close, significant amounts of energy will still transfer. Any of these constants or frequencies that are related to molecules or other matter via heterodynes, can be used to transfer, for example, energy to the matter and hence can directly interact with the matter.

In the reaction in which hydrogen and oxygen are combined to form water, the present invention teaches that the energizing of the reaction intermediates of atomic hydrogen and the hydroxy radical are crucial to sustaining the reaction. In this regard, the physical catalyst platinum energizes both reaction intermediates by directly and indirectly resonating with them. Platinum also energizes the intermediates at multiple energy levels, creating the conditions for energy amplification. The present invention also teaches how to copy platinum's mechanism of action by making use of atomic fine structure frequencies.

The invention has previously discussed resonating with the fine structure frequencies with only slight variations between the frequencies (e.g., 456.676 and 456.686 THz). However, indirectly resonating with the fine structure frequencies, is a significant difference. Specifically, by using the fine splitting frequencies, which are simply the differences or heterodynes between the fine structure frequencies, the present invention teaches that indirect resonance can be achieved. By examining the hydrogen 456 THz fine structure and fine splitting frequencies (see, for example, FIGS. 30 and 31 and Table 3 many heterodynes are shown). In other words, the difference between the fine structure frequencies can be calculated as follows:

$$456.686 \text{ THz} - 456.676 \text{ THz} = 0.0102 \text{ THz} = 10.2 \text{ GHz}$$

Thus, if hydrogen atoms are subjected to 10.2 GHz electromagnetic energy (i.e., energy corresponding to microwaves), then the 456 THz electronic spectrum frequency is energized by resonating with it indirectly. In other words, the 10.2 GHz will add to 456.676 THz to produce the resonant frequency of 456.686 THz. The 10.2 GHz will also subtract from the 456.686 THz to produce the resonant frequency of 456.676 THz. Thus, by introducing 10.2 GHz to a hydrogen atom, the hydrogen atom is excited at the 456 THz frequency. A microwave frequency can be used to stimulate an electronic level.

According to the present invention, it is also possible to use a combination of mimicked catalyst mechanisms. For example, it is possible to: 1) resonate with the hydrogen atom frequencies indirectly through heterodynes (i.e., fine splitting frequencies); and/or 2) resonate with the hydrogen atom at multiple frequencies. Such multiple resonating could occur using a combination of microwave frequencies either simultaneously, in sequence, and/or in chirps or bursts. For example, the individual microwave fine splitting frequencies for hydrogen of 10.87 GHz, 10.2 GHz, 3.23 GHz, 1.38 GHz, and 1.06 GHz could be used in a sequence. Further, there are many fine splitting frequencies for hydrogen that have not been expressly included herein, thus, depending on the frequency range of equipment available, the present invention provides a means for tailoring the chosen frequencies to the capabilities of the available equipment. Thus, the flexibility according to the teachings of the present invention is enormous.

Another method to deliver multiple electromagnetic energy frequencies according to the present invention, is to use a lower frequency as a carrier wave for a higher frequency. This can be done, for example, by producing 10.2 GHz EM energy in short bursts, with the bursts coming at a rate of about 239 MEfz. Both of these frequencies are fine splitting frequencies for hydrogen. This can also be achieved by continuously delivering EM energy and by varying the amplitude at a rate of about 239 MHz. These techniques can be used alone or in combination with the various other techniques disclosed herein.

Thus, by mimicking one or more mechanisms of action of catalysts and by making use of the atomic fine structure and splitting frequencies, it is possible to energize upper levels of atoms using microwave and radiowave frequencies. Accordingly, by selectively energizing or targeting particular atoms, it is possible to catalyze and guide desirable reactions to desired end products. Depending on the circumstances, the option to use lower frequencies may have many advantages. Lower frequencies typically have much better penetration into large reaction spaces and volumes, and may be better suited to large-scale industrial applications. Lower frequencies may be easier to deliver with portable, compact equipment, as opposed to large, bulky equipment which delivers higher frequencies (e.g., lasers). The choice of frequencies for a spectral catalyst may be for as simple a reason as to avoid interference from other sources of EM energy. Thus, according to the present invention, an understanding of the basic processes of heterodyning and fine structure splitting frequencies confers greater flexibility in designing and applying spectral energy catalysts in a targeted manner. Specifically, rather than simply reproducing the spectral pattern of a physical catalyst, the present invention teaches that is possible to make full use of the entire range of frequencies in the electromagnetic spectrum, so long as the teachings of the present invention are followed. Thus, certain desirable frequencies can be applied while other not so desirable frequencies could be left out of an applied spectral energy catalyst targeted to a particular participant and/or component in the reaction system.

As a further example, reference is again made to the hydrogen and oxygen reaction for the formation of water. If it is desired to catalyze the water reaction by duplicating the catalyst's mechanism of action in the microwave region, the present invention teaches that several options are available. Another such option is use of the knowledge that platinum energizes the reaction intermediates of the hydroxy radical. In addition to the hydrogen atom, the B frequency for the hydroxy radical is 565.8 GHz. That means that the actual heterodyned difference between the rotational frequencies is 2B, or 1,131.6 GHz. Accordingly, such a frequency could be utilized to achieve excitement of the hydroxy radical intermediate.

Further, the α constant for the hydroxy radical is 21.4 GHz. Accordingly, this frequency could also be applied to energizing the hydroxy radical. Thus, by introducing hydrogen and oxygen gases into a chamber and irradiating the gases with 21.4 GHz, water will be formed. This particular gigahertz energy is a harmonic heterodyne of the rotational frequencies for the same rotational level but different vibrational levels. The heterodyned frequency energizes all the rotational frequencies, which energize the vibrational levels, which energize the electronic frequencies, which catalyze the reaction. Accordingly, the aforementioned reaction could be catalyzed or targeted with a spectral catalyst applied at several applicable frequencies, all of which match with one or more frequencies in one or more participants and thus permit energy to transfer.

Still further, delivery of frequencies of 565.8 GHz, or even 1,131.6 GHz, would result in substantially all of the rotational levels in the molecule becoming energized, from the ground state all the way up. This approach copies a catalyst mechanism of action in two ways. The first way is by energizing the hydroxy radical and sustaining a crucial reaction intermediate to catalyze the formation of water. The second mechanism copied from the catalyst is to energize multiple levels in the molecule. Because the rotational constant "B" relates to the rotational frequencies, heterodynes occur at all levels in the molecule. Thus, using the frequency "B" energizes all levels in the molecule. This potentiates the establishment of an energy amplification system such as that which occurs with the physical catalyst platinum.

Still further, if a molecule was energized with a frequency corresponding to an l-type doubling constant, such frequency could be used in a substantially similar manner in which a fine splitting frequency from an atomic spectrum is used. The difference between the two frequencies in a doublet is a heterodyne, and energizing the doublet with its' heterodyne frequency (i.e., the splitting frequency) would energize the basic frequency and catalyze the reaction.

A still further example utilizes a combination of frequencies for atomic fine structure. For instance, by utilizing a constant central frequency of 1,131.6 GHz (i.e., the heterodyned difference between rotational frequencies for a hydroxy radical) with a vibrato varying around the central frequency by ±21.4 GHz (i.e., the a constant harmonic for variations between rotational frequencies), use could be made of 1.131.6 GHz EM energy in short bursts, with the bursts coming at a rate of 21.4 GHz.

Since there is slight variation between rotational frequencies for the same level, that frequency range can be used to construct bursts. For example, if the largest "B" is 565.8 GHz, then a rotational frequency heterodyne corresponds to 1,131.6 GHz. If the smallest "B" is 551.2 GHz, this corresponds to a rotational frequency heterodyne of 1,102 GHz. Thus, "chirps" or bursts of energy starting at 1,100 GHz and increasing in frequency to 1,140 GHz, could be used. In fact, the transmitter could be set to "chirp" or burst at a rate of 21.4 GHz.

In any event, there are many ways to make use of the atomic and molecular fine structure frequencies, with their attendant heterodynes and harmonics. An understanding of catalyst mechanisms of action enables one of ordinary skill armed with the teachings of the present invention to utilize a spectral catalyst from the high frequency ultraviolet and visible light regions, down into the sometimes more manageable microwave and radiowave regions. Moreover, the invention enables an artisan of ordinary skill to calculate and/or determine the effects of microwave and radiowave energies on chemical reactions and/or reaction pathways.

Hyperfine Frequencies

Hyperfine structure frequencies are similar to the fine structure frequencies. Fine structure frequencies can be seen by magnifying a portion of a standard frequency spectrum. Hyperfine frequencies can be seen by magnifying a portion of a fine structure spectrum. Fine structure splitting frequencies occur at lower frequencies than the electronic spectra, primarily in the infrared and microwave regions of the electromagnetic spectrum. Hyperfine splitting frequencies occur at even lower frequencies than the fine structure spectra, primarily in the microwave and radio wave regions of the electromagnetic spectrum. Fine structure frequencies are generally caused by at least the electron interacting with its' own magnetic field. Hyperfine frequencies are generally caused by at least the electron interacting with the magnetic field of the nucleus.

Figure 45:
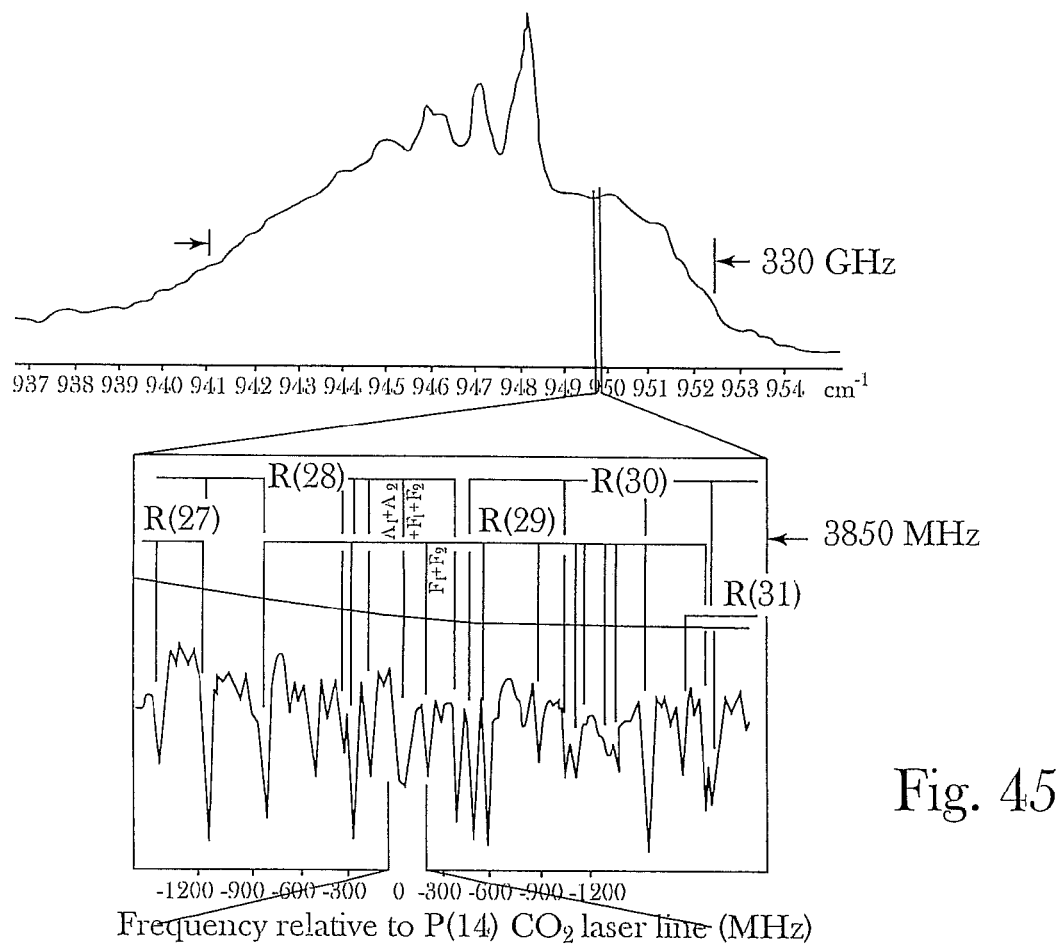
FIG. 45 shows the rotation-vibration band and fine structure frequencies for $SF_6$.

FIG. 36 shows the rotation-vibration band frequency spectra for an $SF_6$ molecule. The rotation-vibration band and fine structure are shown again in FIG. 45. However, the fine structure frequencies are seen by magnifying a small section of the standard vibrational band spectrum (i.e., the lower portion of FIG. 45 shows some of the fine structure frequencies). In many respects, looking at fine structure frequencies is like using a magnifying glass to look at a standard spectrum. Magnification of what looks like a flat and uninteresting portion of a standard vibrational frequency band shows many more curves with lower frequency splitting. These many other curves are the fine structure curves. Similarly, by magnifying a small and seemingly uninteresting portion of the fine structure spectrum of the result is yet another spectrum of many more curves known as the hyperfine spectrum.

A small portion (i.e., from zero to 300) of the $SF_6$ fine structure spectrum is magnified in FIG. 46. The hyperfine spectrum includes many curves split part by even lower frequencies. This time the fine structure spectrum was magnified instead of the regular vibrational spectrum. What is found is even more curves, even closer together. FIGS. 47a and 47b show a further magnification of the two curves marked with asterisks (i.e., "*" and "" in FIG. 46**.

What appears to be a single crisp curve in FIG. 46, turns out to be a series of several curves spaced very close together. These are the hyperfine frequency curves. Accordingly, the fine structure spectra is comprised of several more curves spaced very close together. These other curves spaced even closer together correspond to the hyperfine frequencies.

FIGS. 47a and 47b show that the spacing of the hyperfine frequency curves are very close together and at somewhat regular intervals. The small amount that the hyperfine curves are split apart is called the hyperfine splitting frequency. The hyperfine splitting frequency is also a heterodyne. This concept is substantially similar to the concept of the fine splitting frequency. The difference between two curves that are split apart is called a splitting frequency. As before, the difference between two curves is referred to as a heterodyne frequency. So, hyperfine splitting frequencies are all heterodynes of hyperfine frequencies.

Because the hyperfine frequency curves result from a magnification of the fine structure curves, the hyperfine splitting frequencies occur at only a fraction of the fine structure splitting frequencies. The fine structure splitting frequencies are really just several curves, spaced very close together around the regular spectrum frequency. Magnification of fine structure splitting frequencies results in hyperfine splitting frequencies. The hyperfine splitting frequencies are really just several more curves, spaced very close together. The closer together the curves are, the smaller the distance or frequency separating them. Now the distance separating any two curves is a heterodyne frequency. So, the closer together any two curves are, the smaller (lower) is the heterodyne frequency between them. The distance between hyperfine splitting frequencies (i.e., the amount that hyperfine frequencies are split apart) is the hyperfine splitting frequency. It can also be called a constant or interval.

The electronic spectrum frequency of hydrogen is 2,466 THz. The 2,466 THz frequency is made up of fine structure curves spaced 10.87 GHz (0.01087 THz) apart. Thus, the fine splitting frequency is 10.87 GHz. Now the fine structure curves are made up of hyperfine curves. These hyperfine curves are spaced just 23.68 and 59.21 MHz apart. Thus, 23 and 59 MHz are both hyperfine splitting frequencies for hydrogen. Other hyperfine splitting frequencies for hydrogen include 2.71, 4.21, 7.02, 17.55, 52.63, 177.64, and 1,420.0 MHz. The hyperfine splitting frequencies are spaced even closer together than the fine structure splitting frequencies, so the hyperfine splitting frequencies are smaller and lower than the fine splitting frequencies.

Thus, the hyperfine splitting frequencies are lower than the fine splitting frequencies. This means that rather than being in the infrared and microwave regions, as the fine splitting frequencies can be, the hyperfine splitting frequencies are in the microwave and radiowave regions. These lower frequencies are in the MHz ($10^6$ hertz) and Khz ($10^3$ hertz) regions of the electromagnetic spectrum. Several of the hyperfine splitting frequencies for hydrogen are shown in FIG. 48. (FIG. 48 shows hyperfine structure in the n=2 to n=3 transition of hydrogen).

FIG. 49 shows the hyperfine frequencies for $CH_3I$. These frequencies are a magnification of the fine structure frequencies for that molecule. Since fine structure frequencies for molecules are actually rotational frequencies, what is shown is actually the hyperfine splitting of rotational frequencies.

FIG. 49 shows the hyperfine splitting of just the J=1→2 rotational transition. The splitting between the two tallest curves is less than 100 MHz.

FIG. 50 shows another example of the molecule ClCN. This set of hyperfine frequencies is from the J=1→2 transition of the ground vibrational state for ClCN. Notice that the hyperfine frequencies are separated by just a few megahertz, (MHz) and in a few places by less than even one megahertz.

Figure 51:
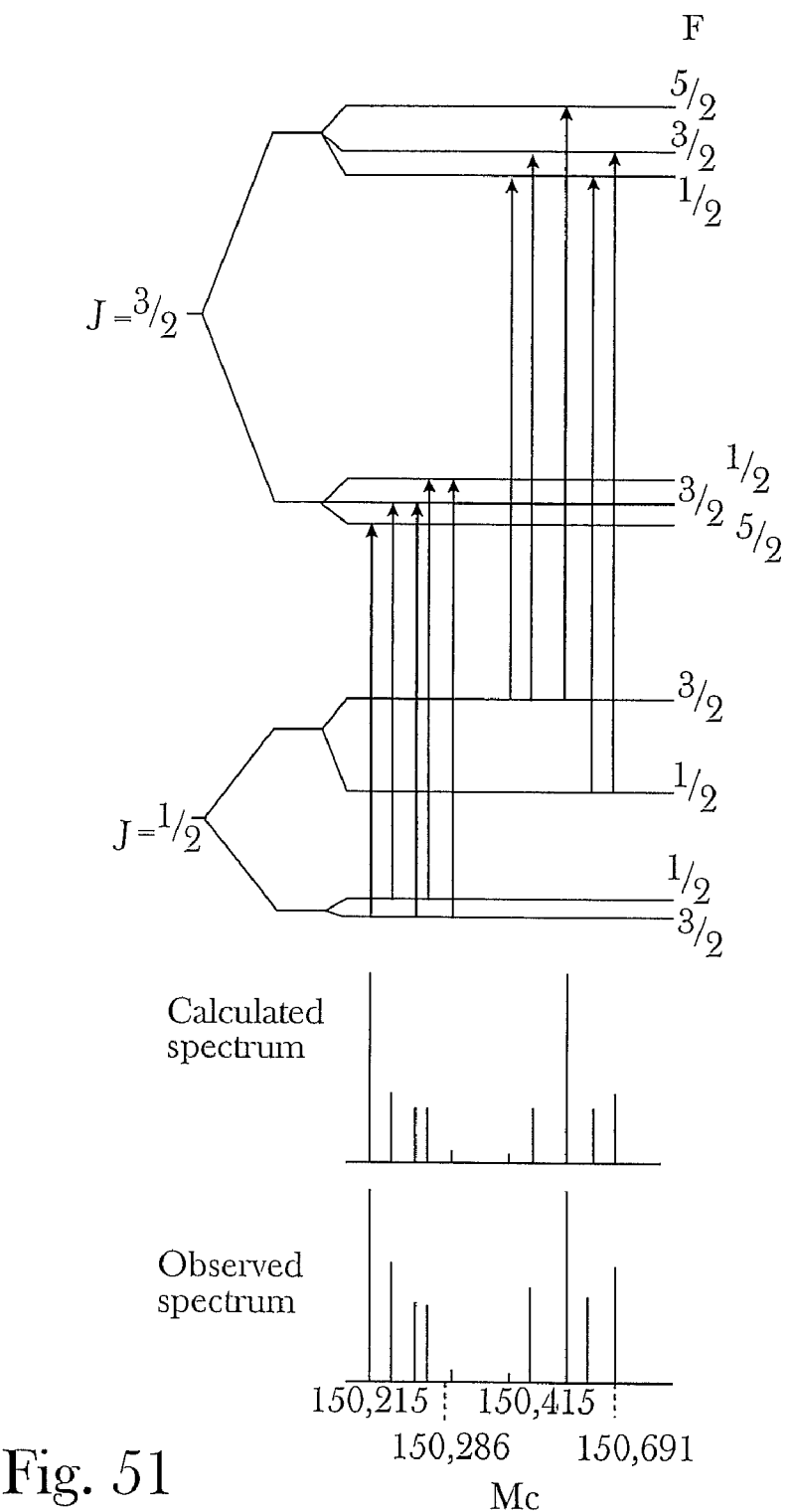
FIG. 51 shows energy level diagrams and hyperfine frequencies for the NO molecule.

The energy-level diagram and spectrum of the J=½→³⁄₂ rotational transition for NO is shown if FIG. 51.

Figure 52:
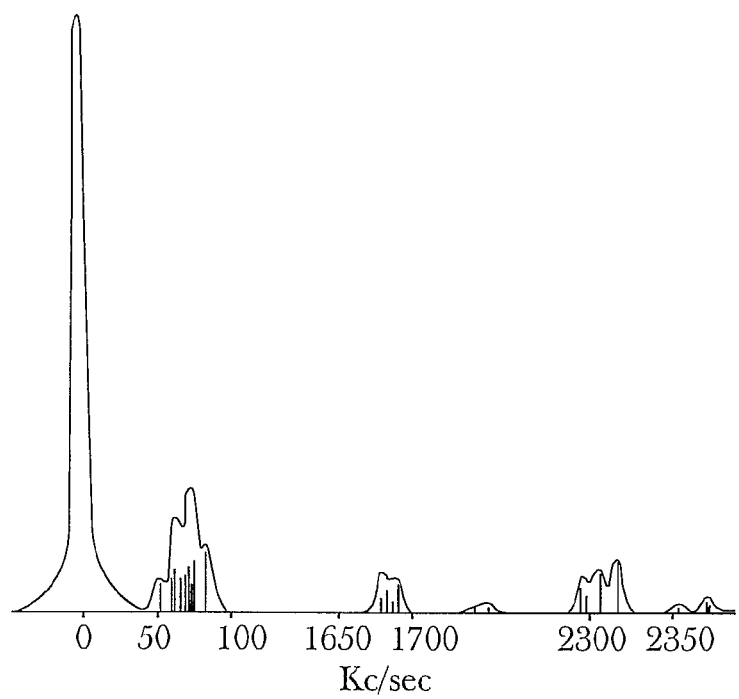
FIG. 52 shows a spectrum corresponding to the hyperfine frequencies for $NH_3$.

In FIG. 52, the hyperfine splitting frequencies for $NH_3$ are shown. Notice that the frequencies are spaced so close together that the scale at the bottom is in kilohertz (Kc/sec). The hyperfine features of the lines were obtained using a beam spectrometer.

Just as with fine splitting frequencies, the hyperfine splitting frequencies are heterodynes of atomic and molecular frequencies. Accordingly, if an atom or molecule is stimulated with a frequency equal to a hyperfine splitting frequency (a heterodyned difference between hyperfine frequencies), the present invention teaches that the energy will equal to a hyperfine splitting frequency will resonate with the hyperfine frequencies indirectly through heterodynes. The related rotational, vibrational, and/or electronic energy levels will, in turn, be stimulated. This is an important discovery. It allows one to use more radio and microwave frequencies to selectively stimulate and target specific reaction system components (e.g., atomic hydrogen intermediates can be stimulated with, for example, (2.55, 23.68 59.2 and/or 1,420 MHz).

Figure 53:
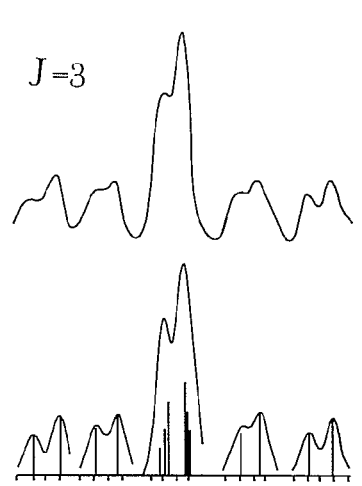
FIG. 53 shows hyperfine structure and doubling of the $NH_3$ spectrum for rotational level J=3. The upper curves in FIG. 53 show experimental data, while the lower curves are derived from theoretical calculations. Frequency increases from left to right in 60 KHz intervals.
Figure 54:
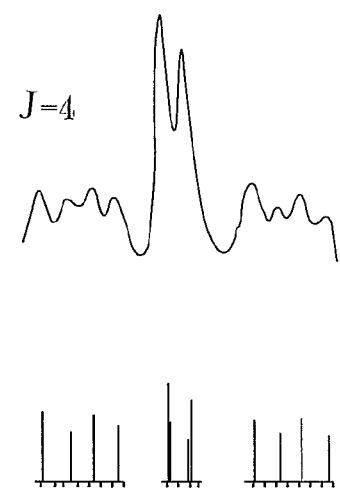
FIG. 54 shows a hyperfine structure and doubling of $NH_3$ spectrum for rotational level J=4. The upper curves in each of FIG. 54 show experimental data, while the lower curves are derived from theoretical calculations. Frequency increases from left to right in 60 KHz intervals.

Hyperfine frequencies, like fine frequencies, also contain features such as doublets. Specifically, in a region where one would expect to find only a single hyperfine frequency curve, there are two curves instead. Typically, one on either side of the location where a single hyperfine frequency was expected. Hyperfine doubling is shown in FIGS. 53 and 54. This hyperfine spectrum is also from $NH_3$. FIG. 53 corresponds to the J=3 rotational level and FIG. 54 corresponds to the J=4 rotational level. The doubling can be seen most easily in the J=3 curves (i.e., FIG. 53). There are two sets of short curves, a tall one, and then two more short sets. Each of the short sets of curves is generally located where one would expect to find just one curve. There are two curves instead, one on either side of the main curve location. Each set of curves is a hyperfine doublet.

There are different notations to indicate the source of the doubling such as l-type doubling, K doubling, and A doubling, etc., and they all have their own constants or intervals. Without going into the detailed theory behind the formation of various types of doublets, the interval between any two hyperfine multiplet curves is also a heterodyne, and thus all of these doubling constants represent frequency heterodynes. Accordingly, those frequency heterodynes (i.e., hyperfine constants) can also be used as spectral energy catalysts according to the present invention.

Specifically, a frequency in an atom or molecule can be stimulated directly or indirectly. If the goal was to stimulate the 2,466 THz frequency of hydrogen for some reason, then, for example, an ultraviolet laser could irradiate the hydrogen with 2,466 THz electromagnetic radiation. This would stimulate the atom directly. However, if such a laser was unavailable, then hydrogen's fine structure splitting frequency of 10.87 GHz could be achieved with microwave equipment. The gigahertz frequency would heterodyne (i.e., add or subtract) with the two closely spaced fine structure curves at 2,466, and stimulate the 2,466 THz frequency band. This would stimulate the atom indirectly.

Still further, the atom could be stimulated by using the hyperfine splitting frequency for hydrogen at 23.68 MHz as produced by radiowave equipment. The 23.68 MHz frequency would heterodyne (i.e., add or subtract) with the two closely spaced hyperfine frequency curves at 2,466, and stimulate the fine structure curves at the 2,466 THz. Stimulation of the fine structure curves would in turn lead to stimulation of the 2,466 THz electronic frequency for the hydrogen atom.

Still further, additional hyperfine splitting frequencies for hydrogen in the radiowave and microwave portions of the electromagnetic spectrum could also be used to stimulate the atom. For example, a radio wave pattern with 2.7 MHz, 4.2 MHz, 7 MHz, 18 MHz, 23 MHz, 52 MHz, and 59 MHz could be used. This would stimulate several different hyperfine frequencies of hydrogen, and it would stimulate them essentially all at the same time. This would cause stimulation of the fine structure frequencies, which in turn would stimulate the electronic frequencies in the hydrogen atom.

Still further, depending on available equipment and/or design, and/or processing constraints, some delivery mode variations can also be used. For example, one of the lower frequencies could be a carrier frequency for the upper frequencies. A continuous frequency of 52 MHz could be varied in amplitude at a rate of 2.7 MHz. Or, a 59 MHz frequency could be pulsed at a rate of 4.2 MHz. There are various ways in which these frequencies can be combined and/or delivered, including different wave shapes durations, intensity shapes, duty cycles, etc. Depending on which of the hyperfine splitting frequencies are stimulated, the evolution of, for example, various and specific transients may be precisely tailored and controlled, allowing precise control over reaction systems using the fine and/or hyperfine splitting frequencies.

Accordingly, a major point of the present invention is once it is understood the energy transfers when frequencies match, then determining which frequencies are available for matching is the next step. This invention discloses precisely how to achieve that goal. Interactions between equipment limitations, processing constraints, etc., can decide which frequencies are best suited for a particular purpose. Thus, both direct resonance and indirect resonance are suitable approaches for the use of spectral energy catalysts.

Electric Fields

Another means for modifying the spectral pattern of substances, is to expose a substance to an electric field. Specifically, in the presence of an electric field, spectral frequency lines of atoms and molecules can be split, shifted, broadened, or changed in intensity. The effect of an electric field on spectral lines is known as the "Stark Effect", in honor of its' discoverer, J. Stark. In 1913, Stark discovered that the Balmer series of hydrogen (i.e., curve II of FIGS. 9a and 9b) was split into several different components, while Stark was using a high electric field in the presence of a hydrogen flame. In the intervening years, Stark's original observation has evolved into a separate branch of spectroscopy, namely the study of the structure of atoms and molecules by measuring the changes in their respective spectral lines caused by an electric field.

The electric field effects have some similarities to fine and hyperfine splitting frequencies. Specifically, as previously discussed herein, fine structure and hyperfine structure frequencies, along with their low frequency splitting or coupling constants, were caused by interactions inside the atom or molecule, between the electric field of the electron and the magnetic field of the electron or nucleus. Electric field effects are similar, except that instead of the electric field coming from inside the atom, the electric field is applied from outside the atom. The Stark effect is primarily the interaction of an external electric field, from outside the atom or molecule, with the electric and magnetic fields already established within the atom or molecule.

When examining electric field effects on atoms, molecules, ions and/or components thereof, the nature of the electric field should also be considered (e.g., such as whether the electric field is static or dynamic). A static electric field may be produced by a direct current. A dynamic electric field is time varying, and may be produced by an alternating current. If the electric field is from an alternating current, then the frequency of the alternating current compared to the frequencies of the, for instance atom or molecule, should also be considered.

In atoms, an external electric field disturbs the charge distribution of the atom's electrons. This disturbance of the electron's own electric field induces a dipole moment in it (i.e., slightly lopsided charge distribution). This lopsided electron dipole moment then interacts with the external electric field. In other words, the external electric field first induces a dipole moment in the electron field, and then interacts with the dipole. The end result is that the atomic frequencies become split into several different frequencies. The amount the frequencies are split apart depends on the strength of the electric field. In other words, the stronger the electric field, the farther apart the splitting.

Figure 55:
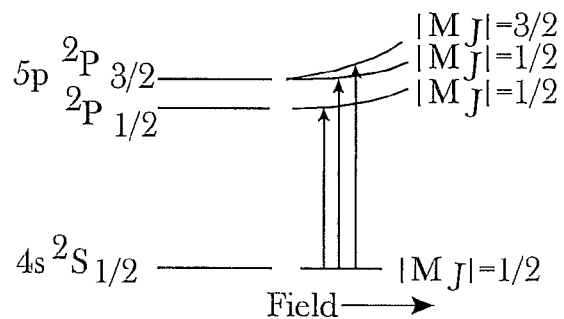
FIG. 55 shows a Stark effect for potassium. In particular, the schematic dependence of the $4_s$ and $5_p$ energy levels on the electric field.
Figure 56:
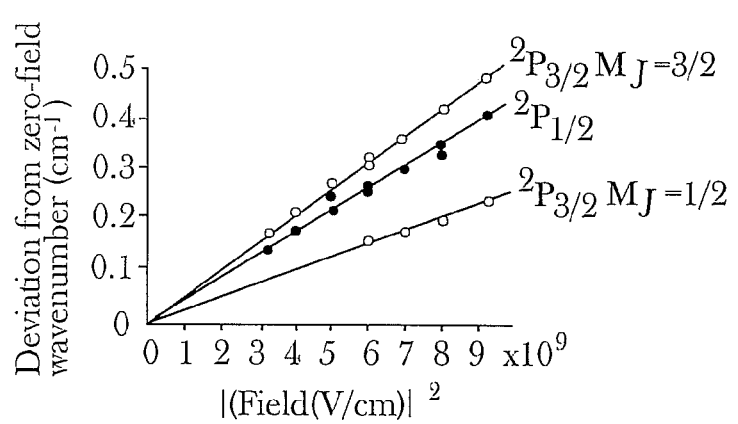
FIG. 56 shows a graph plotting the deviation from zero-field positions of the $5p^2P_{1/2} \leftarrow 4s^2S_{1/2,3/2}$ transition wavenumbers against the square of the electric field.

If the splitting varies directly with the electric field strength, then it is called first order splitting (i.e., $\Delta v = AF$ where $\Delta v$ is the splitting frequency, A is a constant and F is the electric field strength. When the splitting varies with the square of the field strength, it is called a second order or quadriatic effect (i.e., $\Delta v = BF^2$). One or both effects may be seen in various forms of matter. For example, the hydrogen atom exhibits first order Stark effects at low electric field strengths, and second order effects at high field strengths. Other electric field effects which vary with the cube or the fourth power, etc., of the electric field strength are less studied, but produce splitting frequencies nonetheless. A second order electric field effect for potassium is shown in FIGS. 55 and 56. FIG. 55 shows the schematic dependence of the 4s and 5p energy levels on the electric field. FIG. 56 shows a plot of the deviation from zero-field positions of the $5p^2P1/2.3/2 \leftarrow 4s^2S1/2$ transition wavenumbers against the square of the electric field. Note that the frequency splitting or separation of the frequencies (i.e., deviation from zero-field wavenumber) varies with the square of the electric field strength $(v/cm)^2$.

The mechanism for the Stark effect in molecules is simpler than the effect is in atoms. Most molecules already have an electric dipole moment (i.e., a slightly uneven charge distribution). The external electric field simply interacts with the electric dipole moment already inside the molecule. The type of interaction, a first or a second order Stark effect, is different for differently shaped molecules. For example, most symmetric top molecules have first-order Stark effects. Asymmetric rotors typically have second-order Stark effects. Thus, in molecules, as in atoms, the splitting or separation of the frequencies due to the external electric field, is proportional either to the electric field strength itself, or to the square of the electric field strength.

Figure 57:
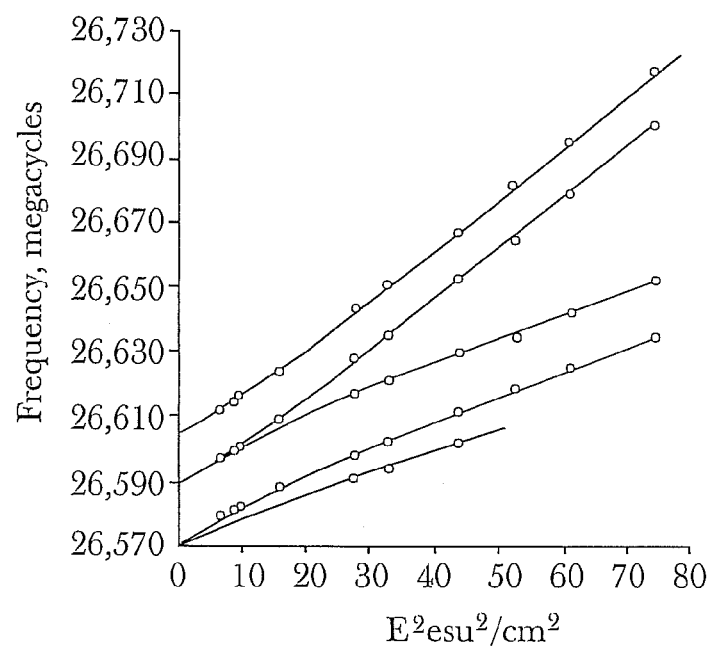
FIG. 57 shows the frequency components of the J=0→1 rotational transition for $CH_3Cl$, as a function of field strength. Frequency is given in megacycles (MHz) and electric field strength (esu cm) is given as the square of the field $E^2$, in $esu^2/cm^2$.

An example of this is shown in FIG. 57, which diagrams how frequency components of the $J=0 \rightarrow 1$ rotational transition for the molecule $CH_3Cl$ respond to an external electric field. When the electric field is very small (e.g., less than $10 E^2$ $esu^2/cm^2$), the primary effect is shifting of the three rotational frequencies to higher frequencies. As the field strength is increased (e.g., between 10 and 20 $E^2$ $esu^2/cm^2$), the three rotational frequencies split into five different frequencies. With continued increases in the electric field strength, the now five frequencies continue to shift to even higher frequencies. Some of the intervals or differences between the five frequencies remain the same regardless of the electric field strength, while other intervals become progressively larger and higher. Thus, a heterodyned frequency might stimulate splitting frequencies at one electric field strength, but not at another.

Figure 58:
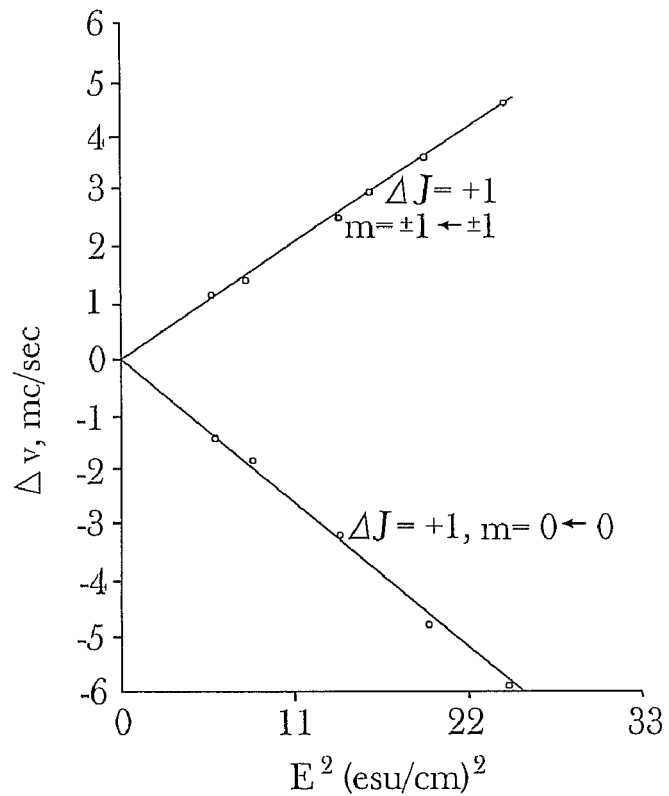
FIG. 58 shows the theoretical and experimental measurements of Stark effect in the J=1→2 transition of the molecule OCS. The unaltered absolute rotational frequency is plotted at zero, and the frequency splitting and shifting is denoted as MHz higher or lower than the original frequency.

Another molecular example is shown in FIG. 58. (This is a diagram of the Stark Effect in the same OCS molecule shown in FIG. 44 for the J=1→2). The J=1→2 rotational transition frequency is shown centered at zero on the horizontal frequency axis in FIG. 58. That frequency centered at zero is a single frequency when there is no external electric field. When an electric field is added, however, the single rotational frequency splits into two. The stronger the electric field is, the wider the splitting is between the two frequencies. One of the new frequencies shifts up higher and higher, while the other frequency shifts lower and lower. Because the difference between the two frequencies changes when the electric field strength changes, a heterodyned splitting frequency might stimulate the rotational level at one electric field strength, but not at another. An electric field can effect the spectral frequencies of reaction participants, and thus impact the spectral chemistry of a reaction.

Broadening and shifting of spectral lines also occurs with the intermolecular Stark effect. The intermolecular Stark effect is produced when the electric field from surrounding atoms, ions, or molecules, affects the spectral emissions of the species under study. In other words, the external electric field comes from other atoms and molecules rather than from a DC or AC current. The other atoms and molecules are in constant motion, and thus their electric fields are inhomogeneous in space and time. Instead of a frequency being split into several easily seen narrow frequencies, the original frequency simply becomes much wider, encompassing most, if not all, of what would have been the split frequencies, (i.e., it is broadened). Solvents, support materials, poisons, promoters, etc., are co+mposed of atoms and molecules and components thereof. It is now understood that many of their effects are the result of the intermolecular Stark effect.

Figure 59:
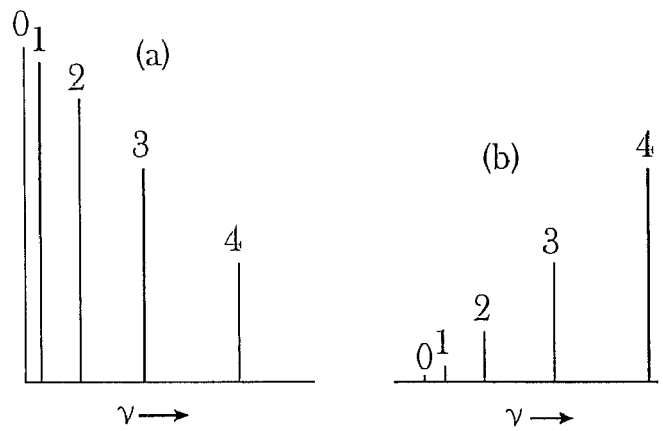
FIG. 59 shows patterns of Stark components for transitions in the rotation of an asymmetric top molecule. Specifically.

The above examples demonstrate how an electric field splits, shifts, and broadens spectral frequencies for matter. However, intensities of the lines can also be affected. Some of these variations in intensity are shown in FIGS. 59*a* and 59*b*. FIG. 59*a* shows patterns of Stark components for transitions in the rotation of an asymmetric top molecule for the J=4→5 transition; whereas FIG. 59*b* corresponds to J=4→4. The intensity variations depend on rotational transitions, molecular structure, etc., and the electric field strength.

An interesting Stark effect is shown in a structure such as a molecule, which has hyperfine (rotational) frequencies. The general rule for the creation of hyperfine frequencies is that the hyperfine frequencies result from an interaction between electrons and the nucleus. This interaction can be affected by an external electric field. If the applied external electric field is weak, then the Stark energy is much less than the energy of the hyperfine energy (i.e., rotational energy). The hyperfine lines are split into various new lines, and the separation (i.e., splitting) between the lines is very small (i.e., at radio frequencies and extra low frequencies).

If the external electric field is very strong, then the Stark energy is much larger than the hyperfine energy, and the molecule is tossed, sometimes violently, back and forth by the electric field. In this case, the hyperfine structure is radically changed. It is almost as though there no longer is any hyperfine structure. The Stark splitting is substantially the same as that which would have been observed if there were no hyperfine frequencies, and the hyperfine frequencies simply act as a small perturbation to the Stark splitting frequencies.

If the external electric field is intermediate in strength, then the Stark and hyperfine energies are substantially equivalent. In this case, the calculations become very complex. Generally, the Stark splitting is close to the same frequencies as the hyperfine splitting, but the relative intensities of the various components can vary rapidly with slight changes in the strength of the external electric field. Thus, at one electric field strength one splitting frequency may predominate, while at an electric field strength just 1% higher, a totally different Stark frequency could predominate in intensity.

All of the preceding discussion on the Stark effect has concentrated on the effects due to a static electric field, such as one would find with a direct current. The Stark effects of a dynamic, or time-varying electric field produced by an alternating current, are quite interesting and can be quite different. Just which of those affects appear, depends on the frequency of the electric field (i.e., alternating current) compared to the frequency of the matter in question. If the electric field is varying very slowly, such as with 60 Hz wall outlet electricity, then the normal or static type of electric field effect occurs. As the electric field varies from zero to maximum field strength, the matter frequencies vary from their unsplit frequencies to their maximally split frequencies at the rate of the changing electric field. Thus, the electric field frequency modulates the frequency of the splitting phenomena.

Figure 16:
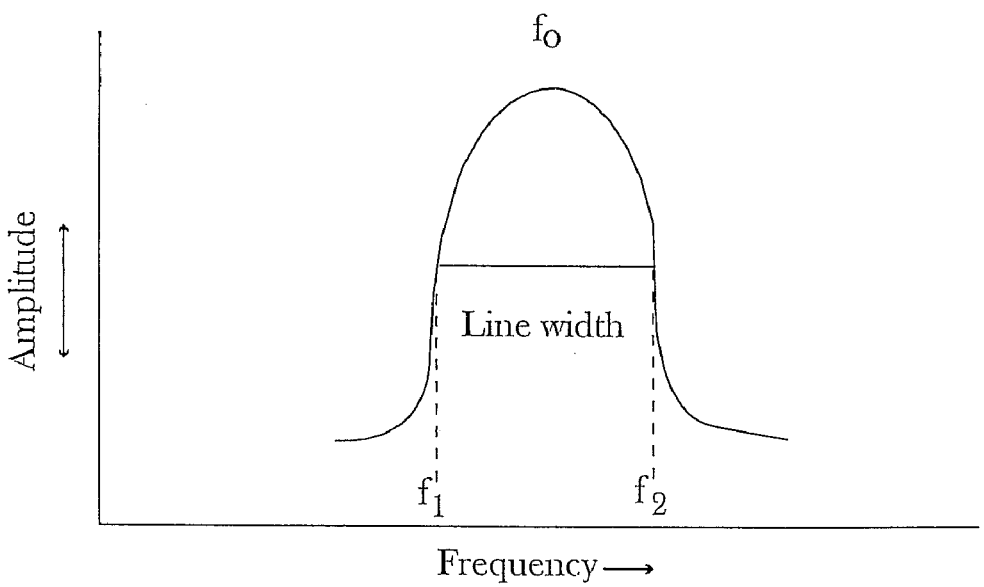
FIG. 16 is spectral curve showing a line width which corresponds to $f_2-f_1$.

However, as the electrical frequency increases, the first frequency measurement it will begin to overtake is the line width (see FIG. 16 for a diagram of line width). The line width of a curve is its' distance across, and the measurement is actually a very tiny heterodyne frequency measurement from one side of the curve to the other side. Line width frequencies are typically around 100 KHz at room temperature. In practical terms, line width represents a relaxation time for molecules, where the relaxation time is the time required for any transient phenomena to disappear. So, if the electrical frequency is significantly smaller than the line width frequency, the molecule has plenty of time to adjust to the slowly changing electric field, and the normal or static-type Stark effects occur.

If the electrical frequency is slightly less than the line width frequency, the molecule changes its' frequencies substantially in rhythm with the frequency of the electric field (i.e., it entrains to the frequency of the electric field). This is shown in FIG. 60 which shows the Stark effect for OCS on the J=1→2 transition with applied electric fields at various frequencies. The letter "a" corresponds to the Stark effect with a static DC electric field; "b" corresponds to a broadening and blurring of the Stark frequencies with a 1 KHz electric field; and "c" corresponds to a normal Stark effect with an electric field of 1,200 KHz. As the electric field frequency approaches the KHz line width range, the Stark curves vary their frequencies with the electric field frequency and become broadened and somewhat blurred. When the electric field frequency moves up and beyond the line width range to about 1,200 KHz, the normal Stark type curves again become crisp and distinguishable. In many respects, the molecule cannot keep up with the rapid electrical field variation and simply averages the Stark effect. In all three cases, the cyclic splitting of the Stark frequencies is modulated with the electrical field frequency, or its' first harmonic (i.e., 2× the electrical field frequency).

The next frequency measurement that an ever-increasing electrical frequency will overtake in a molecule is the transitional frequency between two rotational levels (i.e., hyperfine frequencies). As the electric field frequency approaches a transitional frequency between two levels, the radiation of the transitional frequency in the molecule will induce transitions back and forth between the levels. The molecule oscillates back and forth between both levels, at the frequency of the electric field. When the electric field and transition level frequencies are substantially the same (i.e., in resonance), the molecule will be oscillating back and forth in both levels, and the spectral lines for both levels will appear simultaneously and at approximately the same intensity. Normally, only one frequency level is seen at a time, but a resonant electric field causes the molecule to be at both levels at essentially the same time, and so both transitional frequencies appear in its' spectrum.

Moreover, for sufficiently large electric fields (e.g., those used to generate plasmas) additional transition level frequencies can occur at regular spacings substantially equal to the electric field frequency. Also, splitting of the transition level frequencies can occur, at frequencies of the electric field frequency divided by odd numbers (e.g., electric field frequency "$f_E$" divided by 3, or 5, or 7, i.e., $f_E/3$ or $f_E/5$, etc.).

All the varied effects of electric fields cause new frequencies, new splitting frequencies and new energy level states.

Further, when the electric field frequency equals a transition level frequency of for instance, an atom or molecule, a second component with an opposite frequency charge and equal intensity can develop. This is negative Stark effect, with the two components of equal and opposite frequency charges destructively canceling each other. In spectral chemistry terms this amounts to a negative catalyst or poison in the reaction system, if the transition thus targeted was important to the reaction pathway. Thus, electric fields cause the Stark effect, which is the splitting, shifting, broadening, or changing intensity and changing transitional states of spectral frequencies for matter, (e.g., atoms and molecules). As with many of the other mechanisms that have been discussed herein, changes in the spectral frequencies of reaction systems can affect the reaction rate and/or reaction pathway. For example, consider a reaction system like the following:

where A&B are reactants, C is a physical catalyst, I stands for the intermediates, and D&F are the products.

Assume arguendo that the reaction normally progresses at only a moderate rate, by virtue of the fact that the physical catalyst produces several frequencies that are merely close to harmonics of the intermediates. Further assume that when an electric field is added, the catalyst frequencies are shifted so that several of the catalyst frequencies are now exact or substantially exact harmonics of the intermediates. This will result in, for example, the reaction being catalyzed at a faster rate. Thus, the Stark effect can be used to obtain a more efficient energy transfer through the matching of frequencies (i.e., when frequencies match, energies transfer).

If a reaction normally progresses at only a moderate rate, many "solutions" have included subjecting the reaction system to extremely high pressures. The high pressures result in a broadening of the spectral patterns, which improves the transfer of energy through a matching of resonant frequencies. By understanding the underlying catalyst mechanisms of action, high pressure systems could be replaced with, for example, a simple electric field which produces broadening. Not only would this be less costly to an industrial manufacturer, it could be much safer for manufacturing due to the removal of, for example, high pressure equipment.

Some reactants when mixed together do not react very quickly at all, but when an electric field is added they react rather rapidly. The prior art may refer to such a reaction as being catalyzed by an electric field and the equations would look like this:

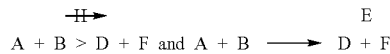

where E is the electric field. In this case, rather than applying a catalyst "C" (as discussed previously) to obtain the products "D+F", an electric field "E" can be applied. In this instance, the electric field works by changing the spectral frequencies (or spectral pattern) of one or more components in the reaction system so that the frequencies come into resonance, and the reaction can proceed along a desired reaction pathway (i.e., when frequencies match, energy is transferred). Understood in this way, the electric field becomes just another tool to change spectral frequencies of atoms and molecules, and thereby affect reaction rates in spectral chemistry.

Reaction pathways are also important. In the absence of an electrical field, a reaction pathway will progress to one set of products:

However, if an electrical field is added, at some particular strength of the field, the spectral frequencies may change so much, that a different intermediate is energized and the reaction proceeds down a different reaction pathway:

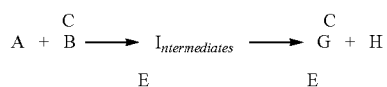

This is similar to the concept discussed earlier herein, regarding the formation of different products depending on temperature. The changes in temperature caused changes in spectral frequencies, and hence different reaction pathways were favored at different temperatures. Likewise, electric fields cause changes in spectral frequencies, and hence different reactions pathways are favored by different electric fields. By tailoring an electric field to a particular reaction system, one can control not only the rate of the reaction but also the reaction products produced.

The ability to tailor reactions, with or without a physical catalyst, by varying the strength of an electric field should be useful in many manufacturing situations. For example, it might be more cost effective to build only one physical set-up for a reaction system and to use one or more electric fields to change the reaction dynamics and products, depending on which product is desired. This would save the expense of having a separate physical set-up for production of each group of products.

Besides varying the strength of an electric field, the frequency of an electric field can also be varied. Assuming that a reaction will proceed at a much faster rate if a particular strength static electric field (i.e., direct current) is added as in the following:

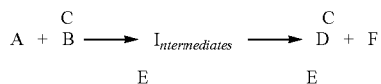

But further assume, that because of reactor design and location, it is much easier to deliver a time-varying electric field with alternating current. A very low frequency field, such as with a 60 Hz wall outlet, can produce the normal or static-type Stark effect. Thus, the reactor could be adapted to the 60 Hz electric field and enjoy the same increase in reaction rate that would occur with the static electric field.

If a certain physical catalyst produces spectral frequencies that are close to intermediate frequencies, but are not exact, it is possible that the activity of the physical catalyst in the past may have been improved by using higher temperatures. As disclosed earlier herein, the higher temperatures actually broadened the physical catalyst's spectral pattern to cause the frequency of the physical catalyst to be at least a partial match for at least one of the intermediates. What is significant here is that high temperature boilers can be minimized, or eliminated altogether, and in their stead a moderate frequency electric field which, for example, broadened the spectral frequencies, could be used. For example, a frequency of around 100 Khz, equivalent to the typical line width frequencies at room temperature, could broaden substantially all of the spectral curves and cause the physical catalyst's spectral curves to match those of, for example, required intermediates. Thus, the electric field could cause the matter to behave as though the temperature had been raised, even though it had not been. (Similarly, any spectral manipulation, (e.g., electric fields acoustics, heterodynes, etc., that cause changes in the spectral line width, may cause a material to behave as though its temperature had been changed).

The cyclic splitting of the Stark frequencies can be modulated with the electrical field frequency or its' first harmonic (i.e., first-order Stark effects are modulated with the electrical field frequency, while second-order Stark effects are modulated by two times the electrical field, frequency). Assume that a metallic platinum catalyst is used in a hydrogen reaction and it is desired to stimulate the 2.7 MHz hyperfine frequency of the hydrogen atoms. Earlier herein it was disclosed that electromagnetic radiation could be used to deliver the 2.7 MHz frequency. However, use of an alternating electric field at 2.7 MHz could be used instead. Since platinum is a metal and conducts electricity well, the platinum can be considered to be a part of the alternating current circuit. The platinum will exhibit a Stark effect, with all the frequencies splitting at a rate of 2.7 MHz. At sufficiently strong electric fields, additional transition frequencies or "sidebands" will occur at regular spacings equal to the electric field frequency. There will be dozens of split frequencies in the platinum atoms that are heterodynes of 2.7 MHz. This massive heterodyned output may stimulate the hydrogen hyperfine frequency of 2.7 MHz and direct the reaction.

Another way to achieve this reaction, of course, would be to leave the platinum out of the reaction altogether. The 2.7 MHz field will have a resonant Stark effect on the hydrogen, separate and independent of the platinum catalyst. Copper is not normally catalytic for hydrogen, but copper could be used to construct a reaction vessel like a Stark waveguide to energize the hydrogen. A Stark waveguide is used to perform Stark spectroscopy. It is shown as FIGS. 61a and 61b. Specifically, FIG. 61a shows the construction of the Stark waveguide, whereas FIG. 61b shows the distribution of fields in the Stark waveguide. The electrical field is delivered through the conducting plate. A reaction vessel could be made for the flow-through of gases and use an economical metal such as copper for the conducting plate. When the 2.7 MHz alternating current is delivered through the electrical connection to the copper conductor plate, the copper spectral frequencies, none of which are particularly resonant with hydrogen, will exhibit a Stark effect with normal-type splitting. The Stark frequencies will be split at a rate of 2.7 MHz. At a sufficiently strong electric field strength, additional sidebands will appear in the copper, with regular spacings (i.e., heterodynes) of 2.7 MHz even though none of the actual copper frequencies matches the hydrogen frequencies, the Stark splitting or heterodynes will match the hydrogen frequency. Dozens of the copper split frequencies may resonate indirectly with the hydrogen hyperfine frequency and direct the reaction (i.e., when frequencies match, energies transfer).

With sophisticated equipment and a good understanding of a particular system, Stark resonance can be used with a transition level frequency. For example, assume that to achieve a particular reaction pathway, a molecule needs to be stimulated with a transition level frequency of 500 MHz. By delivering the 500 MHz electrical field to the molecule, this resonant electrical field may cause the molecule to oscillate back and forth between the two levels at the rate of 500 MHz. This electrically creates the conditions for light amplification (i.e., laser via stimulation of multiple upper energy levels) and any added electromagnetic radiation at this frequency will be amplified by the molecule. In this manner, an electrical field may substitute for the laser effects of physical catalysts.

In summary, by understanding the underlying spectral mechanisms of chemical reactions, electric fields can be used as yet another tool to catalyze and modify those chemical reactions and/or reaction pathways by modifying the spectral characteristics, for example, at least one participant and/or one or more components in the reaction system. Thus, another tool for mimicking catalyst mechanisms of reactions can be utilized.

Magnetic Fields

In spectral terms, magnetic fields behave similar to electric fields in their effect. Specifically, the spectral frequency lines, for instance of atoms and molecules, can be split and shifted by a magnetic field. In this case, the external magnetic field from outside the atom or molecule, interacts with the electric and magnetic fields already inside the atom or molecule.

This action of an external magnetic field on spectral lines is called the "Zeeman Effect", in honor of its' discoverer, Dutch physicist Pieter Zeeman. In 1896, Zeeman discovered that the yellow flame spectroscopy "D" lines of sodium were broadened when the flame was held between strong magnetic poles. It was later discovered that the apparent broadening of the sodium spectral lines was actually due to their splitting and shifting. Zeeman's original observation has evolved into a separate branch of spectroscopy, relating to the study of atoms and molecules by measuring the changes in their spectral lines caused by a magnetic field. This in turn has evolved into the nuclear magnetic resonance spectroscopy and magnetic resonance imaging used in medicine, as well as the laser magnetic resonance and electron spin resonance spectroscopy used in physics and chemistry.

Figure 62A:
FIG. 62a shows the Zeeman effect for sodium "D" lines.
Figure 62B:
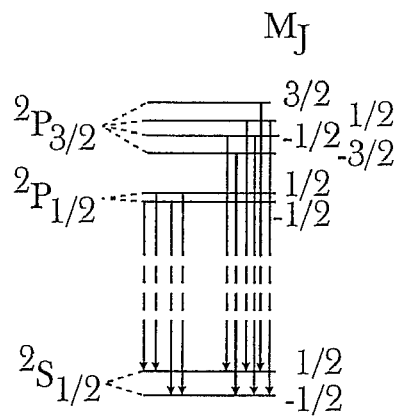
FIG. 62b shows the energy level diagram for transitions in the Zeeman effect for sodium "D" lines.

The Zeeman effect for the famous "D" lines of sodium is shown in FIGS. 62a and 62b. FIG. 62a shows the Zeeman effect for sodium "D" lines; whereas FIG. 62b shows the energy level diagram for the transitions in the Zeeman effect for the sodium "D" lines. The "D" lines are traditionally said to result from transition between the $3p^2P$ and $3s^2S$ electron orbitals. As is shown, each of the single spectral frequencies is split into two or more slightly different frequencies, which center around the original unsplit frequency.

Figure 63:
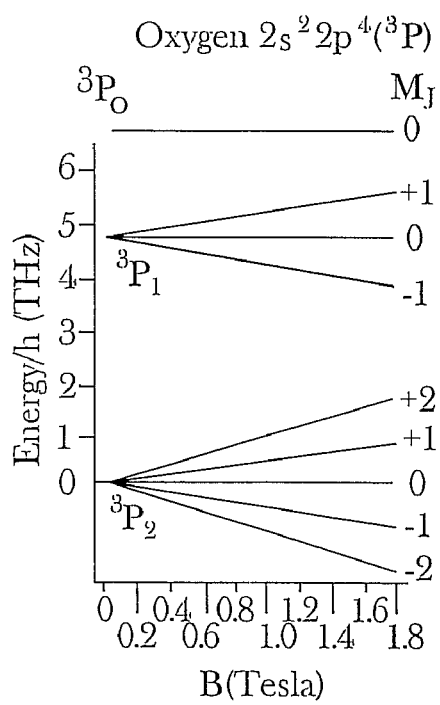
FIG. 63 is a graph which shows the splitting of the ground term of the oxygen atom as a function of magnetic field.

In the Zeeman effect, the amount that the spectral frequencies are split apart depends on the strength of the applied magnetic field. FIG. 63 shows Zeeman splitting effects for the oxygen atom as a function of magnetic field. When there is no magnetic field, there are two single frequencies at zero and 4.8. When the magnetic field is at low strength (e.g., 0.2 Tesla) there is just slight splitting and shifting of the original two frequencies. However, as the magnetic field is increased, the frequencies are split and shifted farther and farther apart.

Figure 64:
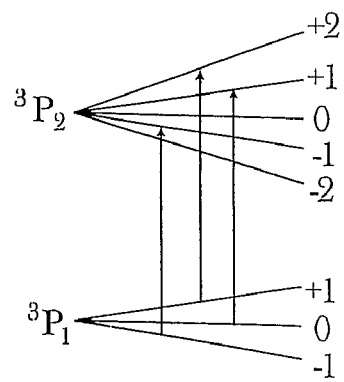
FIG. 64 is a graphic which shows the dependence of the Zeeman effect on magnetic field strength for the "3P" state of silicon.

The degree of splitting and shifting in the Zeeman effect, depending on magnetic field strength, is shown in FIG. 64 for the $^3P$ state of silicon.

As with the Stark effect generated from an external electric field, the Zeeman effect, generated from an external magnetic field, is slightly different depending on whether an atom or molecule is subjected to the magnetic field. The Zeeman effect on atoms can be divided into three different magnetic field strengths: weak; moderate; and strong. If the magnetic field strength is weak, the amount that the spectral frequencies will be shifted and split apart will be very small. The shifting away from the original spectral frequency will still stimulate the shifted frequencies. This is because they will be so close to the original spectral frequency that they will still be well within its resonance curve. As for the splitting, it is so small, that it is even less than the hyperfine splitting that normally occurs. This means that in a weak magnetic field, there will be only very slight splitting of spectral frequencies, translating into very low splitting frequencies in the lower regions of the radio spectrum and down into the very low frequency region. For example, the Zeeman splitting frequency for the hydrogen atom, which is caused by the earth's magnetic field, is around 30 KHz. Larger atoms have even lower frequencies in the lower kilohertz and even hertz regions of the electromagnetic spectrum.

Without a magnetic field, an atom can be stimulated by using direct resonance with a spectral frequency or by using its fine or hyperfine splitting frequencies in the infrared through microwave, or microwave through radio regions, respectively. By merely adding a very weak magnetic field, the atom can be stimulated with an even lower radio or very low frequency matching the Zeeman splitting frequency. Thus, by simply using a weak magnetic field, a spectral catalyst range can be extended even lower into the radio frequency range. The weak magnetic field from the Earth causes Zeeman splitting in atoms in the hertz and kilohertz ranges. This means that all atoms, including those in biological organisms, are sensitive to hertz and kilohertz EM frequencies, by virtue of being subjected to the Earth's magnetic field.

At the other end of magnetic field strength, is the very strong magnetic field. In this case, the splitting apart and shifting of the spectral frequencies will be very wide. With this wide shifting of frequencies, the difference between the split frequencies will be much larger than the difference between the hyperfine splitting frequencies. This translates to Zeeman effect splitting frequencies at higher frequencies than the hyperfine splitting frequencies. This splitting occurs somewhere around the microwave region. Although the addition of a strong magnetic field does not extend the reach in the electromagnetic spectrum at one extreme or the other, as a weak magnetic field does, it still does provide an option of several more potential spectral catalyst frequencies that can be used in the microwave region.

The moderate magnetic field strength case is more complicated. The shifting and splitting caused by the Zeeman effect from a moderate magnetic field will be approximately equal to the hyperfine splitting. Although not widely discussed in the prior art, it is possible to apply a moderate magnetic field to an atom, to produce Zeeman splitting which is substantially equivalent to its' hyperfine splitting. This presents interesting possibilities. Methods for guiding atoms in chemical reactions were disclosed earlier herein by stimulating atoms with hyperfine splitting frequencies. The Zeeman effect provides a way to achieve similar effects without introducing any spectral frequencies at all. For example, by introducing a moderate magnetic field, resonance may be set-up within the atom itself, that stimulates and/or energizes and/or stabilizes the atom.

The moderate magnetic field causes low frequency Zeeman splitting, that matches and hence energizes the low frequency hyperfine splitting frequency in the atom. However, the low hyperfine splitting frequencies actually correspond to the heterodyned difference between two vibrational or fine structure frequencies. When the hyperfine splitting frequency is stimulated, the two electronic frequencies will eventually be stimulated. This in turn causes the atom to be, for example, stimulated. Thus, the Zeeman effect permits a spectral energy catalyst stimulation of an atom by exposing that atom to a precise strength of a magnetic field, and the use of spectral EM frequencies is not required (i.e., so long as frequencies match, energies will transfer). The possibilities are quite interesting because an inert reaction system may suddenly spring to life upon the application of the proper moderate strength magnetic field.

There is also a difference between the "normal" Zeeman effect and the "anomalous" Zeeman effect. With the "normal" Zeeman effect, a spectral frequency is split by a magnetic field into three frequencies, with expected even spacing between them (see FIG. 65a which shows the "normal" Zeeman effects and FIG. 65b which shows the "anomalous" Zeeman effects). One of the new split frequencies is above the original frequency, and the other new split frequency is below the original frequency. Both new frequencies are split the same distance away from the original frequency. Thus, the difference between the upper and original and the lower and original frequencies is about the same. This means that in terms of heterodyne differences, there are at most, two new heterodyned differences with the normal Zeeman effect. The first heterodyne or splitting difference is the difference between one of the new split frequencies and the original frequency. The other splitting difference is between the upper and lower new split frequencies. It is, of course, twice the frequency difference between either of the upper or lower frequencies and the original frequency.

In many instances the Zeeman splitting produced by a magnetic field results in more than three frequencies, or in splitting that is spaced differently than expected. This is called the "anomalous" Zeeman effect (see FIGS. 65 and 66; wherein FIG. 66 shows an anamolous Zeeman effect for zinc 3p→3s.

If there are still just three frequencies, and the Zeeman effect is anomalous because the spacing is different than expected, the situation is similar to the normal effect. However, there are at most, two new splitting frequencies that can be used. If, however, the effect is anomalous because more than three frequencies are produced, then there will be a much more richly varied situation. Assume an easy case where there are four Zeeman splitting frequencies (see FIG. 67a and FIG. 67b). FIG. 67a shows four Zeeman splitting frequencies and FIG. 67b shows four new heterodyned differences.

In this example of anomalous Zeeman splitting, there are a total of four frequencies, where once existed only one frequency. For simplicity's sake, the new Zeeman frequencies will be labeled 1, 2, 3, and 4. Frequencies 3 and 4 are also split apart by the same difference "w". Thus, "w" is a heterodyned splitting frequency. Frequencies 2 and 3 are also split apart by a different amount "x". So far there are two heterodyned splitting frequencies, as in the normal Zeeman effect.

However, frequencies 1 and 3 are split apart by a third amount "y", where "y" is the sum of "w" and "x". And, frequencies 2 and 4 are also split apart by the same third amount "y". Finally, frequencies 1 and 4 are split even farther apart by an amount "z". Once again, "z" is a summation amount from adding "w+x+w". Thus, the result is four heterodyned frequencies: w, x, y, and z in the anomalous Zeeman effect.

If there were six frequencies present from the anomalous Zeeman effect, there would be even more heterodyned differences. Thus, the anomalous Zeeman effect results in far greater flexibility in the choice of frequencies when compared to the normal Zeeman effect. In the normal Zeeman effect the original frequency is split into three evenly spaced frequencies, with a total of just two heterodyned frequencies. In the anomalous Zeeman effect the original frequency is split into four or more unevenly spaced frequencies, with at least four or more heterodyned frequencies.

Now for a discussion of the Zeeman effect in molecules. Molecules come in three basic varieties: ferromagnetic; paramagnetic; and diamagnetic. Ferromagnetic molecules are typical magnets. The materials typically hold a strong magnetic field and are composed of magnetic elements such as iron, cobalt, and nickel.

Paramagnetic molecules hold only a weak magnetic field. If a paramagnetic material is put into an external magnetic field, the magnetic moment of the molecules of the material are lined up in the same direction as the external magnetic field. Now, the magnetic moment of the molecules is the direction in which the molecules own magnetic field is weighted. Specifically, the magnetic moment of a molecule will tip to whichever side of the molecule is more heavily weighted in terms of its own magnetic field. Thus, paramagnetic molecules will typically tip in the same direction as an externally applied magnetic field. Because paramagnetic materials line up with an external magnetic field, they are also weakly attracted to sources of magnetic fields.

Common paramagnetic elements include oxygen, aluminum, sodium, magnesium, calcium and potassium. Stable molecules such as oxygen ($O_2$) and nitric oxide (NO) are also paramagnetic. Molecular oxygen makes up approximately 20% of our planet's atmosphere. Both molecules play important roles in biologic organisms. In addition, unstable molecules, more commonly known as free radicals, chemical reaction intermediates or plasmas, are also paramagnetic. Paramagnetic ions include hydrogen, manganese, chromium, iron, cobalt, and nickel. Many paramagnetic substances occur in biological organisms. For instance the blood flowing in our veins is an ionic solution containing red blood cells. The red blood cells contain hemoglobin, which in turn contains ionized iron. The hemoglobin, and hence the red blood cells, are paramagnetic. In addition, hydrogen ions can be found in a multitude of organic compounds and reactions. For instance, the hydrochloric acid in a stomach contains hydrogen ions. Adenosine triphosphate (ATP), the energy system of nearly all biological organisms, requires hydrogen and manganese ions to function properly. Thus, the very existence of life itself depends on paramagnetic materials.

Diamagnetic molecules, on the other hand, are repelled by a magnetic field, and line up what little magnetic moments they have away from the direction of an external magnetic field. Diamagnetic substances do not typically hold a magnetic field. Examples of diamagnetic elements include hydrogen, helium, neon, argon, carbon, nitrogen, phosphorus, chlorine, copper, zinc, silver, gold, lead, and mercury. Diamagnetic molecules include water, most gases, organic compounds, and salts such as sodium chloride. Salts are really just crystals of diamagnetic ions. Diamagnetic ions include lithium, sodium, potassium, rubidium, caesium, fluorine, chlorine, bromine, iodine, ammonium, and sulphate. Ionic crystals usually dissolve easily in water, and as such the ionic water solution is also diamagnetic. Biologic organisms are filled with diamagnetic materials, because they are carbon-based life forms. In addition, the blood flowing in our veins is an ionic solution containing blood cells. The ionic solution (i.e., blood plasma) is made of water molecules, sodium ions, potassium ions, chlorine ions, and organic protein compounds. Hence, our blood is a diamagnetic solution carrying paramagnetic blood cells.

With regard to the Zeeman effect, first consider the case of paramagnetic molecules. As with atoms, the effects can be categorized on the basis of magnetic field strength. If the external magnetic field applied to a paramagnetic molecule is weak, the Zeeman effect will produce splitting into equally spaced levels. In most cases, the amount of splitting will be directly proportional to the strength of the magnetic field, a "first-order" effect. A general rule of thumb is that a field of one (1) oersted (i.e., slightly larger than the earth's magnetic field) will produce Zeeman splittings of approximately 1.4 MHz in paramagnetic molecules. Weaker magnetic fields will produce narrower splittings, at lower frequencies. Stronger magnetic fields will produce wider splittings, at higher frequencies. In these first order Zeeman effects, there is usually only splitting, with no shifting of the original or center frequency, as was present with Zeeman effects on atoms.

In many paramagnetic molecules there are also second-order effects where the Zeeman splitting is proportional to the square of the magnetic field strength. In these cases, the splitting is much smaller and of much lower frequencies. In addition to splitting, the original or center frequencies shift as they do in atoms, proportional to the magnetic field strength.

Sometimes the direction of the magnetic field in relation to the orientation of the molecule makes a difference. For instance, π frequencies are associated with a magnetic field parallel to an exciting electromagnetic field, while a frequencies are found when it is perpendicular. Both π and σ frequencies are present with a circularly polarized electromagnetic field. Typical Zeeman splitting patterns for a paramagnetic molecule in two different transitions are shown in FIG. 68a and 68b. The π frequencies are seen when $\Delta M=0$, and are above the long horizontal line. The σ frequencies are seen when $\Delta M=\pm 1$, and are below the long horizontal line. If a paramagnetic molecule was placed in a weak magnetic field, circularly polarized light would excite both sets of frequencies in the molecule. Thus, it is possible to control which set of frequencies are excited in a molecule by controlling its orientation with respect to the magnetic field.

When the magnetic field strength is intermediate, the interaction between the paramagnetic molecule's magnetic moments and the externally applied magnetic field produces Zeeman effects equivalent to other frequencies and energies in the molecule. For instance, the Zeeman spitting may be near a rotational frequency and disturb the end-over-end rotational motion of the molecule. The Zeeman splitting and energy may be particular or large enough to uncouple the molecule's spin from its molecular axis.

If the magnetic field is very strong, the nuclear magnetic moment spin will uncouple from the molecular angular momentum. In this case, the Zeeman effects overwhelm the hyperfine structure, and are of much higher energies at much higher frequencies. In spectra of molecules exposed to strong magnetic fields, hyperfine splitting appears as a small perturbation of the Zeeman splitting.

Next, consider Zeeman effects in so called "ordinary molecules" or diamagnetic molecules. Most molecules are of the diamagnetic variety, hence the designation "ordinary". This includes, of course, most organic molecules found in biologic organisms. Diamagnetic molecules have rotational magnetic moments from rotation of the positively charged nucleus, and this magnetic moment of the nucleus is only about $1/1000$ of that from the paramagnetic molecules. This means that the energy from Zeeman splitting in diamagnetic molecules is much smaller than the energy from Zeeman splitting in paramagnetic molecules. The equation for the Zeeman energy in diamagnetic molecules is:

$$Hz = -(g_j J = g_1 I) \cdot \beta H_0$$

where J is the molecular rotational angular momentum, I is the nuclear-spin angular momentum, $g_j$ is the rotational g factor, and $g_1$ is the nuclear-spin g factor. This Zeeman energy is much less, and of much lower frequency, than the paramagnetic Zeeman energy. In terms of frequency, it falls in the hertz and kilohertz regions of the electromagnetic spectrum.

Finally, consider the implications of Zeeman splitting for catalyst and chemical reactions and for spectral chemistry. A weak magnetic field will produce hertz and kilohertz Zeeman splitting in atoms and second order effects in paramagnetic molecules. Virtually any kind of magnetic field will produce hertz and kilohertz Zeeman splitting in diamagnetic molecules. All these atoms and molecules will then become sensitive to radio and very low frequency (VLF) electromagnetic waves. The atoms and molecules will absorb the radio or VLF energy and become stimulated to a greater or lesser degree. This could be used to add spectral energy to, for instance, a particular molecule or intermediate in a chemical reaction system. For instance, for hydrogen and oxygen gases turning into water over a platinum catalyst, the hydrogen atom radical is important for maintaining the reaction. In the earth's weak magnetic field, Zeeman splitting for hydrogen is around 30 KHz. Thus, the hydrogen atoms in the reaction system, could be energized by applying to them a Zeeman splitting frequency for hydrogen (e.g., 30 KHz). Energizing the hydrogen atoms in the reaction system will duplicate the mechanisms of action of platinum, and catalyze the reaction. If the reaction was moved into outer space, away from the earth's weak magnetic field, hydrogen would no longer have a 30 KHz Zeeman splitting frequency, and the 30 KHz would no longer as effectively catalyze the reaction.

The vast majority of materials on this planet, by virtue of existing within the earth's weak magnetic field, will exhibit Zeeman splitting in the hertz and kilohertz regions. This applies to biologics and organics as well as inorganic or inanimate materials. Humans are composed of a wide variety of atoms, diamagnetic molecules, and second order effect paramagnetic molecules. These atoms and molecules all exist in the earth's weak magnetic field. These atoms and molecules in humans all have Zeeman splitting in the hertz and kilohertz regions, because they are in the earth's magnetic field. Biochemical and biocatalytic process in humans are thus sensitive to hertz and kilohertz electromagnetic radiation, by virtue of the fact that they are in the earth's weak magnetic field. As long as humans continue to exist on this planet, they will be subject to spectral energy catalyst effects from hertz and kilohertz EM waves because of the Zeeman effect from the planet's magnetic field. This has significant implications for low frequency communications, as well as chemical and biochemical reactions, diagnostics, and treatment of diseases.

A strong magnetic field will produce splitting greater than the hyperfine frequencies, in the microwave and infrared regions of the EM spectrum in atoms and paramagnetic molecules. In the hydrogen/oxygen reaction, a strong field could be added to the reaction system and transmit MHz and/or GHz frequencies into the reaction to energize the hydroxy radical and hydrogen reaction intermediates. If physical platinum was used to catalyze the reaction, the application of a particular magnetic field strength could result in both the platinum and the reaction intermediate spectra having frequencies that were split and shifted in such a way that even more frequencies matched than without the magnetic field. In this way, Zeeman splitting can be used to improve the effectiveness of a physical catalyst, by copying its mechanism of action (i.e., more frequencies could be caused to match and thus more energy could transfer).

A moderate magnetic field will produce Zeeman splitting in atoms and paramagnetic molecules at frequencies on par with the hyperfine and rotational splitting frequencies. This means that a reaction system can be energized without even adding electromagnetic energy. Similarly, by placing the reaction system in a moderate magnetic field that produces Zeeman splitting equal to the hyperfine or rotational splitting, increased reaction would occur. For instance, by using a magnetic field that causes hyperfine or rotational splitting in hydrogen and oxygen gas, that matches the Zeeman splitting in hydrogen atom or hydroxy radicals, the hydrogen or hydroxy intermediate would be energized and would proceed through the reaction cascade to produce water. By using the appropriately tuned moderate magnetic field, the magnetic field could be used to turn the reactants into catalysts for their own reaction, without the addition of physical catalyst platinum or the spectral catalyst of platinum. Although the magnetic field would simply be copying the mechanism of action of platinum, the reaction would have the appearance of being catalyzed solely by an applied magnetic field.

Finally, consider the direction of the magnetic field in relation to the orientation of the molecule. When the magnetic field is parallel to an exciting electromagnetic field, $\pi$ frequencies are produced. When the magnetic field is perpendicular to an exciting electromagnetic field, $\sigma$ frequencies are found. Assume that there is an industrial chemical reaction system that uses the same (or similar) starting reactants, but the goal is to be able to produce different products at will. By using magnetic fields combined with spectral energy or physical catalysts, the reaction can be guided to one set of products or another. For the first set of products, the electromagnetic excitation is oriented parallel to the magnetic field, producing one set of $\pi$ frequencies, which leads to a first set of products. To achieve a different product, the direction of the magnetic field is changed so that it is perpendicular to the exciting electromagnetic field. This produces a different set of $\sigma$ frequencies, and a different reaction pathway is energized, thus producing a different set of products. Thus, according to the present invention, magnetic field effects, Zeeman splitting, splitting and spectral energy catalysts can be used to fine tune the specificity of many reaction systems.

In summary, by understanding the underlying spectral mechanism to chemical reactions, magnetic fields can be used as yet another tool to catalyze and modify those chemical reactions by modifying the spectral characteristics of at least one participant and/or at least one component in the reaction system.

Reactor Vessel Size, Shape and Composition

An important consideration in the use of spectral chemistry is the reactor vessel size, shape and composition. The reactor vessel size and shape can affect the vessel's NOF to various wave energies (e.g., EM, acoustic, electrical current, etc). This in turn may affect reaction system dynamics. For instance, a particularly small bench-top reactor vessel may have an EM NOF of 1,420 MHz related to a 25 cm dimension. When a reaction with an atomic hydrogen intermediate is performed in the small bench-top reactor, the reaction proceeds quickly, due in part to the fact that the reactor vessel and the hydrogen hyperfine splitting frequencies match (1,420 MHz). This allows the reactor vessel and hydrogen intermediates to resonate, thus transferring energy to the intermediate and promoting the reaction pathway.

When the reaction is scaled up for large industrial production, the reaction would occur in a much larger reactor vessel with an EM NOF of, for example, 100 MHz. Because the reactor vessel is no longer resonating with the hydrogen intermediate, the reaction proceeds at a slower rate. This deficiency in the larger reactor vessel can be compensated for, by, for example, supplementing the reaction with 1,420 MHz radiation, thereby restoring the faster reaction rate.

Likewise, reactor vessel composition may play a similar role in reaction system dynamics. For example, a stainless steel bench-top reactor vessel may produce vibrational frequencies which resonate with vibrational frequencies of a reactant, thus, for example, promoting disassociation of a reactant into reactive intermediates. When the reaction is scaled up for industrial production, it may be placed into, for example, a ceramic-lined metal reactor vessel. The new reactor vessel typically will not produce the reactant vibrational frequency, and the reaction will proceed at a slower rate. Once again, this deficiency in the new reactor vessel, caused by its different composition, can be compensated for either by returning the reaction to a stainless steel vessel, or by supplementing, for example, the vibrational frequency of the reactant into the ceramic-lined vessel It should now be understood that all the aspects of spectral chemistry previously discussed (resonance, targeting, poisons, promoters, supporters, electric and magnetic-fields both endogenous and exogenous to reaction system components, etc.) apply to the reactor vessel, as well as to, for example, any participant placed inside it. The reactor vessel may be comprised of matter (e.g., stainless steel, plastic, glass, and/or ceramic, etc.) or it may be comprised of a field or energy (e.g., magnetic bottle, light trapping, etc.) A reactor vessel, by possessing inherent properties such as frequencies, waves, and/or fields, may interact with other components in the reaction system and/or at least one participant. Likewise, holding vessels, conduits, etc., some of which may interact with the reaction system, but in which the reaction does not actually take place, may interact with one or more components in the reaction system and may potentially affect them, either positively or negatively. Accordingly, when reference is made to the reactor vessel, it should be understood that all portions associated therewith may also be involved in desirable reactions.

EXAMPLES

The invention will be more clearly perceived and better understood from the following specific examples.

Example 1

Replacing a Physical Catalyst With a Spectral Catalyst in a Gas Phase Reaction

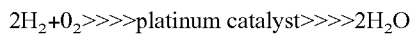

Water can be produced by the method of exposing $H_2$ and $O_2$ to a physical platinum (Pt) catalyst but there is always the possibility of producing a potentially dangerous explosive risk. This experiment replaced the physical platinum catalyst with a spectral catalyst comprising the spectral pattern of the physical platinum catalyst, which resonates with and transfers energy to the hydrogen and hydroxy intermediates.

To demonstrate that oxygen and hydrogen can combine to form water utilizing a spectral catalyst, electrolysis of water was performed to provide stoichiometric amounts of oxygen and hydrogen starting gases. A triple neck flask was fitted with two (2) rubber stoppers on the outside necks, each fitted with platinum electrodes encased in glass for a four (4) inch length. The flask was filled with distilled water and a pinch of salt so that only the glass-encased portion of the electrode was exposed to air, and the unencased portion of the electrode was completely under water. The central neck was connected via a rubber stopper to vacuum tubing, which led to a Drierite column to remove any water from the produced gases.

After vacuum removal of all gases in the system (to about 700 mm Hg), electrolysis was conducted using a 12 V power source attached to the two electrodes. Electrolysis was commenced with the subsequent production of hydrogen and oxygen gases in stoichiometric amounts. The gases passed through the Drierite column, through vacuum tubing connected to positive and negative pressure gauges and into a sealed 1,000 ml, round quartz flask. A strip of filter paper, which contained dried cobalt, had been placed in the bottom of the sealed flask. Initially the cobalt paper was blue, indicating the absence of water in the flask. A similar cobalt test strip exposed to the ambient air was also blue.

The traditional physical platinum catalyst was replaced by spectral catalyst platinum emissions from a Fisher Scientific Hollow Cathode Platinum Lamp which was positioned approximately 2 cm from the flask. This allowed the oxygen and hydrogen gases in the round quartz flask to be irradiated with emissions from the spectral catalyst. A Cathodeon Hollow Cathode Lamp Supply C610 was used to power the Pt lamp at 80% maximum current (12 mAmps). The reaction flask was cooled using dry ice in a Styrofoam container positioned directly beneath the round quartz flask, offsetting any effects of heat from the Pt lamp. The Pt lamp was turned on and within two days of irradiation, a noticeable pink color was evident on the cobalt paper strip indicating the presence of water in the round quartz flask. The cobalt test strip exposed to ambient air in the lab remained blue. Over the next four to five days, the pink colored area on the cobalt strip became brighter and larger. Upon discontinuation of the Pt emission, $H_2O$ diffused out of the cobalt strip and was taken up by the Drierite column. Over the next four to five days, the pink coloration of the cobalt strip in the quartz flask faded. The cobalt strip exposed to the ambient air remained blue.

Example 2

Replacing a Physical Catalyst With a Spectrl Catalyst in a Liquid Phase Reaction

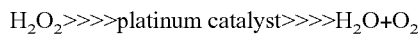

$H_2O_2 \ggg$ platinum catalyst $\ggg H_2O + O_2$

The decomposition of hydrogen peroxide is an extremely slow reaction in the absence of catalysts. Accordingly, an experiment was performed which showed that the physical catalyst, finely divided platinum, could be replaced with the spectral catalyst having the spectral pattern of platinum. Hydrogen peroxide, 3%, filled two (2) nippled quartz tubes. (the nippled quartz tubes consisted of a lower portion 17 mm internal diameter and 150 mm in length, narrowing over a 10 mm length to an upper capillary portion being 2.0 mm internal diameter and 140 mm in length and were made from PhotoVac Laser quartz tubing). Both quartz tubes were inverted in 50 ml beaker reservoirs filled with (3%) hydrogen peroxide to 40 ml and were shielded from incident light (cardboard cylinders covered with aluminum foil). One of the light shielded tubes was used as a control. The other shielded tube was exposed to a Fisher Scientific Hollow Cathode Lamp for platinum (Pt) using a Cathodeon Hollow Cathode Lamp Supply C610, at 80% maximum current (12 mA). The experiment was performed several times with an exposure time ranging from 24-96 hours. The shielded tubes were monitored for increases in temperature (there was none) to assure that any reaction was not due to thermal effects. In a typical experiment the nippled tubes were prepared with hydrogen peroxide (3%) as described above herein. Both tubes were shielded from light, and the Pt tube was exposed to platinum spectral emissions, as described above, for about 24 hours. Gas production in the control tube A measured about four (4) mm in length in the capillary (i.e., about 12.5 mm³), while gas in the Pt (tube B) measured about 50 mm (i.e., about 157 mm³). The platinum spectral catalyst thus increased the reaction rate about 12.5 times.

The tubes were then switched and tube A was exposed to the platinum spectral catalyst, for about 24 hours, while tube B served as the control. Gas production in the control (tube B) measured about 2 mm in length in the capillary (i.e., about 6 nu3) while gas in the Pt tube (tube A) measured about 36 mm (i.e., about 113 mm³), yielding about a 19 fold difference in reaction rate.

As a negative control, to confirm that any lamp would not cause the same result, the experiment was repeated with a sodium lamp at 6 mA (80% of the maximum current). Na in a traditional reaction would be a reactant with water releasing hydrogen gas, not a catalyst of hydrogen peroxide breakdown. The control tube measured gas to be about 4 mm in length (i.e., about 12 mm³) in the capillary portion, while the Na tube gas measured to be about 1 mm in length (i.e., about 3 mm³). This indicated that while spectral emissions can substitute for catalysts, they cannot yet substitute for reactants. Also, it indicated that the simple effect of using a hollow cathode tube emitting heat and energy into the hydrogen peroxide was not the cause of the gas bubble formation, but instead, the spectral pattern of Pt replacing the physical catalyst caused the reaction.

Example 3

Replacing a Physical Catalyst With a Spectral Catalyst in a Solid Phase Reaction It is well known that certain micro-organisms have a toxic reaction to silver Ag. It is now understood through this invention, that high intensity spectral frequencies produced in the silver electronic spectrum match with ultraviolet frequencies that are lethal to bacteria (by creation of free radicals and by causing bacterial DNA damage) but are harmless to mammalian cells. Thus, it was theorized that the known medicinal and anti-microbial uses of silver are due to a spectral catalyst effect. In this regard, an experiment was conducted which showed that the spectral catalyst emitting the spectrum of silver demonstrated a toxic or inhibitory effect on micro-organisms.

Bacterial cultures were placed onto standard growth medium in two petri dishes (one control and one Ag) using standard plating techniques covering the entire dish. Each dish was placed at the bottom of a light shielding cylindrical chamber. A light shielding foil-covered, cardboard disc with a patterned slit was placed over each culture plate. A Fisher Scientific Hollow Cathode Lamp for Silver (Ag) was inserted through the top of the Ag exposure chamber so that only the spectral emission pattern from the silver lamp was irradiating the bacteria on the Ag culture plate (i.e., through the patterned slit). A Cathodeon Hollow Cathode Lamp Supply C610 was used to power the Ag lamp at 80% maximum current (3.6 mA). The control plate was not exposed to emissions of an Ag lamp, and ambient light was blocked. Both control and Ag plates were maintained at room temperature (e.g., about 70-74° F.) during the silver spectral emission exposure time, which ranged from about 12-24 hours in the various experiments. Afterwards, both plates were incubated using standard techniques (37° C., aerobic Forma Scientific Model 3157, Water-Jacketed Incubator) for about 24 hours.

The following bacteria (obtained from the Microbiology Laboratory at People's Hospital in Mansfield, Ohio, US), were studied for effects of the Ag lamp spectral emissions:
1. *E. coli;*
2. *Strep. pneumoniae;*
3. *Staph. aureus;* and
4. *Salmonella typhi.*

This group included both Gram⁺ and Gram⁻ species, as well as cocci and rods.

Results were as follows:
1. Controls—all controls showed full growth covering the culture plates;
2. The Ag plates
   areas unexposed to the Ag spectral emission pattern showed full growth.
   areas exposed to the Ag spectral emission pattern showed:
   a. *E. coli*—no growth;
   b. *Strep. pneumoniae*—no growth; and
   c. *Staph. agreus*—no growth;
   d. *Salmoinella tyhli*—inhibited growth.

Example 4

Replacing a Physical Catalyst With a Spectral Catalyst, and Comparing Results to Physical Catalyst Results in a Biologic Preparation To further demonstrate that certain susceptible organisms which have a toxic reaction to silver would have a similar reaction to the spectral catalyst emitting the spectrum of silver, cultures were obtained from the American Type Culture Collection (ATCC) which included *Escherichia coli* #25922, and *Klebsiella pneumonia,* subsp *Pneumoniae,* #13883. Control and Ag plate cultures were performed as described above. After incubation, plates were examined using a binocular microscope. The *E. coli* exhibited moderate resistance to the bactericidal effects of the spectral silver emission, while the Klebsiella exhibited moderate sensitivity. All controls exhibited full growth.

Accordingly, an experiment was performed which demonstrated a similar result using the physical silver catalyst as was obtained with the Ag spectral catalyst. Sterile test discs were soaked in an 80 ppm, colloidal silver solution. The same two (2) organisms were again plated, as described above. Colloidal silver test discs were placed on each Ag plate, while the control plates had none. The plates were incubated as described above and examined under the binocular microscope. The collodial silver E. coli exhibited moderate resistance to the bactericidal effects of the physical colloidal silver, while the Klebsiella again exhibited moderate sensitivity. All controls exhibited full growth.

Example 5

Augmenting a Physical Catalyst With a Spectral Catalyst

To demonstrate that oxygen and hydrogen can combine to form water utilizing a spectral catalyst to augment a physical catalyst, electrolysis of water was performed to provide the necessary oxygen and hydrogen starting gases, as in Example 1.

Two quartz flasks (A and B) were connected separately after the Drierite column, each with its own set of vacuum and pressure gauges. Platinum powder (31 mg) was placed in each flask. The flasks were filled with electrolytically produced stoichiometric amounts of $H_2$ and $O_2$ to 120 mm Hg. The flasks were separated by a stopcock from the electrolysis system and from each other. The pressure in each flask was recorded over time as the reaction proceeded over the physical platinum catalyst. The reaction combines three (3) moles of gases, (i.e., two (2) moles H2 and one (1) mole O2), to produce two (2) moles $H_2O$. This decrease in molarity, and hence progress of the reaction, can be monitored by a decrease in pressure "P" which is proportional, via the ideal gas law, (PV=nRT), to molarity "n". A baseline rate of reaction was thus obtained. Additionally, the test was repeated filling each flask with $H_2$ and $O_2$ to 220 mm Hg. Catalysis of the reaction by only the physical catalyst yielded two baseline reaction curves which were in good agreement between flasks A and B, and for both the 110 mm and 220 mm Hg tests.

Next, the traditional physical platinum catalyst in flask A was augmented with spectral catalyst platinum emissions from two (2) parallel Fisher Scientific Hollow Cathode Platinum Lamps, as in Example 1, which were positioned approximately two (2) cm from flask A. The test was repeated as described above, separating the two (2) flasks from each other and monitoring the rate of the reaction via the pressure decrease in each. Flask B served as a control flask. In flask A, the oxygen and hydrogen gases, as well as the physical platinum catalyst, were directly irradiated with emissions from the Pt lamp spectral catalyst.

Rate of reaction in the control flask B, was in good agreement with previous baseline rates. Rate of reaction in flask "A", wherein physical platinum catalyst was augmented with the platinum spectral pattern, exhibited an overall mean increase of 60%, with a maximal increase of 70% over the baseline and flask B.

Example 6

Replacing a Physical Catalyst With a Fine Structure Heterodyned Frequency and Replacing a Physical Catalyst With a Fine Structure Frequency the Alpha Rotation-Vibration Constant Water was electrolyzed to produce stoichiometric amounts of hydrogen and oxygen gases as described above herein. Additionally, a dry ice cooled stainless steel coil was placed immediately after the Drierite column. After vacuum removal of all gases in the system, electrolysis was accomplished using a 12 V power source attached to the two electrodes, resulting in a production of hydrogen and oxygen gases. After passing through the Drierite column, the hydrogen and oxygen gases passed through vacuum tubing connected to positive and negative pressure gauges, through the dry ice cooled stainless steel coil and then to a 1,000 ml round, quartz flask. A strip of filter paper impregnated with dry (blue) cobalt was in the bottom of the quartz flask, as an indicator of the presence or absence of water.

The entire system was vacuum evacuated to a pressure of about 700 mm Hg below atmospheric pressure. Electrolysis was performed, producing hydrogen and oxygen gases in stoichiometric amounts, to result in a pressure of about 220 mm Hg above atmospheric pressure. The center of the quartz flask, now containing hydrogen and oxygen gases was irradiated for approximately 12 hours with continuous microwave electromagnetic radiation emitted from a Hewlett Packard microwave spectroscopy system which included an HP 83350B Sweep Oscillator, an HP 8510B Network Analyzer, and an HP 8513A Reflection Transmission Test Set. The frequency used was 21.4 GHz, which corresponds to a fine splitting constant, the alpha rotation-vibration constant, of the hydroxy intermediate, and is thus a harmonic resonant heterodyne for the hydroxy radical. The cobalt strip changed strongly in color to pink which indicated the presence of water in the quartz flask, whose creation was catalyzed by a harmonic resonant heterodyne frequency for the hydroxy radical.

Example 7

Replacing a Physical Catalyst With a Hyperfine Splitting Frequency

An experimental dark room was prepared, in which there is no ambient light, and which can be totally darkened. A shielded, ground room (Ace Shielded Room, Ace, Philadelphia, Pa., US, Model A6H$_3$-16; 8 feet wide, 17 feet long, and 8 feet high copper mesh) was installed inside the dark room.

Hydrogen peroxide (3%) was placed in nippled quartz tubes, which were then inverted in beakers filled with (3%) hydrogen peroxide, as described in greater detail herein. The tubes were allowed to rest for about 18 hours in the dark room, covered with non-metallic light blocking hoods (so that the room could be entered without exposing the tubes to light). Baseline measurements of gases in the nippled tubes were then performed.

Three nippled RF tubes were placed on a wooden grid table in the shielded room, in the center of grids 4, 54, and 127; corresponding to distances of about 107 cm, 187 cm, and 312 cm respectively, from a frequency-emitting antenna (copper tubing 15 mm diameter, 4.7 m octagonal circumference, with the center frequency at approximately 6.5 MHz. A 25 watt, 17 MHz signal was sent to the antenna. This frequency corresponds to a hyperfine splitting frequency of the hydrogen atom, which is a transient in the dissociation of hydrogen peroxide. The antenna was pulsed continuously by a BK Precision RF Signal Generator Model 2005A, and amplified by an Amplifier Research amplifier, Model 25A-100. A control tube was placed on a wooden cart immediately adjacent to the shielded room, in the dark room. All tubes were covered with non-metallic light blocking hoods.

After about 18 hours, gas production from dissociation of hydrogen peroxide and resultant oxygen formation in the nippled tubes was measured. The RF tube closest to the antenna produced 11 mm length gas in the capillary (34 mm$^3$), the tube intermediate to the antenna produced a 5 mm length (10 mm$^3$) gas, and the RF tube farthest from the antenna produced no gas. The control tube produced 1 mm gas. Thus, it can be concluded that the RF hyperfine splitting frequency for hydrogen increased the reaction rate approximately five (5) to ten (10) times.

Example 8

Replacing a Physical Catalyst With a Magnetic Field

Hydrogen peroxide (15%) was placed in nippled quartz tubes, which were then inverted in beakers filled with (15%) hydrogen peroxide, as described above. The tubes were allowed to rest for four (4) hours on a wooden table in a shielded cage, in a dark room. Baseline measurements of gases in the nippled tubes were then performed.

Remaining in the shielded cage, in the dark room, two (2) control tubes were left on a wooden table as controls. Two (2) magnetic field tubes were placed on the center platform of an ETS Helmholtz single axis coil, Model 6402, 1.06 gauss/Ampere, pulsed at about 83 Hz by a BK Precision 20 MHz Sweep/Function Generator, Model 4040. The voltage output of the function generator was adjusted to produce an alternating magnetic field of about 19.5 milliGauss on the center platform of the Helmholtz Coil, as measured by a Holaday Model HI-3627, three (3) axis ELF magnetic field meter and probe. Hydrogen atoms, which are a transient in the dissociation of hydrogen peroxide, exhibit nuclear magnetic resonance via Zeeman splitting at this applied frequency and applied magnetic field strength. Thus, frequency of the alternating magnetic field was resonant with the hydrogen transients.

After about 18 hours, gas production from dissociation of hydrogen peroxide and resultant oxygen formation in the nippled tubes was measured. The control tubes averaged about 180 mm gas formation (540 mm$^3$) while the tubes exposed to the alternating magnetic field produced about 810 mm gas (2,430 mm$^3$), resulting in an increase in the reaction rate of approximately four (4) times.

Example 9

Negatively Catalyzing a Reaction With an Electric Field

Hydrogen peroxide (15%) was placed in four (4) nippled quartz tubes which were inverted in hydrogen peroxide (15%) filled beakers, as described in greater detail above herein. The tubes were placed on a wooden table, in a shielded room, in a dark room. After four (4) hours, baseline measurements were taken of the gas in the capillary portion of the tubes.

An Amplifier Research self-contained electromagnetic mode cell ("TEM") Model TC1510A had been placed in the shielded, darkened room. A sine wave signal of about 133 MHz was provided to the TEM cell by a BK Precision RF Signal Generator, Model 2005A, and an Amplifier Research amplifier, Model 25A100. Output levels on the signal generator and amplifier wave adjusted to produce an electric field (E-field) of about five (5) V/m in the center of the TEM cell, as measured with a Holaday Industries electric field probe, Model HI-4433GRE, placed in the center of the lower chamber.

Two of the hydrogen peroxide filled tubes were placed in the center of the upper chamber of the TEM cell, about 35 cm from the wall of the shielded room. The other two (2) tubes served as controls and were placed on a wooden table, also about 35 cm from the same wall of the shielded, dark room, and removed from the immediate vicinity of the TEM cell, so that there was no ambient electric field, as confirmed by E-field probe measurements.

The 133 MHz alternating sine wave signal delivered to the TEM cell was well above the typical line width frequency at room temperature (e.g., about 100 KHz) and was theorized to be resonant with an n=20 Rydberg state of the hydrogen atom as derived from $$\Delta E = cE^{3/4}$$

where E is the change in energy in cm$^{-1}$, c is 7.51±0.02 for the hydrogen state n=20 and E is the electric field intensity in (Kv/cm)$^2$.

After about five (5) hours of exposure to the electric field, the mean gas production in the tubes subjected to the E-field was about 17.5 mm, while mean gas production in the control tubes was about 58 mm.

While not wishing to be bound by any particular theory or explanation, it is believed that the alternating electric field resonated with an upper energy level in the hydrogen atoms, producing a negative Stark effect, and thereby negatively catalyzing the reaction.

Example 10

Augmentation of a Physical Catalyst By Irradiating Reactants/Transients With a Spectral Catalyst Hydrogen and oxygen gases were produced in stoichiometric amounts by electrolysis, as previously described in greater detail above herein. A stainless steel coil cooled in dry ice was placed immediately after the Drierite column. Positive and negative pressure gauges were connected after the coil, and then a 1,000 ml round quartz flask was sequentially connected with a second set of pressure gauges.

At the beginning of each experimental run, the entire system was vacuum evacuated to a pressure of about minus 650 mm Hg. The system was sealed for about 15 minutes to confirm the maintenance of the generated vacuum and integrity of the connections. Electrolysis of water to produce hydrogen and oxygen gases was performed, as described previously.

Initially, about 10 mg of finely divided platinum was placed into the round quartz flask. Reactant gases were allowed to react over the platinum and the reaction rate was monitored by increasing the rate of pressure drop over time, as previously described. The starting pressure was approximately in the mid-90's mm Hg positive pressure, and the ending pressure was approximately in the low 30's over the amount of time that measurements were taken. Two (2) control runs were performed, with reaction rates of about 0.47 mm Hg/minute and about 0.48 mm Hg/minute.

For the third run, a single platinum lamp was applied, as previously described, except that the operating current was reduced to about eight (8) mA and the lamp was positioned through the center of the flask to irradiate only the reactant/transient gases, and not the physical platinum catalyst. The reaction rate was determined, as described above, and was found to be about 0.63 mm Hg/minute, an increase of 34%.

Example 11

Apparent Poisoning of a Reaction By the Spectral Pattern of a Physical Poison

The conversion of hydrogen and oxygen gases to water, over a stepped platinum physical catalyst, is known to be poisoned by gold. Addition of gold to this platinum catalyzed reaction reduces reaction rates by about 95%. The gold blocks only about one sixth of the platinum binding sites, which according to prior art, would need to be blocked to poison the physical catalyst to this degree. Thus, it was theorized that a spectral interaction of the physical gold with the physical platinum and/or reaction system could also be responsible for the poisoning effects of gold on the reaction. It was further theorized that addition of the gold spectral pattern to the reaction catalyzed by physical platinum could also poison the reaction.

Hydrogen and oxygen gases were produced by electrolysis, as described above in greater detail. Finely directed platinum, about 15 mg, was added to the round quartz flask. Starting pressures were about in the 90's mm Hg positive pressure, and ending pressures were about in the 20's mm Hg over the amount of time that measurements were taken. Reaction rates were determined as previously described. The first control run revealed a reaction rate of about 0.81 mm Hg/minute.

In the second run, a Fisher Hollow Cathode Gold lamp was applied, as previously described, at an operating frequency of about eight (8) mA, (80% maximum current), through about the center of the round flask. The reaction rate increased to about 0.87 mm Hg/minute.

A third run was then performed on the same reaction flask and physical platinum that had been in the flask exposed to the gold spectral pattern. The reaction rate decreased to about 0.75 mm Hg/minute.

What is claimed is:

1. A method for controlling a water formation reaction system comprising:
   direct resonance targeting atomic hydrogen in a reaction system comprising hydrogen, oxygen and atomic hydrogen, said direct resonance targeting of said atomic hydrogen occurring with electromagnetic emissions from a platinum lamp.

2. The method of claim 1, wherein said reaction system further comprises hydroxyl radical.

3. The method of claim 2, wherein said hydroxyl radical is direct resonance targeted with electromagnetic emissions from said platinum lamp.

4. The method of claim 1, wherein said reaction system further comprises physical platinum.

5. The method of claim 4, wherein said physical platinum comprises platinum powder.

6. The method of claim 1, wherein said platinum lamp comprises a hollow cathode lamp.

7. A method for increasing the rate of a water formation reaction comprising:
   irradiating a reaction system comprising hydrogen, oxygen and atomic hydrogen with a spectral energy catalyst, said spectral energy catalyst consisting of platinum electromagnetic emissions.

8. The method of claim 7, wherein said reaction system further comprises physical platinum.

9. The method of claim 8, wherein said physical platinum comprises platinum powder.

10. The method of claim 8, wherein said reaction system further comprises hydroxyl radical.

11. The method of claim 10, wherein said hydroxyl radical is direct resonance targeted with said platinum electromagnetic emissions.

12. A method for increasing the rate of a water formation reaction comprising:
    direct resonance targeting atomic hydrogen in a reaction system comprising hydrogen, oxygen and atomic hydrogen, said direct resonance targeting of said atomic hydrogen occurring by irradiating said reaction system with a spectral energy catalyst consisting of platinum electromagnetic emissions.

13. The method of claim 12, wherein said reaction system further comprises hydroxyl radical.

14. The method of claim 13, wherein said hydroxyl radical is direct resonance targeted with said spectral energy catalyst.

15. The method of claim 12, wherein said reaction system further comprises physical platinum.

16. The method of claim 15, wherein said physical platinum comprises platinum powder.

17. A method for controlling a water formation reaction system comprising:
    forming a reaction system comprising hydrogen, oxygen, atomic hydrogen and physical platinum; and
    direct resonance targeting said atomic hydrogen with electromagnetic emissions from a platinum lamp.

18. The method of claim 17, wherein said physical platinum comprises platinum powder.

19. A method for increasing the rate of a water formation reaction comprising:
    forming a reaction system comprising hydrogen, oxygen, atomic hydrogen and physical platinum;
    providing a spectral energy catalyst consisting of platinum electromagnetic emissions; and
    irradiating said reaction system with said spectral energy catalyst.

20. The method of claim 19, wherein said physical platinum comprises platinum powder.

* * * * *